US012599666B2

(12) United States Patent
Han et al.

(10) Patent No.: US 12,599,666 B2
(45) Date of Patent: Apr. 14, 2026

(54) PHOTOLYTIC COMPOUNDS AND TRIPLET-TRIPLET ANNIHILATION MEDIATED PHOTOLYSIS

(71) Applicant: University of Massachusetts, Boston, MA (US)

(72) Inventors: Gang Han, Shrewsbury, MA (US); Ling Huang, Worcester, MA (US)

(73) Assignee: University of Massachusetts, Westborough, MA (US)

(*) Notice: Subject to any disclaimer, the term of this patent is extended or adjusted under 35 U.S.C. 154(b) by 884 days.

(21) Appl. No.: 17/765,251

(22) PCT Filed: Oct. 7, 2020

(86) PCT No.: PCT/US2020/054478
§ 371 (c)(1),
(2) Date: Mar. 30, 2022

(87) PCT Pub. No.: WO2021/071876
PCT Pub. Date: Apr. 15, 2021

(65) Prior Publication Data

US 2022/0387590 A1 Dec. 8, 2022

Related U.S. Application Data

(60) Provisional application No. 62/913,701, filed on Oct. 10, 2019.

(51) Int. Cl.

| | |
|---|---|
| ***A61K 41/00*** | (2020.01) |
| ***A61K 31/196*** | (2006.01) |
| ***A61K 39/395*** | (2006.01) |
| ***A61K 47/54*** | (2017.01) |

(52) U.S. Cl.
CPC ........ *A61K 41/0042* (2013.01); *A61K 31/196* (2013.01); *A61K 39/3955* (2013.01); *A61K 47/54* (2017.08); *A61K 47/545* (2017.08)

(58) Field of Classification Search
CPC .................................................. A61K 41/0042
See application file for complete search history.

(56) References Cited

FOREIGN PATENT DOCUMENTS

WO WO2016077311 A1 * 5/2016 ............... C07K 1/00

* cited by examiner

*Primary Examiner* — Paul V Ward
(74) *Attorney, Agent, or Firm* — Milstein Zhang & Wu LLC

(57) ABSTRACT

The invention provides novel photolytic compounds and prodrugs, nanoparticles and compositions thereof, and methods of conducting photolysis mediated by triplet-triplet annihilation.

12 Claims, 48 Drawing Sheets

$Ir(ppy)_3$

Cou (1)

PHOTOLYTIC COMPOUNDS AND TRIPLET-TRIPLET ANNIHILATION MEDIATED PHOTOLYSIS

PRIORITY CLAIMS AND RELATED APPLICATIONS

This application is the U.S. national phase of and claims priority to PCT/US20/54478, filed Oct. 7, 2020, which claims the benefit of priority to U.S. Provisional Application No. 62/913,701, filed Oct. 10, 2019, the entire content of each of which is incorporated herein by reference for all purposes.

TECHNICAL FIELDS OF THE INVENTION

The invention generally relates to chemical and biological photolysis and photolytic compounds. More particularly, the invention provides novel photolytic compounds, prodrugs, nanoparticles and compositions thereof, and methods of conducting chemical and biological photolysis mediated by triplet-triplet annihilation.

BACKGROUND OF THE INVENTION

Photolysis is a chemical reaction in which a chemical compound is broken down by light to yield a different chemical compound. Due to the unique and precise spatiotemporal controllability, photolysis is a powerful approach with vast applications from organic synthesis, drug discovery to numerous biological applications, such as developmental biology, neuromodulation, as well as cancer treatments. In general, a photolytic molecule consists of three key components: a payload, a photolabile linkage and a photoremovable protecting group (PPG). In photolysis, PPG absorbs high-energy photons and then transitions to an excited state, causing the photolabile linkage to break down, resulting in the release of the payload molecule. Unfortunately, most of the existing PPGs, such as coumarin (Cou), anthracene (An) and perylene (Py), boron-dipyrromethene (BDP) only respond to high energy short wavelength single photon light excitation for subsequent photolytic reactions (FIG. 1A). (Klán, et al. 2013 *Chem. Rev.* 113, 119-191.)

Photolysis has enabled numerous discoveries in chemistry, drug discovery and biology. The use of short wavelength light for photolysis, however, has inherent drawbacks. For instance, the shallow penetration of short wavelength light through colored reaction solvents or media leads to poor photolytic reaction yields, especially in large-scale chemical reactions. In addition, short wavelength photons cause the rapid photodamage and photobleaching of PPGs. (Ravetz, et al. 2019 *Nature* 565, 343-346.) Moreover, in regard to photolysis applications in biology, the term "photouncaging" has been coined to describe the technique of using light to remove the PPGs and activate biological compounds so as to noninvasively probe different biological processes, neuronal connections, as well as to develop disease treatments. However, photouncaging using conventional short wavelength light also encounter serious problems, such as inevitable phototoxicity and shallow tissue penetration depths. (Mitsunaga, et al. 2011 *Nat. Med.* 17, 1685.)

Efforts to address these challenges by using lower energy long wavelength light, such as far red light and near infrared light that has much higher penetration depth through various media and biological tissue, have not been successful. (Welsher, et al. 2009 *Nat. Nano.* 4, 773.) To date, there are only a pair of state-of-the-art long wavelength activation photolytic methods in the reported literature. For example, the femtosecond pulsed two-photon laser can be used to remove PPGs. (Richers, et al. 2017 *Angew. Chem. Int. Ed.* 56, 193-197.) This process, however, is quite inadequate for photolysis as the two-photon absorption cross-sectional area of PPGs is quite weak and the reactions can only take place in the tiny area of the laser focal point. (Klán, et al. 2013 *Chem. Rev.* 113, 119-191.) (FIG. 1B).

Meanwhile, lanthanide-doped upconversion nanoparticles (UCNPs)-assisted photolysis have emerged as an appealing method. (Carling, et al. 2009 *J. Am. Chem. Soc.* 131, 10838-10839.) Yet, owing to low absorption and emission cross-sections, the lanthanide-doped UCNPs typically suffer from the need for high power light excitation ($10^1$-$10^4$ $W \cdot cm^{-2}$) and inherently low quantum yields. (Dong, et al. 2015 *Chem. Rev.* 115, 10725-10815.) In addition, upconversion luminescence resonance energy transfer (LRET) from inorganic UCNP nanoparticles to conjugated PPGs is generally inefficient. (FIG. 1C).

There is a dearth of efficient long wavelength light mediated photolysis. An ongoing need exists for novel photolytic methodologies as well as compounds and compositions that are suitable for improved photolytic yield and versatility.

SUMMARY OF THE INVENTION

The invention provides novel photolytic compounds, prodrugs, nanoparticles and compositions thereof, as well as methods of conducting photolysis mediated by triplet-triplet annihilation. More particularly, disclosed herein is a highly efficient and versatile triplet-triplet annihilation mediated photolysis (TTAP) method that enables long wavelength single photon driven photolytic reactions to occur for a wide variety of photolytic molecules. The present disclosure also demonstrates the therapeutic potentials of photolytic compounds and methods based in the present invention in diverse biopharmaceutical fields, such as anti-inflammation and anti-tumor immunotherapy in ambient air-stable nanoparticle formations.

In a TTAP, as depicted in FIG. 1D, photosensitizers (Sen) absorb low energy long wavelength photons, reach their singlet excited state ($^1$[Sen]*) and subsequently populate their long-lived triplet excited state ($^3$[Sen]*) through rapid intersystem crossing (ISC). The resultant lifetime of this photosensitizer triplet excited state is long enough to allow collisions of the targeted photolytic molecules (PPGs-X) to occur. The energy of $^3$[Sen]* can thus be efficiently transferred to PPGs-X. Consequently, the triplet-triplet annihilation (TTA) of *[PPGs-X]$^1$ drives photolytic reactions to take place, thus breaking down the photolabile linkage and releasing and activating the targeted molecules. Because of the much greater light absorption of photosensitizers than PPGs themselves and the highly efficient triplet-triplet energy transfer (TTET) from photosensitizers to PPGs-X, the long wavelength single photon driven TTAP method can outperform existing short-wavelength single photon direct activation and two long wavelength activation methods.

In one aspect, the invention generally relates to a compound having the formula,

PPG-X, wherein PPG is a photoremovable protecting group and X is L-Y, wherein L is a photolabile linker and Y an active moiety.

In another aspect, the invention generally relates to a composition that comprises a compound disclosed herein.

In yet another aspect, the invention generally relates to a pharmaceutical composition comprising a compound disclosed herein and one or more pharmaceutically acceptable excipients, carriers or diluents.

In yet another aspect, the invention generally relates to a light-activatable prodrug comprising is a photoremovable protecting group linked to a bioactive agent via a photolabile linker.

In yet another aspect, the invention generally relates to a pharmaceutical composition comprising a light-activatable prodrug disclosed herein and one or more pharmaceutically acceptable excipients, carriers or diluents.

In yet another aspect, the invention generally relates to a composition comprising a pair of a photosensitizer and a photolytic compound, wherein the photosensitizer and the photolytic compound are selected as follows: the photosensitizer is capable of light absorption of single low energy photon in the range of about 400 nm to about 1,000 nm thereby reaching a singlet excited state and subsequently generating a photosensitizer triplet excited state through rapid intersystem crossing; and the triplet excited state is characterized by a lifetime sufficient to allow collision with the photolytic molecule to occur thereby capable of transferring energy to the photolytic molecule via triplet-triplet annihilation so as to cause a photolytic reaction of the photolytic compound.

In yet another aspect, the invention generally relates to a nanoparticle comprising a polymer with encapsulated therein one or more photosensitizers and one or more photolytic compounds.

In yet another aspect, the invention generally relates to a pharmaceutical composition comprising nanoparticles disclosed herein and one or more pharmaceutically acceptable excipients, carriers or diluents.

In yet another aspect, the invention generally relates to a method for inhibiting cancer cell growth, comprising administering to a subject in need there of a pharmaceutical composition comprising a compound disclosed herein.

In yet another aspect, the invention generally relates to a method for inhibiting cancer cell growth, comprising administering to a subject in need there of a pharmaceutical composition comprising nanoparticles disclosed herein.

In yet another aspect, the invention generally relates to a method for performing immunotherapy, comprising administering to a subject in need there of a pharmaceutical composition comprising a compound disclosed herein.

In yet another aspect, the invention generally relates to a method for performing immunotherapy, comprising administering to a subject in need there of a pharmaceutical composition comprising nanoparticles disclosed herein.

In yet another aspect, the invention generally relates to a method for reducing inflammation, comprising administering to a subject in need there of a pharmaceutical composition comprising a compound disclosed herein.

In yet another aspect, the invention generally relates to a method for reducing inflammation, comprising administering to a subject in need there of a pharmaceutical composition comprising nanoparticles disclosed herein.

In yet another aspect, the invention generally relates to a method for conducting photolysis, comprising: providing a photosensitizer; causing a light absorption by the photosensitizer under conditions to reach a singlet excited state and subsequently generate a photosensitizer triplet excited state through rapid intersystem crossing; and contacting the photosensitizer triplet excited state with a photolytic molecule to transfer energy from the photosensitizer triplet excited state to the photolytic molecule via triplet-triplet annihilation so as to cause a photolytic reaction of the photolytic compound.

DETAILED DESCRIPTION OF THE INVENTION

Figure 1:
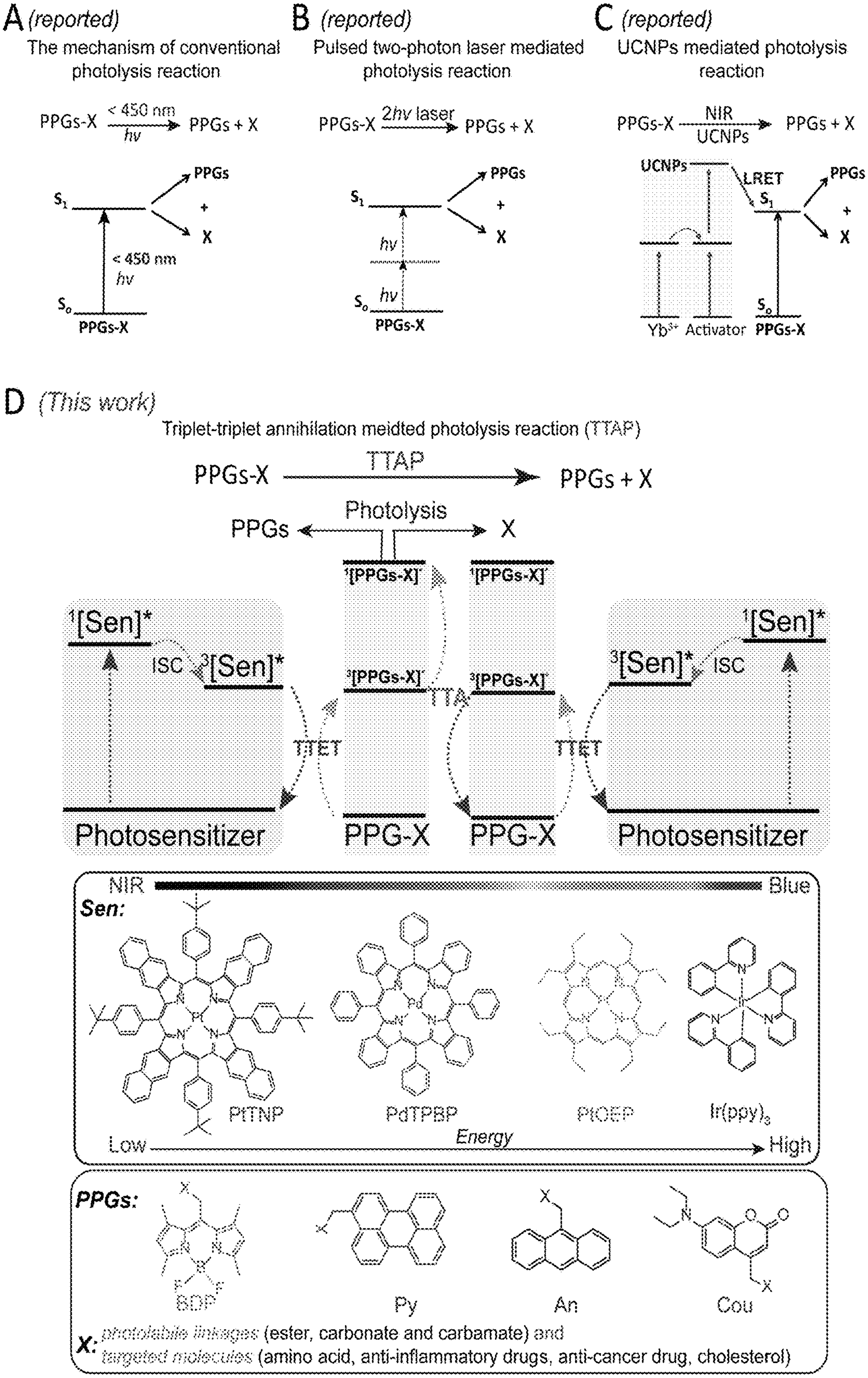
FIG. 1. The mechanism of reported state-of-the-art photolytic reactions and the TTAP mechanism in this work. (a) The reported conventional short wavelength direct activation (b) pulsed two photon laser strategy mechanism for photolytic reaction, hv: single photon, 2 hv: two photon; (c) The reported lanthanide ion doped upconversion nanoparticles (UCNPs) mediated photolytic reaction, LRET: luminescence resonance energy transfer; (d) The mechanism of triplet-triplet annihilation mediated photolysis (TTAP, this work), ISC: intersystem crossing, TTET: triplet-triplet energy transfer, TTA: triplet-triplet annihilation, 1[Sen]*: the singlet excited state of the photosensitizer; $^3$[Sen]*: the triplet excited state of the photosensitizer; PPGs: photoremovable protecting group, X: targeted molecules (amino acids, anti-inflammatory drugs, anti-cancer drug, cholesterol) and photolabile linkage (ester bond, carbonate, carbamate); the molecular structures of photosensitizers, including PtTNP, PdTPBP, PtOEP and $Ir(ppy)_3$; The molecular structures of PPGs, including BDP, Py, An and Cou moieties.

The invention is based in part on the discovery of a novel, highly efficient and robust photolysis platform methodology where long wavelength single photon is employed to drive a wide array of photolytic reactions via triplet-triplet annihilation photolysis. This methodology is highly versatile and can be adapted to a broad range of wavelengths on the electromagnetic spectrum as well as to diverse chemical structures of photoremovable protecting groups, photolabile linkages, in addition to a broad array of payload molecules. The TTAP approach not only remarkably surpasses photolytic quantum efficiency but also resolves the photobleaching of the existing photolysis methods, regardless of whether they are a single photon or multiple photon associated. Furthermore, air-stable TTAP nanoparticles are disclosed herein that can exert highly effective ultra-low power far red light activated photolysis to activate anticancer prodrugs to potentiate anti-tumor immunotherapy.

In one aspect, the invention generally relates to a compound having the formula,

PPG-X, wherein PPG is a photoremovable protecting group and X is L-Y, wherein L is a photolabile linker and Y an active moiety.

In certain embodiments, the PPG comprises a moiety selected from the group consisting of coumarin, anthracene and perylene, boron-dipyrromethene, or a derivative or analog thereof.

In certain embodiments, the PPG comprises a coumarin or a derivative or analog thereof.

In certain embodiments, the PPG comprises a anthracene or a derivative or analog thereof.

In certain embodiments, L comprises an ester bond.

In certain embodiments, L comprises carbonate bond.

In certain embodiments, L comprises a carbamate.

In certain embodiments, L comprises a quaternary ammonium salt moiety.

In certain embodiments, Y is a bioactive moiety.

In certain embodiments, Y is a therapeutic agent.

In certain embodiments, Y is a diagnostic agent or probe.

In certain embodiments, Y is a chemically active moiety.

In certain embodiments, Y is an anti-inflammatory agent.

In certain embodiments, Y is an anti-nonsteroidal agent.

In certain embodiments, Y is an anti-tumor agent.

In certain embodiments, Y is cholesterol.

In certain embodiments, Y is a peptide.

In another aspect, the invention generally relates to a composition that comprises a compound disclosed herein.

In yet another aspect, the invention generally relates to a pharmaceutical composition comprising a compound disclosed herein.

In yet another aspect, the invention generally relates to a light-activatable prodrug comprising is a photoremovable protecting group linked to a bioactive agent via a photolabile linker.

In certain embodiments, the light-activatable prodrug has the structure

PPG-X, wherein PPG is a photoremovable protecting group; and X is L-Y, wherein L is a photolabile linker and Y an active moiety.

In certain embodiments, the bioactive agent is a therapeutic agent.

In certain embodiments, the bioactive agent is a diagnostic or imaging agent or probe.

In certain embodiments, the bioactive agent is an anti-inflammatory agent. In certain embodiments, the bioactive agent is an anti-nonsteroidal agent.

In certain embodiments, the bioactive agent is an anti-tumor agent.

In certain embodiments, the bioactive agent is cholesterol.

In certain embodiments, the bioactive agent is an amino acid.

In certain embodiments, the PPG comprises a moiety selected from the group consisting of coumarin, anthracene and perylene, boron-dipyrromethene, or a derivative or analog thereof.

In certain embodiments, the PPG comprises a coumarin or a derivative or analog thereof.

In certain embodiments, the PPG comprises an anthracene or a derivative or analog thereof.

In certain embodiments, L comprises an ester, carbonate, carbamate, quaternary ammonium salt moiety.

In certain embodiments, L comprises an ester group.

In certain embodiments, L comprises a carbonate group.

In certain embodiments, L comprises a carbamate group.

In yet another aspect, the invention generally relates to a pharmaceutical composition comprising a light-activatable prodrug disclosed herein.

In yet another aspect, the invention generally relates to a composition comprising a pair of a photosensitizer and a photolytic compound, wherein the photosensitizer and the photolytic compound are selected as follows: the photosensitizer is capable of light absorption of single low energy photon in the range of about 400 nim to about 1,000 nm thereby reaching a singlet excited state and subsequently generating a photosensitizer triplet excited state through rapid intersystem crossing; and the triplet excited state is characterized by a lifetime sufficient to allow collision with the photolytic molecule to occur thereby capable of transferring energy to the photolytic molecule via triplet-triplet annihilation so as to cause a photolytic reaction of the photolytic compound.

In certain embodiments of the composition, the photolytic compound has the formula,

PPG-X, wherein PPG is a photoremovable protecting group and X comprises is a photolabile group.

In certain embodiments, X is L-Y, wherein L is a photolabile linker and Y an active moiety.

In certain embodiments, the PPG comprises a moiety selected from the group consisting of coumarin, anthracene and perylene, boron-dipyrromethene, or a derivative or analog thereof.

In certain embodiments, L comprises an ester, carbonate, carbamate, quaternary ammonium salt moiety.

In certain embodiments, Y is a chemically active moiety.

In certain embodiments, Y is a bioactive moiety.

In certain embodiments, Y is a therapeutic agent.

In certain embodiments, Y is a diagnostic agent or probe.

In certain embodiments, the photosensitizer is capable of light absorption of single low energy photon in the range of about 400 nm to about 1,000 nm (e.g., about 400 nm to about 900 nm, about 400 nm to about 800 nm, about 400 nm to about 700 nm, about 500 nm to about 1,000 nm, about 600 nm to about 1,000 nm, about 700 nm to about 1,000 nm, about 800 nm to about 1,000 nm, about 450 nm to about 750 nm).

In certain embodiments, the photosensitizer is selected from the group consisting of PtTNP, PdTPBP, PtOEP and $Ir(ppy)_3$ or a derivative or analog thereof.

In certain embodiments, the composition further comprises a polymer in the form of nanoparticles wherein the pair of a photosensitizer and a photolytic compound are encapsulated.

In certain embodiments, the composition comprises an oxygen scavenger.

In certain embodiments, the polymer is an amphiphilic polymer (e.g., oleylamine substituted amphiphilic polymer).

In certain embodiments, the composition is in the form of ultra-small sized nanoparticles having a dimension less than about 35 nm (e.g., less than about 30 nm, less than about 25 nm).

The composition disclosed herein may comprise one or more pharmaceutically acceptable excipients, carriers or diluents.

In yet another aspect, the invention generally relates to a nanoparticle comprising a polymer with encapsulated therein one or more photosensitizers and one or more photolytic compounds.

In certain embodiments, the nanoparticle is air-stable.

In certain embodiments, the nanoparticle is monodispersed.

In certain embodiments, the nanoparticle is ultra-small having a dimension less than about 35 nm (e.g., less than about 30 nm, less than about 25 nm).

In certain embodiments, the nanoparticle is water dispersed.

In certain embodiments, the nanoparticle comprises an oxygen scavenger.

In certain embodiments, the polymer is an amphiphilic polymer.

In certain embodiments, the amphiphilic polymer is capable of scavenging oxygen.

In certain embodiments, the amphiphilic polymer is an oleylamine substituted amphiphilic polymer.

In certain embodiments of the nanoparticle, the photolytic compound has the formula, PPG-X, wherein PPG is a photoremovable protecting group and X comprises is a photolabile group.

In certain embodiments, X is L-Y, wherein L is a photolabile linker and Y an active moiety.

In certain embodiments, the PPG comprises a moiety selected from the group consisting of coumarin, anthracene and perylene, boron-dipyrromethene, or a derivative or analog thereof.

In certain embodiments, L comprises an ester, carbonate, carbamate, quaternary ammonium salt moiety.

In certain embodiments of the nanoparticle, the photosensitizer is capable of light absorption of single low energy photon in the range of about 450 nm to about 750 nm.

In certain embodiments, the photosensitizer is selected from the group consisting of PtTNP, PdTPBP, PtOEP and $Ir(ppy)_3$, or a derivative or analog thereof.

In certain embodiments, Y is a chemically active moiety.

In certain embodiments, Y is a bioactive moiety.

In certain embodiments, Y is a therapeutic agent.

In certain embodiments, the therapeutic agent is an anti-inflammatory agent.

In certain embodiments, the therapeutic agent is an anti-nonsteroidal agent.

In certain embodiments, the therapeutic agent is an anti-tumor agent.

In certain embodiments, Y is a diagnostic agent or probe.

In yet another aspect, the invention generally relates to a pharmaceutical composition comprising nanoparticles disclosed herein.

In yet another aspect, the invention generally relates to a method for inhibiting cancer cell growth, comprising administering to a subject in need there of a pharmaceutical composition comprising a compound disclosed herein.

In yet another aspect, the invention generally relates to a method for inhibiting cancer cell growth, comprising administering to a subject in need there of a pharmaceutical composition comprising nanoparticles disclosed herein.

In yet another aspect, the invention generally relates to a method for performing immunotherapy, comprising administering to a subject in need there of a pharmaceutical composition comprising a compound disclosed herein.

In yet another aspect, the invention generally relates to a method for performing immunotherapy, comprising administering to a subject in need there of a pharmaceutical composition comprising nanoparticles disclosed herein.

In yet another aspect, the invention generally relates to a method for reducing inflammation, comprising administering to a subject in need there of a pharmaceutical composition comprising a compound disclosed herein.

In yet another aspect, the invention generally relates to a method for reducing inflammation, comprising administering to a subject in need there of a pharmaceutical composition comprising nanoparticles disclosed herein.

In certain embodiments of the methods, the subject is a mammal (e.g., a human).

In yet another aspect, the invention generally relates to a method for conducting photolysis, comprising: providing a photosensitizer; causing a light absorption by the photosensitizer under conditions to reach a singlet excited state and subsequently generate a photosensitizer triplet excited state through rapid intersystem crossing; and contacting the photosensitizer triplet excited state with a photolytic molecule to transfer energy from the photosensitizer triplet excited state to the photolytic molecule via triplet-triplet annihilation so as to cause a photolytic reaction of the photolytic compound.

In certain embodiments of the method, the photosensitizer is capable of light absorption of single low energy photon in the range of about 400 nm to about 1,000 nm (e.g., about 400 nm to about 900 nm, about 400 nm to about 800 nm, about 400 nm to about 700 nm, about 500 nm to about 1,000 nm, about 600 nm to about 1,000 nm, about 700 nm to about 1,000 nm, about 800 nm to about 1,000 nm, about 450 nm to about 750 nm) thereby reaching a singlet excited state.

In certain embodiments, the photosensitizer is selected from the group consisting of PtTNP, PdTPBP, PtOEP and $Ir(ppy)_3$, or a derivative or analog thereof.

In certain embodiments, the photolytic compound has the formula,

PPG-X, wherein PPG is a photoremoveavle protecting group and X comprises is a photolabile group.

In certain embodiments, wherein X is L-Y, wherein L is a photolabile linker and Y an active moiety.

In certain embodiments, wherein the PPG comprises a moiety selected from the group consisting of coumarin, anthracene and perylene, boron-dipyrromethene, or a derivative or analog thereof.

In certain embodiments, L comprises an ester, carbonate, carbamate, quaternary ammonium salt moiety.

A key aspect of the disclosed invention is the design and selection of a pair of PPG and photosensitizer that work together to achieve TTAP. Examples of such pairs are provided below.

(1) the Pair of Coumarin Derivatives (PPGs) and Iridium Complexes (Sen).

TABLE 1

| The molecular structures of coumarin derivatives. | |
|---|---|
| 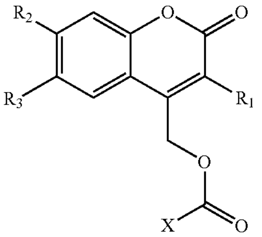 | Cou-1 |
| 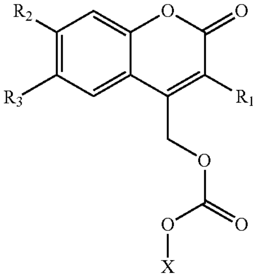 | Cou-2 |

TABLE 1-continued

| The molecular structures of coumarin derivatives. | |
|---|---|
| 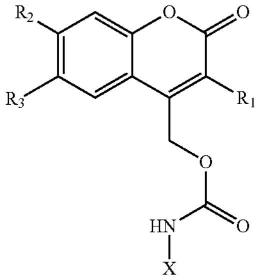 | Cou-3 |
| 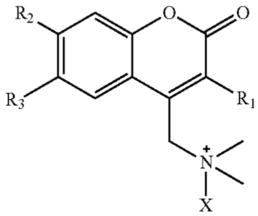 | Cou-4 |

$R_1$ =

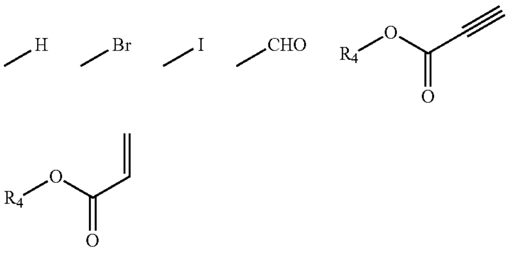

$R_4$ =

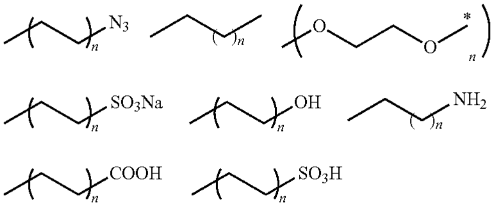

$R_2$ =

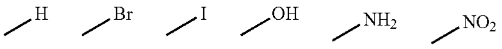

$R_3$ =

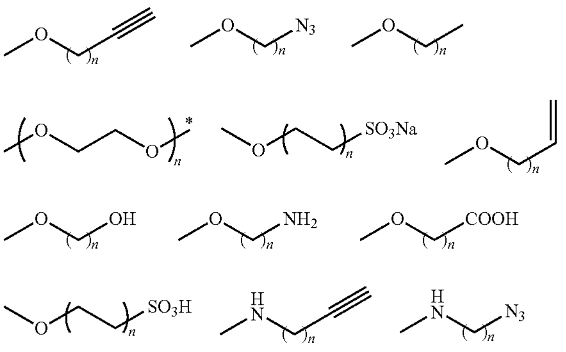

TABLE 1-continued

| The molecular structures of coumarin derivatives. |
|---|
| 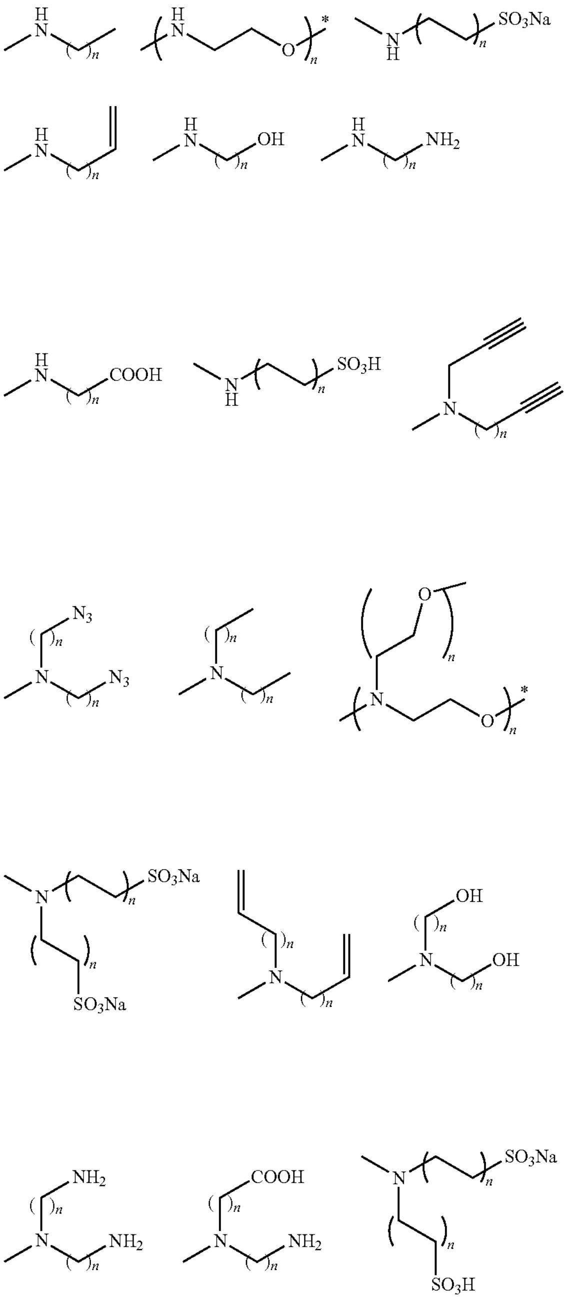 |

wherein $R_1$ is selected from: hydrogen, bromo, iodio, and aldehyde, alkynyl and alkenyl;

$R_2$ is selected from: hydrogen, bromo, iodio, hydroxy, amino and nitro;

$R_3$ is selected from: alkynyl, alkyl, alkenyl, azide, PEG, amine, carboxylic acid, sulfonate and hydroxyl;

$R_4$ is selected from: alkynyl, alkyl, alkenyl, azide, PEG, amine, carboxylic acid, sulfonate and hydroxyl; and n is an integer selected from 0 to 7.

TABLE 2

| The molecular structures of iridium complex (Sen) derivatives. | |
|---|---|
| 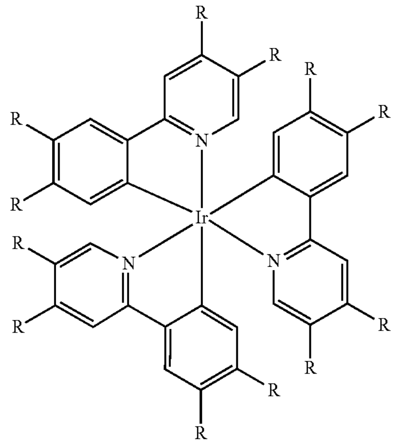 | Ir-1 |
| 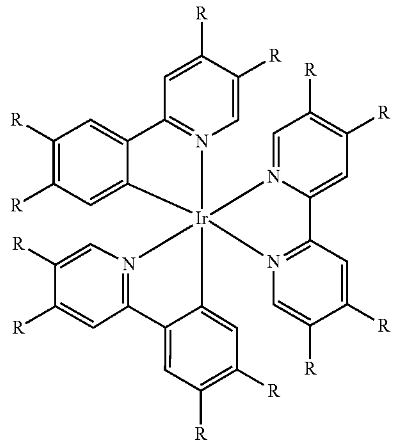 | Ir-2 |
| 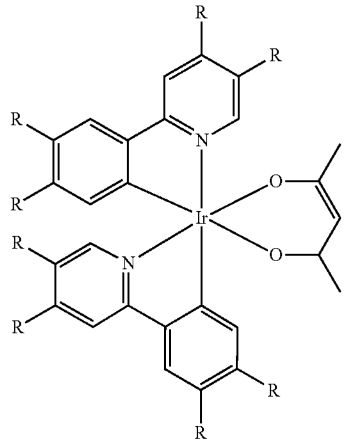 | Ir-3 |

R =

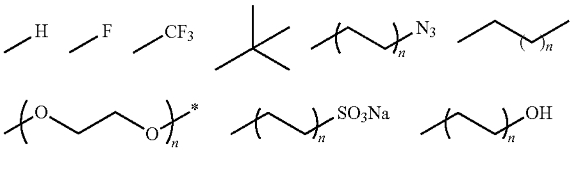

TABLE 2-continued

| The molecular structures of iridium complex (Sen) derivatives. |
|---|
| 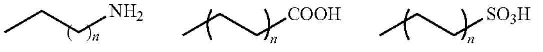 |

wherein

R is selected from: hydrogen, fluoro, trifluoromethyl, tert-butyl, alkyl, azide, PEG, amine, carboxylic acid, sulfonate and hydroxyl; and n is an integer selected from 1 to 7.

(2) The Pair of Anthracene Derivatives (PPGs) and Porphyrin Derivatives.

TABLE 3

| The molecular structures of anthracene derivatives. | |
|---|---|
| 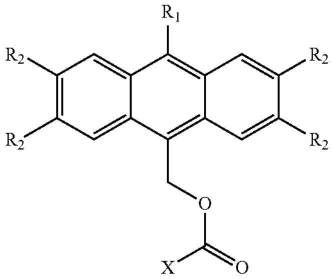 | An-1 |
| 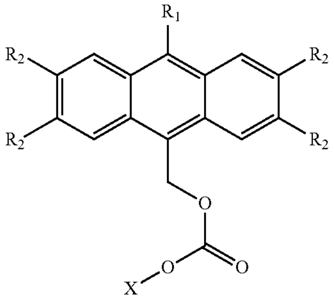 | An-2 |
| 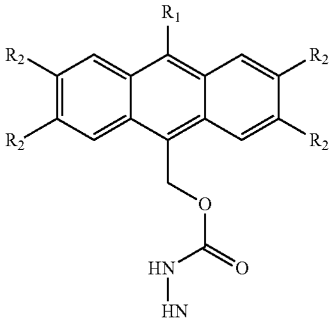 | An-3 |
| 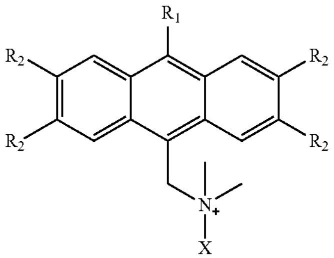 | An-4 |

TABLE 3-continued

The molecular structures of anthracene derivatives.

$R_1$ =

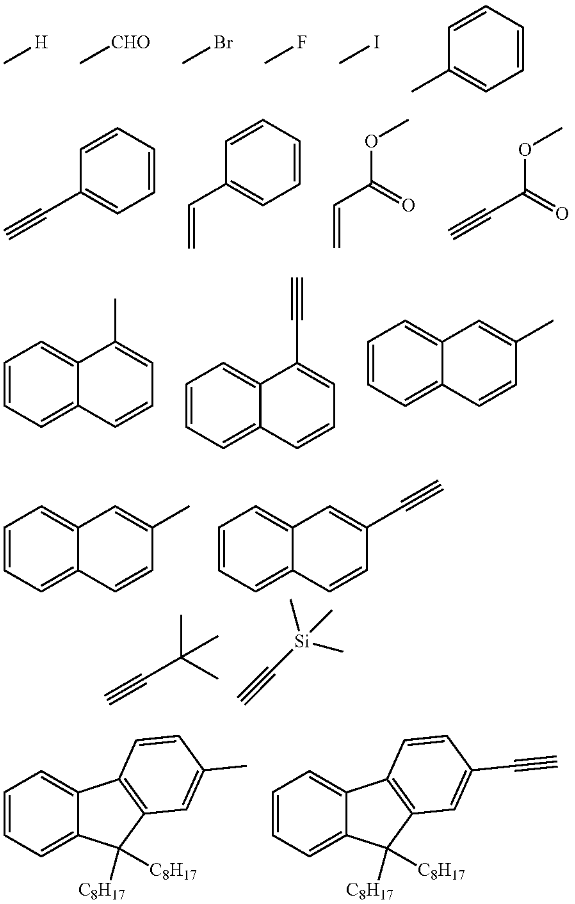

$R_2$ =

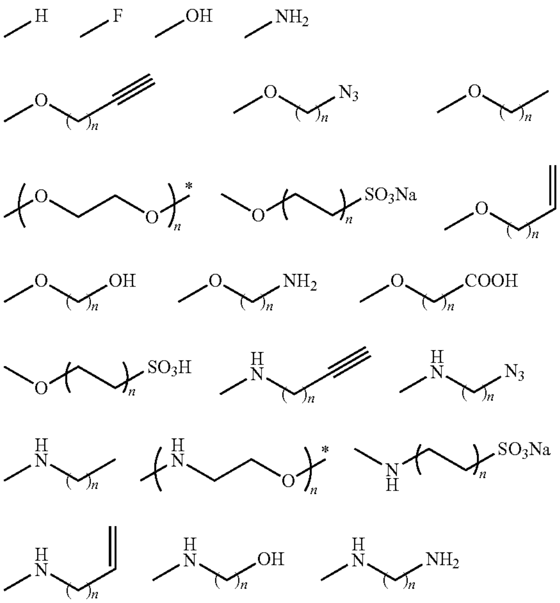

TABLE 3-continued

| The molecular structures of anthracene derivatives. | | |
|---|---|---|
| 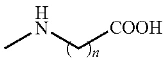 | 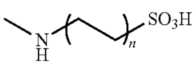 | 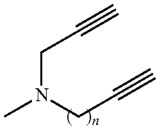 |
| 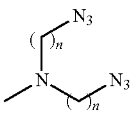 | 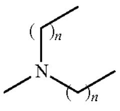 | 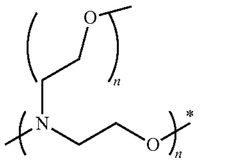 |
| 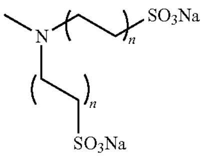 | 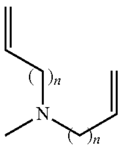 | 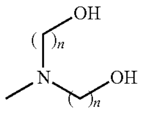 |
| 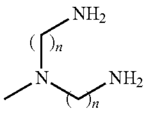 | 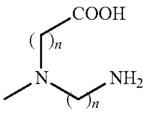 | 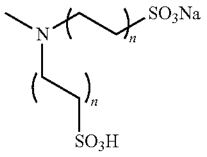 |

wherein $R_1$ is selected from: hydrogen, bromo, iodio, fluro, 1-naphthyl, 1-naphthalenyl, 1-naphthyloro, aldehyde, phenyl, styryl, phenylethynyl, alkynyl, vinyl, 2-naphthyl, 2-naphthalenyl, 2-naphthyl, 2-fluorenyl, 2-fluorenyl alkynyl.

$R_2$ is selected from: hydrogen, fluro, hydroxy, amino, alkynyl, alkyl, alkenyl, azide, PEG, amine, carboxylic acid, sulfonate and hydroxyl.

n is an integer selected from 1 to 7.

TABLE 4

| The molecular structures of porphyrin derivatives. |
|---|
| 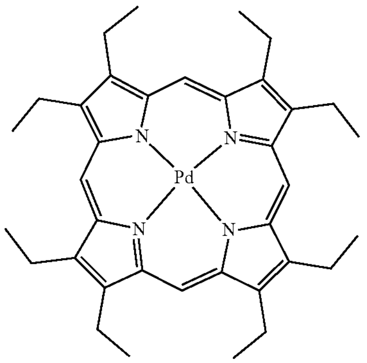 |

TABLE 4-continued

| The molecular structures of porphyrin derivatives. |
|---|
| 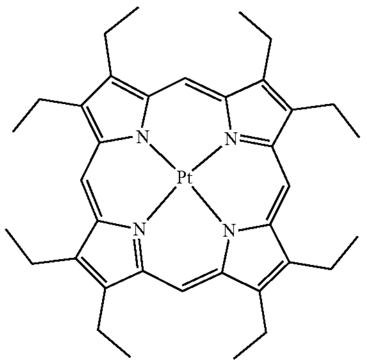 |
| 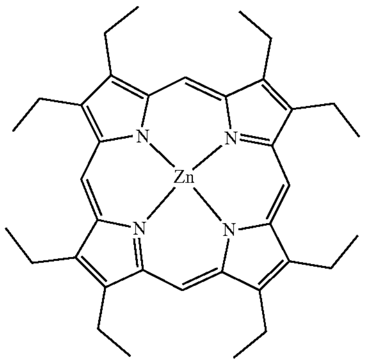 |
| 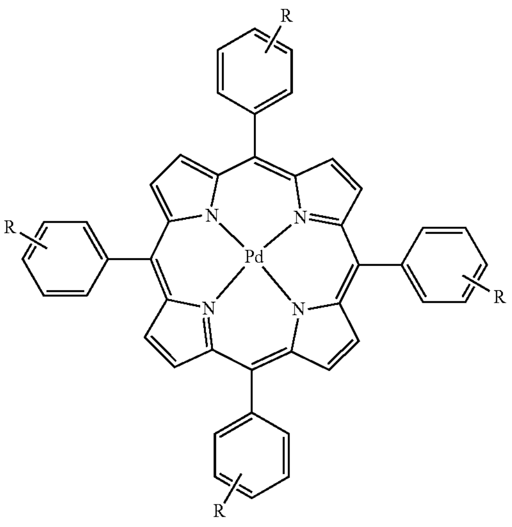 |

TABLE 4-continued
| The molecular structures of porphyrin derivatives. |
| --- |
| 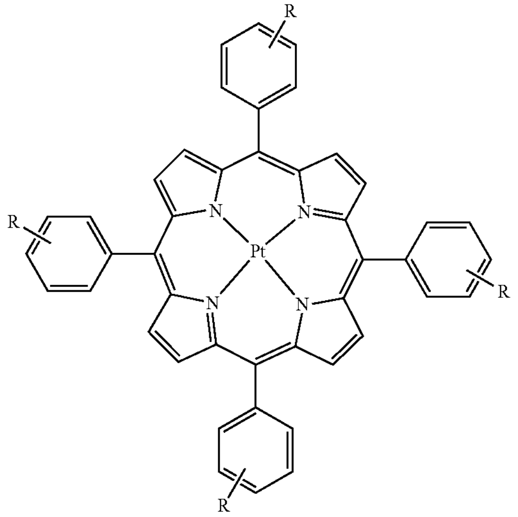 |
| 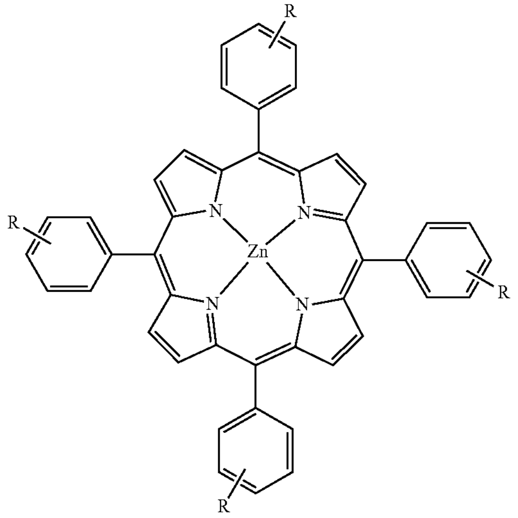 |
| R = |
| 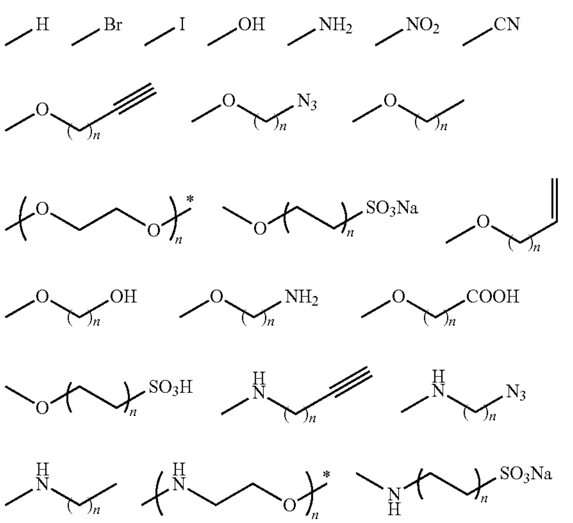 |
| 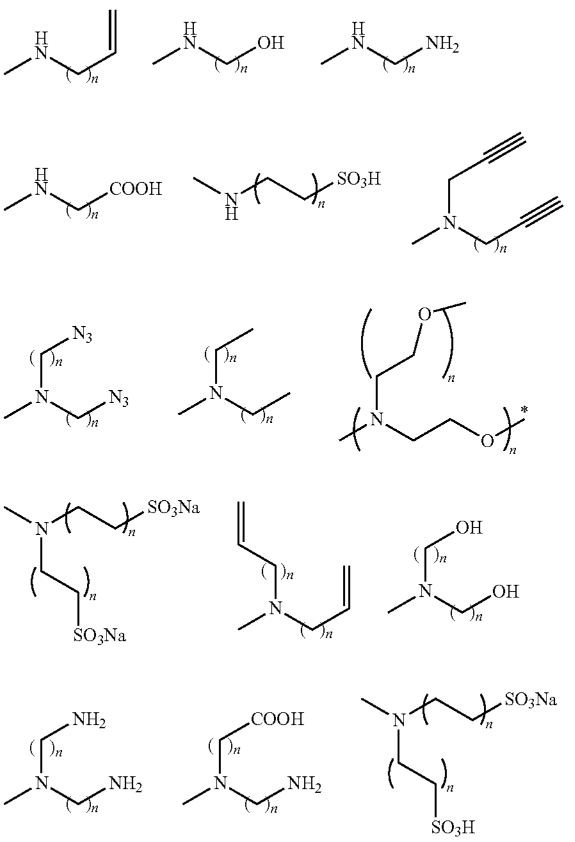 |
wherein
R is elected from: hydrogen, bromo, iodio, fluro, cyan, hydroxy, amino, alkynyl, alkyl, alkenyl, azide, PEG, amine, carboxylic acid, sulfonate and hydroxyl.
n is an integer selected from 1 to 7.
TABLE 5
| The molecular structures of perylene derivatives. | | |
| --- | --- | --- |
| 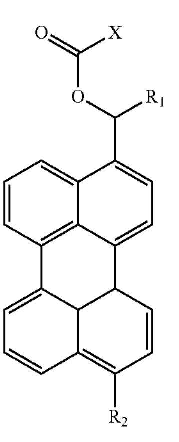 | 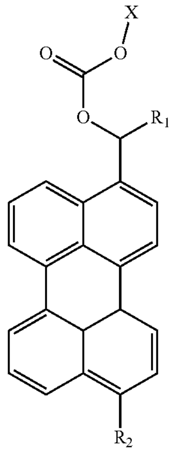 | 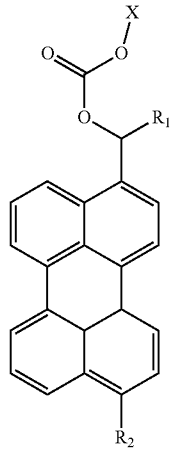 |

TABLE 5-continued
| The molecular structures of perylene derivatives. |
|---|
| 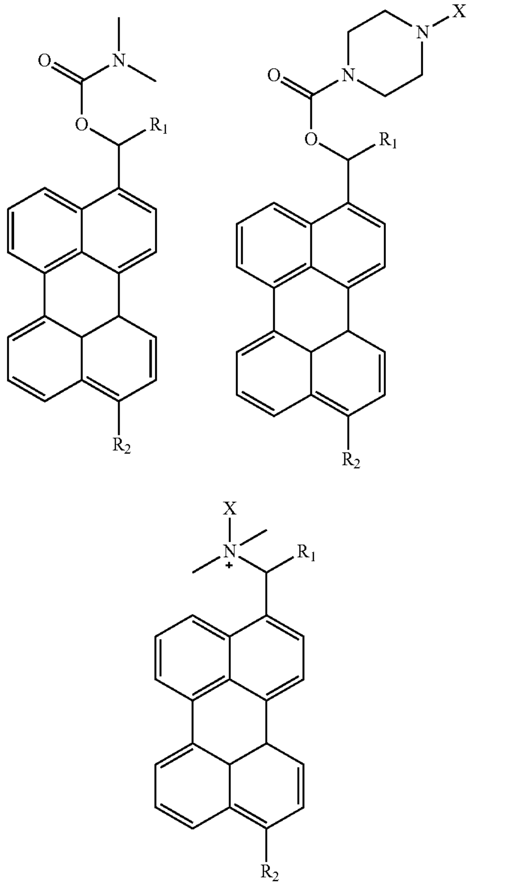 |
| $R_1$ = |
| 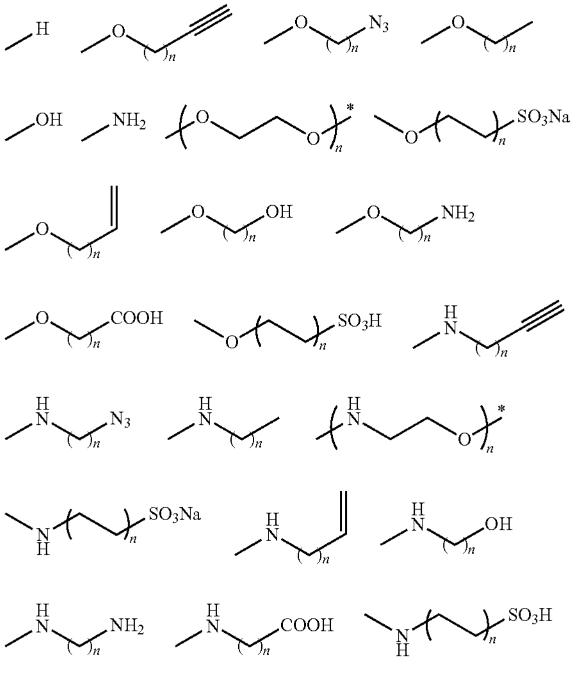 |
| 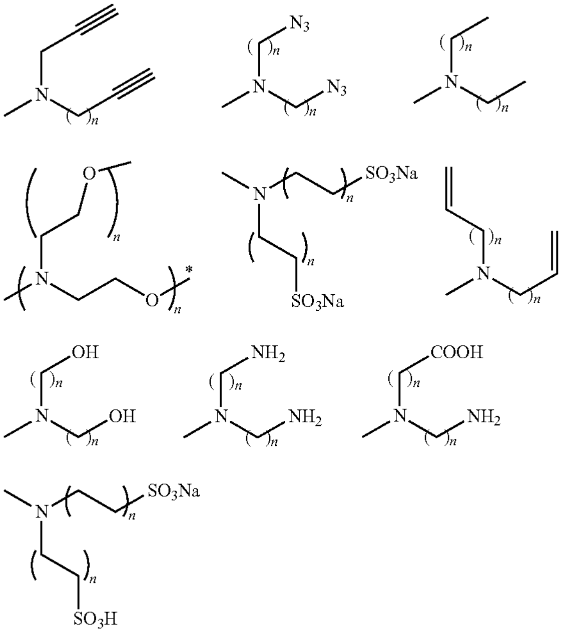 |
| $R_2$ = |
| 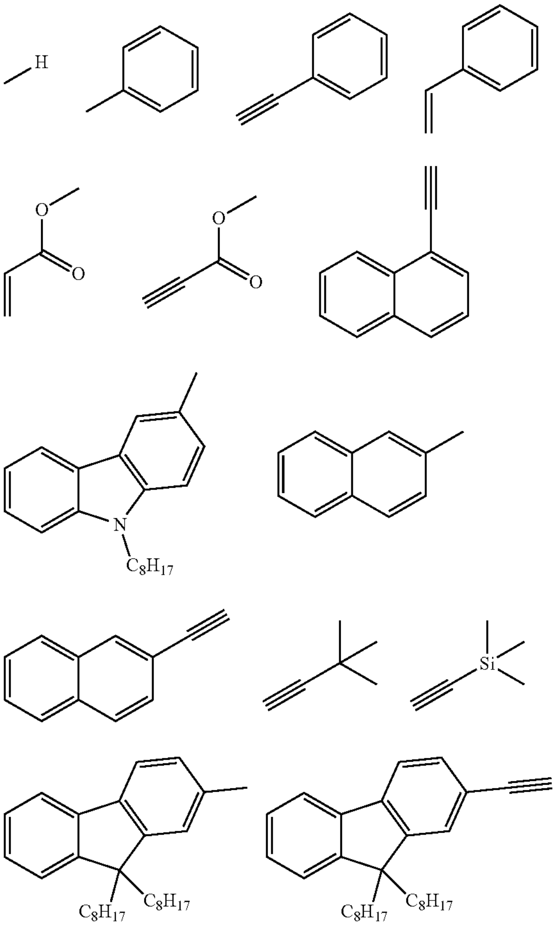 |

TABLE 5-continued

| The molecular structures of perylene derivatives. |
| --- |
| 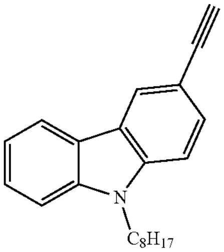 |

wherein $R_1$ is elected from: hydrogen, hydroxy, amino, alkynyl, alkyl, alkenyl, azide, PEG, amine, carboxylic acid and sulfonate;

$R_2$ is elected from: hydrogen, bromo, iodio, fluro, 1-naphthyl, 1-naphthalenyl, 1-naphthyloro, aldehyde, phenyl, styryl, phenylethynyl, alkynyl, vinyl, 2-naphthyl, 2-naphthalenyl, 2-naphthyl, 2-fluorenyl, 2-fluorenyl alkynyl, carbazolyl and carbazolyl alkynyl; and n is an integer selected from 1 to 7.

TABLE 6

| The molecular structures of BODIPY derivatives. | | |
| --- | --- | --- |
| 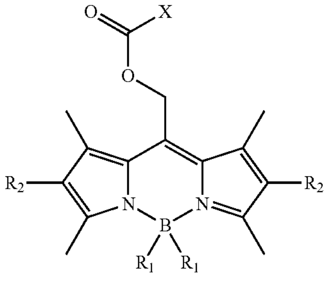 | 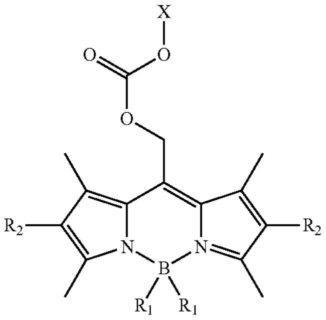 | 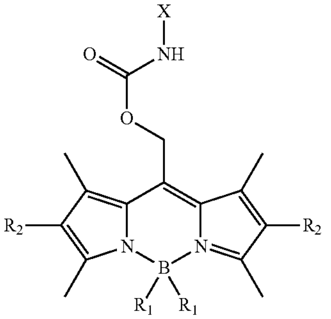 |
| 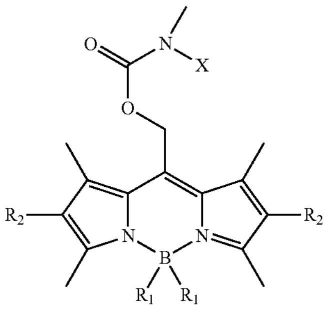 | 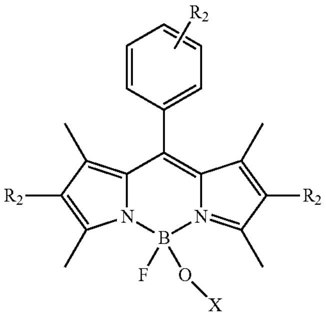 | |
| R2 = 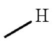 | 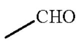 | 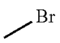 |
| 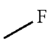 | 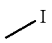 | |
| 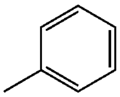 | 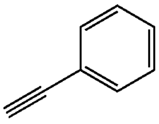 | 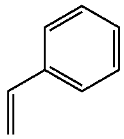 |
| 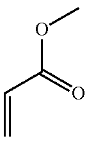 | 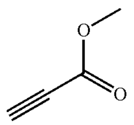 | 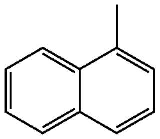 |

TABLE 6-continued
| The molecular structures of BODIPY derivatives. | | |
|---|---|---|
| 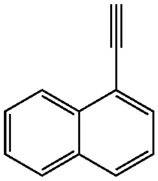 | 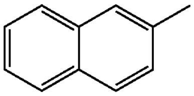 | 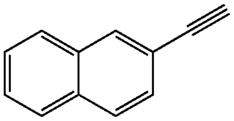 |
| 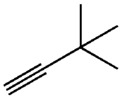 | 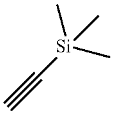 | 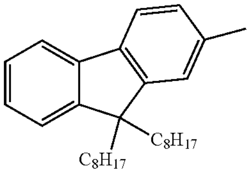 |
| 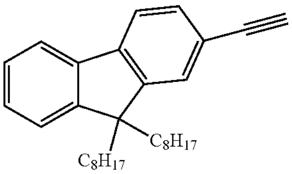 | 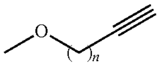 | 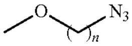 |
| 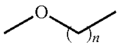 | 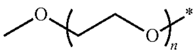 | 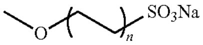 |
| 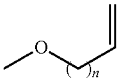 | 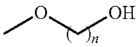 | 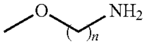 |
| 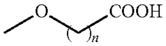 | 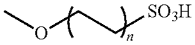 | 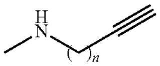 |
| 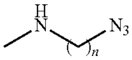 | 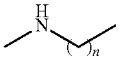 | 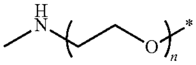 |
| 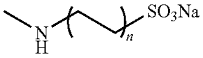 | 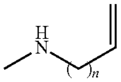 | 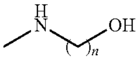 |
| 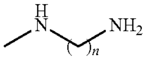 | 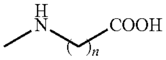 | 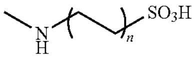 |
| 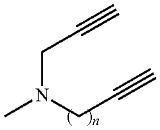 | 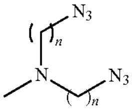 | 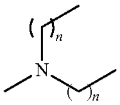 |
| 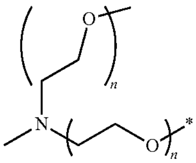 | 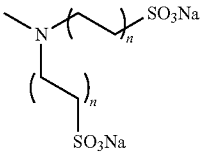 | 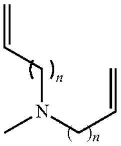 |
| 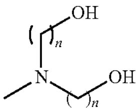 | 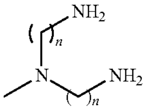 | 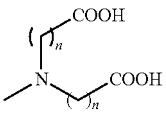 |

TABLE 6-continued

| The molecular structures of BODIPY derivatives. |
| --- |
| 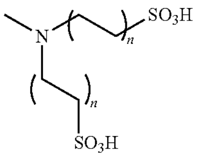 |

wherein $R_1$ is elected from: alkynyl, fluro, alkyl.

$R_2$ is elected from: hydrogen, bromo, iodio, fluro, 1-naphthyl, 1-naphthalenyl, 1-naphthyloro, aldehyde, phenyl, styryl, phenylethynyl, alkynyl, vinyl, 2-naphthyl, 2-naphthalenyl, 2-naphthyl, 2-fluorenyl, 2-fluorenyl alkynyl, carbazolyl, carbazolyl alkynyl, alkynyl, hydroxy, amino, alkynyl, alkyl, alkenyl, azide, PEG, amine, carboxylic acid, sulfonate and hydroxyl.

n is an integer selected from 1 to 7.

TABLE 7

| The molecular structures of benzoporphyrin derivatives. | |
| --- | --- |
| 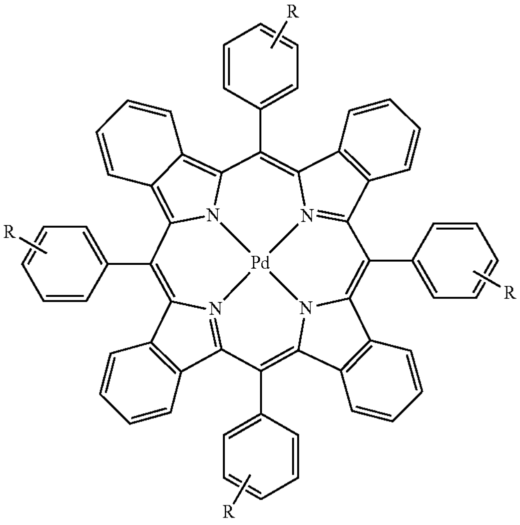 | 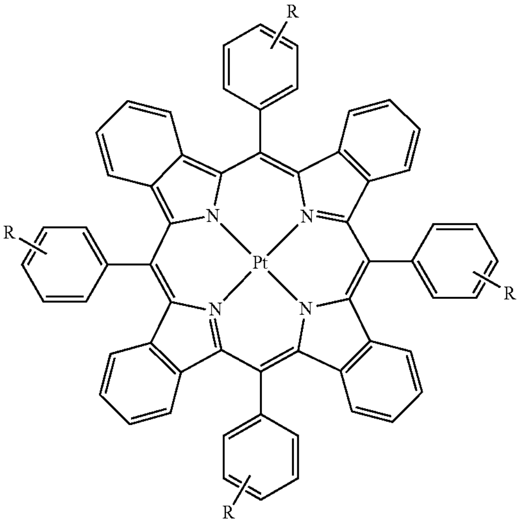 |
| 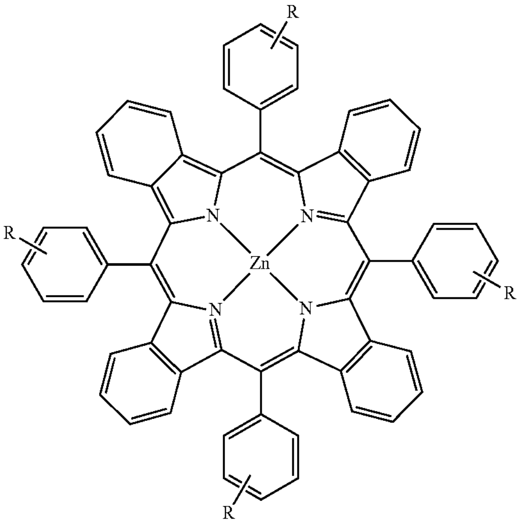 | 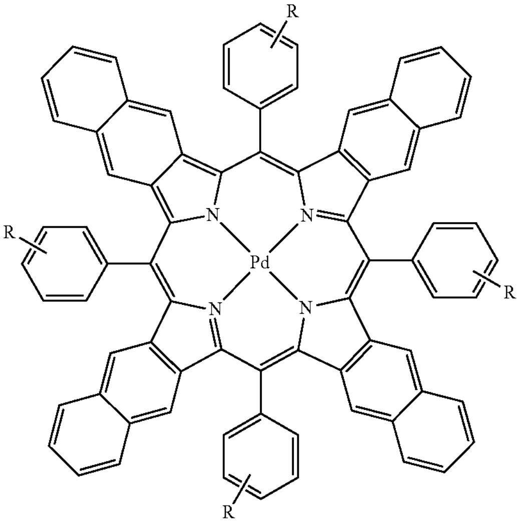 |

TABLE 7-continued
The molecular structures of benzoporphyrin derivatives.
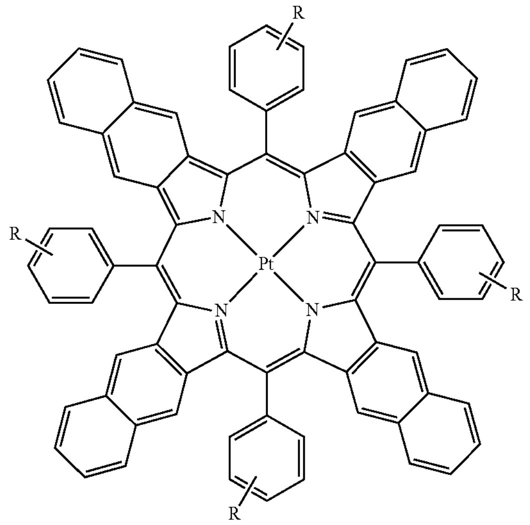
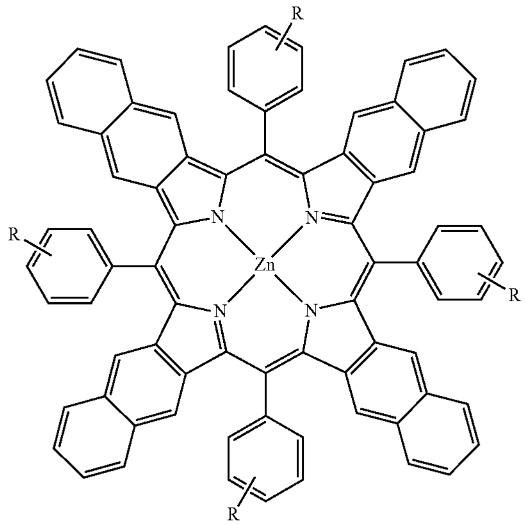
R =
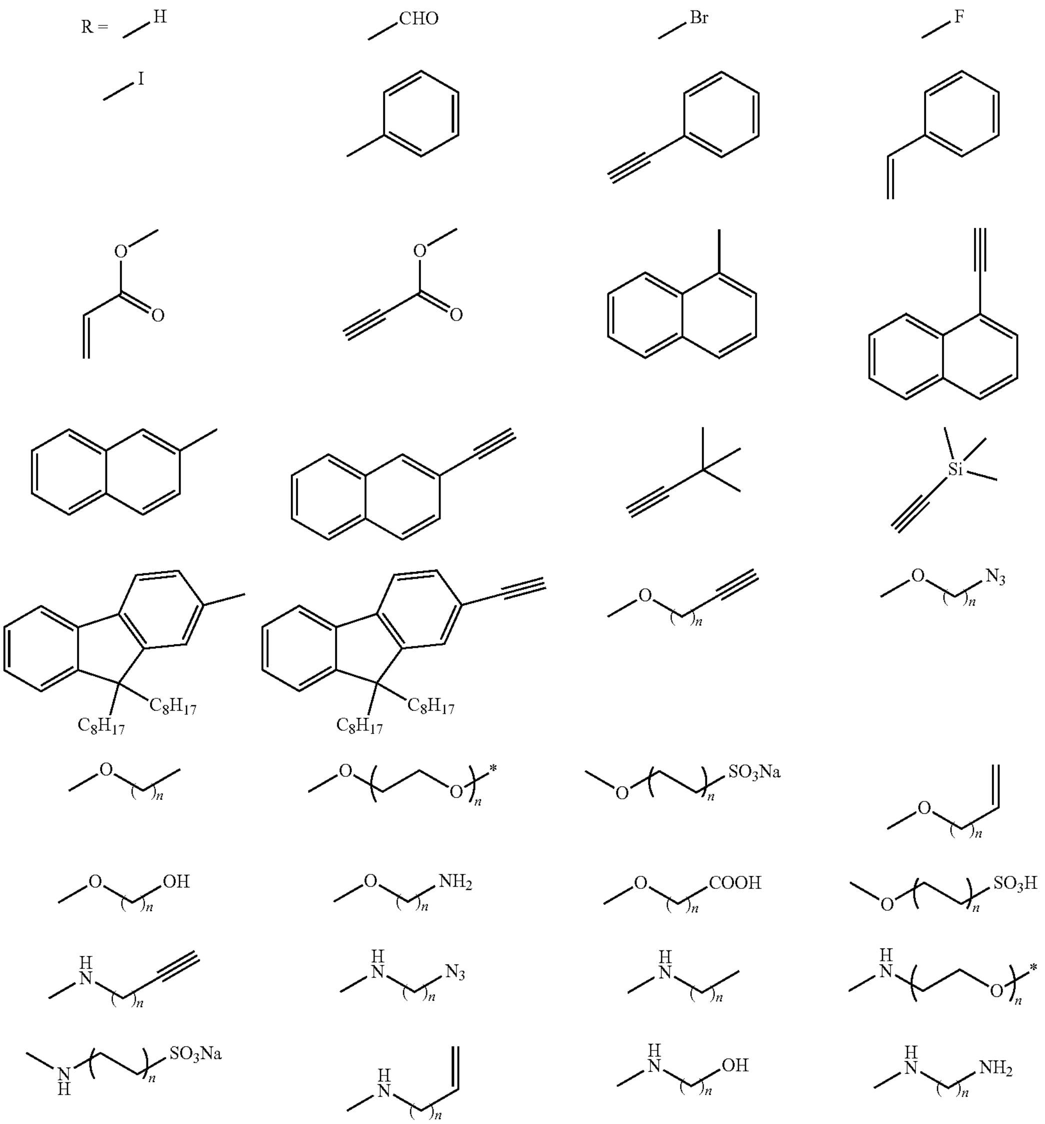

TABLE 7-continued

| The molecular structures of benzoporphyrin derivatives. | | | |
|---|---|---|---|
| 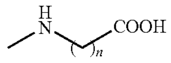 | 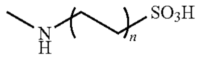 | 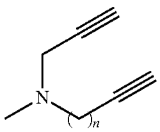 | 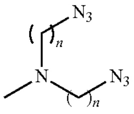 |
| 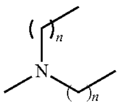 | 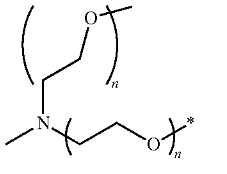 | 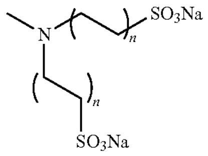 | 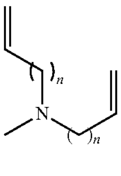 |
| 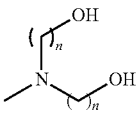 | 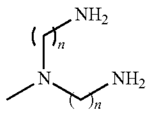 | 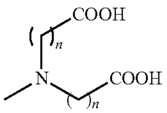 | 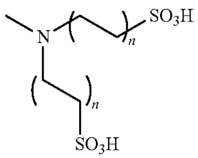 |

wherein

R is selected from: hydrogen, bromo, iodio, fluro, 1-naphthyl, 1-naphthalenyl, 1-naphthyloro, aldehyde, phenyl, styryl, phenylethynyl, alkynyl, vinyl, 2-naphthyl, 2-naphthalenyl, 2-naphthyl, 2-fluorenyl, 2-fluorenyl alkynyl, carbazolyl, carbazolyl alkynyl, alkynyl, hydroxy, amino, alkynyl, alkyl, alkenyl, azide, PEG, amine, carboxylic acid, sulfonate and hydroxyl.

The following examples are meant to be illustrative of the practice of the invention and not limiting in any way.

EXAMPLES

In regard to the TTAP process, there are two general rules in designing an effective TTAP system: (1) the PPGs should have a lower laying triplet excited state than that of the triplet excited state of the photosensitizer ($^{3}$[PPGs]*$<^{3}$[Sen]*), allowing the efficient TTET process to occur from Sen to PPGs; (2) the doubled energy of the triplet excited state of the PPGs should be higher than that of the singlet excited state of the PPGs (2x$^{3}$[PPGs]*$>^{1}$[PPGs]*), enabling the ultimate TTA to take place (FIG. 1D). (Zhou, et al. 2015 *Chem. Rev.* 115, 395-465; Zhao, et al. 2015 *Chem. Soc. Rev.* 44, 8904-8939; Singh-Rachford, et al. 2010 *Coord. Chem. Rev.* 254, 2560-2573.)

Figure 6:
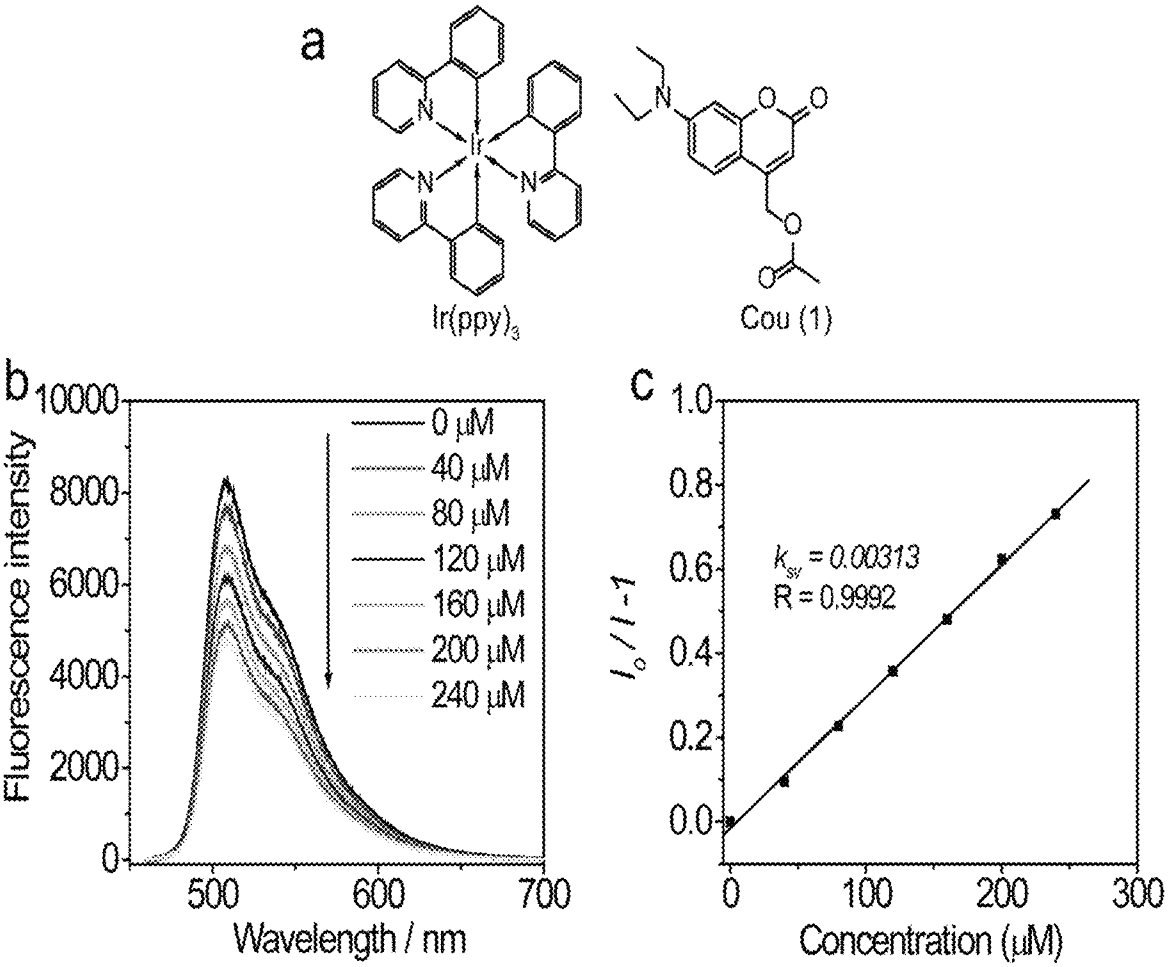
FIG. 6. (a) Molecular structure of $Ir(ppy)_3$ and Cou (compound 1); (b) Phosphorescence intensity quenching of $Ir(ppy)_3$ (10 μM) in the presence of different concentration of compound 1, $\lambda_{ex}$=410 nm; (c) Stern-Volmer plots generated from the phosphorescence intensity quenching of $Ir(ppy)_3$ as a function of compound 1 concentration.

As disclosed herein, we began our TTAP investigations with a widely used PPG of the coumarin group ($T_1$=2.18 eV) (Huang, et al. 2013 *Photochem. Photobiol. Sci.* 12, 872-882.). Here, due to its broad presence in pharmaceuticals and natural products, we tested the ester bond as the photolabile linkage for protecting carboxylate (acetic acid) in compound 1. After considering the energetic requirements of the TTAP system, Ir(ppy)$_3$ ($T_1$=2.4 eV) was chosen as the initial coupling photosensitizer partner (Experimental, section 3) After considering the energetic requirements of the TTAP system, Ir(ppy)$_3$ ($T_1$=2.4 eV) was chosen as the initial coupling partner (Experimental, section 3) (Hofbeck, et al. 2010 *Inorg. Chem.* 49, 9290-9299.) The TTET process from Ir(ppy)$_3$ to compound 1 was studied via Stern-Volmer photoluminescence quenching assays under oxygen-free conditions. When we titrated compound 1 into the Ir(ppy)$_3$ solution, the phosphorescence decreased dramatically. (FIG. 6.) The respective Stern-Volmer constants ($k_{sv}$) were calculated to be 3.13x10$^3$ M$^{-1}$. Next, when combining the Ir(ppy)$_3$ with 1, we observed the photolytic product in 73% of the yield under the characteristic absorption of Ir (ppy)$_3$ (476 nm, LED, 20 mW/cm$^2$) illumination. In contrast, in the absence of Ir(ppy)$_3$, no photolytic product was observed under such light irradiation as the PPG of the coumarin group typically requires 360 nm short wavelength light direct activation (Table 11). This experiment clearly validated the feasibility of our proposed TTAP concept.

Inspired by the above mentioned TTAP experimental results, we decided to examine whether this TTAP concept is general enough to be adapted to a wide spectrum of electron-magnetic wavelengths. To do so, we tested a series of long wavelength absorbing sensitizers, ranging from green (PtOEP), far-red (PdTPBP) to near infrared light (PtTNP) (FIG. 1D), as well as a broad array of PPGs (An, Py and BDP) (FIG. 1D). Through extensive analysis of the photophysical properties (Experimental, section 3), we identified a family of potential TTAP pair candidates based on the energetic match among these sensitizers and PPGs. These pairs are: PtOEP: An; PtOEP: Py; PdTPBP:Py; PdTPBP:BDP; PtTNP:Py and PtTNP:BDP. To further support our theoretical spectrum analysis, we then tested the Stern-Volmer constants ($k_{sv}$) (Experimental, section 5-7) in regard to all of these selected combinations.

As shown in Table 8, the compound 2 with PPGs of anthracene ($T_1$=1.77 eV) and the compound 8 with PPGs of perylene ($T_1$=1.52 eV) demonstrate significant quenching of the photoluminescence of green light absorbing photosensitizer of PtOEP ($T_1$=1.92 eV). (Ji, et al. 2011 *Angew. Chem. Int. Ed.* 50, 1626-1629; Cui, et al. 2014 *J. Am. Chem. Soc.* 136, 9256-9259.) Meanwhile, for far-red light absorbing photosensitizer of PdTPBP, PPG-X of compound 7 with PPG of BDP ($T_1$=1.49 eV) and PPG-X of compound 8 with PPG of perylene exhibited obvious quenching effects on the photoluminescence of PdTPBP ($T_1$=1.55 eV). Moreover, regarding NIR light absorbing photosensitizer of PtTNP, compound 8 and compound 7 also show quenching effect on its photoluminescence ($T_1$=1.43 eV). The TTA upconversion of the above-mentioned combinations (Sen and PPGs) were also further measured. The upconversion quantum yields are respectively recorded to be 8.7% (PtOEP: compound 2), 9.5% (PtOEP: compound 8), 5.8% (PdTPBP: compound 8), 8.4% (PdTPBP: compound 7), 0.05% (PtTNP: compound 8), and 0.3% (PtTNP: compound 7).

Figure 2:
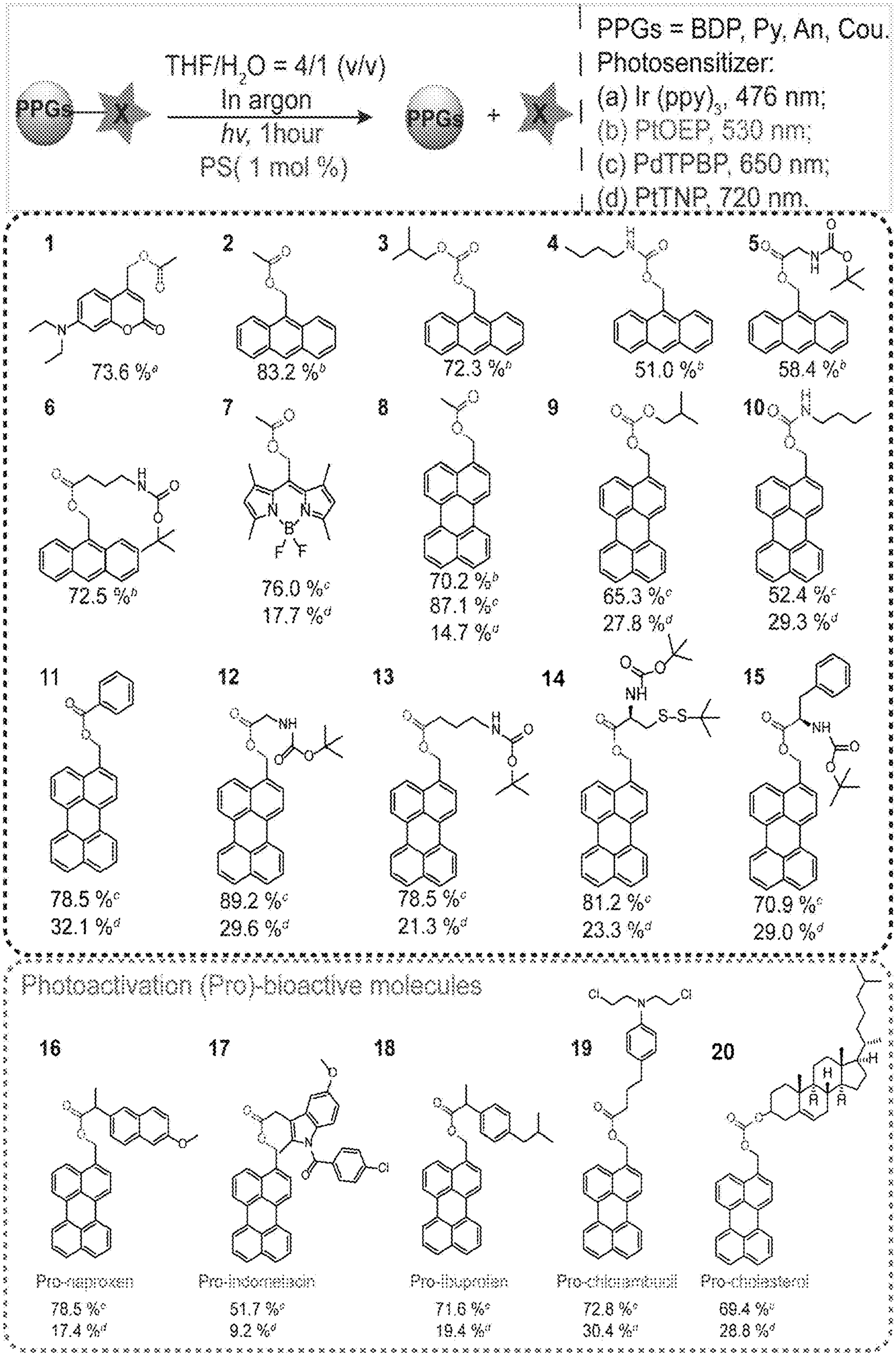
FIG. 2. Triplet-triplet annihilation mediated photolytic reactions under diverse low power long wavelength LED irradiation. The superscripts (a-d) next to the reaction yields represent the sensitizers used and their respective operation light wavelengths.

Next, we then measured the photolysis yields of the above mentioned TTAP systems (FIG. 2). Specifically, we first tested the two green light activating TTAP systems, including PtOEP: compound 2 and PtOEP: compound 8. We found that their photolytic yield is outstanding: 83% for An containing compound 2 and 70% for Py containing compound 8 respectively under 20 mW/cm$^2$ 532 nm LED light. In a similar manner, we also observed significant photolytic yield at 76% and 87% for our far-red light activating TTAP pair candidates (PdTPBP: compound 7, PdTPBP: compound 8) respectively under 20 mW/cm$^2$ 650 nm LED light. Moreover, we tested our NIR light activating TTAP candidates (PtTNP: compound 8, PtTNP: compound 7). Notable photolytic yield at 14.7% and 17.7% were also respectively observed under 1 h illumination of 20 mW/cm$^2$ 720 nm NIR LED light.

Compared to conventionally used PPGs in peptide synthesis that are involved with harsh chemical conditions such as acid/base- or redox-sensitive groups, PPGs have been emerging as a traceless and green alternative to allow "reagent-free" deprotection under light illumination. (DeForest, et al. 2011 *Nat Chem.* 3, 925-931.) Thus, herein we expanded our TTAP concept to a variety of amino acids such as glycine, cysteine and phenylalanine. As a result, we observed excellent low power long wavelength light driven photo-deprotection for these amino acids containing target molecules. For PPGs of An for protecting glycine (compound 5), we observed the photolytic yield is 58.4% in conjunction with PtOEP under green LED illumination. For PPGs of Py for protecting glycine (compound 12), in conjunction with PdTPBP and PtTNP, the photolytic yield is 89.2%, 29.6% respectively. For PPGs of Py for protecting cysteine (compound 14), when PdTPBP and PtTNP are used as photosensitizers, the photolysis yields are 81.2% and 23.3%. In addition, for PPGs of Py for protecting phenylalanine, with PdTPBP and PtTNP as photosensitizers, the photolytic yields are 70.9% and 29.0% respectively. These results show the potential of our TTAP technology in a wide array of applications in functional peptide synthesis. (FIG. 2)

Excitingly, we further found that such low energy long wavelength activation can indeed surpass the traditionally needed high energy short-wavelength light direct activation. For example, an identical photolytic reaction on compound 8 was irradiated with a typically needed 20 mW/cm$^2$ short wavelength blue LED (445 nm) instead of a far-red LED (20 mW/cm$^2$, 650 nm) for TTAP. Only a 59% photolytic yield was obtained under blue light in the same reaction time (Table 18). Thanks to the intense absorbance of Sen and the effective TTET process from Sen to PPGs, our TTAP system is able to improve the photolytic yield to 87.1% for such PPG-X by reducing the byproducts generation under far red-light illumination. We further quantitatively compared the photolytic quantum efficiency ($\eta_P=\Phi_p\times\varepsilon$) (Goswami, et al. 2015 *J. Am. Chem. Soc.* 137, 3783-3786) for our TTAP ($\eta_p=\Phi_{p(PPGs)}\times\varepsilon_{(sen)}$) under short wavelength light direct illumination photolysis ($\eta_p=\Phi_p$ (PPGs)$\lambda\varepsilon$(PPGs)) (Table 19). For the PPG of Cou group, under direct light illumination $\eta_{p\ (direct)}$ is 806, while in conjunction with Ir(ppy)$_3$, $\eta_{p\ (TTAP)}$ increases by 274% to 2210. Similarly, the $\eta_{p\ (direct)}$ is 976 for PPG of An group, while $\eta_{p\ (TTAP)}$ goes up 638% to 6230 in the presence of PtOEP. Moreover, the $\eta_{p\ (direct)}$ is 3627 for the PPG of Py group, and $\eta_{p\ (TTAP)}$ is boosted by 342% to 12400 (PtTNP), 282% to 10230 (PdTPBP) and 179% to 6510 (PtOEP), respectively. In addition, the $\eta_{p,\ (direct)}$ is 70 for the PPG of BDP group, and then $\eta_{p\ (TTAP)}$ increases by 188% to 132 (PtTNP) and by 155% to 108.9 (PdTPBP), respectively. Our TTAP system shows a remarkable photocleavage quantum yield, which increased by 1.6-6.4-fold as compared to the conventional direct short wavelength direct photolysis (Table 19).

Having identified our TTAP systems enable photolytic ester bonds, we then turned our attention to evaluate the scope of this method with other typically used photolabile linkages of carbonate (compound 3, compound 9) and carbamate (compound 4, compound 10) in the alcohols and amines containing targeted molecules. We found that PtOEP: compound 3 and PtOEP: compound 4 were effectively photolyzed under green light illumination, respectively, in 72.3%, 51.0% yield. PdTPBP: compound 9 and PdTPBP: compound 10 were also efficiently photocleaved under far red-light illumination, the photolytic yields are 65.3%, 52.4% respectively. Moreover, NIR light activated TTAP systems including PtTNP: compound 9 and PtTNP: compound 10, were all compatible with this method, affording 27.8%, 29.3% photolytic yield.

In addition to the amino acids, we also explored the possibility of extending TTAP compatible targeted molecules to small molecule drugs in current clinical use. In particular, small molecule drugs such as anti-inflammatory and anti-tumor drugs, are known to have server systematic off-target side effects. To this end, light-activatable prodrugs constitute emerging major targets for utilization in drug discovery, due to their high spatiotemporal resolution in the treatment of complex diseases. (Hoelder, et al. 2012 *Mol. Oncol.* 6, 155-176; Muralidharan, et al. 2014 *Pain Med.* 15, 93-110; Ivanenkov, et al. 2011 *Mini. Rev. Med. Chem.* 11, 55-78; Li, et al. 2016 *Nat. Rev. Mater* 1, 16071; Mitragotri, et al. 2014 *Nat. Rev. Drug. Discov.* 13, 655.)

Here, we constructed a series of TTAP compatible prodrugs via the conjugation of anti-nonsteroidal and anti-inflammatory drugs (naproxen, indometacin, ibuprofen) with perylene via esterification. This group of compounds (16, 17, 18) was denoted as pro-NSAIDs. In conjunction with far red light or NIR light absorbing PdTPBP or PtTNP, these resultant compounds (compounds 16, 17, 18) were denoted as pro-naproxen, pro-indomethacin and pro-ibuprofen. In conjunction with the far-red light photosensitizer (PdTPBP) or the NIR light photosensitizer (PtTNP), we observed that pro-naproxen (compound 16) has excellent photolytic reaction yields of 78.5% (PdTPBP) and 17.4% (PtTNP). For the pro-indomethacin (compound 17), the photolytic reaction yield is 51.7% (PdTPBP) and 9.2% (PtTNP). In addition, the photolytic reaction yields are also found to be quite effective: 71.6% (PdTPBP), and 19.4% (PtTNP) for pro-ibuprofen (compound 18).

Next, in order to conceptually demonstrate the in vivo biological feasibility via TTAP, we chose chlorambucil, which is an FDA approved anti-cancer drug to evaluate the effect of cancer treatment. (Bosch, et al. 2019 *Nat. Rev. Clin. Oncol.* 1.). In this regard, we conjugated Py with chlorambucil to obtain pro-chlorambucil (compound 19). Then, when PdTPBP or PdTNP were used as the coupling partners, we observed the respective photolytic yield of 72.8% (PdTPBP) and 30.4% (PtTNP). We then designed an oleylamine substituted amphiphilic polymer (PSMA-PEG-OAm) encapsulated TTAP nanoparticles to resolve the noxious di-oxygen quenching of the triplet states of Sen and PPGs-X under ambient air conditions.

This unsaturated olefin-modified amphiphilic polymer was found to be able to encapsulate Sen and PPG-X to form air-stable monodispersed and water soluble ultra-small sized TTAP nanoparticles (TTAP NPs).

Via $^1$H-NMR spectra and the phosphorescence quenching experiments (Experimental, section 10), we found that the unsaturated olefins can react with singlet oxygen to exhaust oxygen from the stored solution under light illumination. Due to the outstanding photolytic yield of the combination PdTPBP: compound 19 of PtTNP: compound 19, we prepared TTAP nanoparticles (TTAP NPs) that contain PdTPBP: compound 19. The entrapment and drug loading efficiency are measured to be 89% and 16% in TTAPNPs. Via TEM and DLS characterization, the TTAP NPs have ultra-small size (12.9±2.6 nm, 29.7±4.6 nm). Moreover, after 30 days, the size also stayed at ~30 nm via DLS, indicating the excellent stability of TTAP NPs. (Experimental, section 11) We then tested the photolytic kinetic process of TTAP NPs. After 60 min 20 $mWcm^2$. 650 nm LED illumination, the 64% prodrug was effectively photolyzed. Moreover, the photolysis process was clearly dependent on the ON-OFF pattern of the LED excitation (Experimental, section 12). This result demonstrated the feasibility of the use of our TTAP system in aqueous solution under ambient air. The dose and duration of the prodrug activation can be precisely interrogated by our TTAP nanoparticles.

Figure 17:
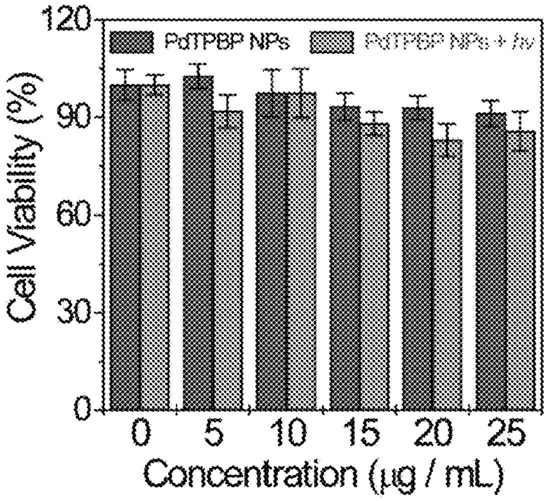
FIG. 17. Hela cell viability in different concentrations of PdTPBP NPs with and without light irradiation.

We then conducted in vitro and in vivo studies of our TTAP NPs. Firstly, via MTT assays, we demonstrated that TTAP NPs significantly enable the inhibition of many types of cancer cell growth (Experimental, section 13). This result indicates that via TTAP, the prodrug (pro-chlorambucil) was photolyzed and released from TTAP NPs into cancer cells, causing cancer cell death under far red-light illumination. Moreover, we evaluated the phototoxicity of PdTPBP NPs. However, we did not observe obvious cell death in the presence of the light, indicating the negligible phototoxicity of PdTPBP. We reasoned that the unsaturated olefins in the PSMA-PEG-OAm can efficiently exhausted the singlet oxygen in PdTPBP nanoparticles (FIG. 17).

Figure 3:
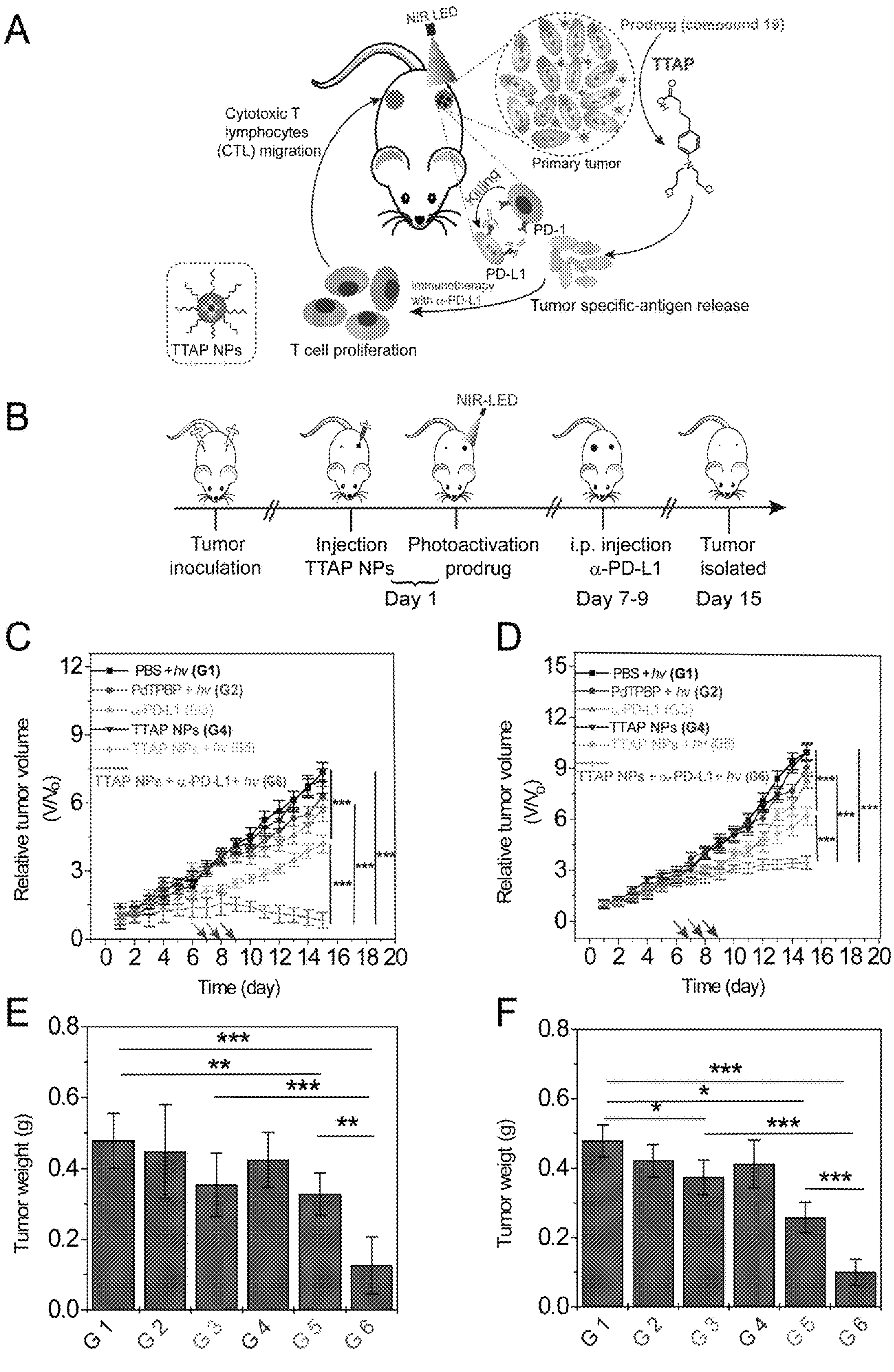
FIG. 3. TTAP NPs mediated synergistic immunotherapy to cure metastatic tumors. (a) A schematic illustration of the in vivo study TTAP NPs mediated combination photoactivation prodrug with checkpoint blockade antibody to realize synergistic immunotherapy in a bilateral model of 4T1 tumor bearing BALB/c mice, the right side tumor stands for (primary tumor), the left side tumor stands for (distant tumor or "metastatic tumor"); (b) A schematic illustration of the experimental immunotherapy process, the 4T1 cells were seeded at mice right back and the left mice back, waiting for the right side tumor volume reached to 100 $mm^3$, the TTAP NPs was intratumorally injected, then NIR LED (20 $mW/cm^2$, 650 nm) illuminated the right side tumor; at 7 th, 8 th and 9 th, the α-PD-L1 was i.p. injected for mice (group 3 and group 6). (c) The growth curves of primary tumors; (d) The growth curves of distant tumors, the red arrow stands for i.p. injection α-PD-L1 for group 3 and group 6 at 7th, 8th and 9th day. (e) The primary tumor weight and (d) the distant tumor weight. "G" is the abbreviation of group, values are means±s.e.m. (n=5 mice per group). *$p<0.05$, $p<0.01$ and *$p<0.001$.

Next, we went on to examine the synergistic the anti-tumor immunotherapy effect of our TTABP system in conjunction with the checkpoint blockade PD-L1 anti-body (a-PD-L1) in a bilateral model of 4T1 tumor bearing BALB/c mice. (Nam, et al. 2019 *Nat. Rev. Mater* 4, 398-414; Duan, et al. 2019 *Nat. Commun.* 10, 1899.) As shown in FIG. 3A, the tumor on the right represented the primary tumor that was subjected to the injection of TTAP NPs and the subsequent light treatment. The tumor on the left was left untreated and served to mimic a distant metastatic tumor. When the tumor on the right reached 100 $mm^3$, TTAP NPs were intratumorally injected. After 4 hours, this tumor was exposed to NIR light (650 nm, 20 $mW/cm^2$) for 30 min. At the $7^{th}$, $8^{th}$ and $9^{th}$ day, the mice were i.p. injected with the a-PD-Li (75 μg/mouse) (FIG. 3B). The therapeutic efficacy of different treatment groups was evaluated by measuring tumor volume and weight. The volume growth rates for the tumor on the right are presented in FIG. 3C. In group 5 (TTAP NPs+hv), we only observed that the right tumor volume was more suppressed than that observed in groups 1-4. In contrast, in group 6 (TTAP NPs+hv+α-PD-L1), both the right and left tumor volume showed obvious reduction (FIG. 3D). Moreover, after 15, the right- and left tumors were isolated respectively, and then weighed the tumor mass, as shown in FIG. 3E and FIG. 3F, the results were consistent with tumor volume growth. These experimental results clearly demonstrated that the TTABP mediated prodrug photolytic system potentiated the checkpoint blockade immunotherapy efficacy and promoted abscopal effects.

We next explored the mechanism by which TTAP mediated prodrug photolysis enhanced the efficacy of immunotherapy (Experimental, section 14). In particular, we first analyzed immune cell profiling in the spleen. The cytotoxic $CD8^+$ T cell and helper $CD4^+$ T cell levels significantly increased in the treated group, as compared to those in the PBS treatment group (group 1). After stimulation with PMA/ionomycin for 4 hours, the cytokine of IFN-γ produced in $CD4^+$ and $CD8^+$ T cells were counted. The number of antigen-specific IFN-γ producing T cells significantly increased in group 6, indicating that TTABP plus α-PD-L1 treatment induced a tumor-specific T cell response. We further profiled infiltrating leukocytes in the primary and the distant tumors. Flow cytometry measurements for group 6 showed a significant increase in tumor-infiltration of $CD4^+$ and $CD8^+$ T cells in both primary and distant tumors. These results demonstrated TTABP-mediated prodrug plus α-PD-L1 treatment increased the infiltration of the effector T cells to treat the metastasis.

Figure 23:
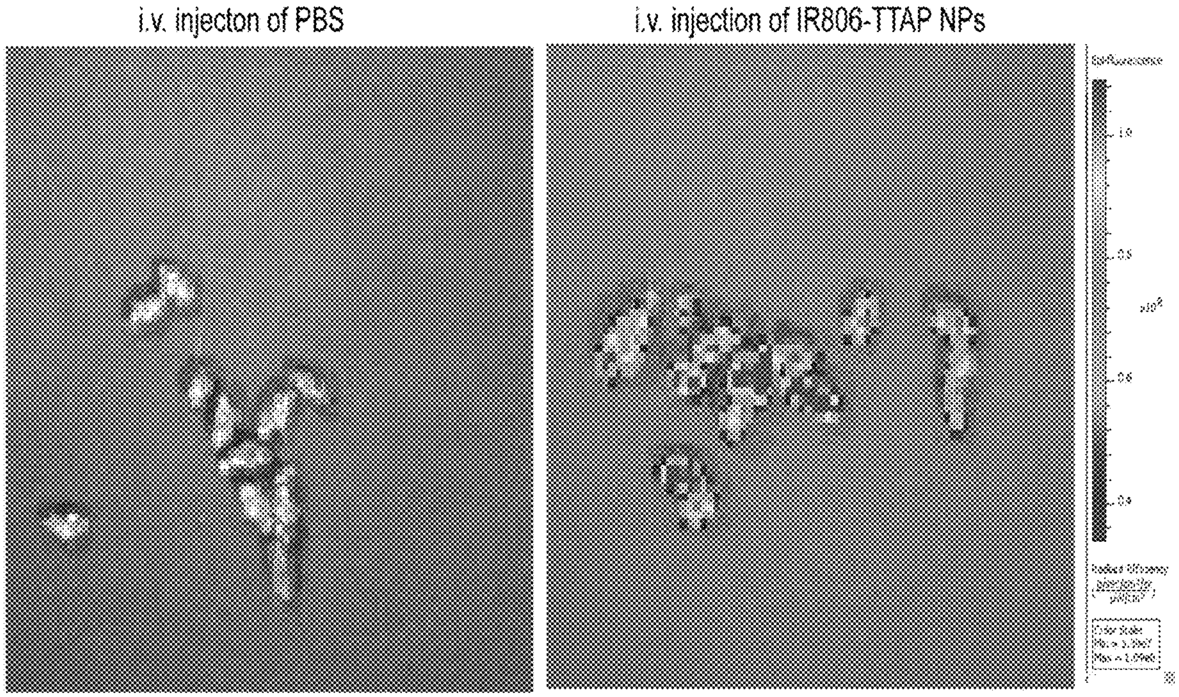
FIG. 23. IVS imaging of the mice feces for i.v. injection PBS (control) and i.v. injection of IR806-TTAP NPs.
Figure 24:
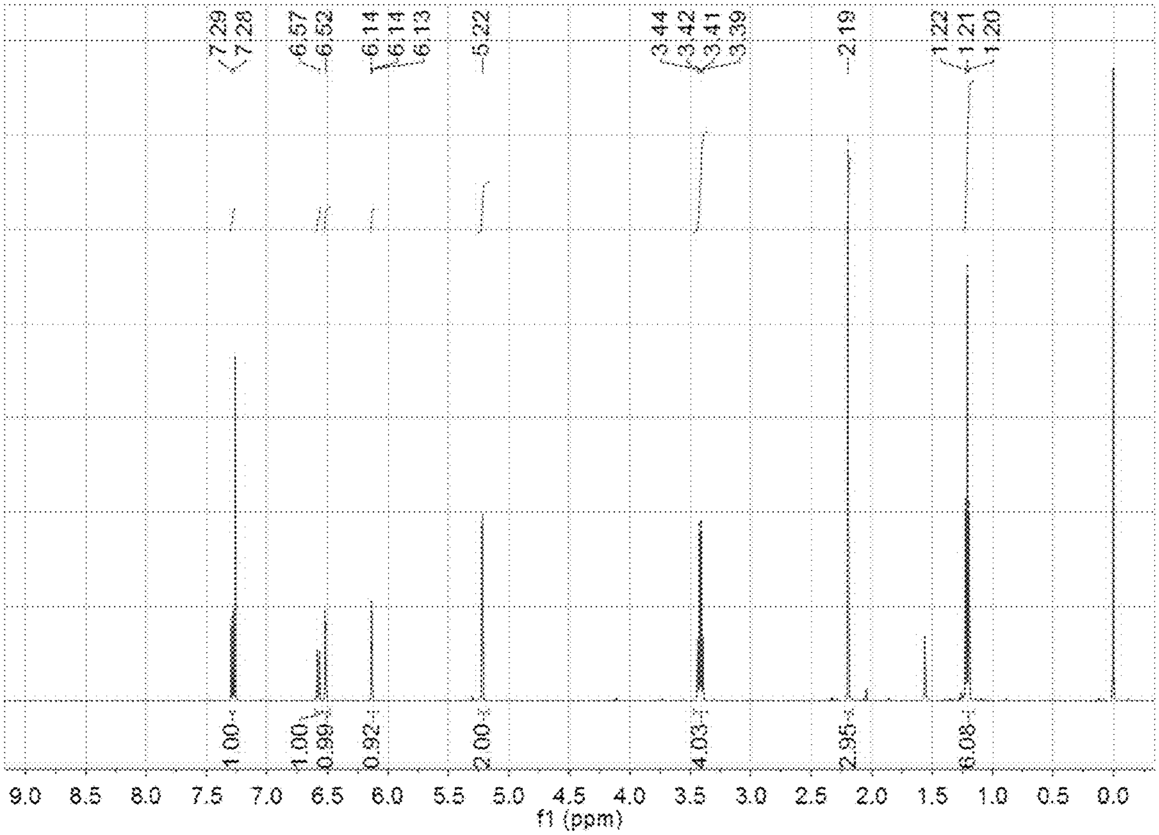
FIG. 24 shows $^1$HNMR of 1 (500 MHz, $CDCl_3$).
Figure 25:
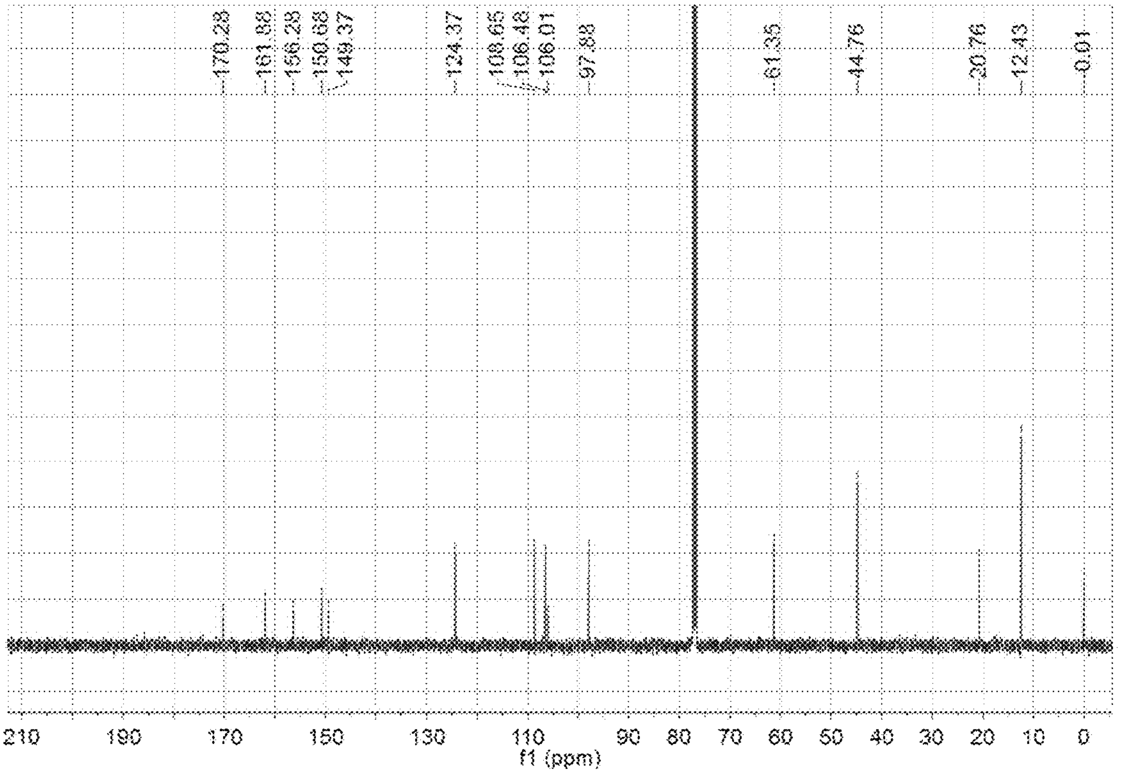
FIG. 25 shows $^{13}$CNMR of 1 (125 MHz, $CDCl_3$).
Figure 26:
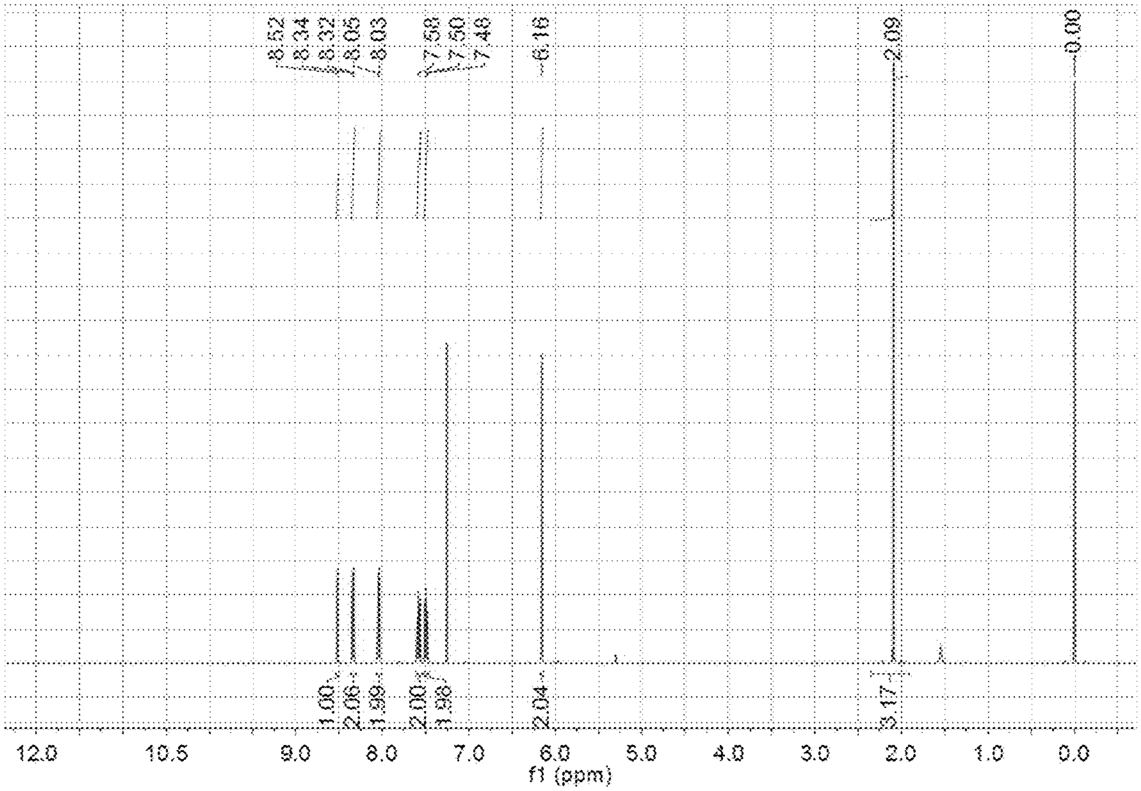
FIG. 26 shows $^1$HNMR of 2 (500 MHz, $CDCl_3$).
Figure 27:
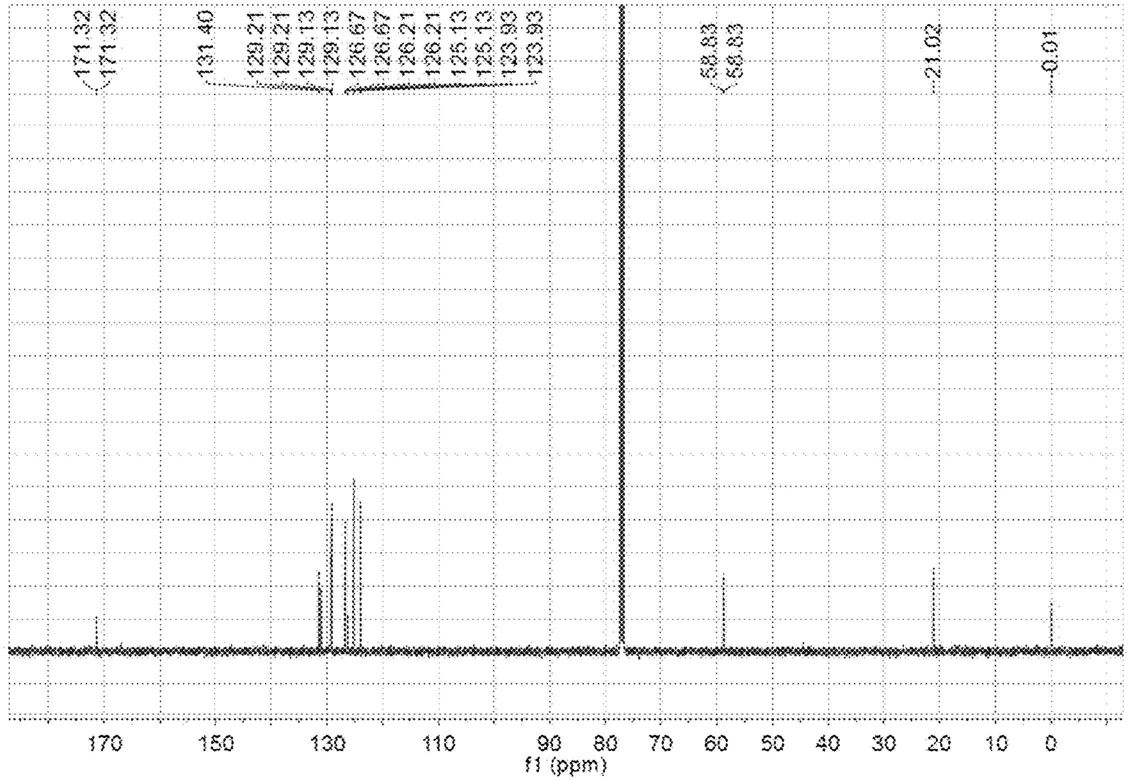
FIG. 27 shows $^{13}$CNMR of 2 (125 MHz, $CDCl_3$).
Figure 28:
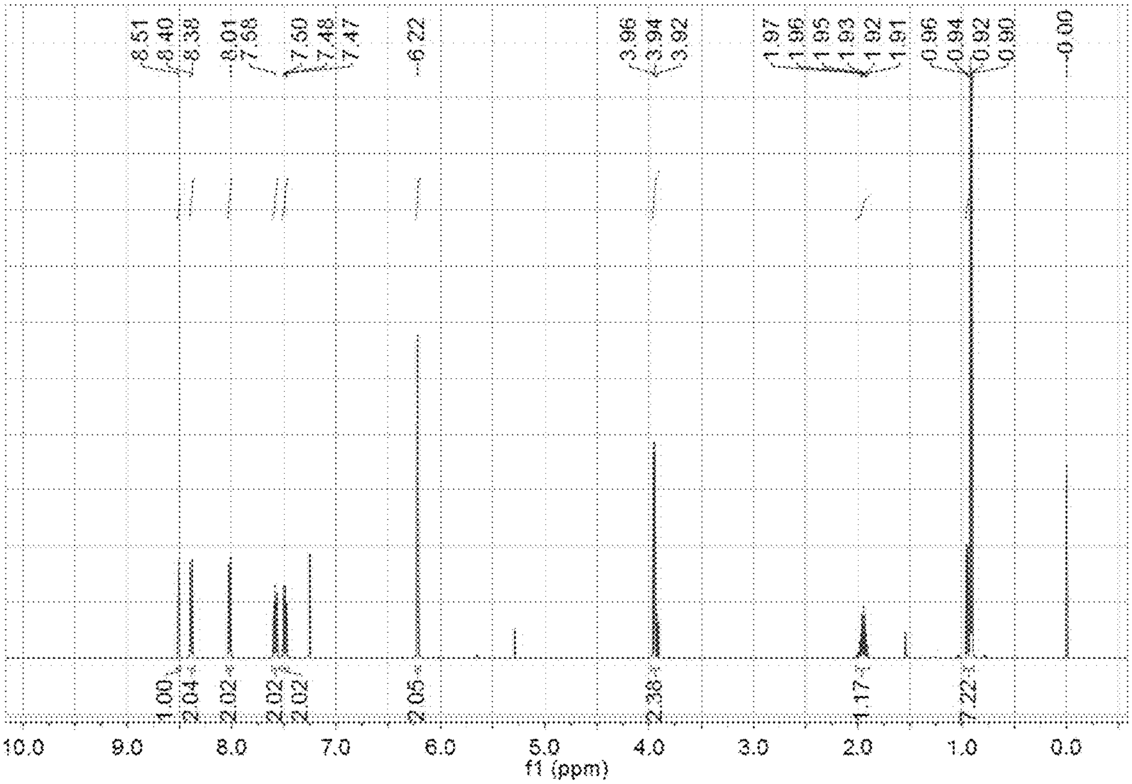
FIG. 28 shows $^1$NMR of 3 (500 MHz, $CDCl_3$).
Figure 29:
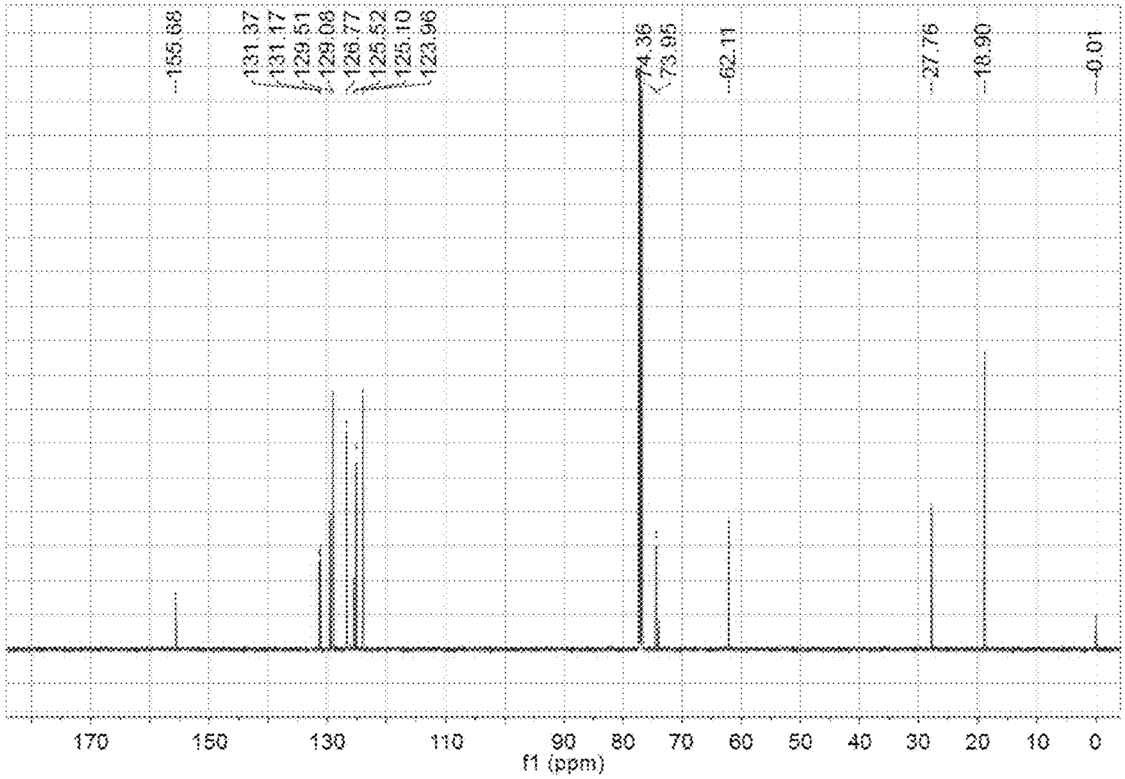
FIG. 29 shows $^{13}$CNMR of 3 (125 MHz, $CDCl_3$).
Figure 30:
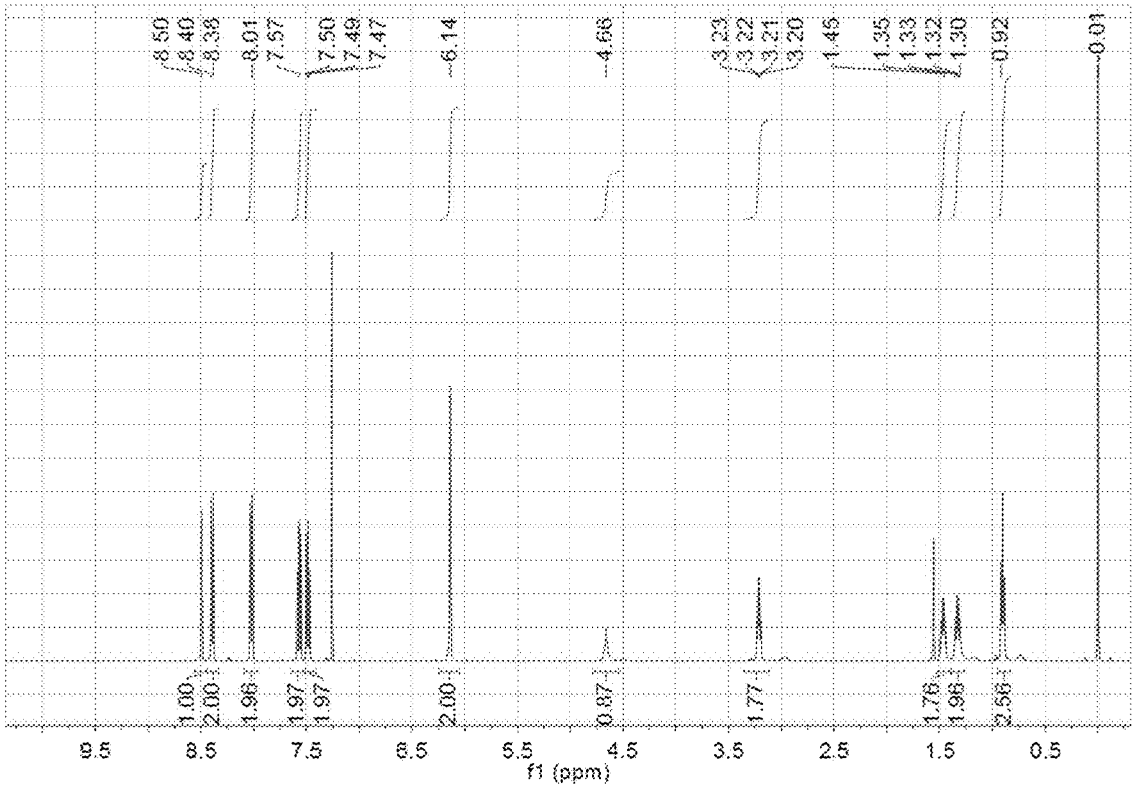
FIG. 30 shows $^1$HNMR of 4 (500 MHz, $CDCl_3$).
Figure 31:
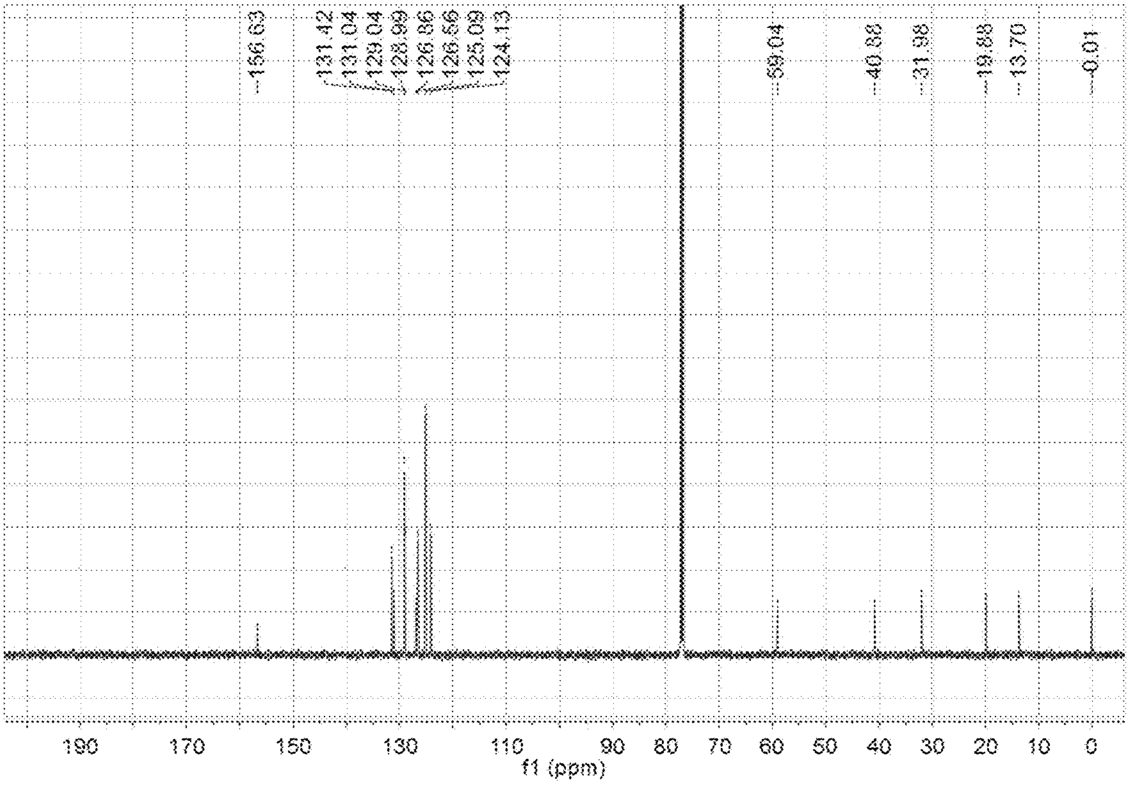
FIG. 31 shows $^{13}$CNMR of 4 (125 MHz, $CDCl_3$).
Figure 32:
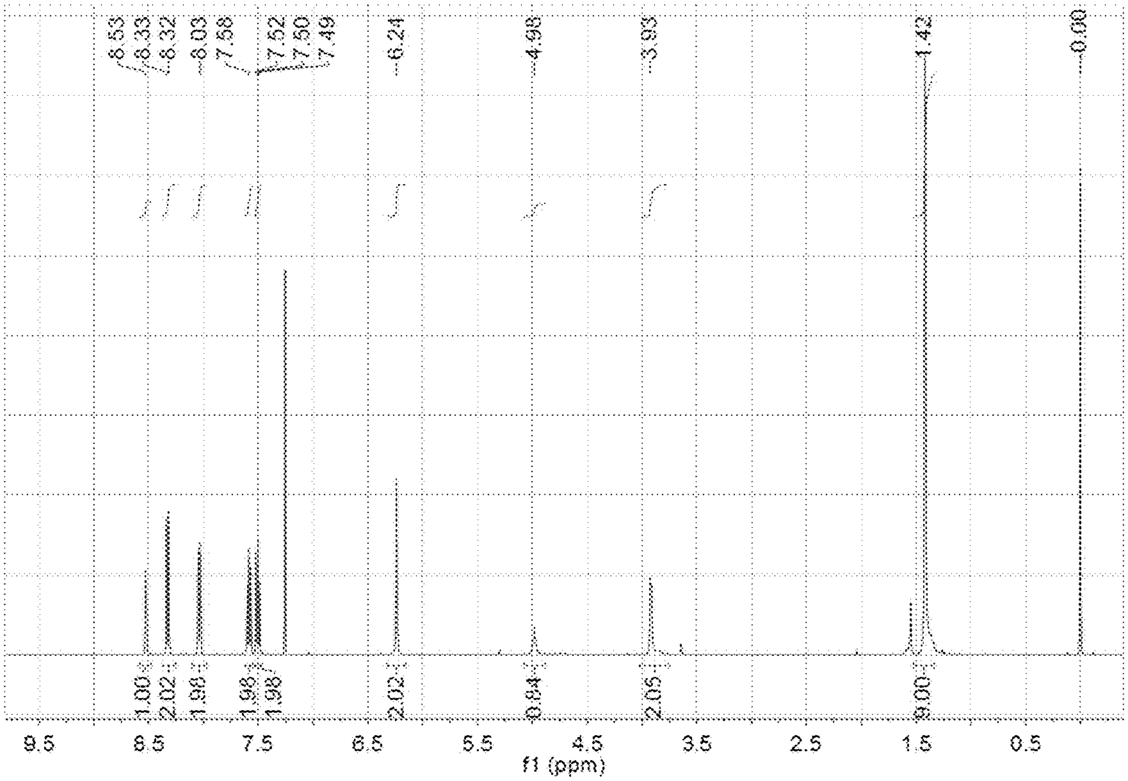
FIG. 32 shows $^1$HNMR of 5 (500 MHz, $CDCl_3$).
Figure 33:
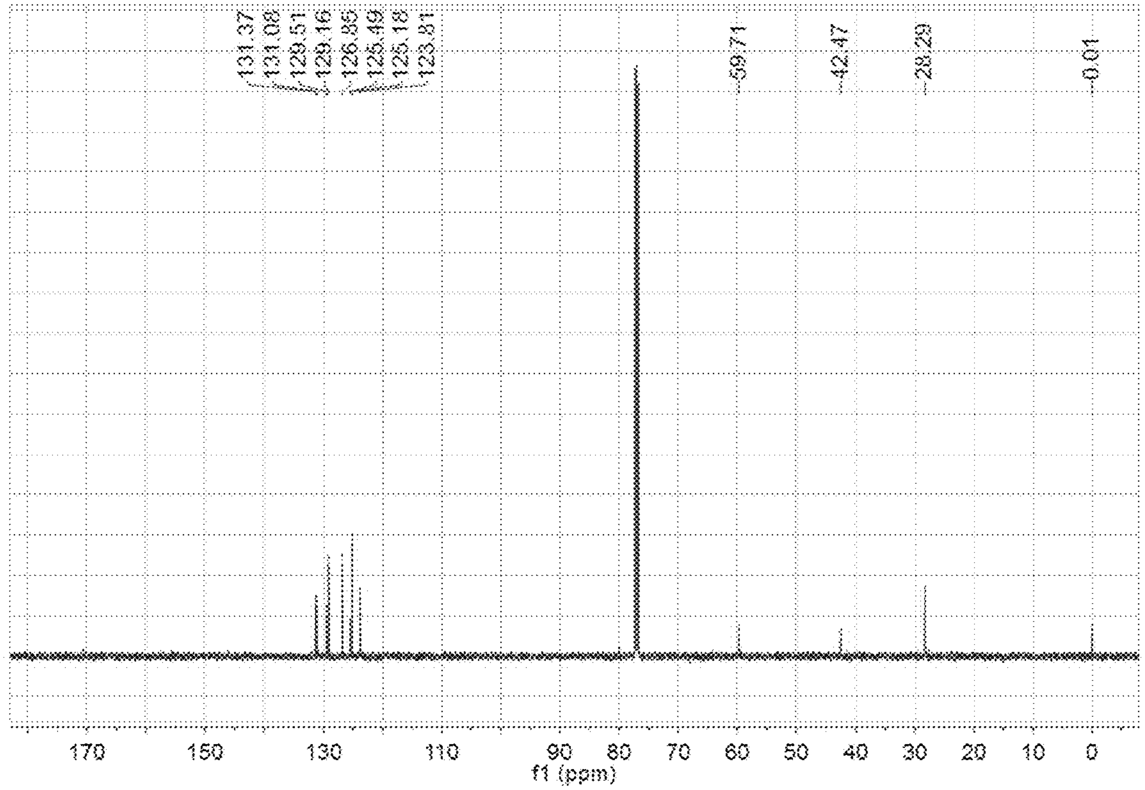
FIG. 33 shows $^{13}$CNMR of 5 (125 MHz, $CDCl_3$).
Figure 34:
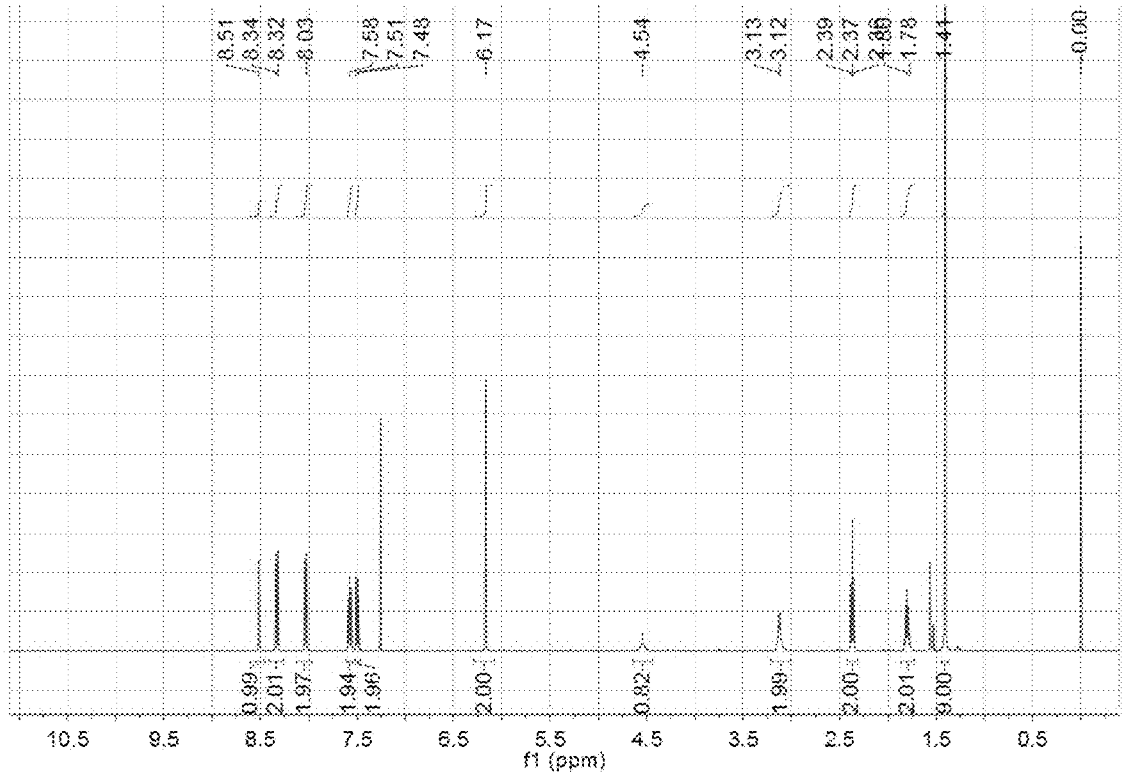
FIG. 34 shows $^1$HNMR of 6 (500 MHz, $CDCl_3$).
Figure 35:
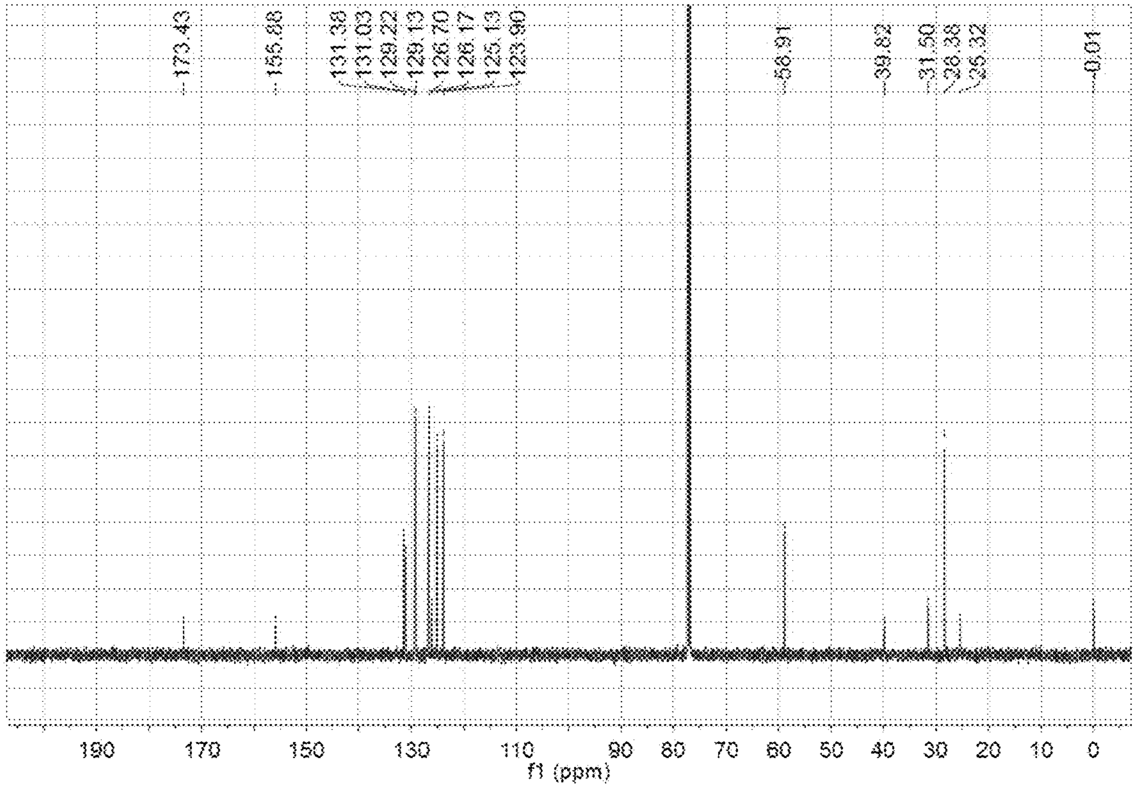
FIG. 35 shows $^{13}$CNMR of 6 (125 MHz, $CDCl_3$).
Figure 36:
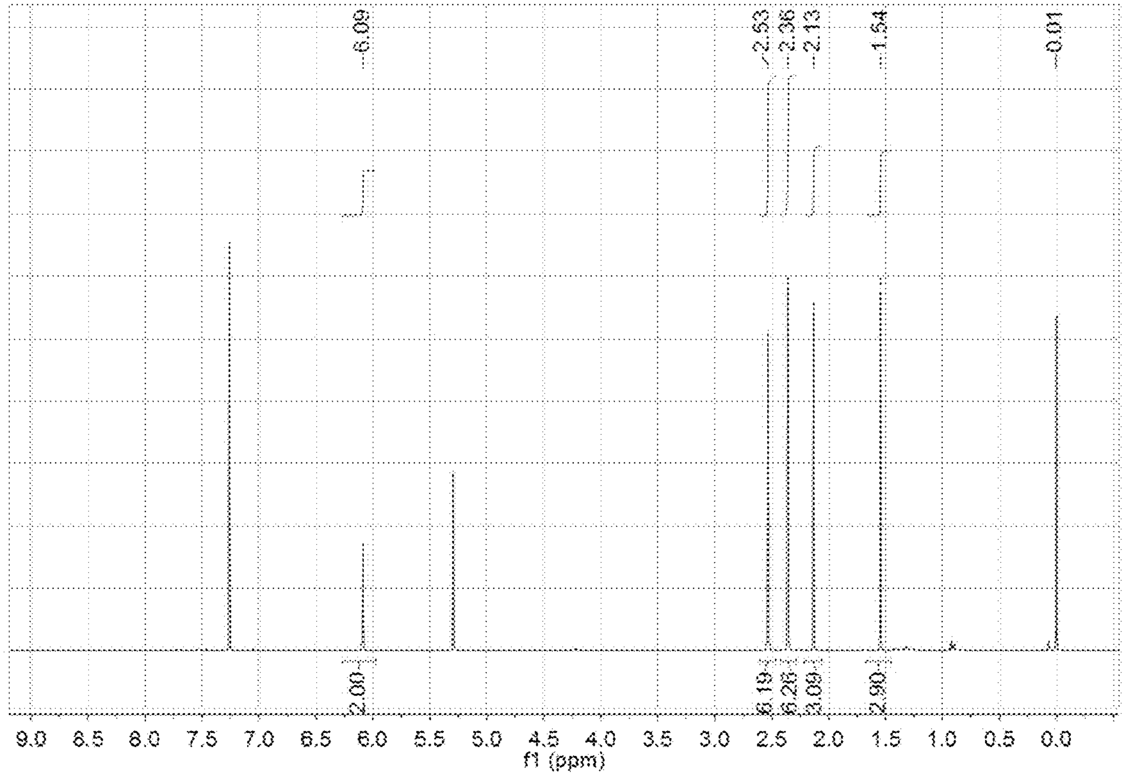
FIG. 36 shows $^1$HNMR of 7 (500 MHz, $CDCl_3$).
Figure 37:
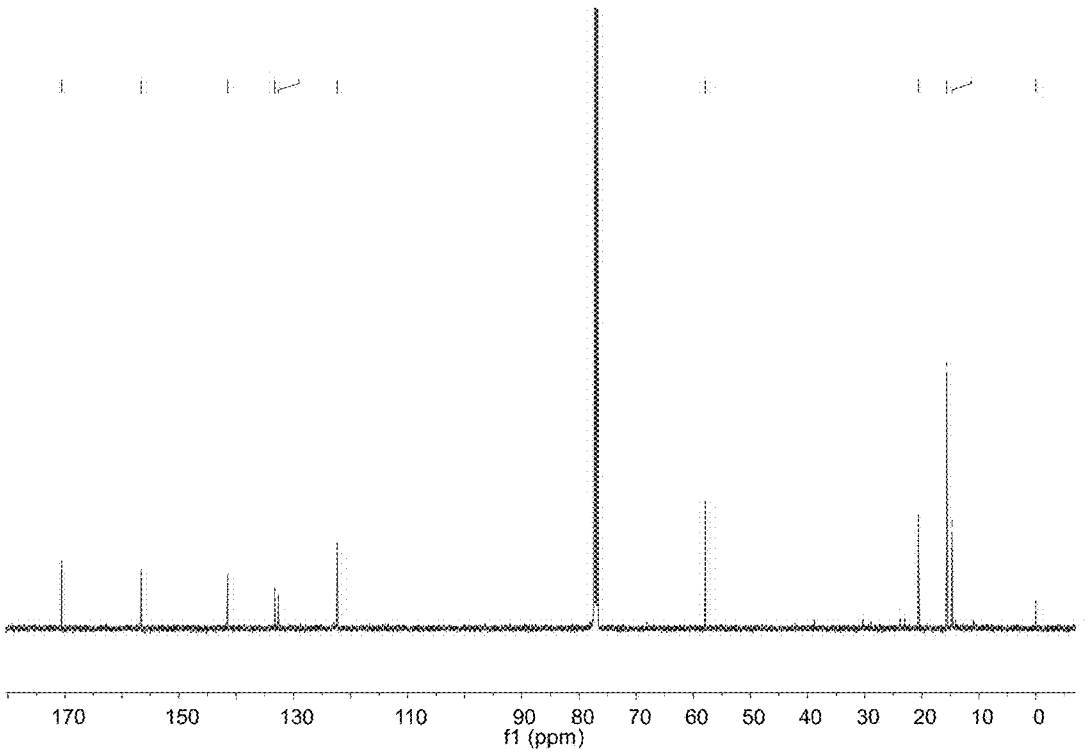
FIG. 37 shows $^{13}$CNMR of 7 (125 MHz, $CDCl_3$).
Figure 38:
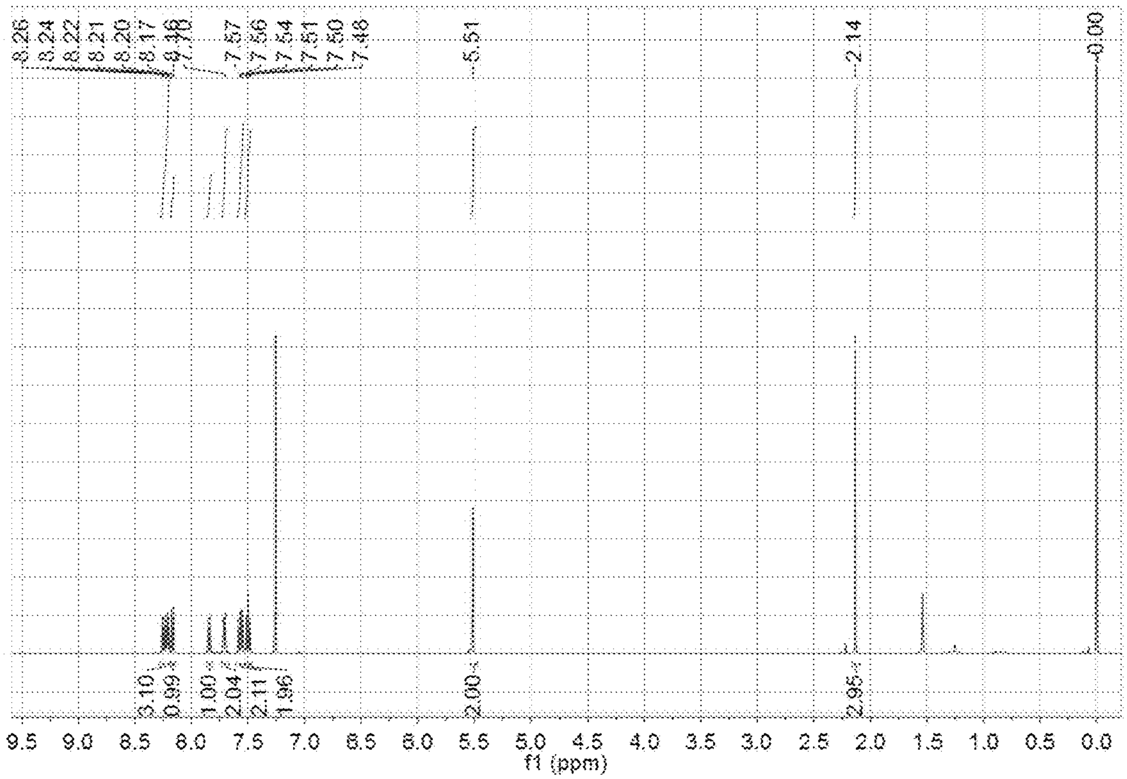
FIG. 38 shows $^1$HNMR of 8 (500 MHz, $CDCl_3$).
Figure 39:
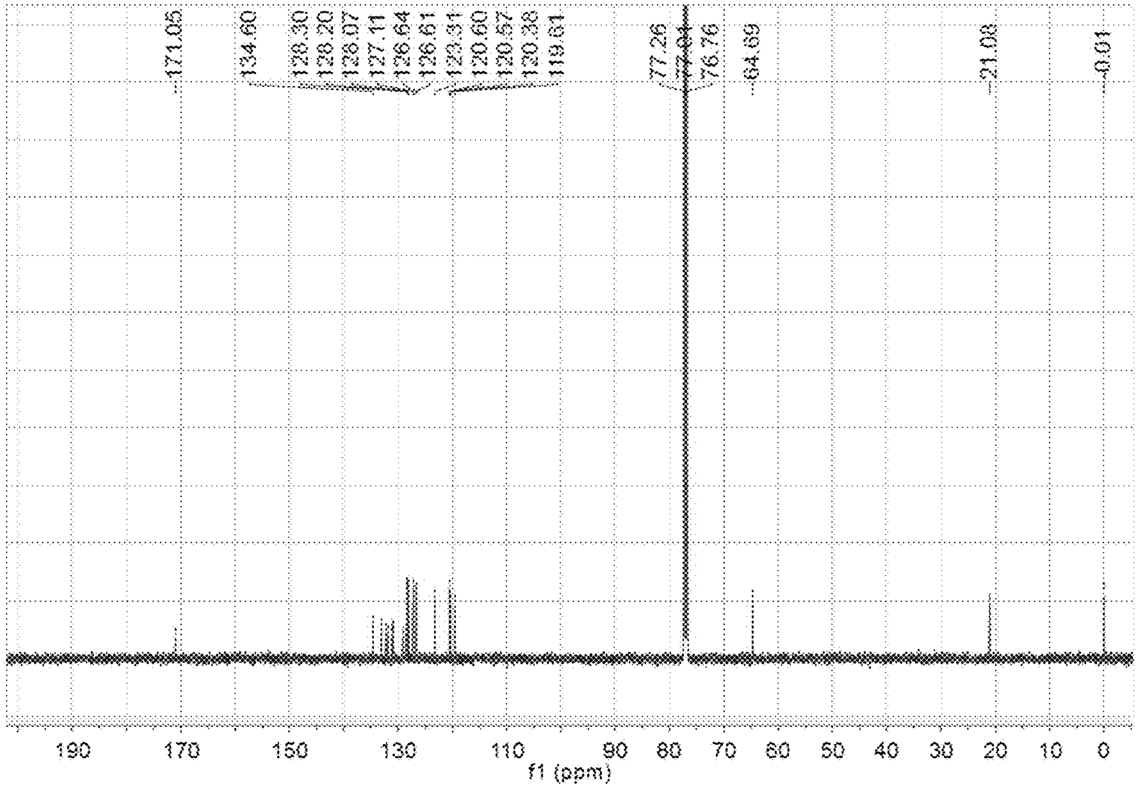
FIG. 39 shows $^{13}$CNMR of 8 (125 MHz, $CDCl_3$).
Figure 40:
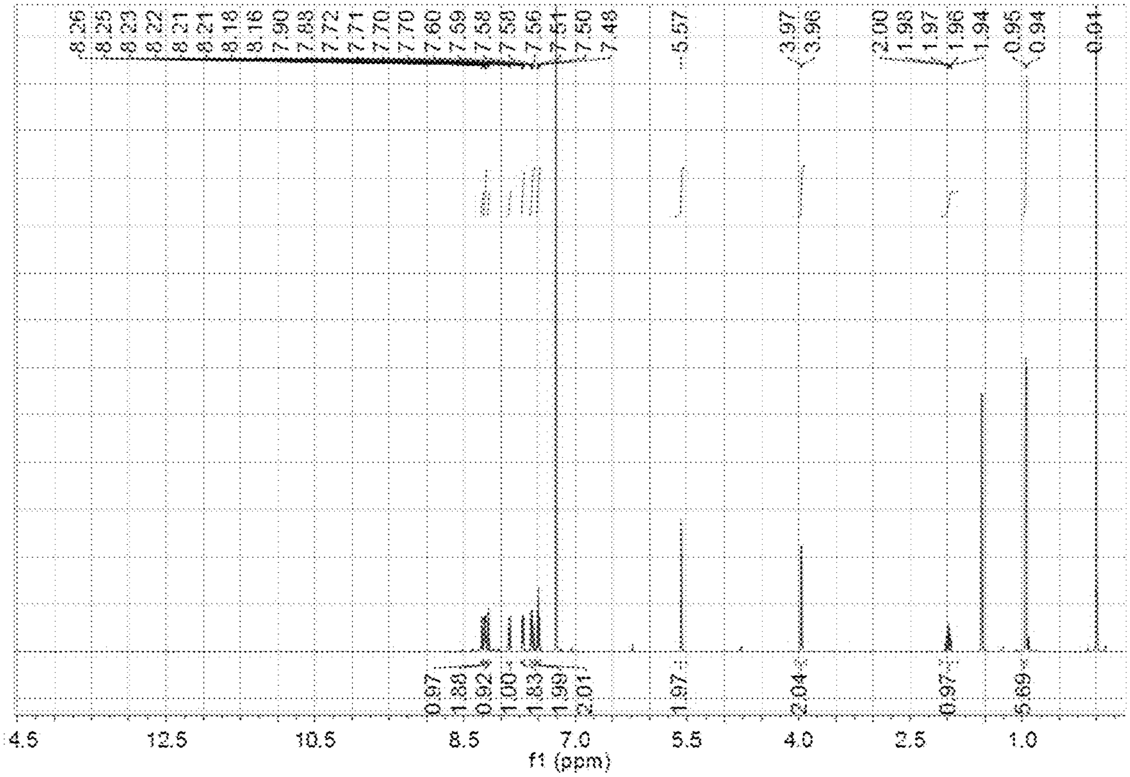
FIG. 40 shows $^1$HNMR of 9 (500 MHz, $CDCl_3$).
Figure 41:
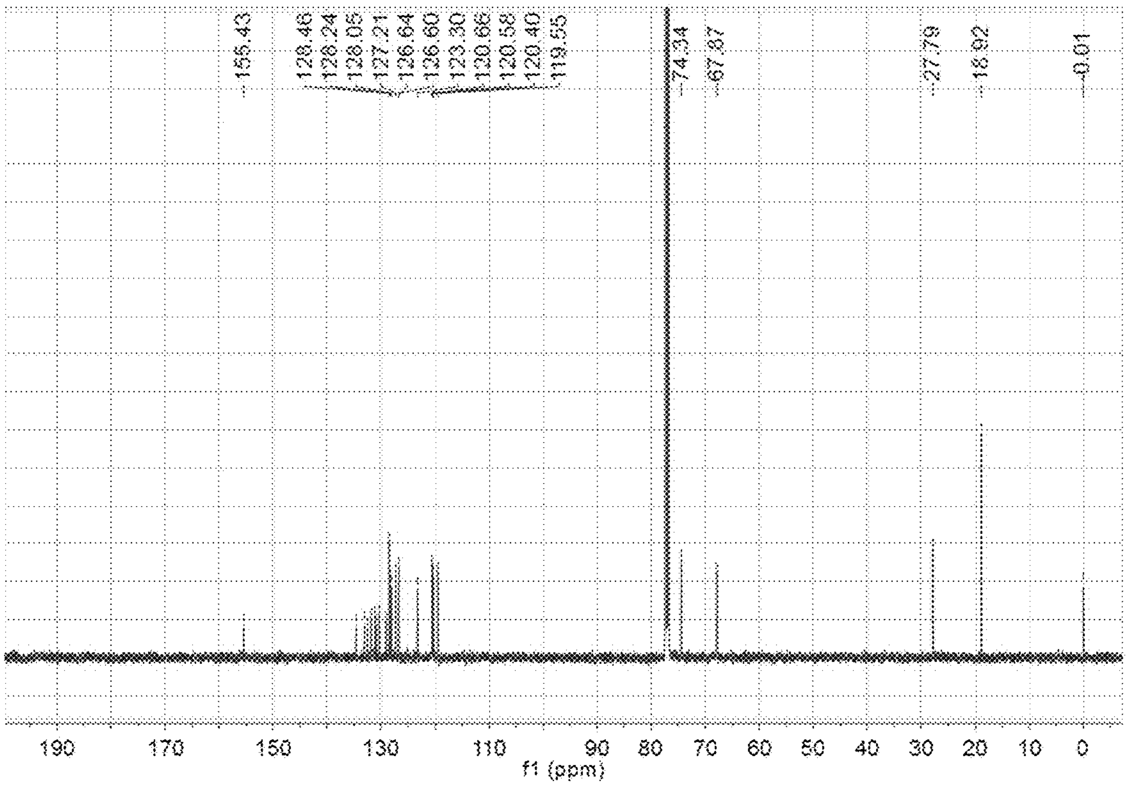
FIG. 41 shows $^{13}$CNMR of 9 (125 MHz, $CDCl_3$).
Figure 42:
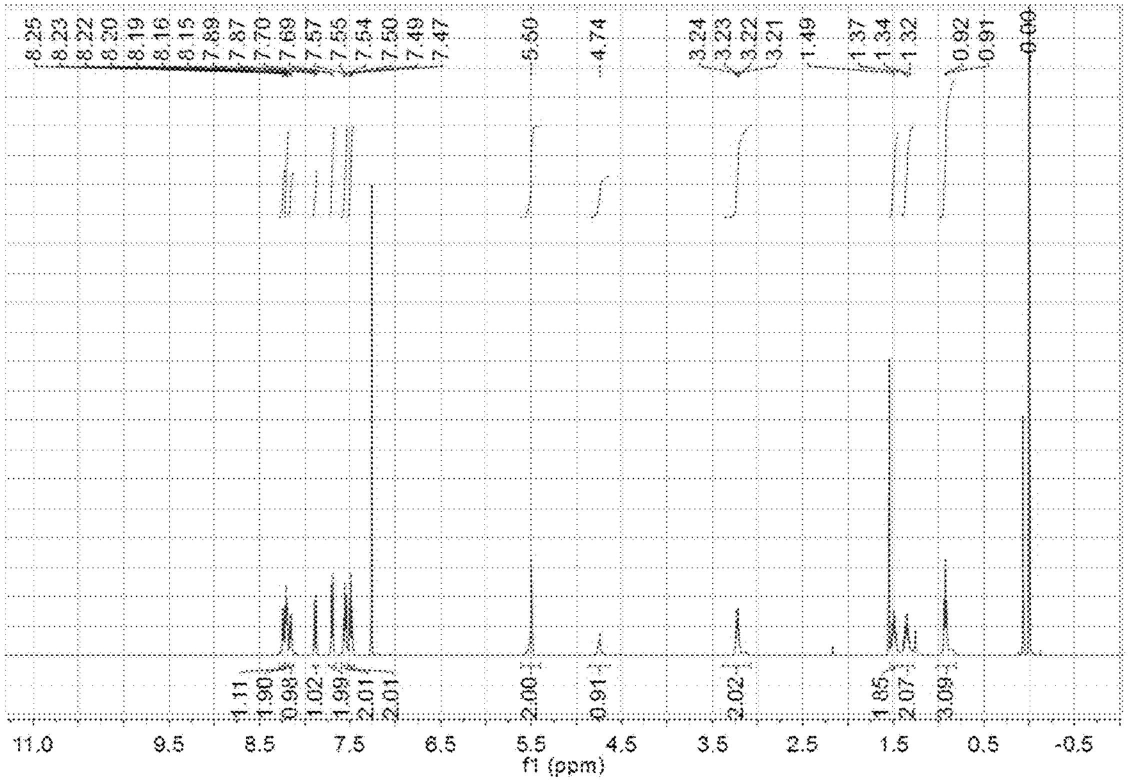
FIG. 42 shows $^1$HNMR of 10 (500 MHz, $CDCl_3$).
Figure 43:
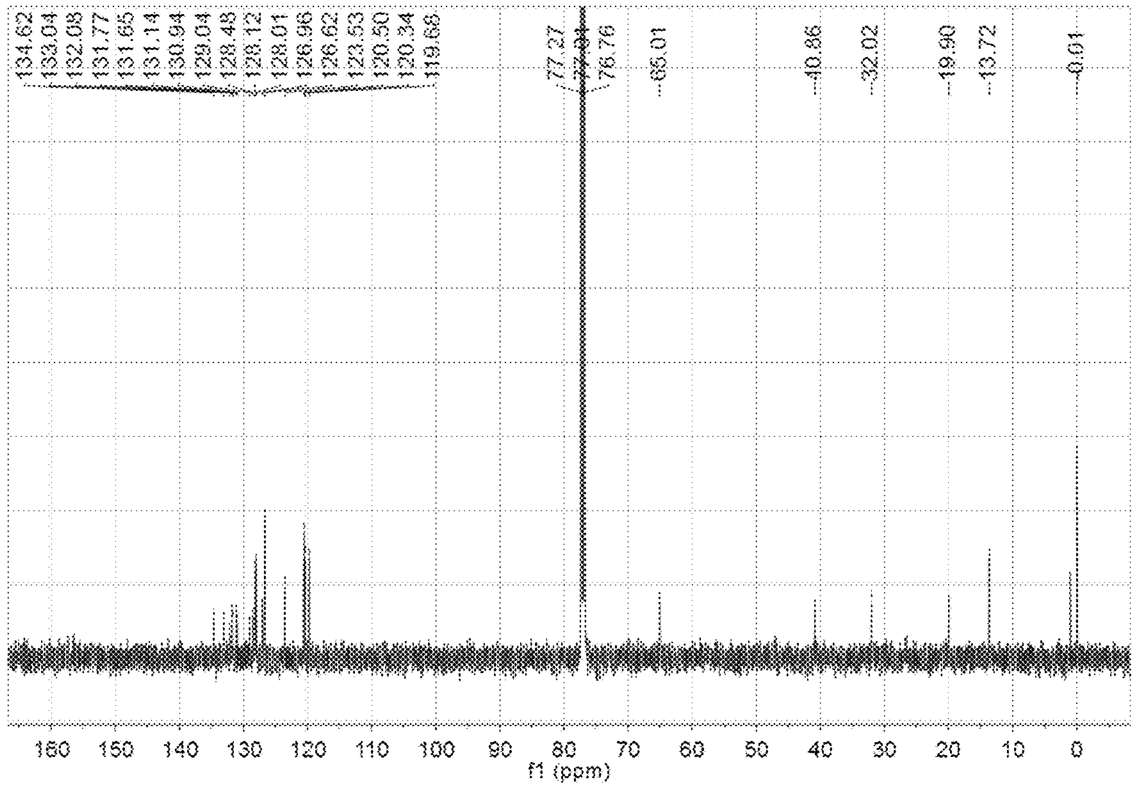
FIG. 43 shows $^{13}$CNMR of 10 (125 MHz, $CDCl_3$).
Figure 44:
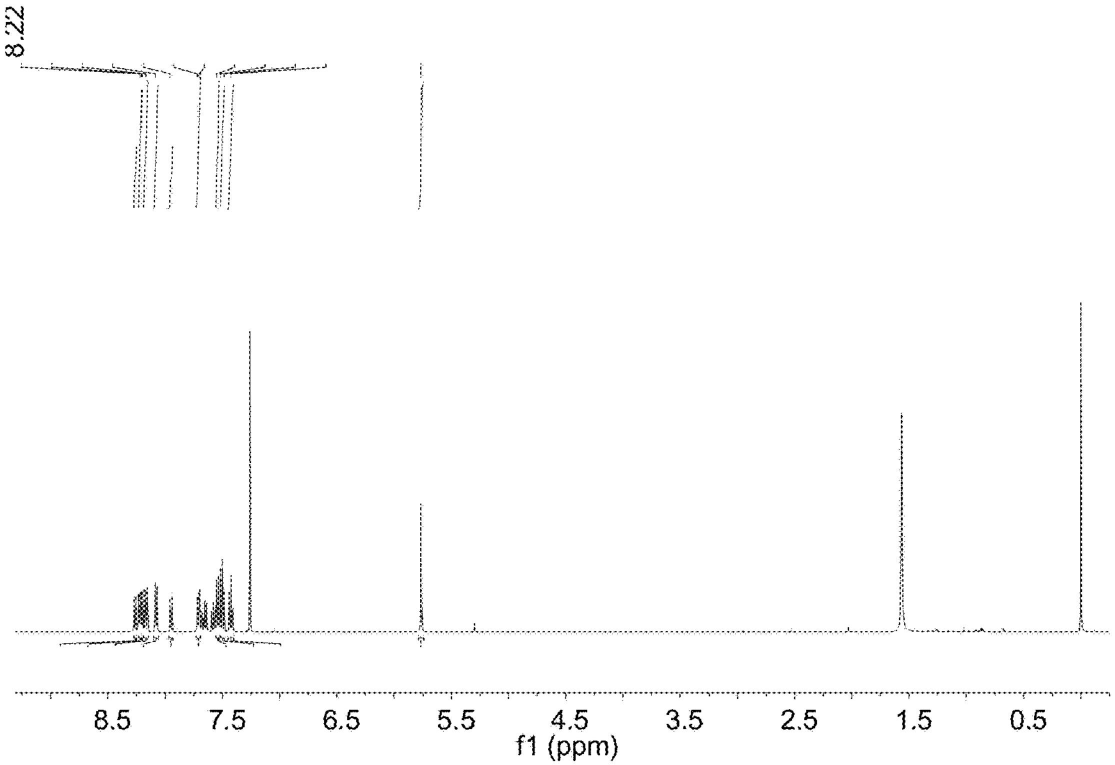
FIG. 44 shows $^1$HNMR of 11 (500 MHz, $CDCl_3$).
Figure 45:
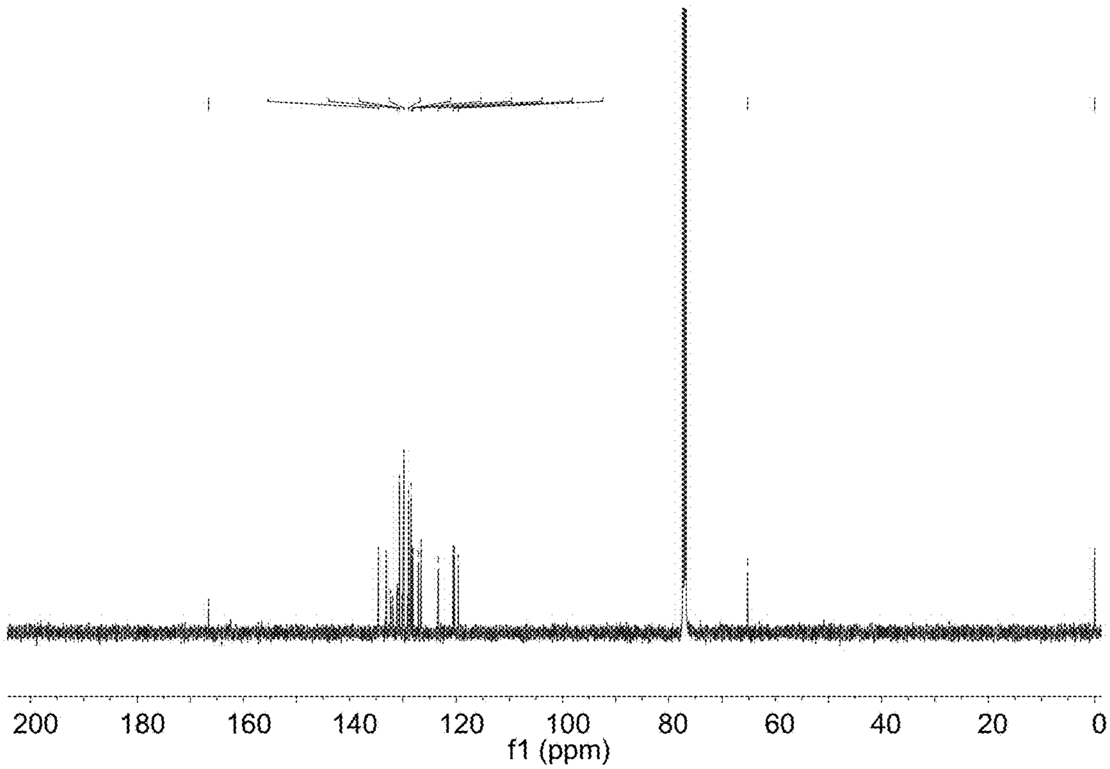
FIG. 45 shows $^{13}$CNMR of 11 (125 MHz, $CDCl_3$).
Figure 46:
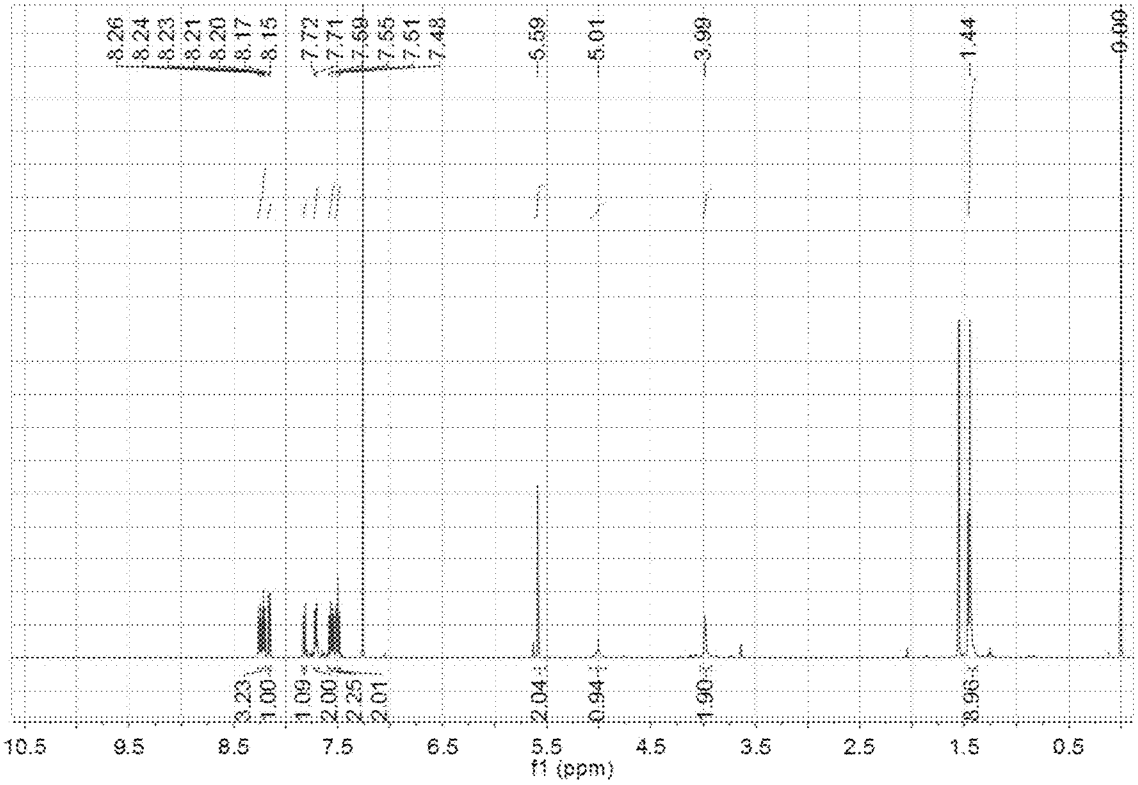
FIG. 46 shows $^1$HNMR of 12 (500 MHz, $CDCl_3$).
Figure 47:
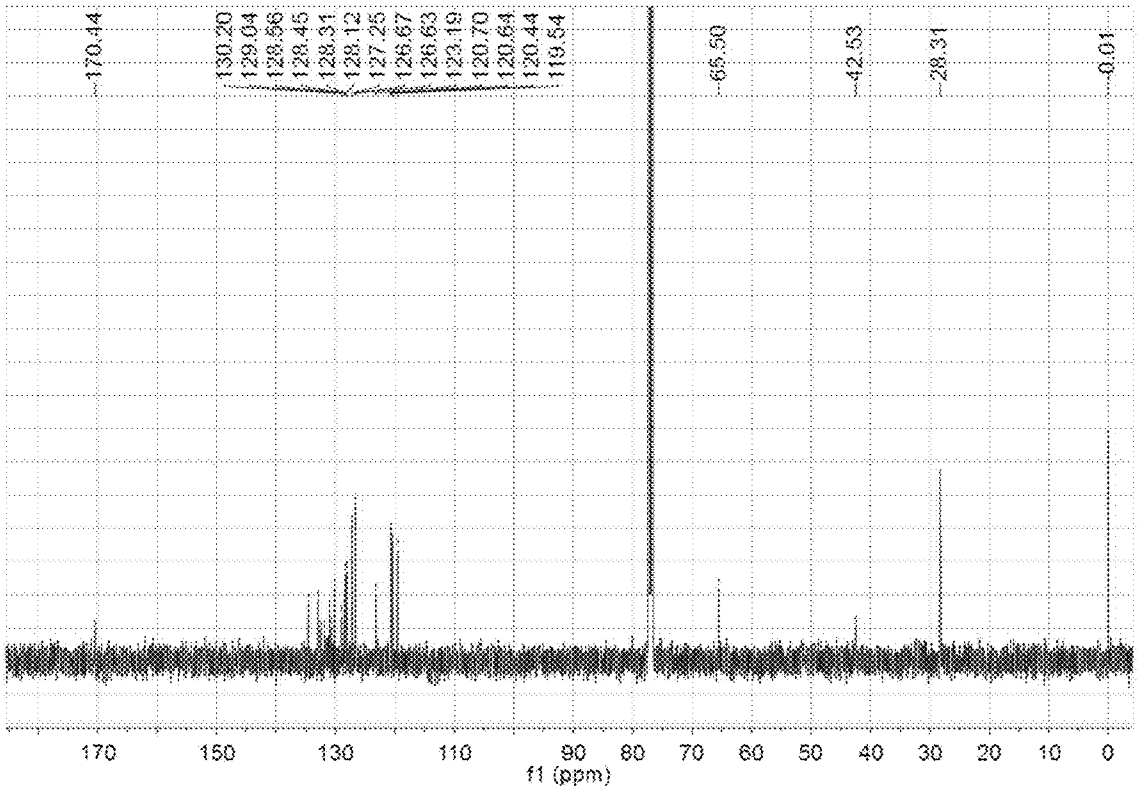
FIG. 47 shows $^{13}$CNMR of 12 (125 MHz, $CDCl_3$).
Figure 48:
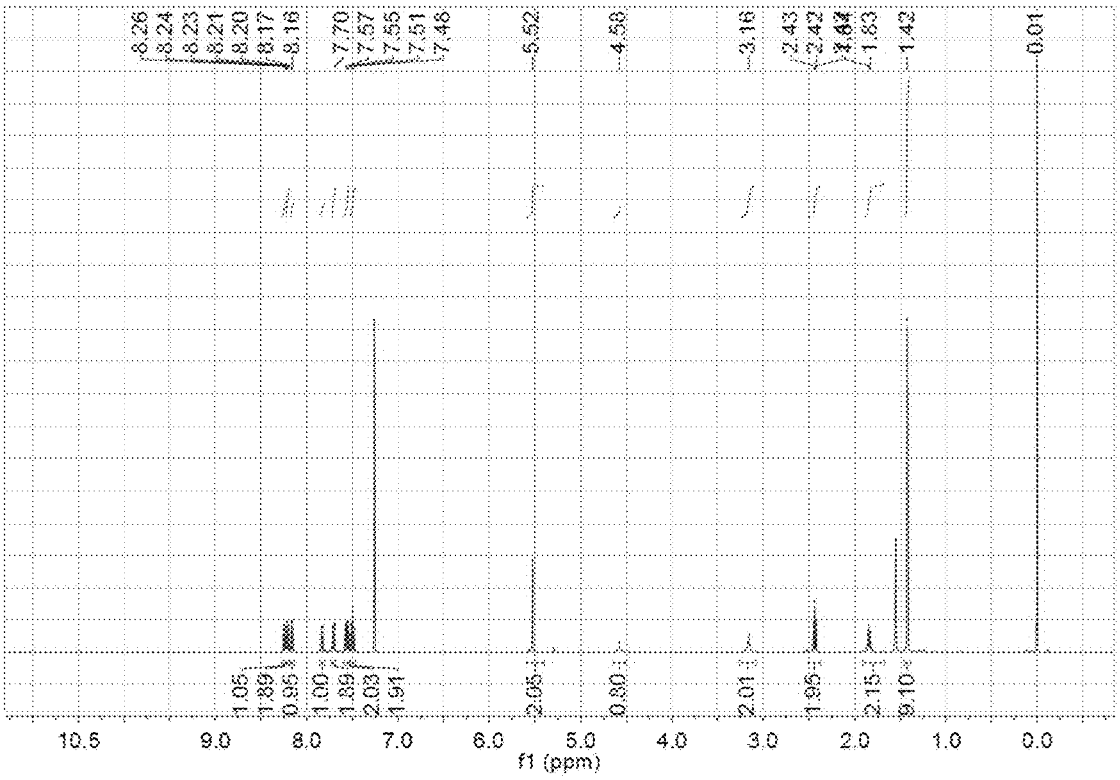
FIG. 48 shows $^1$HNMR of 13 (500 MHz, $CDCl_3$).
Figure 49:
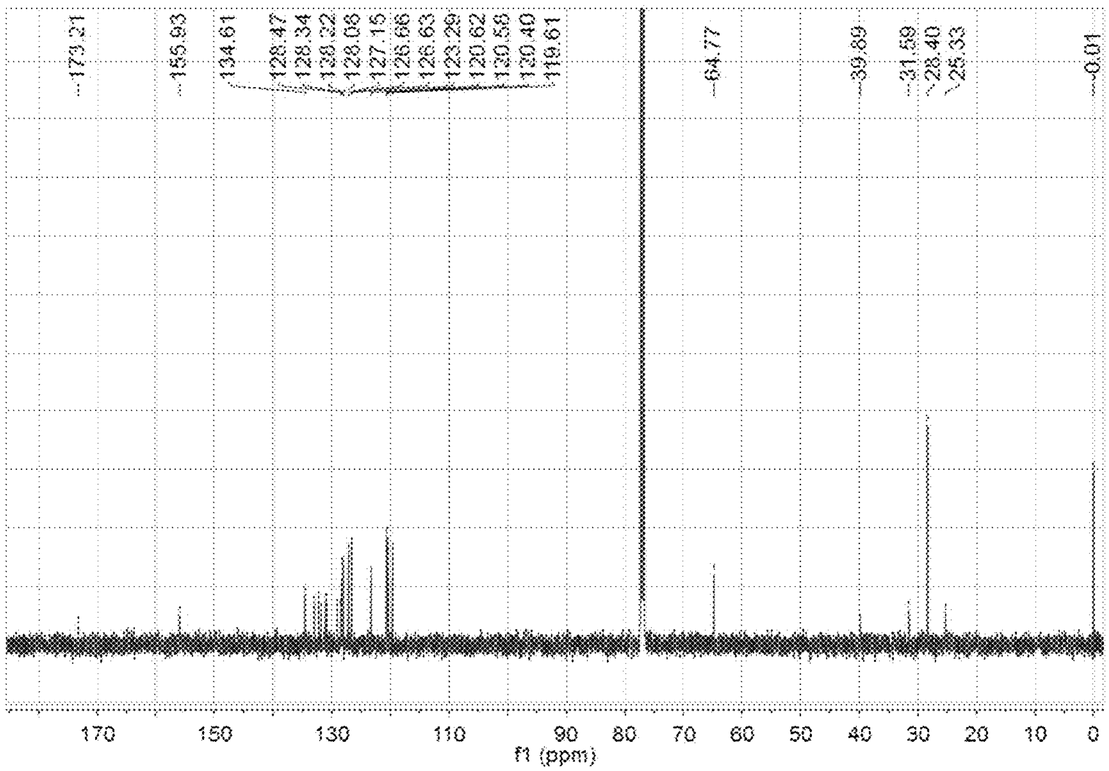
FIG. 49 shows $^{13}$CNMR of 13 (125 MHz, $CDCl_3$).
Figure 50:
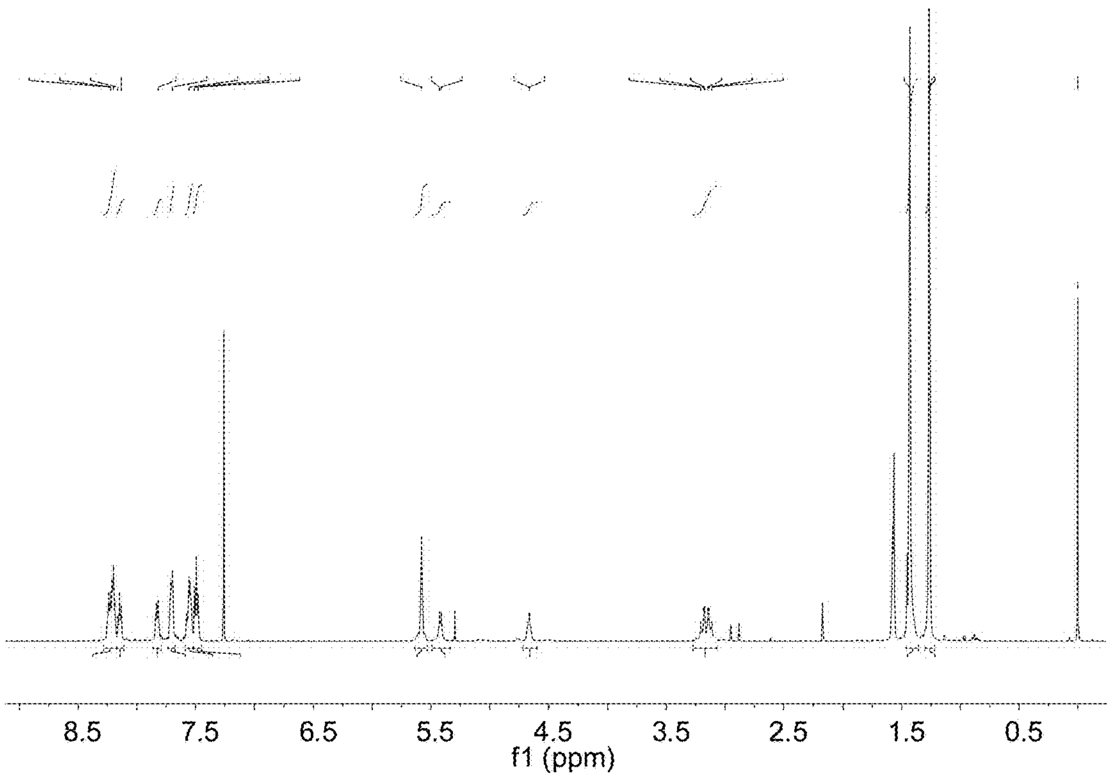
FIG. 50 shows $^1$HNMR of 14 (500 MHz, $CDCl_3$).
Figure 51:
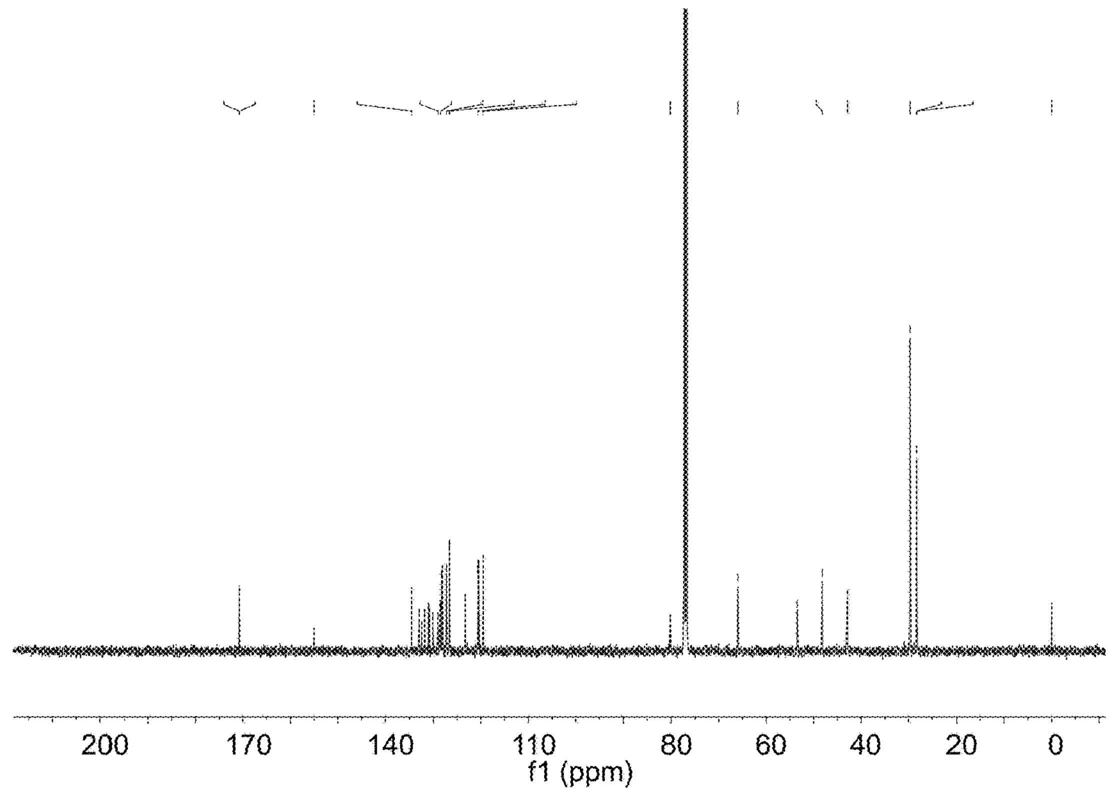
FIG. 51 shows $^{13}$CNMR of 14 (125 MHz, $CDCl_3$).
Figure 52:
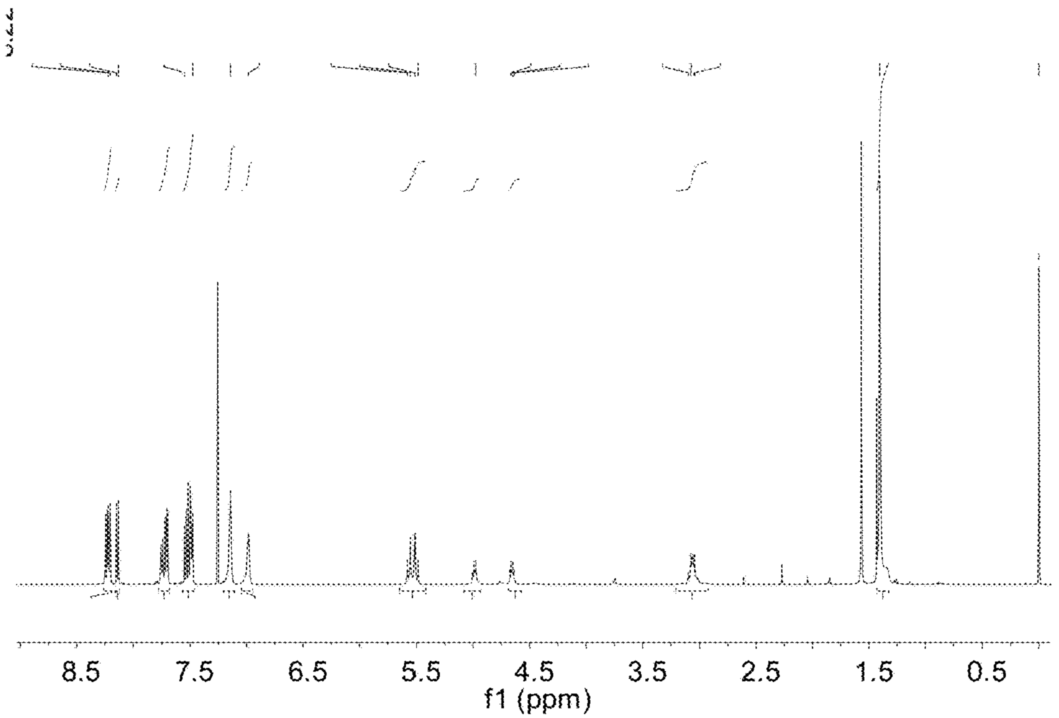
FIG. 52 shows $^1$HNMR of 15 (500 MHz, $CDCl_3$).
Figure 53:
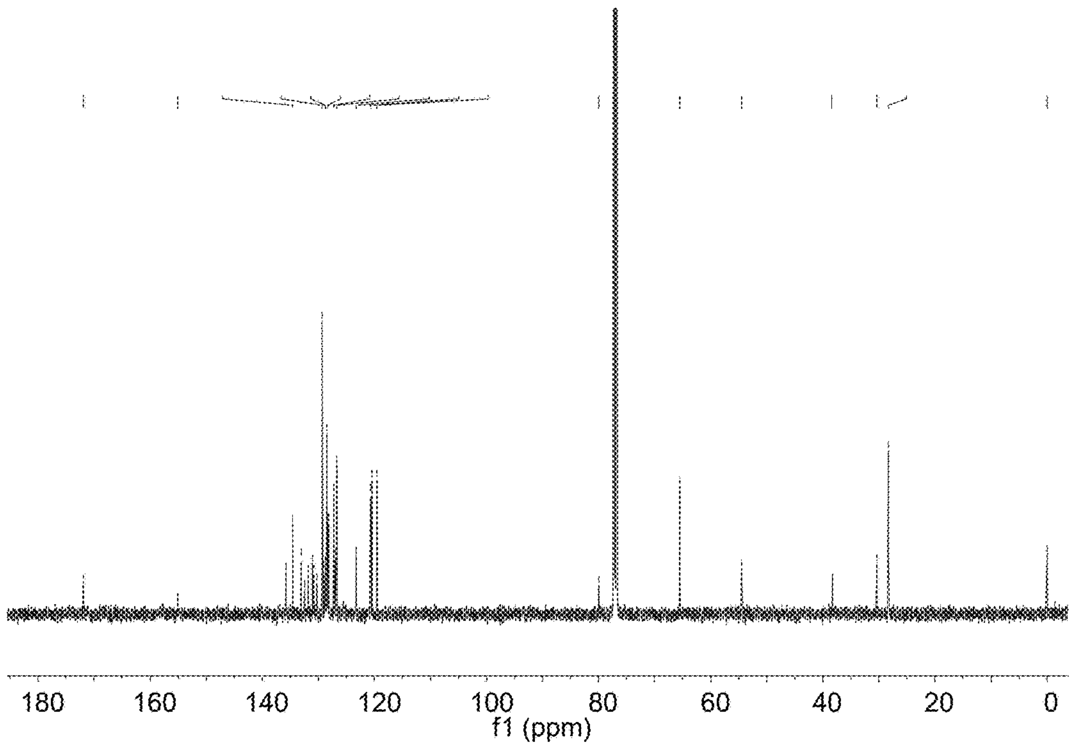
FIG. 53 shows $^{13}$CNMR of 15 (125 MHz, $CDCl_3$).
Figure 54:
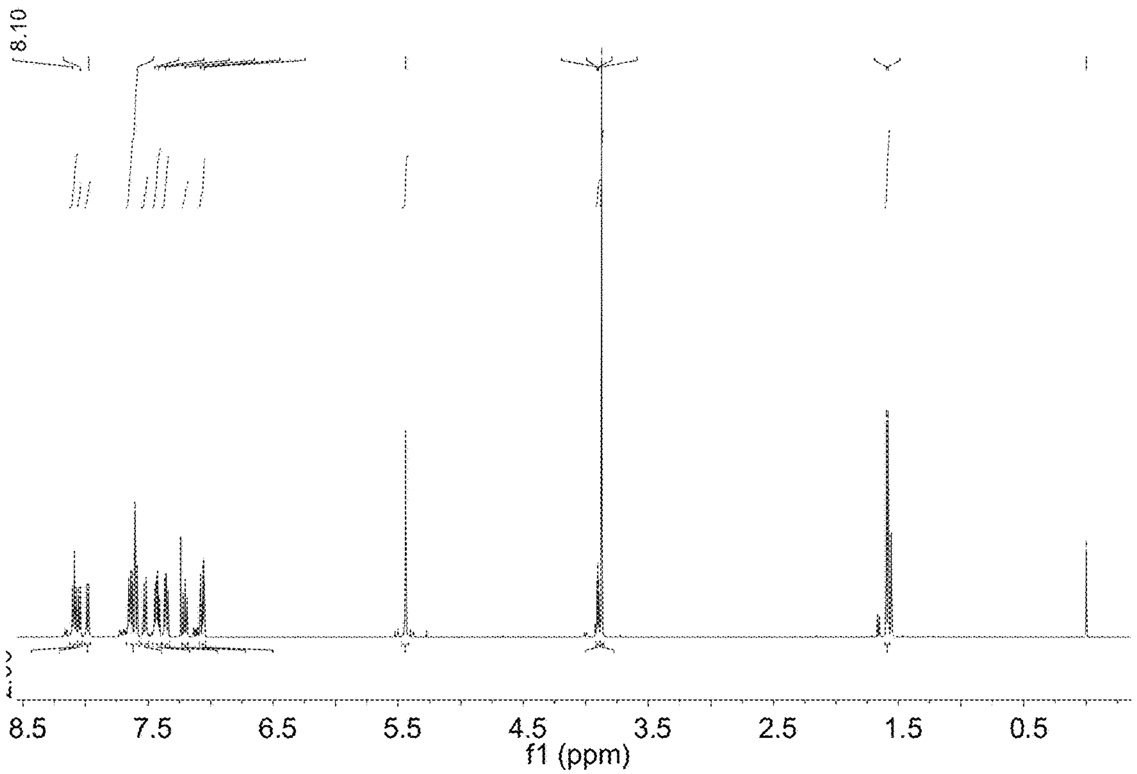
FIG. 54 shows $^{1}$HNMR of 16 (500 MHz, $CDCl_3$).
Figure 55:
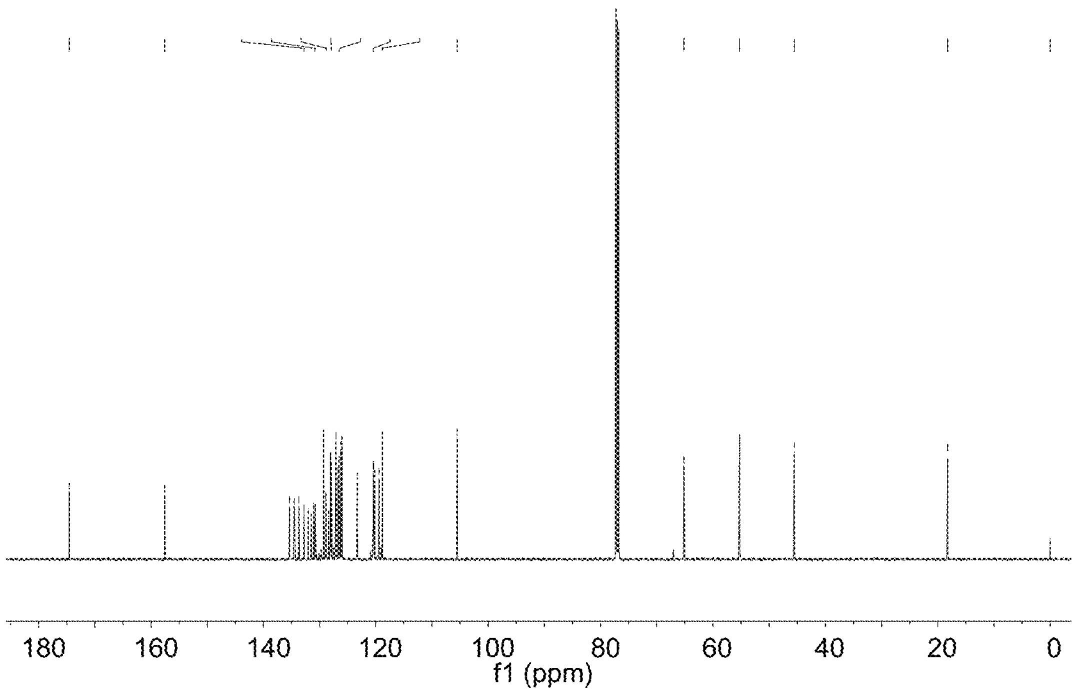
FIG. 55 shows $^{13}$CNMR of 16 (125 MHz, $CDCl_3$).
Figure 56:
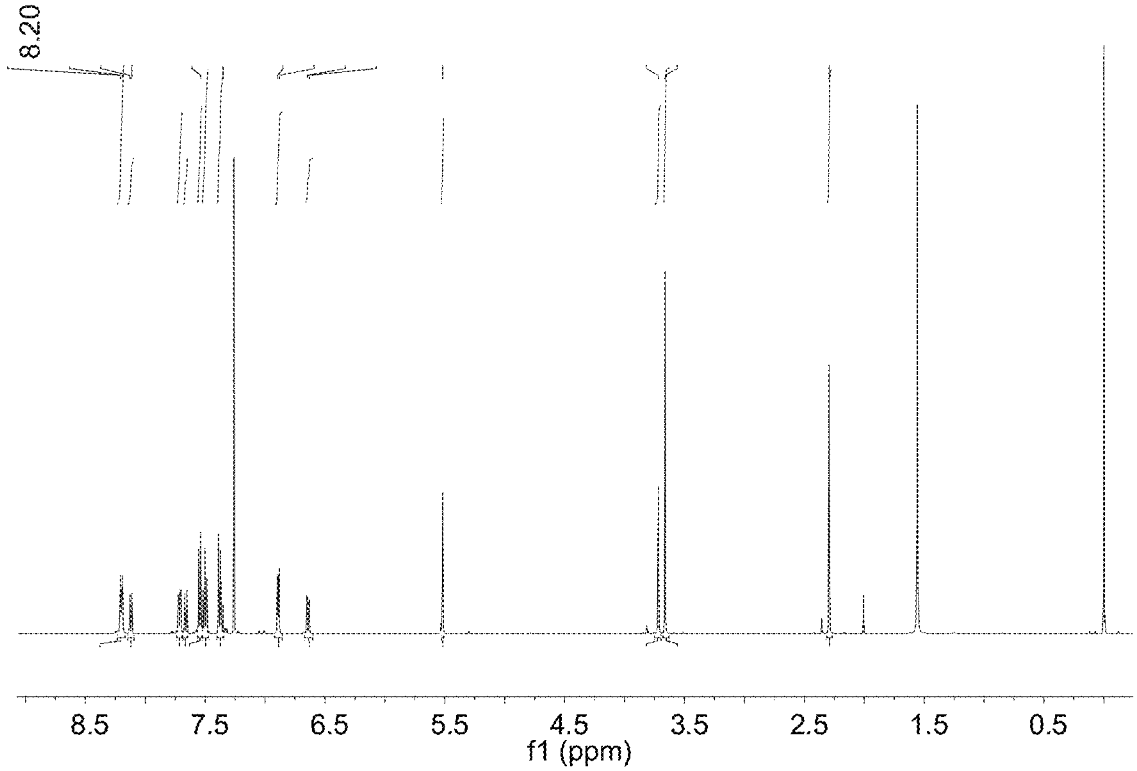
FIG. 56 shows $^{1}$HNMR of 17 (500 MHz, $CDCl_3$).
Figure 57:
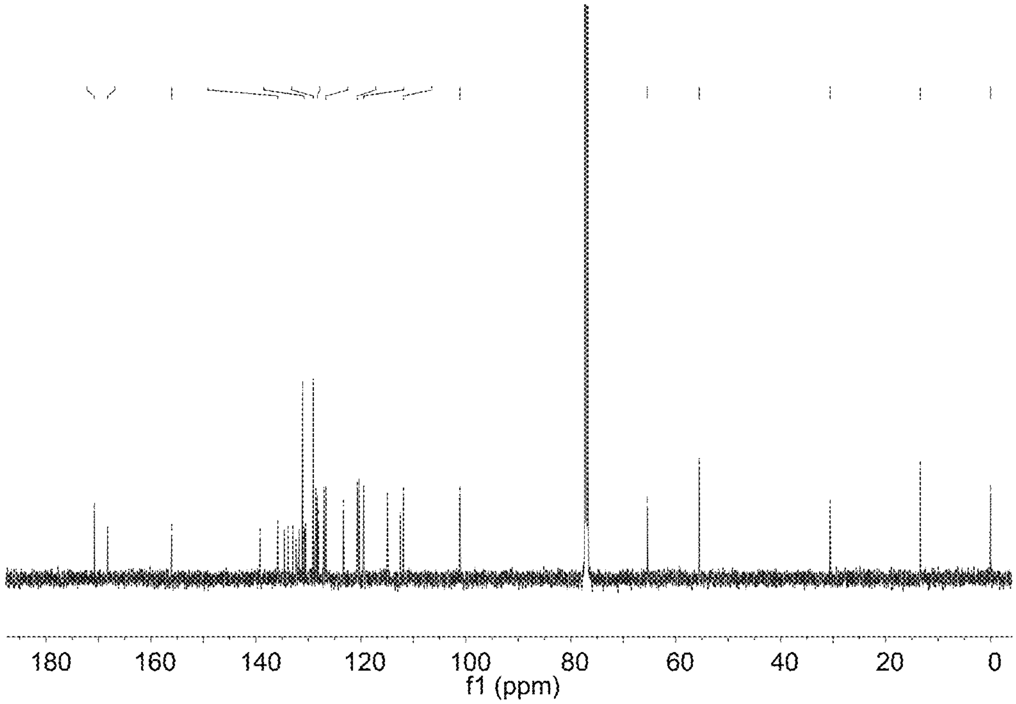
FIG. 57 shows $^{13}$CNMR of 17 (125 MHz, $CDCl_3$).
Figure 58:
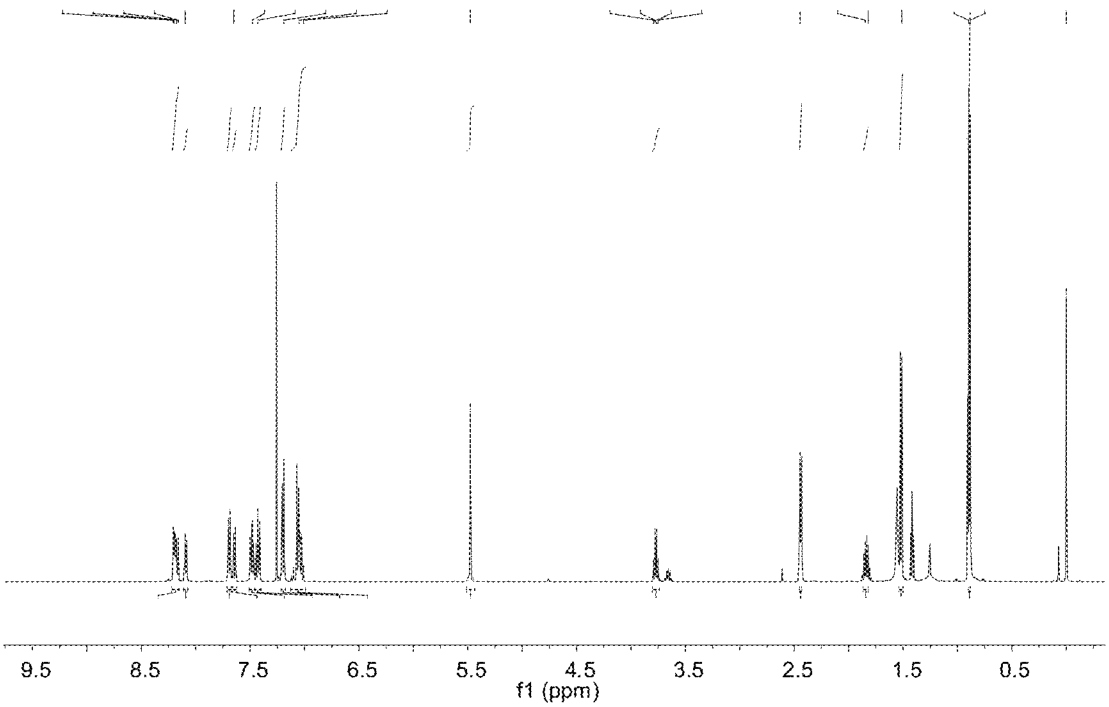
FIG. 58 shows $^{1}$HNMR of 18 (500 MHz, $CDCl_3$).
Figure 59:
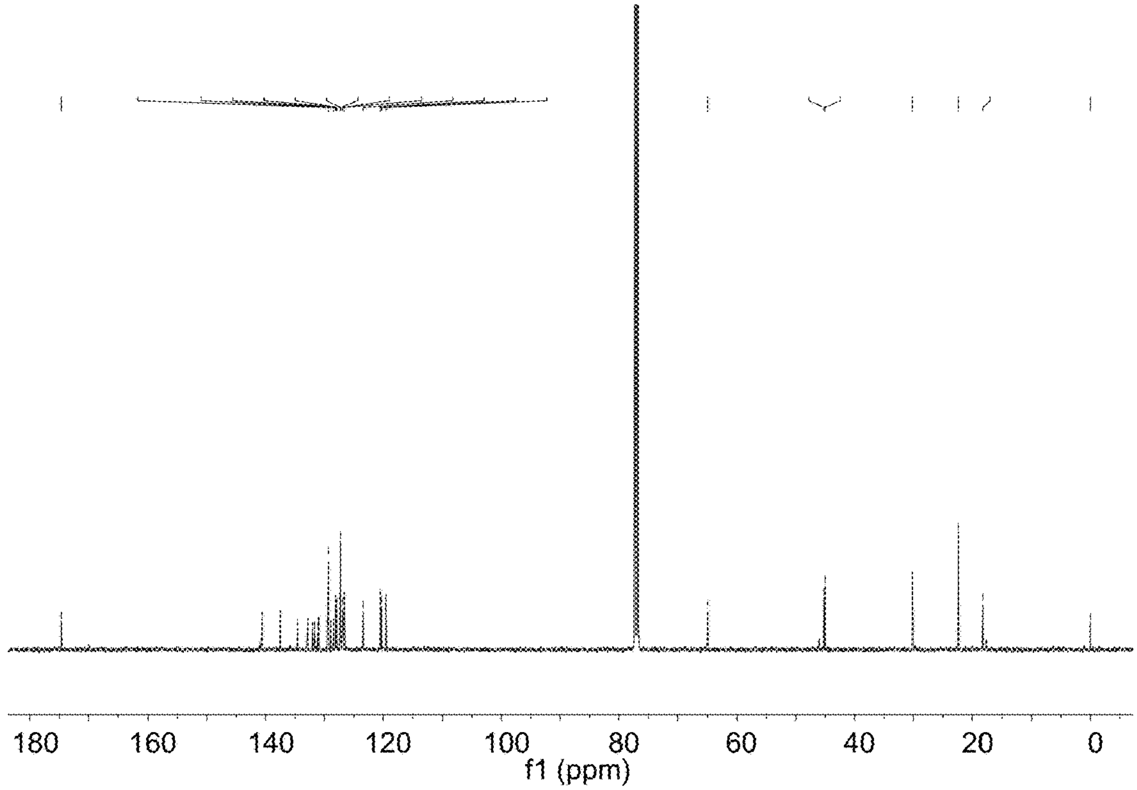
FIG. 59 shows $^{13}$CNMR of 18 (125 MHz, $CDCl_3$).
Figure 60:
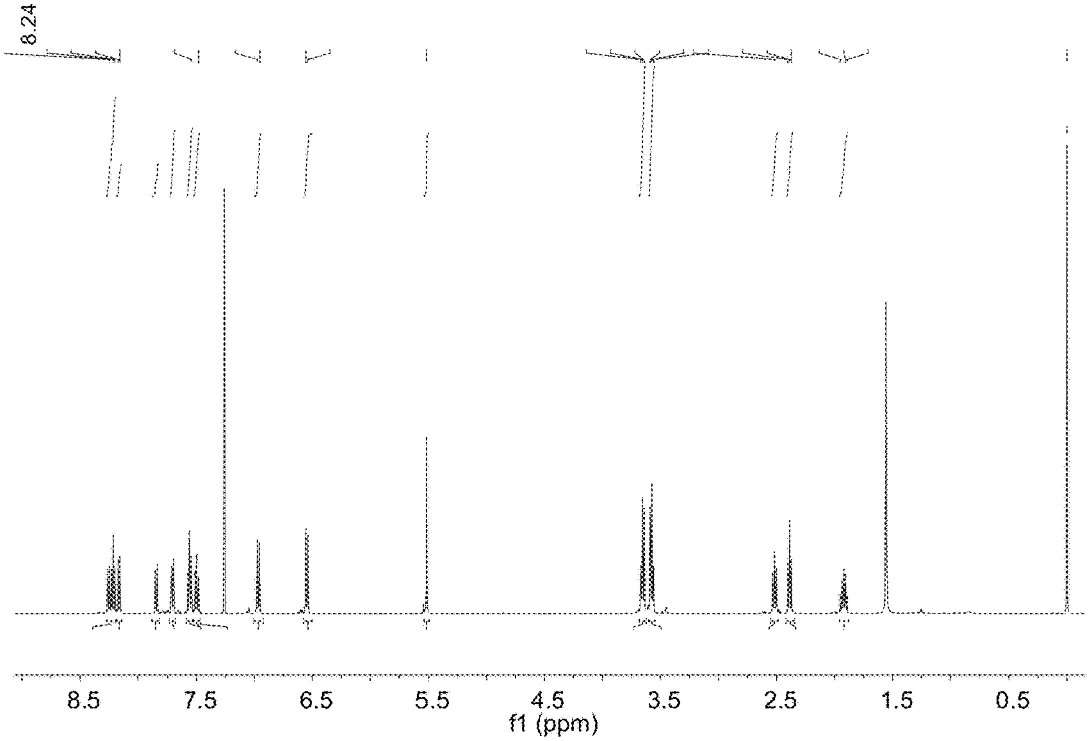
FIG. 60 shows $^{1}$HNMR of 19 (500 MHz, $CDCl_3$).
Figure 61:
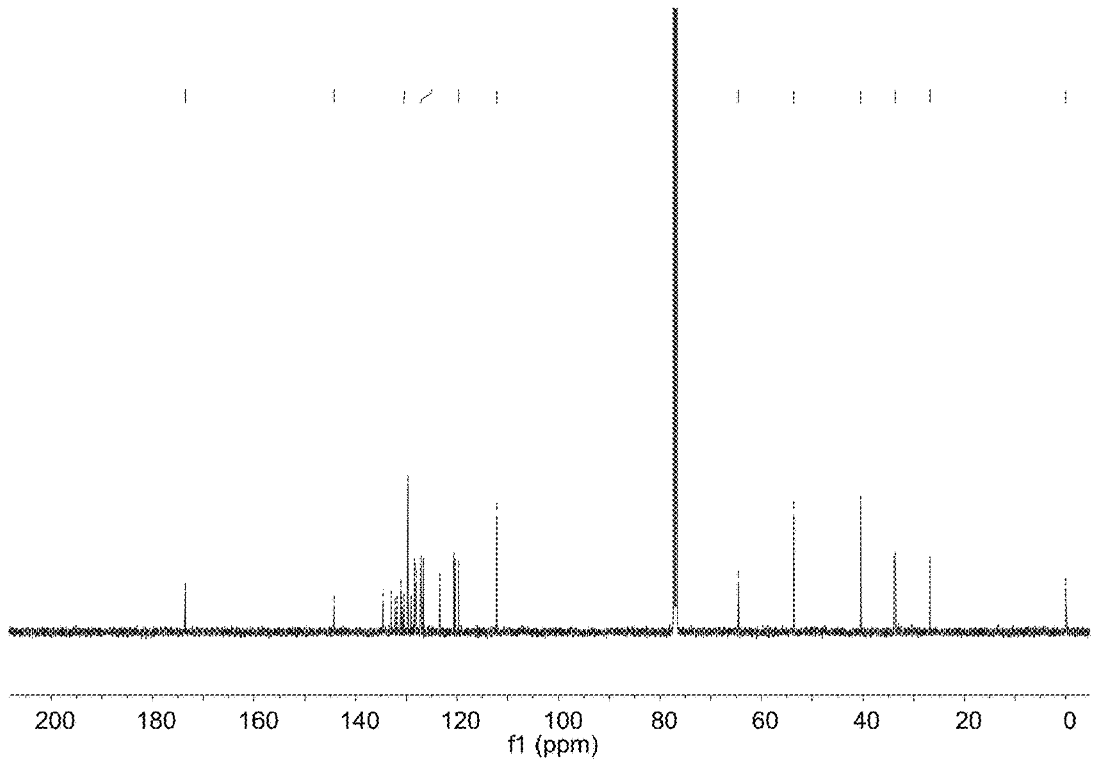
FIG. 61 shows $^{13}$CNMR of 19 (125 MHz, $CDCl_3$).
Figure 62:
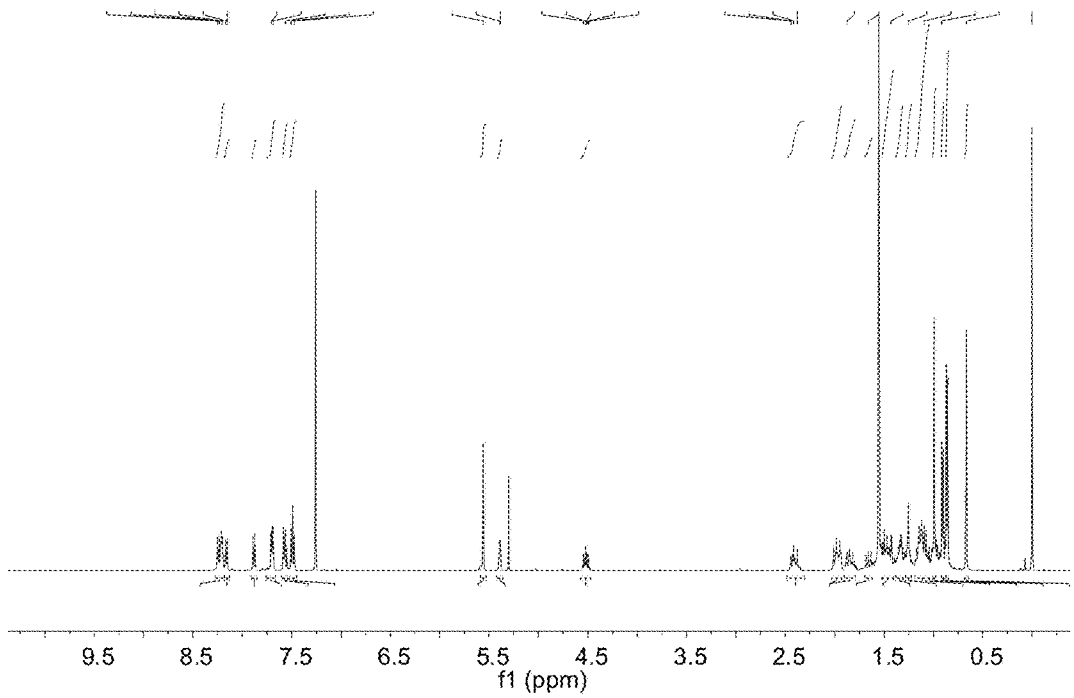
FIG. 62 shows $^{1}$HNMR of 20 (500 MHz, $CDCl_3$).
Figure 63:
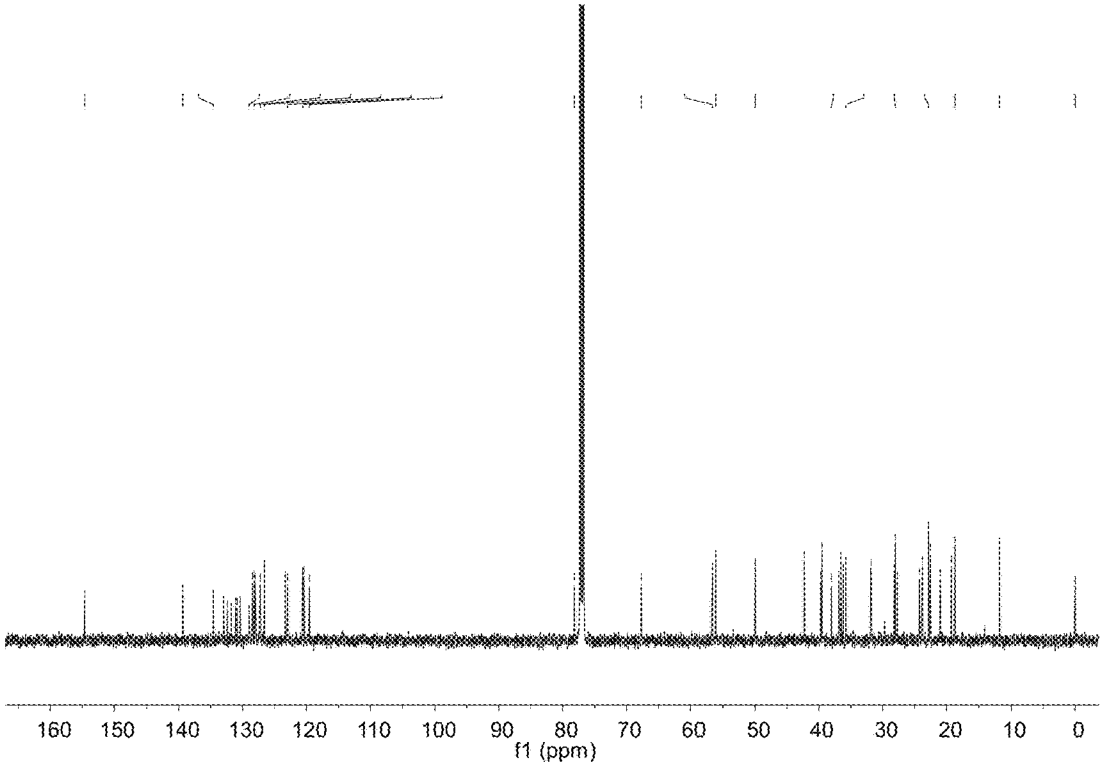
FIG. 63 shows $^{13}$CNMR of 20 (125 MHz, $CDCl_3$).
Figure 64:
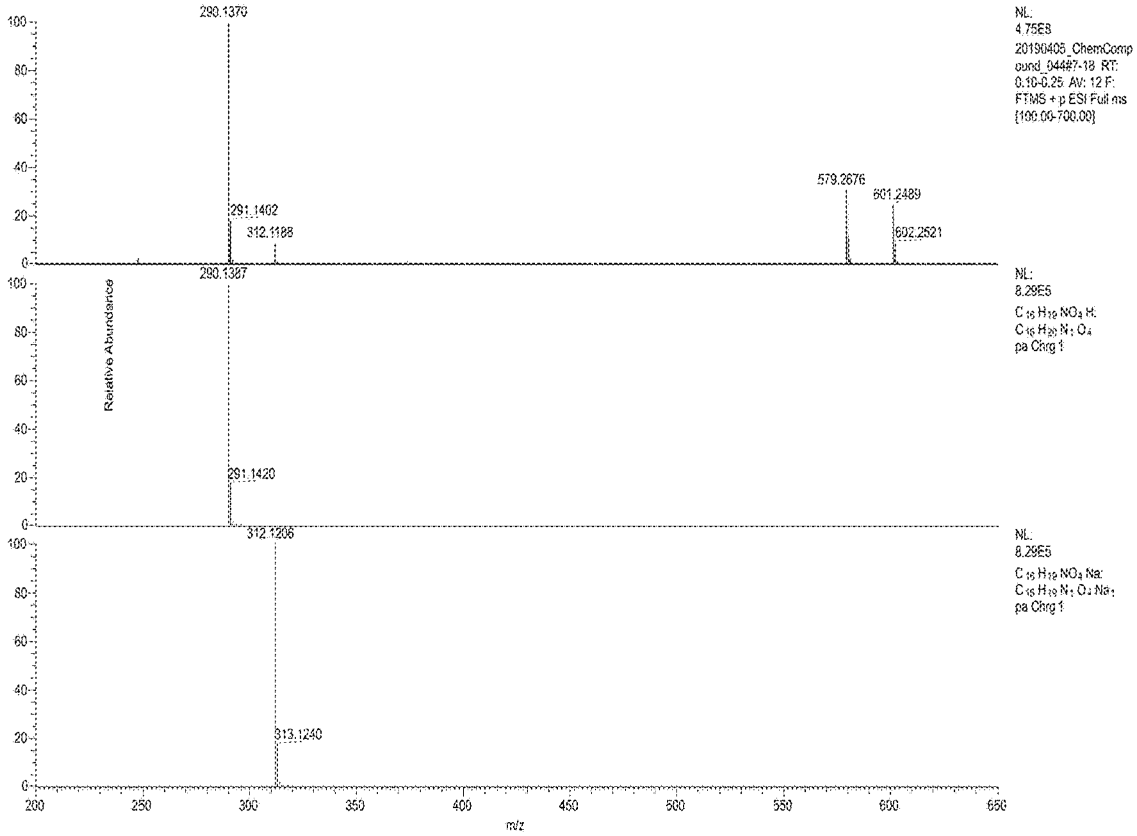
FIG. 64 shows HRMS (ESI) of 1.
Figure 65:
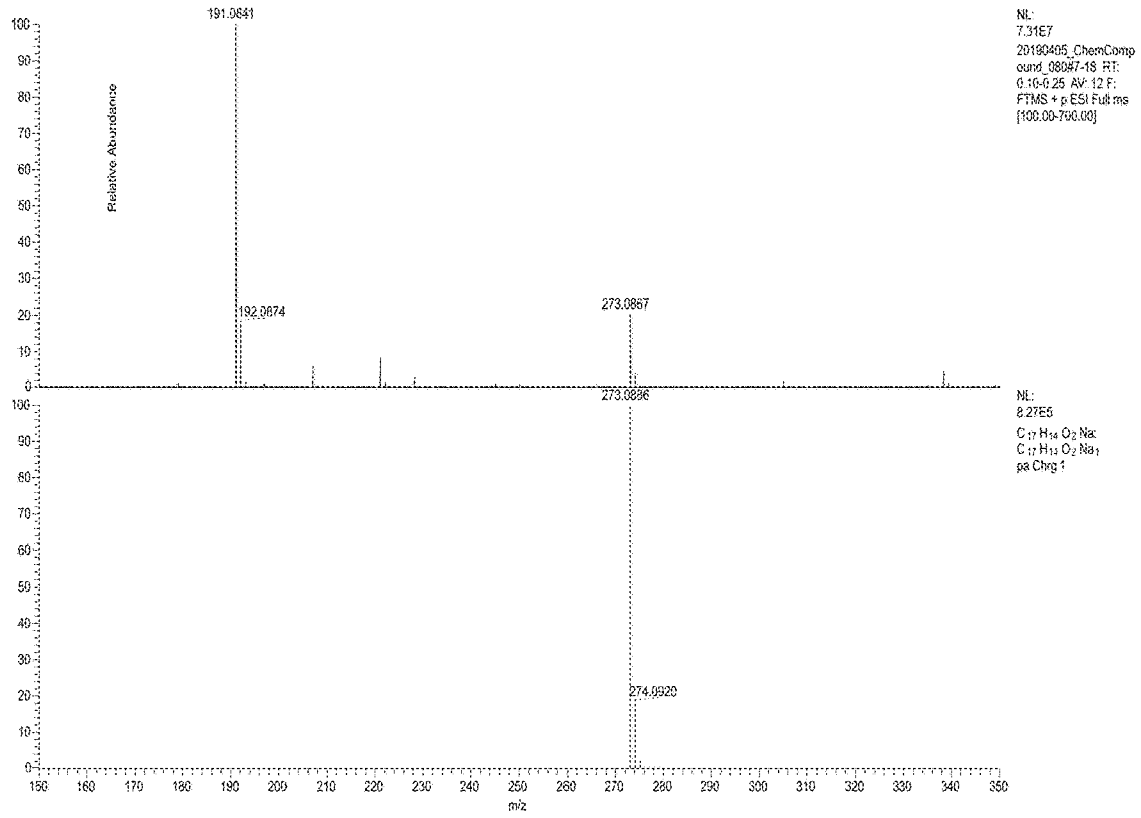
FIG. 65 shows HRMS (ESI) of 2.
Figure 66:
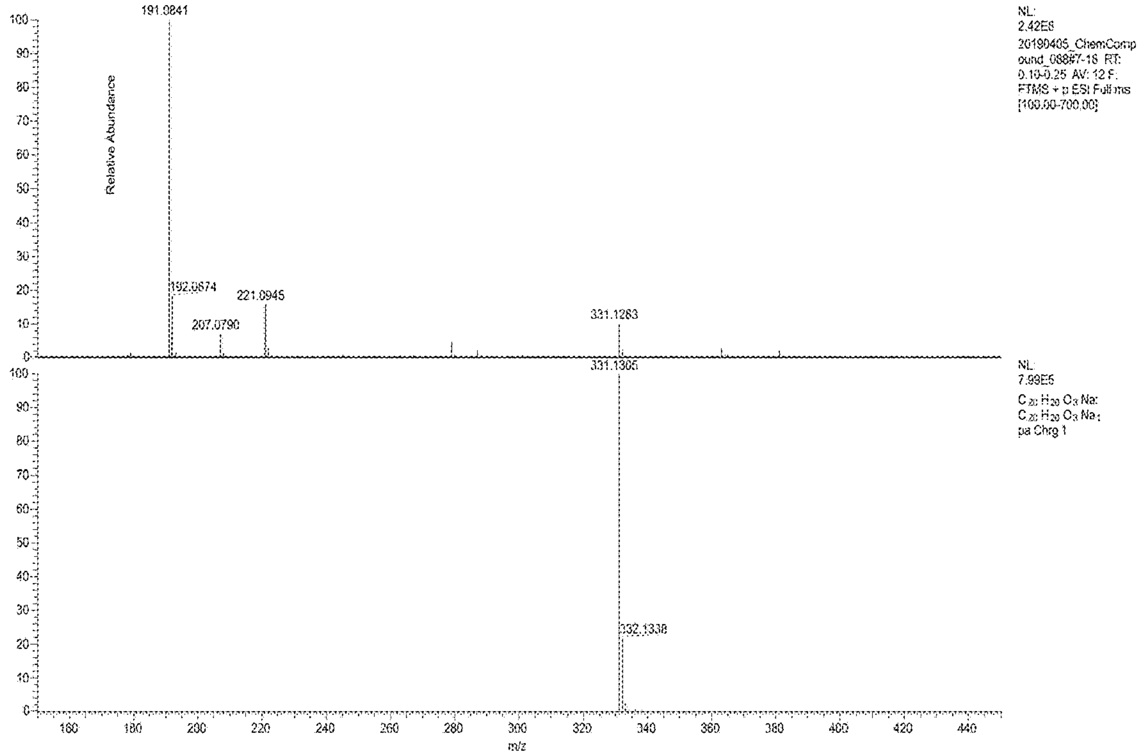
FIG. 66 shows HRMS (ESI) of 3.
Figure 67:
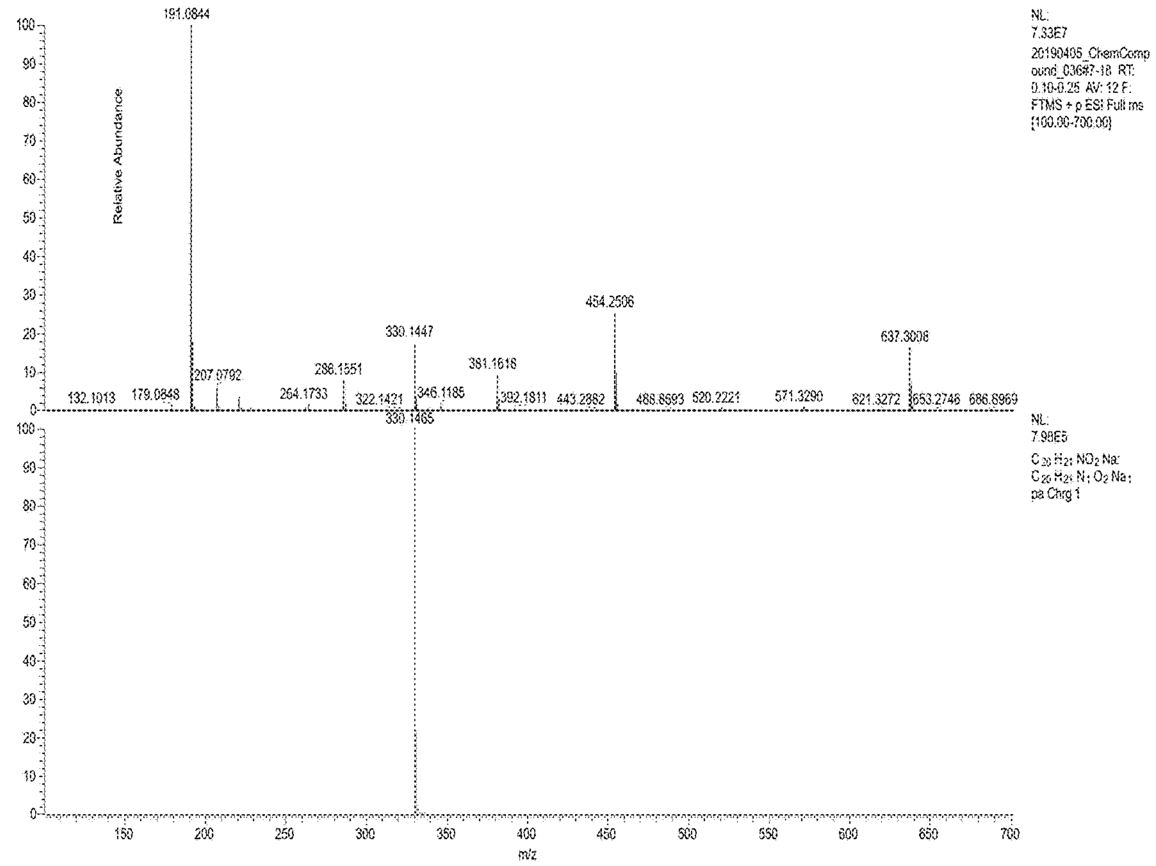
FIG. 67 shows HRMS (ESI) of 4.
Figure 68:
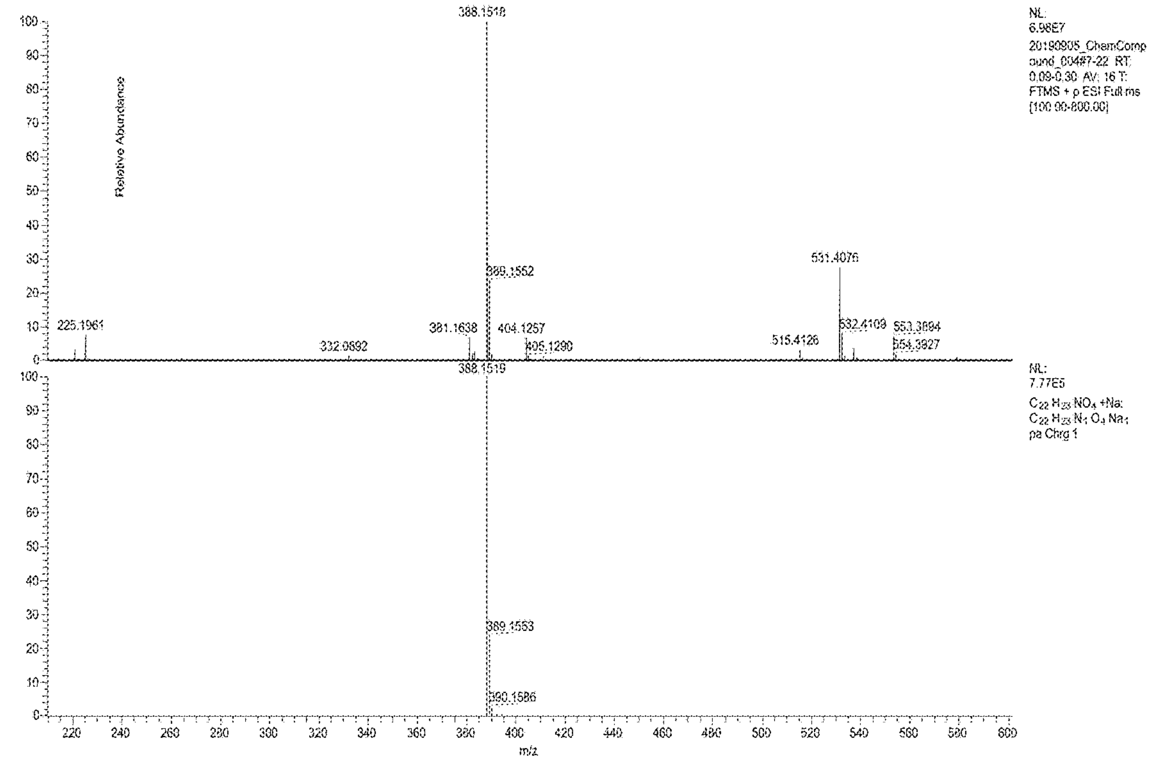
FIG. 68 shows HRMS (ESI) of 5.
Figure 69:
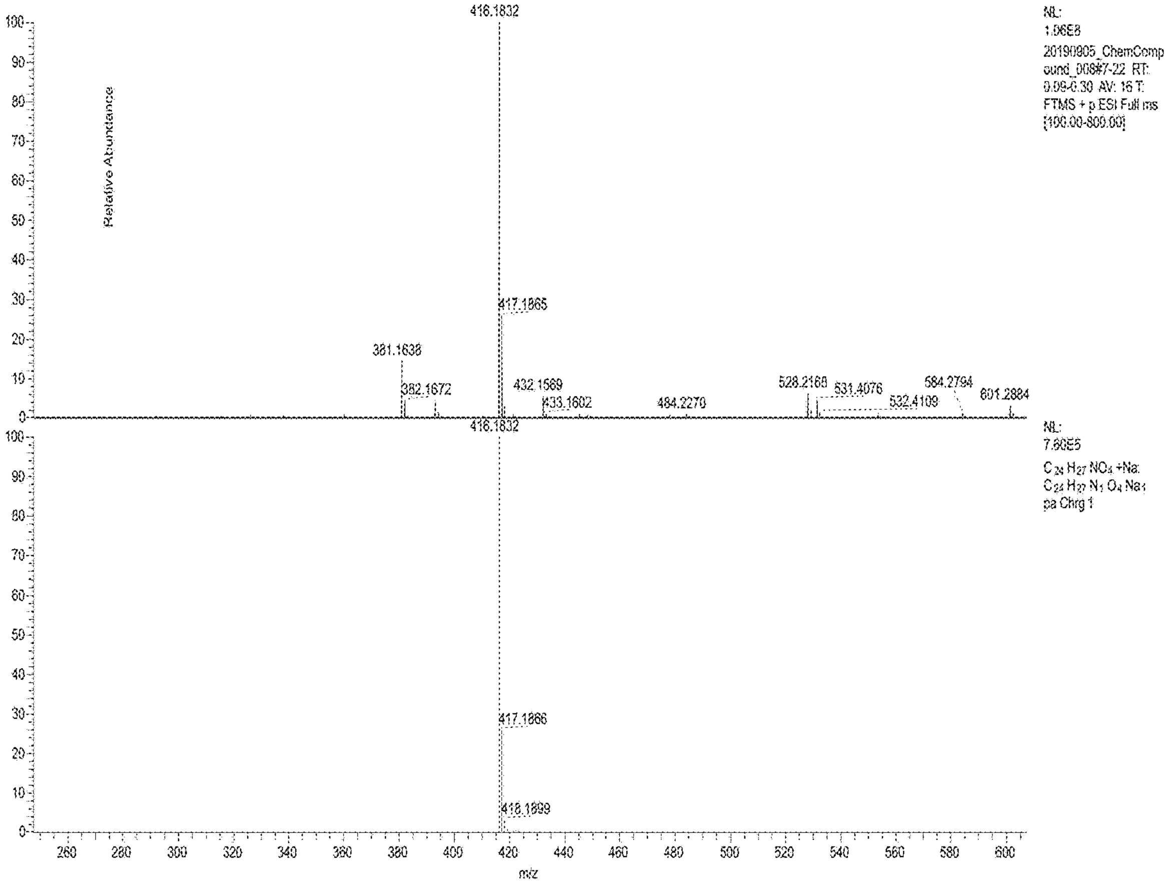
FIG. 69 shows HRMS (ESI) of 6.
Figure 70:
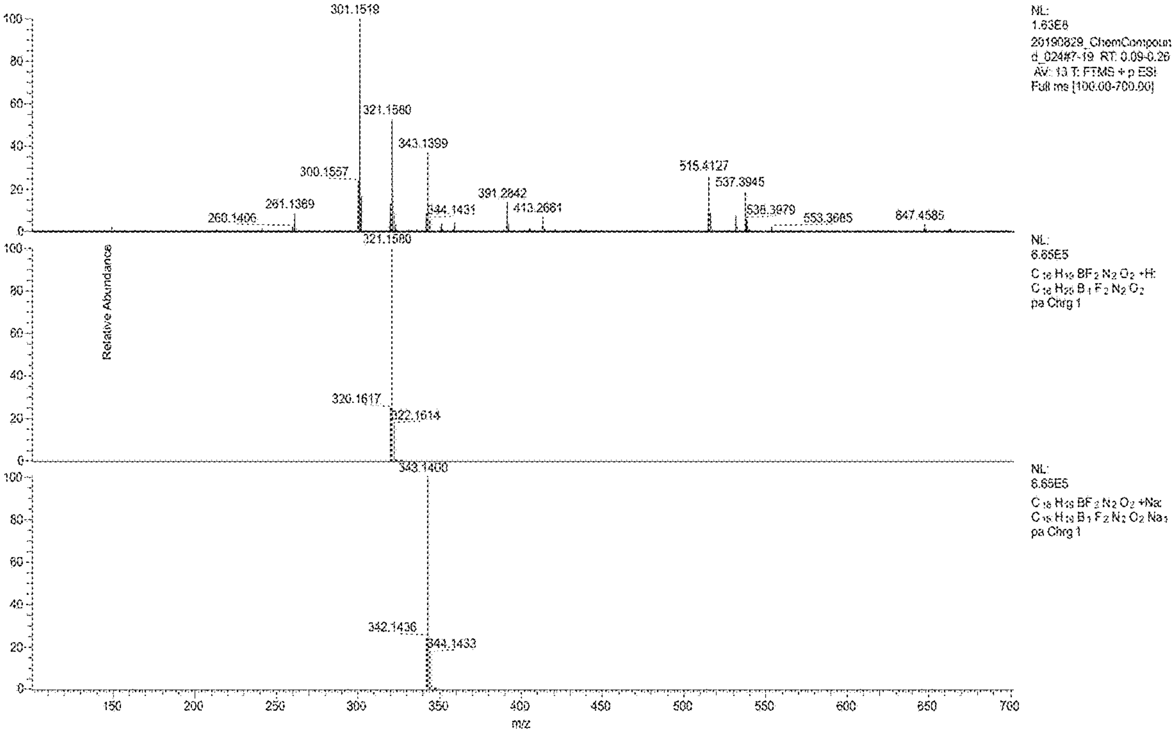
FIG. 70 shows HRMS (ESI) of 7.
Figure 71:
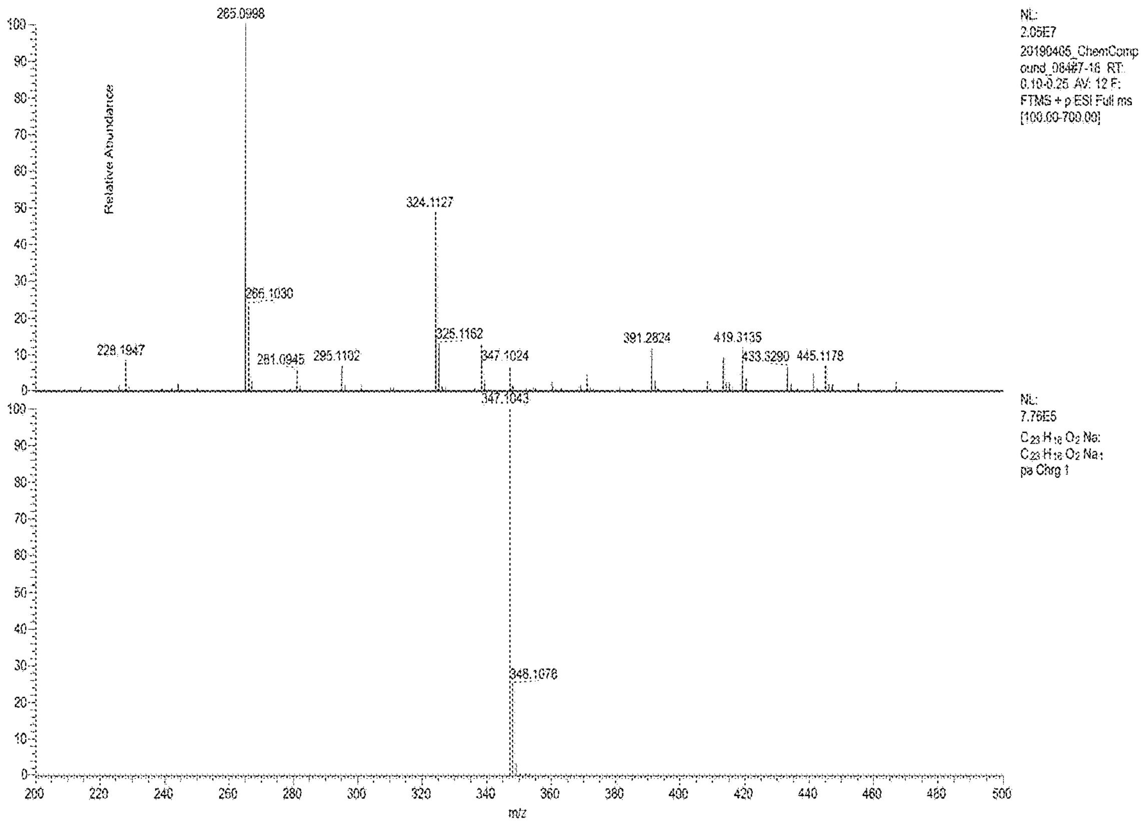
FIG. 71 shows HRMS (ESI) of 8.
Figure 72:
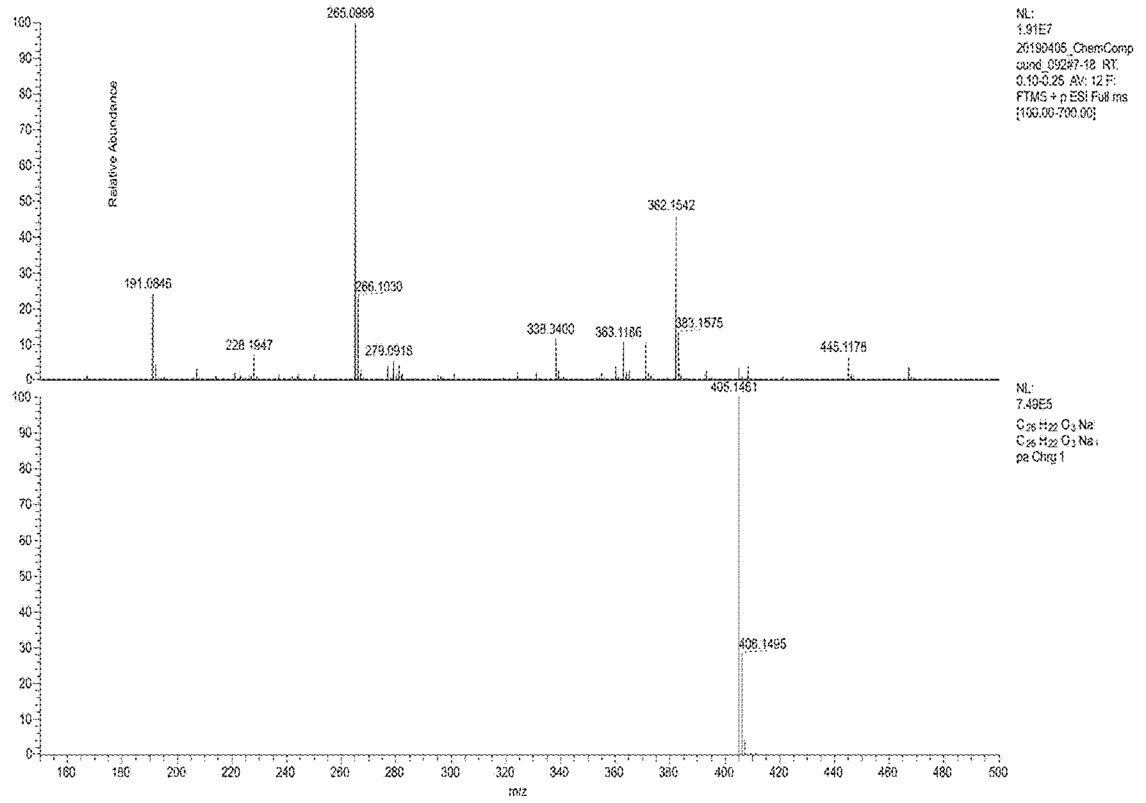
FIG. 72 shows HRMS (ESI) of 9.
Figure 73:
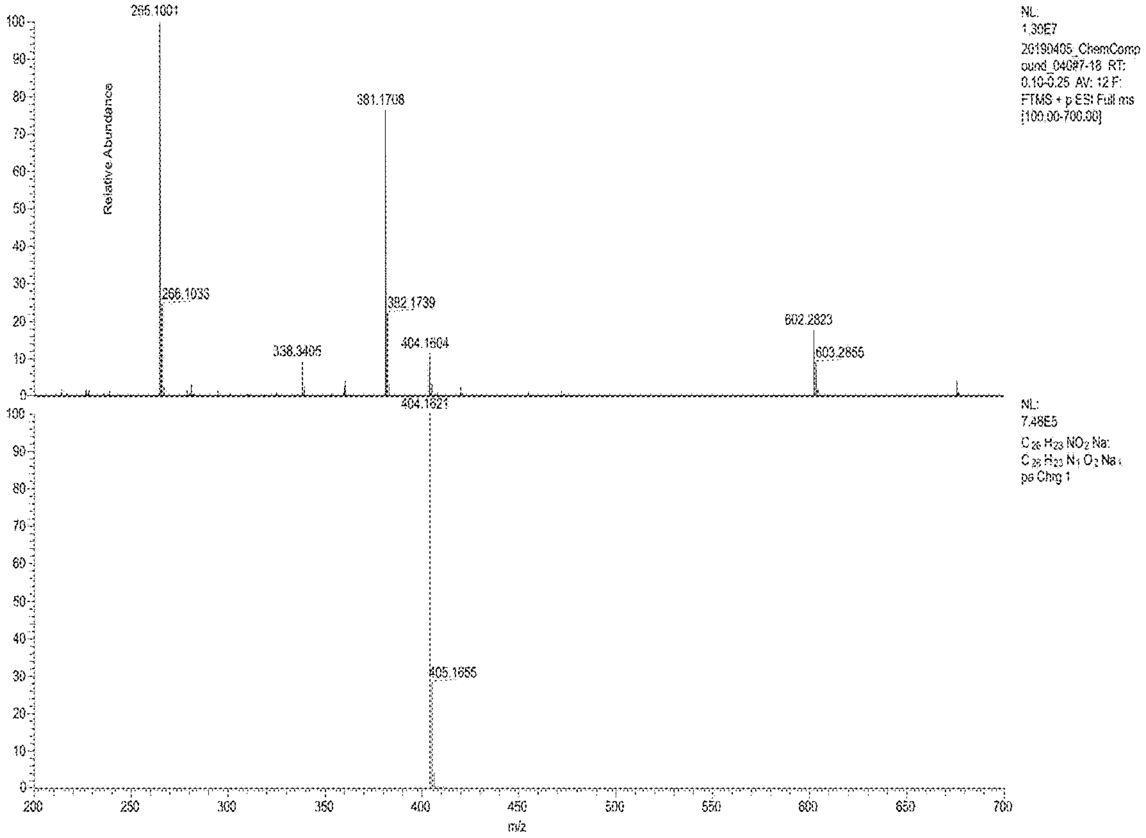
FIG. 73 shows HRMS (ESI) of 10.
Figure 74:
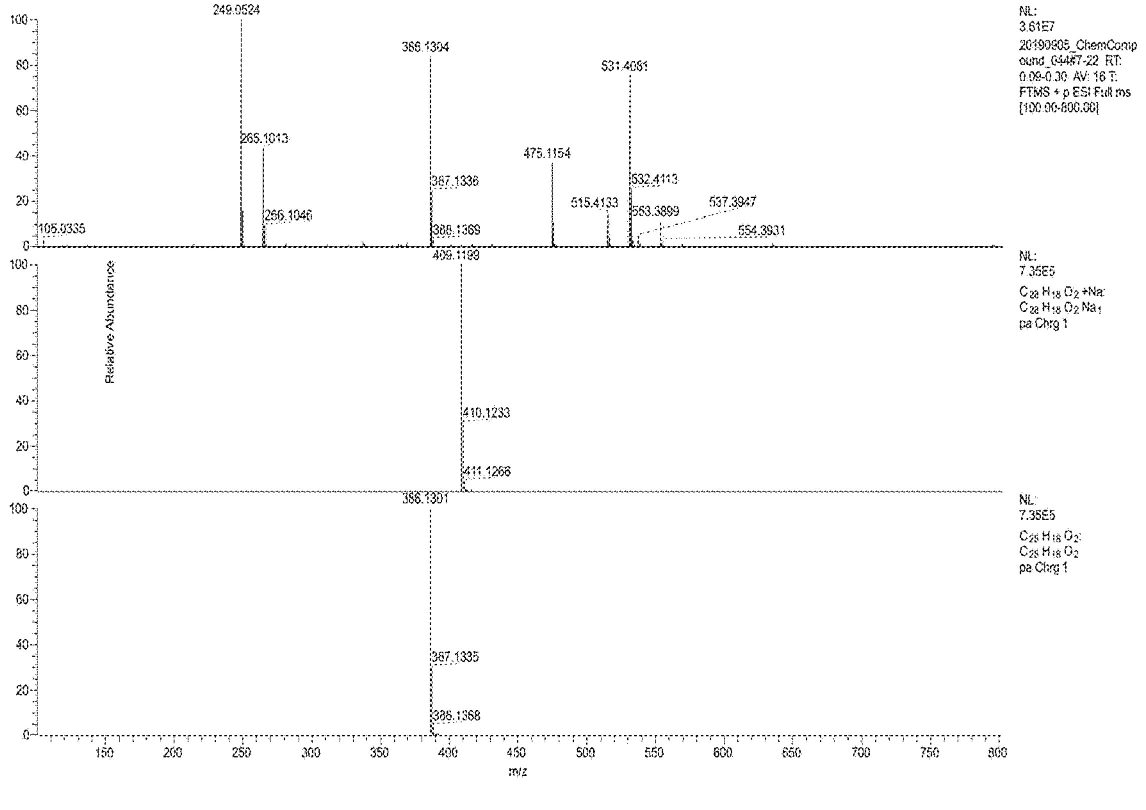
FIG. 74 shows HRMS (ESI) of 11.
Figure 75:
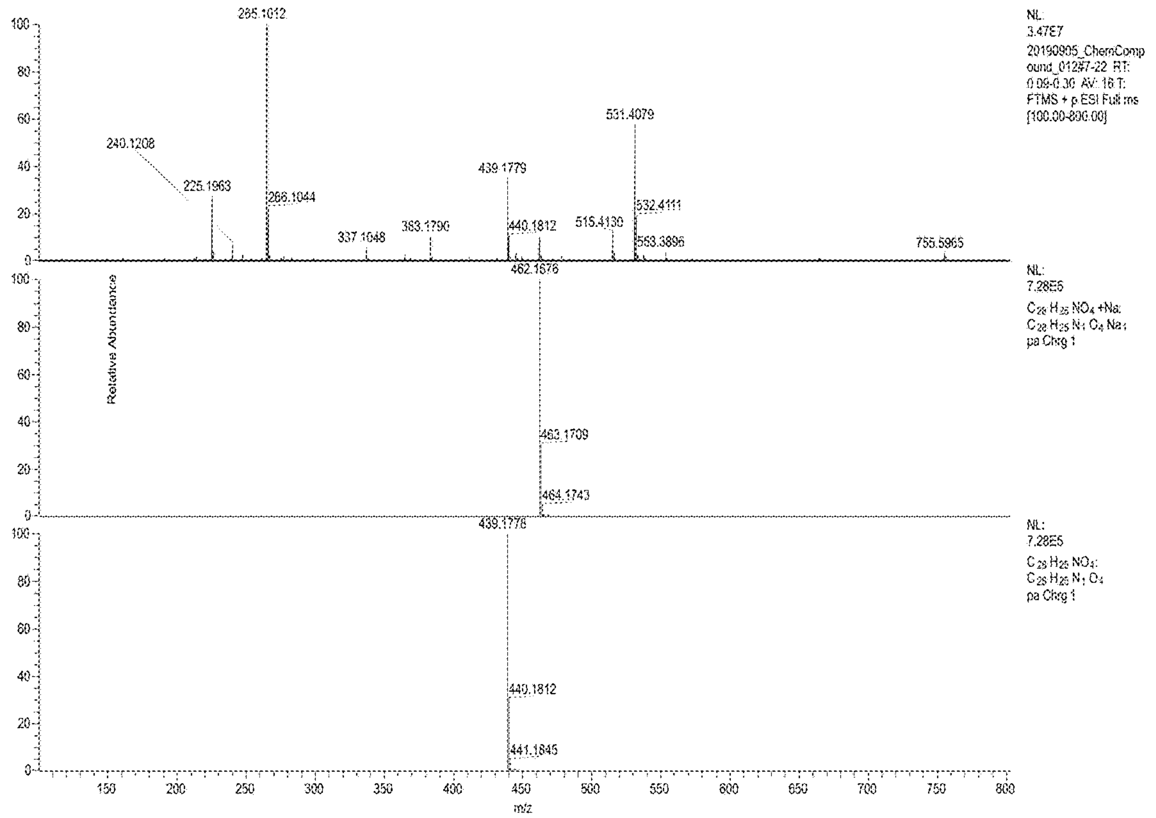
FIG. 75 shows HRMS (ESI) of 12.
Figure 76:
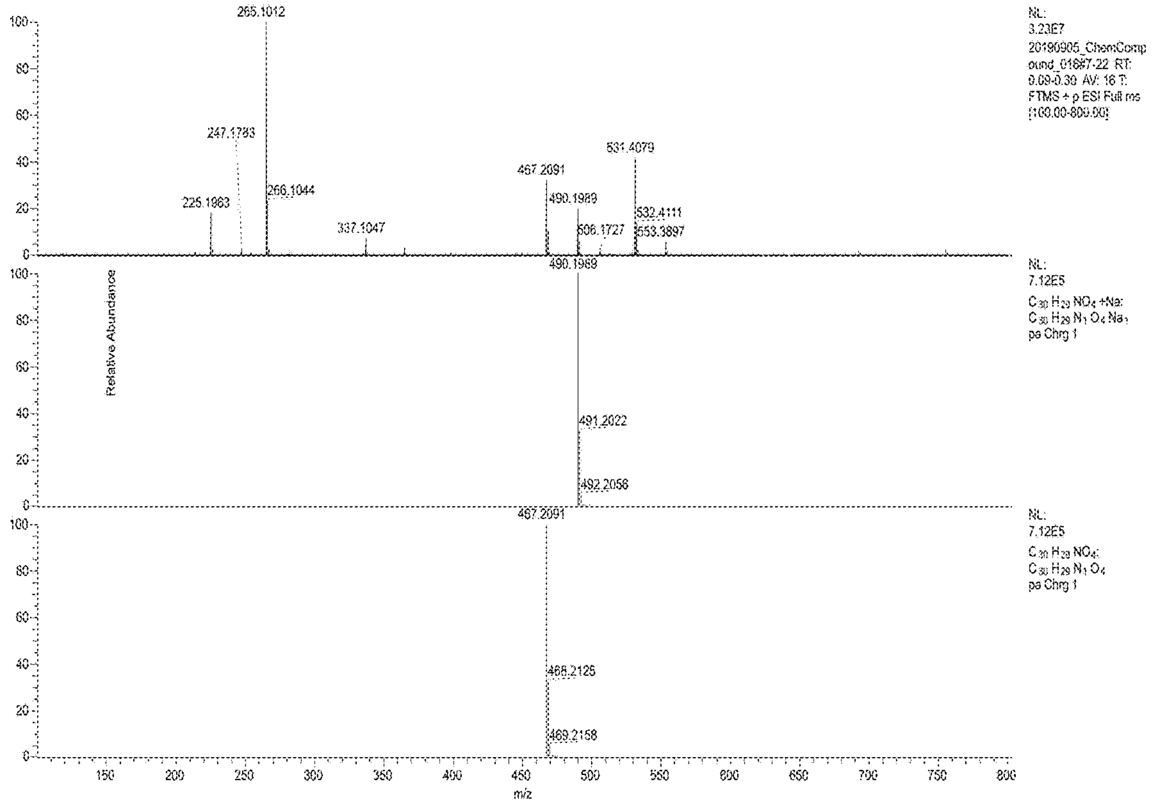
FIG. 76 shows HRMS (ESI) of 13.
Figure 77:
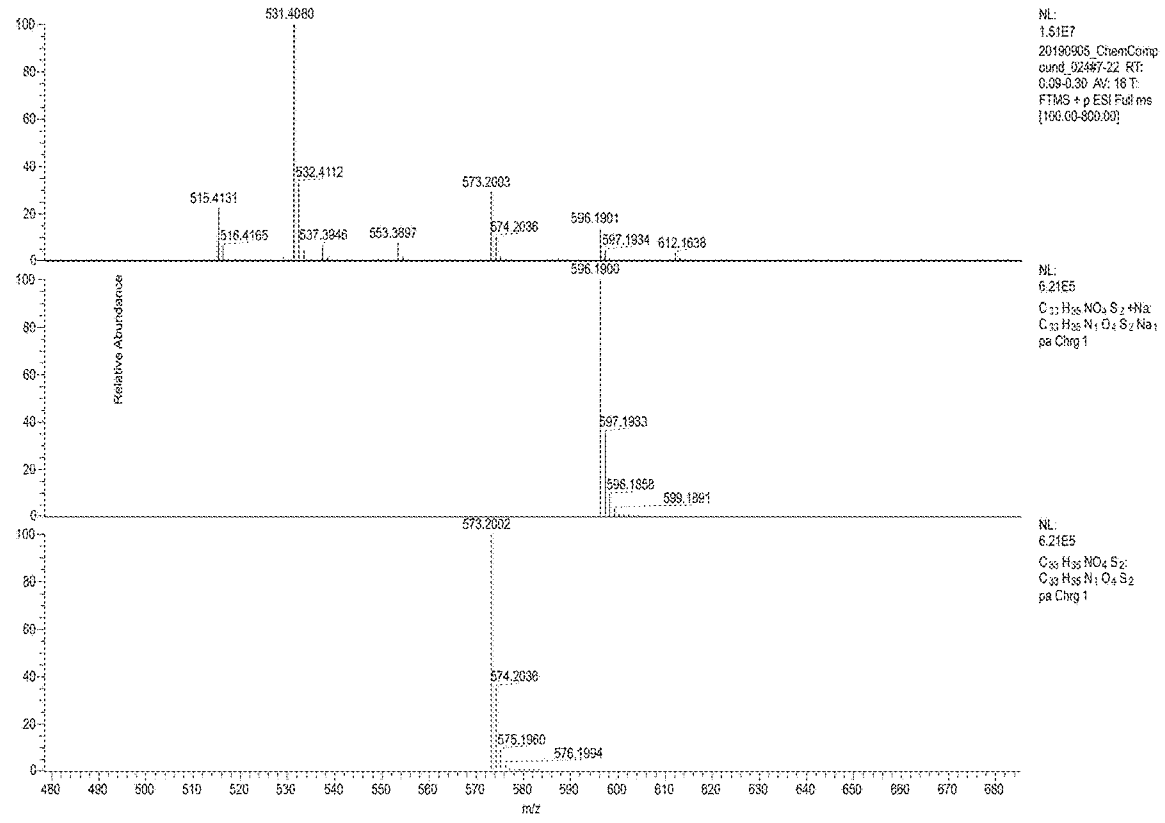
FIG. 77 shows HRMS (ESI) of 14.
Figure 78:
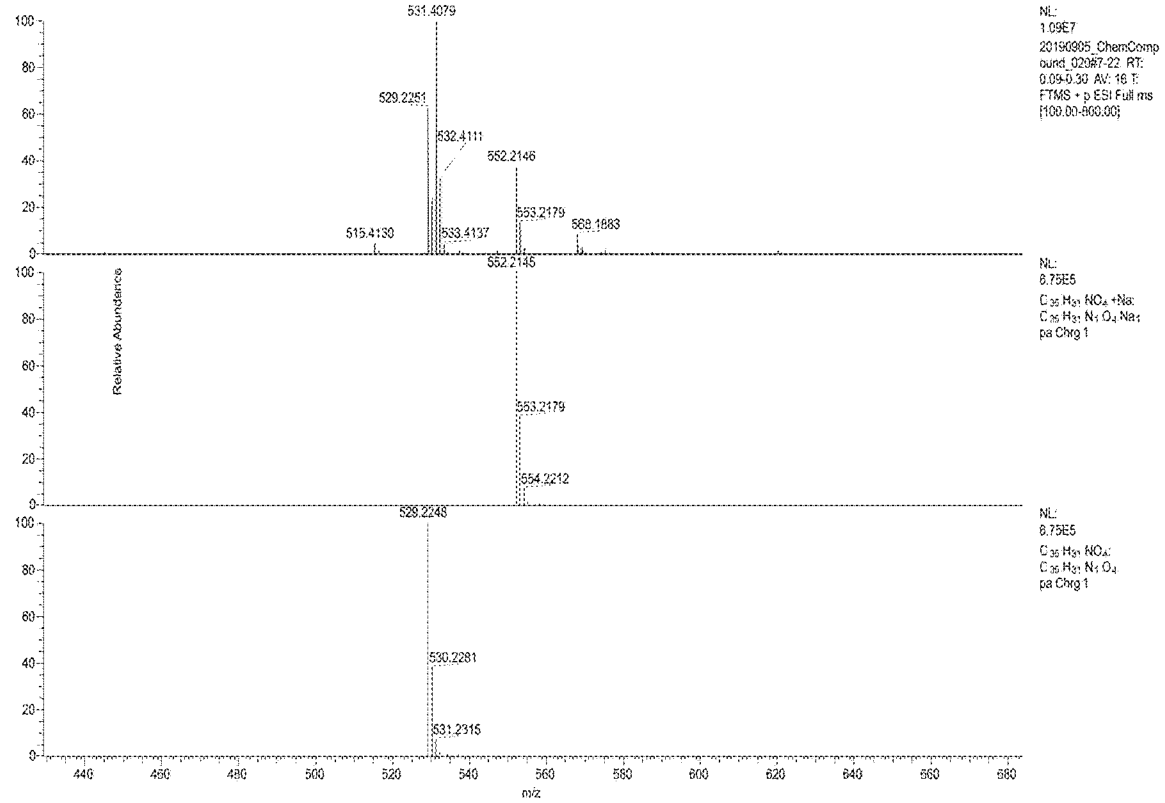
FIG. 78 shows HRMS (ESI) of 15.
Figure 79:
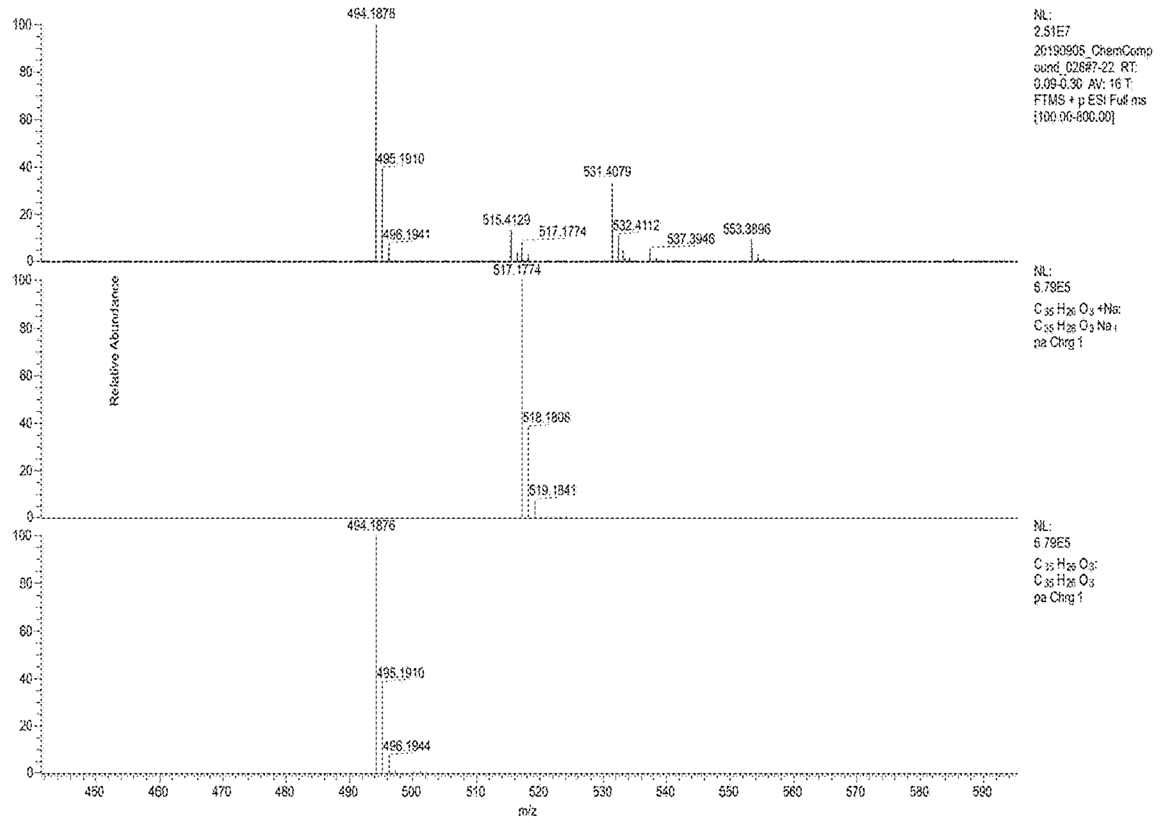
FIG. 79 shows HRMS (ESI) of 16.
Figure 80:
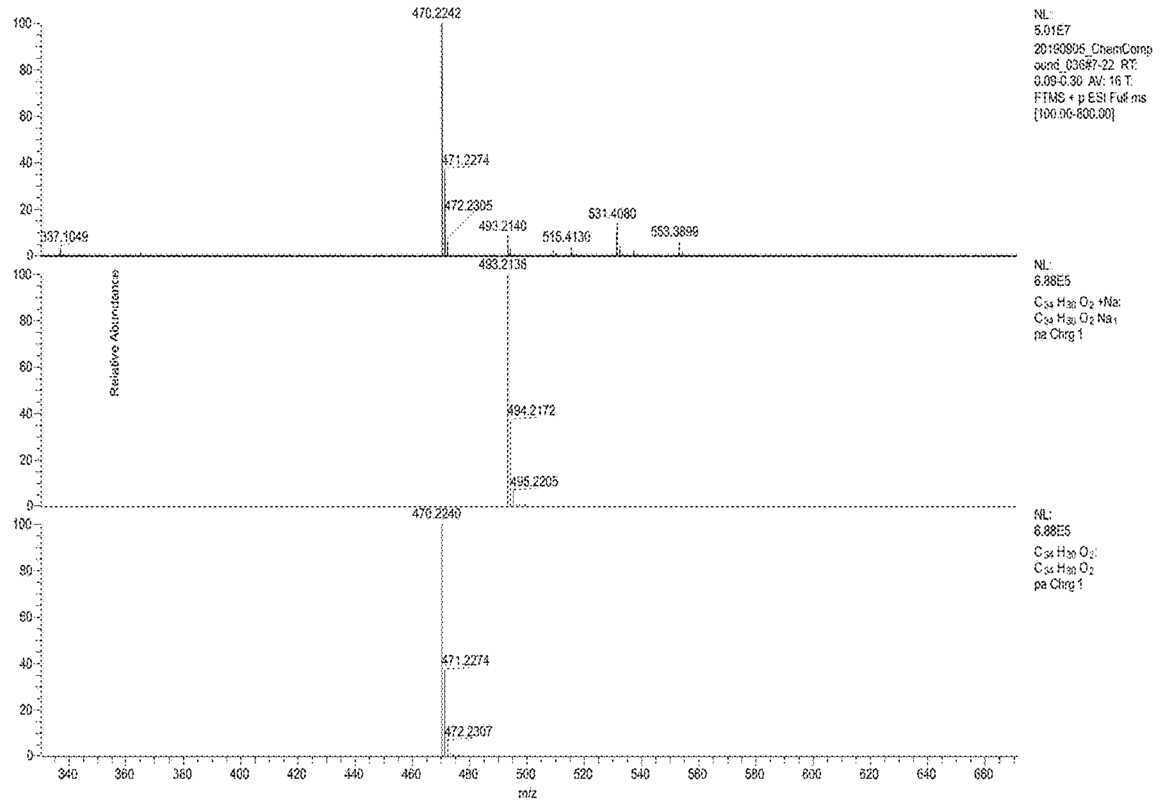
FIG. 80 shows HRMS (ESI) of 17.
Figure 81:
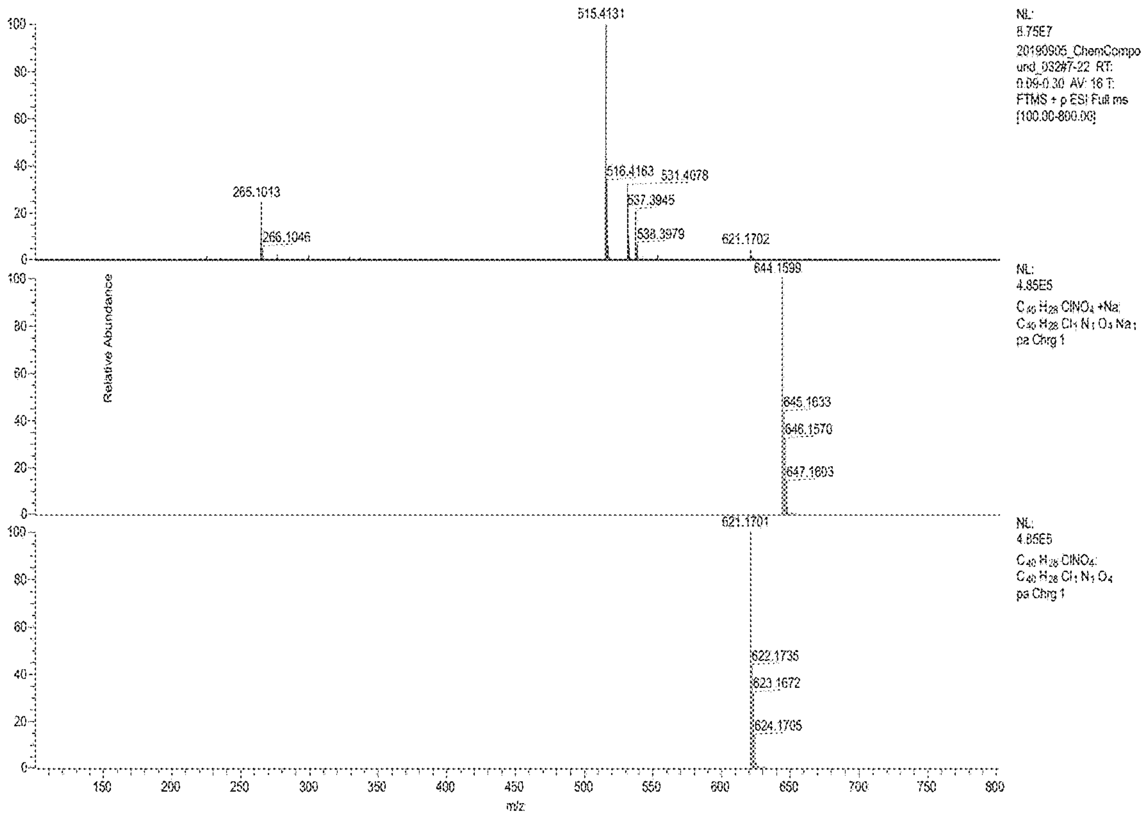
FIG. 81 shows HRMS (ESI) of 18.
Figure 82:
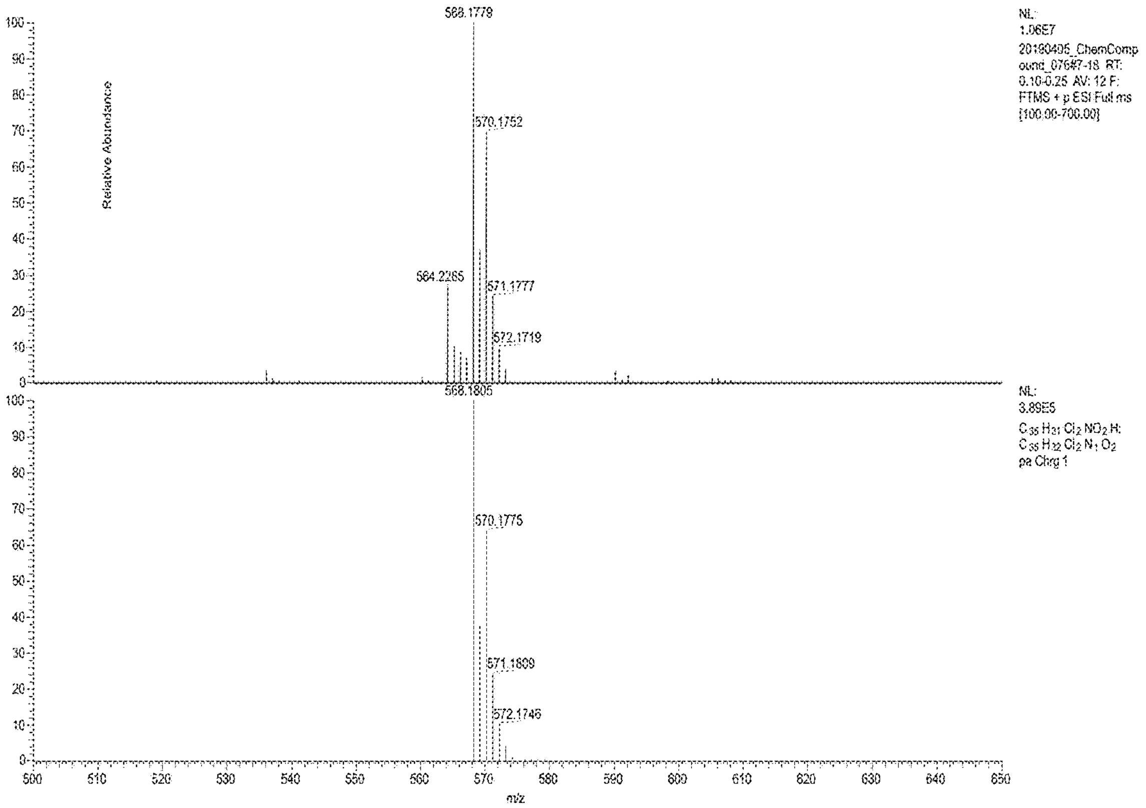
FIG. 82 shows HRMS (ESI) of 19.
Figure 83:
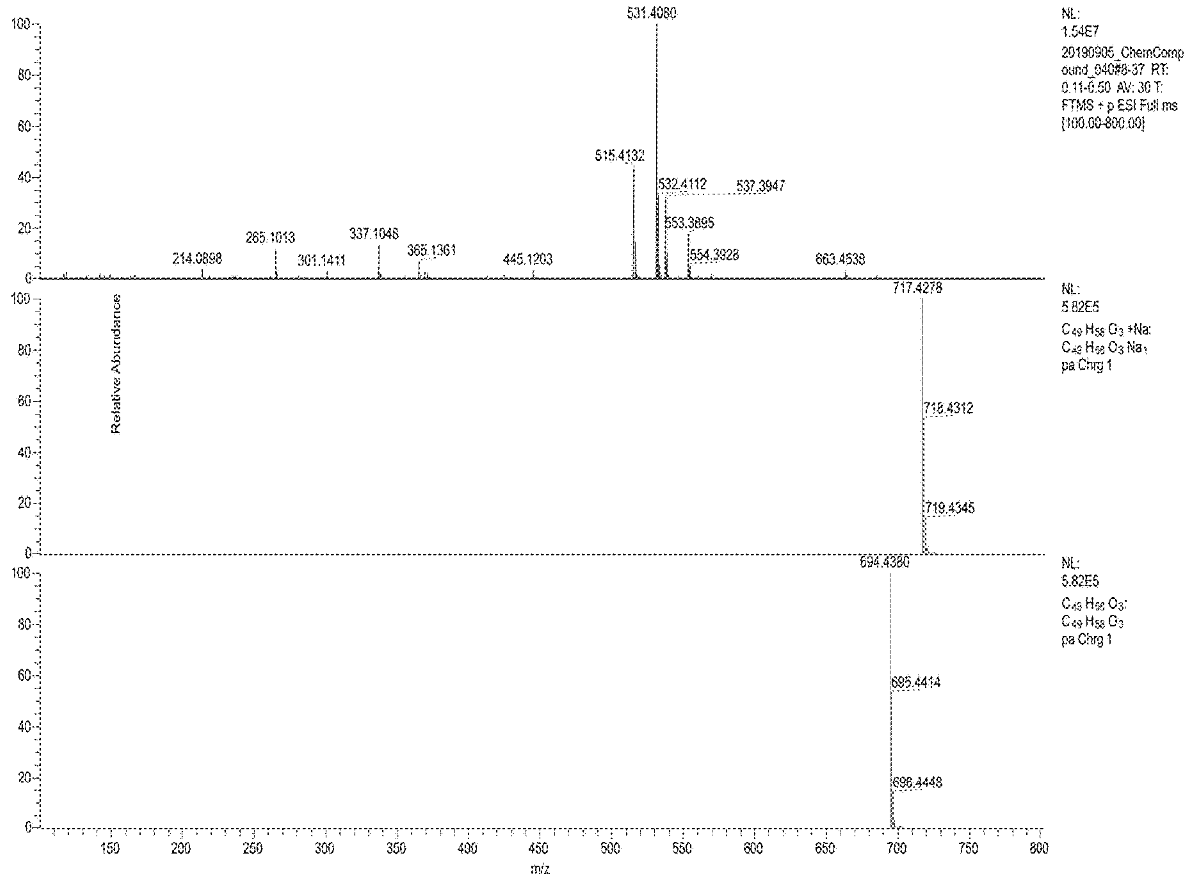
FIG. 83 shows HRMS (ESI) of 20.

Finally, we also tested whether there was any in vivo toxicity by measuring the body weight of mice in each cohort (Experimental, section 15). The body weight experiment showed negligible side-effects. Furthermore, we compared H&E stained images of the major organs (heart, liver, spleen, lung, and kidney) from normal mice to those treated with TTAP NPs and light. Neither results displayed noticeable organ damage or inflammation lesions, indicating that no obvious heart, liver, spleen, lung, or kidney dysfunction for the mice were induced by the photoactivatable process using TTAP NPs. Further, as shown in Table 23, we did not observe abnormal results from the serum analysis experiments, which indicates that no observable unwanted inflammation was induced. Excrement from the mice 96 h after an IR 806 dye conjugated TTAP nanoparticle i.v. injection was also collected. Compared to the PBS-injected control group, we detected the fluorescence of the IR-806 dye signal in the excrement of mice in the nanoparticle treated group (FIG. 23), indicating that TTAP NPs can be cleared from the body. All of these results demonstrate that the as-designed TTAP NPs possess high biosafety and are highly biocompatible.

In sum, photolytic reaction has powerful and important applications in numerous aspects of chemistry, materials as well as biology. Our discovery of long wavelength single photon driven TTAP overcomes the key problems (low effectiveness and high photodamage) in all existing methods. This method is "LEGO"-like and highly modular. The light partners (the photosensitizers and the PPGs-X) can be energetically matched to adapt to the needs of a wide range of electromagnetic spectrum wavelengths and numerous chemical structures of photoremovable protecting groups, photolabile linkages, and a broad range of targeted molecules. Moreover, we exemplified the biological applications of TTAP via creating an ambient air-stable, ultra-small, water-soluble TTAP nanoparticle. Such nanoparticles achieve highly effective, ultra-low power, long wavelength single photon driven anticancer prodrug activation and, in turn, potentiated anti-tumor immunotherapeutic responses.

Experimental

Chemicals: perylene, tris [2-phenylpyridinato-$C_2$, N] iridium (III) ($Ir(ppy)_3$) were purchased from TCI chemicals. The solvents of dimethylformamide (DMF), phosphoryl chloride ($POCl_3$), sodium borohydride ($NaBH_4$), methanol, acetyl chloride, pyridine, dicyclohexylcarbodiimide (DCC), 4-(dimethylamino) pyridine (DMAP); triethylamine (TEA) N-butylamine, dry $CH_2Cl_2$, 3-(4,5-dimethylthiazol-2-yl)-2, 5-diphenyltetrazolium bromide (MTT), propidium iodide (PI), 9-anthracenemethanol, 4-nitrophenylchloroformate, chloro (3-methylbutoxy) methanone, N-pivaloyl glycine, 4-[(2,2-dimethylpropanoyl)amino]butanoic acid and poly (styrene-co-maleic anhydride) (PSMA, $M_w$=1600) were purchased from Sigma-Aldrich (St. Louis, MO, USA). meso-tetraphenyltetrabenzoporphine palladium complex (PdTPBP) and platinum octaethylporphyrin (PtOEP) were purchased from Frontier Scientific, Inc. Dulbecco's Modified Eagle Medium (DMEM), fetal bovine serum (FBS), penicillin-streptomycin, trypsin-EDTA (EDTA=ethylenediaminetetraacetic acid), and phosphate-buffered saline solution (PBS) were obtained from Invitrogen (Carlsbad, CA, USA). Ultrapure water was prepared by using a Millipore Simplicity System (Millipore, Bedford, USA). All of the above-mentioned chemicals were used as received without further purification.

Characterization: $^1$H NMR spectra were recorded with a Bruker 500 MHz spectrometer. UV-Vis spectra were recorded on an Agilent Cary-5 spectrophotometer. Steady-state fluorescence spectra were measured on a HITACHI F-7000 spectrometer. The morphology of the TTAP NPs was characterized by using a JEOL JEM-200CX transmission electron microscope (TEM) operated at 80 kV. The sample for TEM measurement was prepared by dropping the solution onto a carbon-coated copper grid following negative staining with 2.0% (w/v) phosphotungstic acid. The particle size and size distribution were measured by using dynamic light scattering (DLS) on a Malvern Nano-ZS particle size analyzer, excitation wavelength 532 nm. All samples in the Stern-Volmer quenching plots experiments were deaerated with argon for ca. 15 min before measurement and the gas flow was maintained during the measurements. For the TTA upconversion spectra measurement, the diode pumped solid-state laser (650 nm, continues wave, CW, Hi-Teach company, China) was used as the excitation light source and a modified spectrofluorometer was used to record the upconversion spectra. For the prodrug photolytic experiment, an All LED (Mightex Company) was used as the excitation light source.

Photolytic molecule experiment: The NIR LED (720 nm), far red LED (650 nm), green LED (530 nm), blue LED (476 nm) and deep blue (455 nm) were used for photolytic reactions. The mixed solution of the photosensitizers (PtTNP, PdTPBP, PtOEP, $Ir(ppy)_3$) and PPG-X (BDP, perylene, anthracene or coumarin) were degassed for at least 15 min with Ar in $THF/H_2O$ (4/1, v/v). Then, the solution was excited with a LED (20 mW/cm$^2$) at 37° C. After the photolytic reaction, the raw product was dried and re-dissolved in $CH_3CN/H_2O$=(2/1, v/v) and HPLC was used to analyze the yield of product.

The Stern-Volmer quenching plots experiment ($k_{sv}$): photoluminescence of photosensitizers (PtTNP, PdTPBP, PtOEP, and $Ir(ppy)_3$) in the presence of different concentrations of PPGs (BDP, perylene, anthracene and coumarin). The mixed solutions were degassed for at least 15 min with Ar in toluene. The $k_{sv}$ constants were calculated with eq 1, where $\mathbf{I}_o$ and $I_t$ stand for photoluminescence intensity of photosensitizer in the absence of PPGs-X and the photoluminescence intensity of photosensitizer in the presence PPGs-X. Q is the concentration of PPGs-X. Biomolecular quenching constants ($k_q$) were calculated by eq2. The Tr is the phosphorescence lifetime of photosensitizer in argon.

$$\frac{I_O}{I_t} = 1 + k_{sv}Q \tag{1}$$

$$k_{sv} = k_q \times \tau_T \tag{2}$$

The upconversion quantum yields ($\Phi_{UC}$): The upconversion quantum yields were calculated with the eq 3, where $\Phi_{UC}$ and $\Phi_{std}$ stand for upconversion luminescence quantum yield of sample TTA-UC and fluorescence quantum yield of reference compounds, respectively. $A_{unk}$ and $A_{std}$ stand for absorbance of the TTA-UC and reference compound, respectively. $I_{unk}$ and $I_{std}$ stand for integrated upconversion luminescence intensity of the TTA-UC and fluorescence intensity of reference compounds, respectively. $\eta_{unk}$ and $\mu_{std}$ stand for the refractive index of water. The equation is multiplied by a factor of 2 to make the maximum quantum yield of two unified emitters.

$$\Phi_{UC} = 2 \times \Phi_{std} \times \frac{A_{std}}{A_{unk}} \times \frac{I_{unk}}{I_{std}} \times \left(\frac{\eta_{unk}}{\eta_{std}}\right)^2 \tag{3}$$

The upconversion experiments were deaerated with argon for ca. 15 min before measurement and the argon gas flow was kept during the measurement.

Section 1: Preparation and Characterization of PPGs-X.

Compounds 4-benzyl alcohol coumarin, 1-benzyl alcohol perylene were synthesized according to the previous synthesis protocols. (Lin, et al. 2010 *J. Am. Chem. Soc.* 132, 10645; Mahmood, et al. 2016 *J. Org. Chem.* 81, 587.)

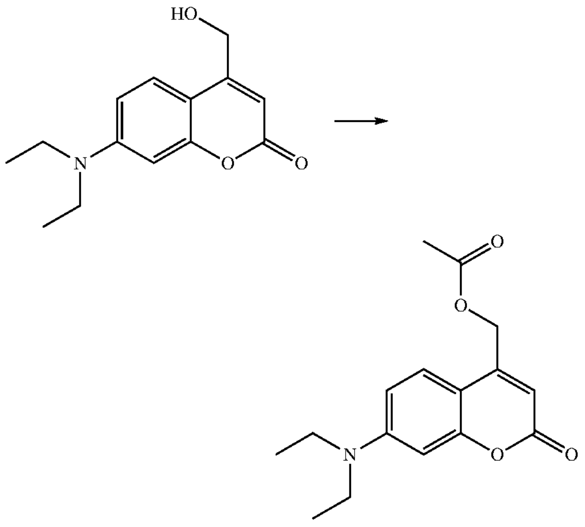

1

Compound 1: 4-benzyl alcohol coumarin (247.1 mg, 1.0 mmol) dissolved in dry dichloromethane (DCM) (10 mL) and pyridine (50 µL) were mixed. Acetyl chloride (2.0 mmol) was dissolved in dry DCM (10 mL) and added dropwise to the mixture over 10 min and then stirred for 2 hours. After the reaction, the solvents were removed under vacuum condition. The raw 1 was purified by silica gel flash column chromatography with DCM/n-hexane=1/1 (v/v) as elute. The yellow band was collected and yield determined to be 92% (266.9 mg). $^1$H-NMR (500 MHz, $CDCl_3$): δ=7.29-7.28 (d, 1H, J=5.0 Hz), 6.59-6.57 (d, 1H, J=10.0 Hz), 6.52 (s, 1H), 6.14-6.13 (d, 1H, J=5.0 Hz), 5.22 (s, 2H), 3.44-3.39 (m, 4H), 2.19 (s, 3H), 1.22-1.20 ppm (m, 6H). $^{13}$C-NMR (125 MHz, $CDCl_3$): δ=150.7, 149.4, 124.4, 108.7, 106.5, 106.0, 97.9, 61.4, 44.8, 20.8, 12.4 ppm. HRMS (ESI) exact mass calculated for $[M+H]^+$ ($C_{16}Hi_9NO_4$+$H^+$) requires m/z 290.1392, found m/z 290.1387.

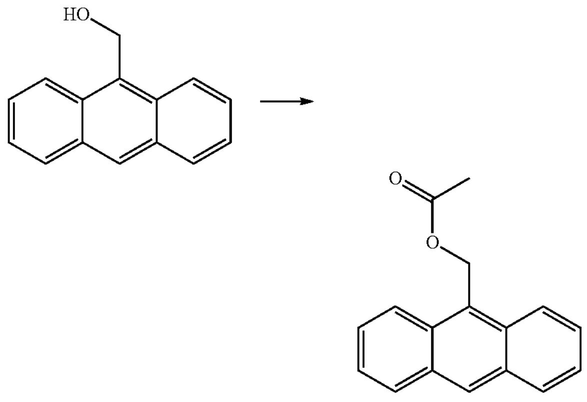

2

Compound 2: 4-benzyl alcohol anthracene (208 mg, 1.0 mmol) dissolved in dry dichloromethane (DCM) (10 mL) and pyridine (50 μL) were mixed. Acetyl chloride (2.0 mmol) was dissolved in dry DCM (10 mL) and added dropwise to the mixture over 10 min and then stirred for 2 hours. After the reaction, the solvents were removed under vacuum condition. The raw 2 was purified by silica gel flash column chromatography with DCM/n-hexane=1/2 (v/v) as elute. The yellow band was collected and yield determined to be 85% (212.5 mg). $^1$H-NMR (500 MHz, $CDCl_3$): δ=8.52 (s, 1H), 8.34-8.32 (d, 2H, J=10.0 Hz), 8.05-8.03 (d, 2H, J=9.5 Hz), 7.58-7.56 (m, 2H), 7.50-7.48 (m, 2H), 6.16 (s, 2H), 2.09 ppm (s, 3H). $^{13}$C-NMR (125 MHz, $CDCl_3$): S=171.3, 131.4, 131.1, 129.2, 129.1, 126.7, 126.2, 125.1, 123.9, 58.8, 21.0 ppm. HRMS (ESI) exact mass calculated for $[M+Na^+](C_{17}H1_4O_2+Na^+)$ requires m/z 273.0891, found m/z 273.0886.

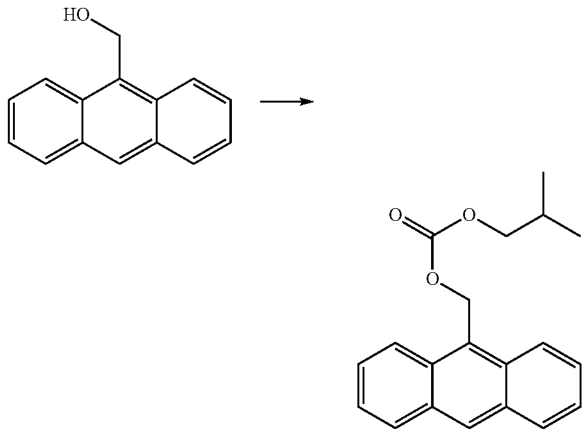

3

Compound 3: 4-benzyl alcohol anthracene (208 mg, 1.0 mmol) dissolved in dry dichloromethane (DCM) (10 mL) and pyridine (50 μL) were mixed. Isobutyl chloroformate (2.0 mmol) was dissolved in dry DCM (10 mL) and added dropwise to the mixture over 10 min and then stirred for 2 hours. After the reaction, the solvents were removed under vacuum condition. The raw 3 was purified by silica gel flash column chromatography with DCM/n-hexane=1/2 (v/v) as elute. The yellow band was collected and yield determined to be 65% (200.2 mg). $^1$H-NMR (500 MHz, $CDCl_3$): δ=8.51 (s, 1H), 8.40-8.38 (d, 2H, J=10.0 Hz), 8.03-8.01 (d, 2H, J=9.5 Hz), 7.60-7.56 (m, 2H), 7.50-7.47 (m, 2H), 6.22 (s, 2H), 3.96-3.94 (d, 2H, J=10.0 Hz), 1.98-1.91 (m, 1H), 0.92 (s, 3H), 0.90 ppm (s, 3H). $^{13}$C-NMR (125 MHz, $CDCl_3$): δ=155.68, 131.37, 131.17, 129.51, 129.08, 126.77, 125.10, 123.96, 123.96, 74.36, 73.95, 62.11, 27.76, 18.90 ppm. HRMS (ESI) exact mass calculated for $[M+Na]^+$ $(C_{20}H_{20}O_3+Na^+)$ requires m/z 331.1310, found m/z 331.1305.

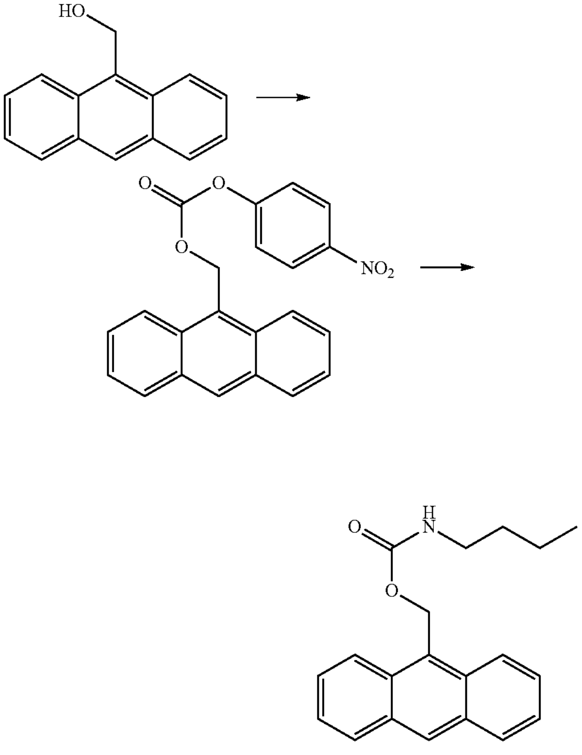

4

Compound 4: 4-benzyl alcohol anthracene (208 mg, 1.0 mmol) dissolved in dry dichloromethane (DCM) (10 mL) and pyridine (50 μL) were mixed. 4-nitrophenyl chloroformate (1.2 mmol) was dissolved in dry DCM (10 mL) and added dropwise to the mixture over 10 min and then stirred for 2 hours. Next, the butylamine (2.0 mmol) was added and stirred for another 12 hours in room temperature. After the reaction, 50 mL $CH_2Cl_2$ was added. The solutions were washed with saturated aqueous solution of sodium bicarbonate (30 mL). The organic layer was collected and dried by $Na_2SO_4$; the solvents were removed under vacuum condition. The raw 4 was purified by silica gel flash column chromatography with DCM/n-hexane=1/1 (v/v) as elute. The shallow yellow band was collected and yield determined to be 60% (184.2 mg). $^1$H-NMR (500 MHz, $CDCl_3$): δ=8.50 (s, 1H), 8.40-8.38 (m, 2H), 8.03-8.01 (d, 2H, J=9.0 Hz), 7.57-7.55 (m, 2H), 7.50-7.47 (m, 2H), 6.14 (s, 2H), 4.66 (s, 1H), 3.23-3.20 (m, 2H), 1.50-1.44 (m, 2H), 1.35-1.30 (m, 2H), 0.92-0.90 ppm (m, 3H). $^{13}$C-NMR (125 MHz, $CDCl_3$): δ=156.6, 131.4, 131.0, 129.1, 129.0, 126.9, 126.6, 125.1, 124.1, 59.0, 40.9, 32.0, 19.9, 13.7 ppm. HRMS (ESI) exact mass calculated for $[M+Na]^+$ $(C_{20}H_{21}NO_2+Na^+)$ requires m/z 330.1470, found m/z 330.1465.

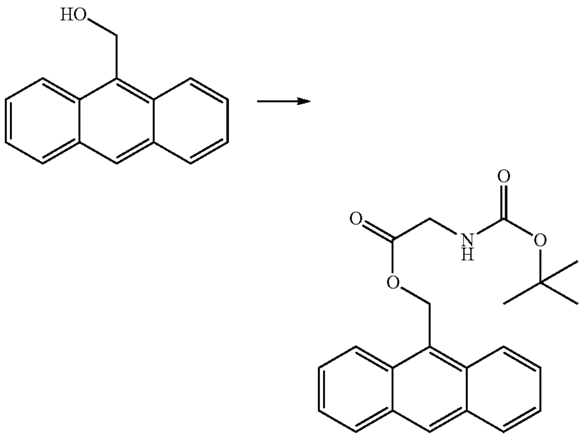

5

Compound 5: 4-benzyl alcohol anthracene (208 mg, 1.0 mmol) and Boc-Gly-OH (1.5 mmol) dissolved in dry dichloromethane (DCM) (10 mL) in 0° C. Next, the 4-dimethylaminopyridine (DMAP, 0.2 mmol) and N, N'-dicyclohexylcarbodiimide (DCC, 1.2 mmol) were added to the mixture and then stirred for 12 hours. After the reaction, the solvents were removed under vacuum condition. The raw 5 was purified by silica gel flash column chromatography with DCM/n-hexane=1/1 (v/v) as elute. The shallow yellow band was collected and yield determined to be 71% (260 mg). $^{1}$H-NMR (500 MHz, $CDCl_3$): δ=8.53 (s, 1H), 8.33-8.32 (d, 2H, J=5.0 Hz), 8.04-8.03 (d, 2H, J=5.0 Hz), 7.60-7.57 (m, 2H), 7.52-7.49 (m, 2H), 6.24 (s, 2H), 4.98 (s, 1H), 3.93 (s, 2H), 1.42 ppm (s, 9H). $^{13}$C-NMR (125 MHz, $CDCl_3$): δ=131.4, 131.1, 129.5, 129.2, 126.9, 125.2, 123.8, 59.7, 42.5, 28.3 ppm. HRMS (ESI) exact mass calculated for $[M+Na]^+$ ($C_{22}H_{23}NO_4+Na^+$) requires m/z 388.1525, found m/z 388.1519.

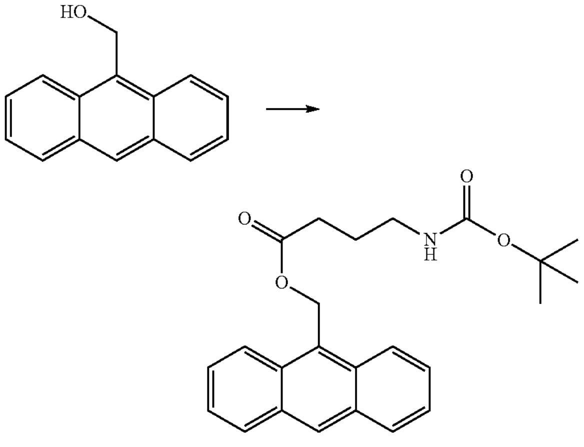

6

Compound 6: 4-benzyl alcohol anthracene (208 mg, 1.0 mmol) and Boc-GABA-OH (1.5 mmol) dissolved in dry dichloromethane (DCM) (10 mL) in 0° C. Next, 4-dimethylaminopyridine (DMAP, 0.2 mmol) and N, N'-dicyclohexylcarbodiimide (DCC, 1.2 mmol) were added to the mixture and then stirred for 12 hours. After the reaction, the solvents were removed under vacuum condition. The raw 6 was purified by silica gel flash column chromatography with DCM/n-hexane=1/1 (v/v) as elute. The shallow yellow band was collected and yield determined to be 80% (314 mg). $^{1}$H-NMR (500 MHz, $CDCl_3$): δ=8.51 (s, 1H), 8.34-8.32 (d, 2H, J=10.0 Hz), 8.04-8.03 (d, 2H, J=5.0 Hz), 7.59-7.56 (m, 2H), 7.51-7.48 (m, 2H), 6.17 (s, 2H), 4.54 (s, 1H), 3.13-3.12 (d, 2H, J=5.0 Hz), 2.39-2.36 (m, 2H), 1.82-1.78 (m, 2H), 1.41 ppm (s, 9H). $^{13}$C-NMR (125 MHz, $CDCl_3$): δ=173.4, 155.9, 131.4, 131.0, 129.2, 129.1, 126.7, 126.2, 125.1, 123.9, 58.9, 39.8, 31.1, 28.4, 25.3 ppm. HRMS (ESI) exact mass calculated for $[M+Na]^+$ ($C_{24}H_{27}NO_4+Na^+$) requires m/z 416.1838, found m/z 416.1832.

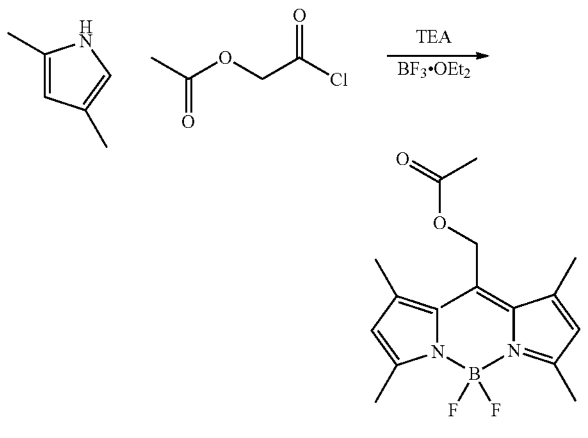

7

Compound 7: 2,4-dimethylpyrrole (980 mg, 10 mmol) and acetoxyacetyl chloride (5.0 mmol) dissolved in dry dichloromethane (DCM) (300 mL) at 0° C. and then stirred for 12 hours. After the reaction, 5 mL $BF_3$·$OEt_2$ was dropwise for 20 min at 0° C. and stirred another 4 hours, the solvents were removed under vacuum condition. The raw 7 was purified by silica gel flash column chromatography with DCM/n-hexane=1/1 (v/v) as elute. The shallow yellow band was collected and yield determined to be 15% (480 mg). $^{1}$H-NMR (500 MHz, $CDCl_3$): δ=6.09 (s, 2H), 2.53 (s, 6H), 2.36 (s, 6H), 2.13 (s, 3H), 1.54 ppm (s, 2H). $^{13}$C-NMR (125 MHz, $CDCl_3$): δ=170.6, 156.6, 141.5, 133.3, 132.7, 122.3, 57.9, 20.6, 13.6, 14.7 ppm. HRMS (ESI) exact mass calculated for $[M+H]^+$ ($C_{16}H_{19}BF_2N_2O_2+H^+$) requires m/z 321.1586, found m/z 321.1580.

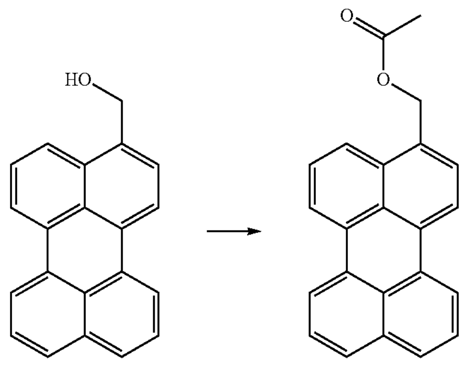

8

Compound 8: 4-benzyl alcohol perylene (140 mg, 0.5 mmol) dissolved in dry dichloromethane (DCM) (30 mL) and pyridine (50 μL) were mixed. Acetyl chloride (1.0 mmol) was dissolved in dry DCM (10 mL) and added dropwise to the mixture over 10 min and then stirred for 2 hours. After the reaction, the solvents were removed under vacuum condition. The raw 8 was purified by silica gel flash column chromatography with DCM/n-hexane=1/2 (v/v) as elute. The yellow band was collected and yield determined to be 95% (150 mg). $^{1}$H-NMR (500 MHz, $CDCl_3$): δ=8.26-8.24 (d, 1H, J=10.0 Hz), 8.22-8.20 (m, 3H), 8.17-8.16 (d, 1H, J=5.0 Hz), 7.72-7.70 (m, 2H), 7.58-7.54 (m, 2H), 7.51-7.48 (m, 2H), 5.51 (s, 2H), 2.14 ppm (s, 3H). $^{1}$C-NMR (125 MHz, $CDCl_3$): δ=171.1, 134.6, 133.0, 132.2, 131.9, 131.1, 130.9, 130.8, 129.0, 128.5, 128.3, 128.2, 128.1, 127.1, 126.6, 126.5, 123.3, 120.6, 120.5, 120.4, 119.6, 64.7, 21.1 ppm. HRMS (ESI) exact mass calculated for $[M+Na]^+$ ($C_{23}H_{16}O_2+Na^+$) requires m/z 347.1043, found m/z 347.1042.

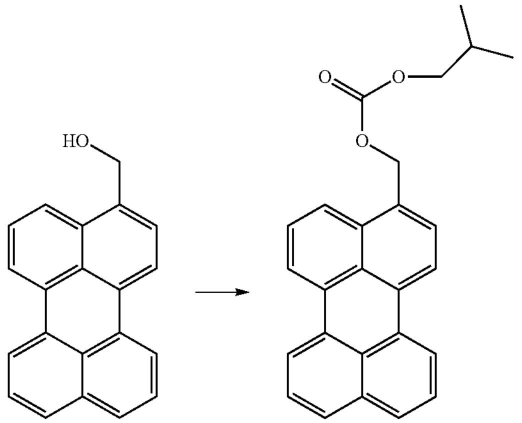

9

Compound 9: 4-benzyl alcohol perylene (140 mg, 0.5 mmol) dissolved in dry dichloromethane (DCM) (30 mL) and pyridine (50 μL) were mixed. Isobutyl chloroformate (1.0 mmol) was dissolved in dry DCM (10 mL) and added dropwise to the mixture over 10 min and then stirred for 2 hours. After the reaction, the solvents were removed under vacuum condition. The raw 9 was purified by silica gel flash column chromatography with DCM/n-hexane=1/2 (v/v) as elute. The yellow band was collected and yield determined to be 85% (107 mg). $^{1}$H-NMR (500 MHz, $CDCl_3$): δ=8.26-8.25 (d, 1H, J=5.0 Hz), 8.23-8.21 (m, 2H), 8.18-8.16 (d, 1H, J=10.0 Hz), 7.90-7.88 (d, 1H, J=9.0 Hz), 7.72-7.70 (m, 2H), 7.60-7.56 (m, 2H), 7.51-7.48 (m, 2H), 5.57 (s, 2H), 3.97-3.96 (d, J=5.0 Hz, 2H), 2.00-1.94 (m, 1H), 0.95 (s, 3H), 0.94 ppm (s, 3H). $^{1}$C-NMR (125 MHz, $CDCl_3$): δ=155.4, 134.6, 133.0, 132.4, 131.8, 130.8, 130.3, 129.0, 128.0, 127.2, 126.6, 126.5, 123.3, 120.7, 120.6, 120.4, 119.6, 74.3, 67.9, 27.8, 18.9 ppm. HRMS (ESI) exact mass calculated for $[M+Na]^+$ ($C_{26}H_{23}O_3+Na^+$) requires m/z 406.1539, found m/z 406.1495.

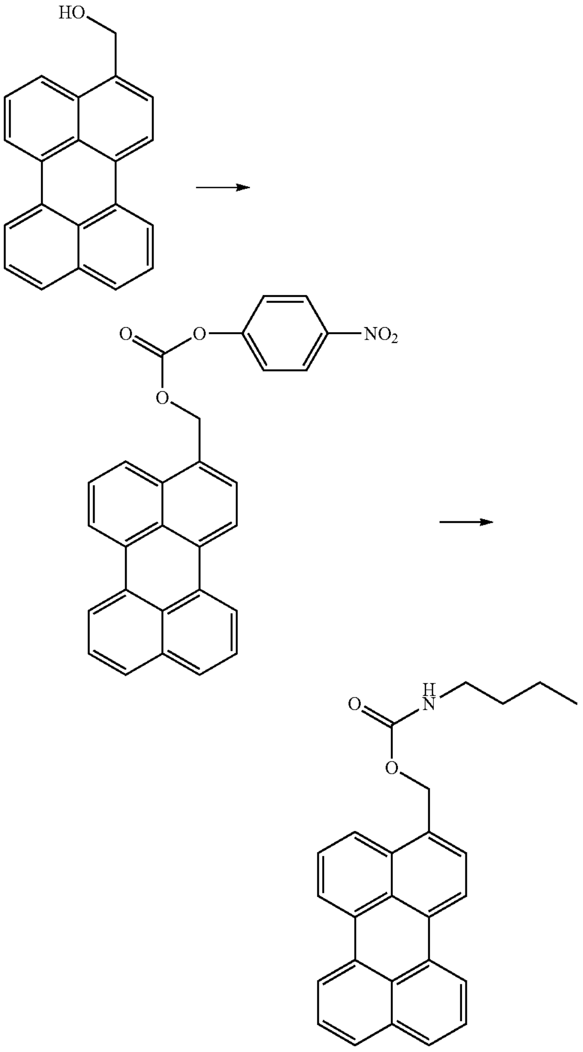

10

Compound 10: 4-benzyl alcohol perylene (140 mg, 0.5 mmol) dissolved in dry dichloromethane (DCM) (30 mL) and pyridine (50 μL) were mixed. 4-nitrophenyl chloroformate (0.6 mmol) was dissolved in dry DCM (10 mL) and added dropwise to the mixture over 10 min and then stirred for 2 hours. Next, the butylamine (2.0 mmol) was added and stirred for another 12 hours in room temperature. After the reaction, 50 mL $CH_2Cl_2$ was added. The solutions were washed with saturated aqueous solution of sodium bicarbonate (30 mL). The organic layer was collected and dried by $Na_2SO_4$; the solvents were removed under vacuum condition. The raw 10 was purified by silica gel flash column chromatography with DCM/n-hexane=1/1 (v/v) as elute. The shallow yellow band was collected and yield determined to be 45% (91 mg). $^{1}$H-NMR (500 MHz, $CDCl_3$): δ=8.25-8.23 (d, 1H, J=10.0 Hz), 8.22-8.19 (m, 2H), 8.16-8.15 (d, 1H, J=5.0 Hz), 7.89-7.87 (d, 111, J=10.0 Hz), 7.70-7.69 (d, 2H, J=5.0 Hz), 7.57-7.54 (m, 2H), 7.50-7.47 (m, 2H), 5.50 (s, 2H), 4.74 (s, 1H), 3.24-3.21 (m, 2H), 1.49-1.47 (m, 2H), 1.39-1.32 (m, 2H), 0.94-0.91 ppm (m, 311). $^{13}$C-NMR (125 MHz, $CDCl_3$): δ=134.6, 133.0, 132.1, 131.8, 131.7, 131.1, 130.9, 129.0, 128.5, 128.1, 128.0, 127.0, 126.6, 123.5, 120.3, 119.7, 65.0, 40.9, 32.0, 19.9, 13.7 ppm. HRMS (ESI) exact mass calculated for $[M+Na]^+$ ($C_{26}H_{23}NO_2+Na^+$) requires m/z 404.1626, found m/z 404.1621.

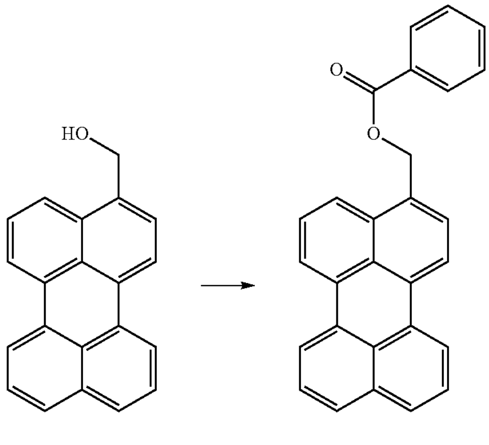

11

Compound 11: 4-benzyl alcohol perylene (140 mg, 0.5 mmol) dissolved in dry dichloromethane (DCM) (30 mL) and triethylamine (100 μL) were mixed. Benzoyl chloride (0.6 mmol) was dissolved in dry DCM (10 mL) and added dropwise to the mixture over 10 min and then stirred for 12 hours. After the reaction, 50 mL $CH_2Cl_2$ was added. The solutions were washed with saturated aqueous solution of sodium bicarbonate (30 mL). The organic layer was collected and dried by $Na_2SO_4$; the solvents were removed under vacuum condition. The raw 11 was purified by silica gel flash column chromatography with DCM/n-hexane=1/1 (v/v) as elute. The shallow yellow band was collected and yield determined to be 80% (154 mg). $^1$H-NMR (500 MHz, $CDCl_3$): δ=8.27-8.25 (d, 1H, J=10.0 Hz), 8.22-8.20 (m, 2H), 8.19-8.16 (m, 2H), 8.09-8.07 (m, 2H), 7.96-7.94 (d, 1H, J=9.0 Hz), 7.72-7.70 (m, 2H), 7.55-7.53 (d, 2H, J=10.0 Hz), 7.52-7.49 (m, 2H), 7.44-7.43 (m, 2H), 5.76 ppm (s, 2H). $^{13}$C-NMR (125 MHz, $CDCl_3$): δ=166.6, 134.6, 134.5, 133.1, 133.0, 132.3, 131.9, 131.0, 130.9, 130.6, 130.1, 129.8, 129.1, 128.9, 128.4, 128.3, 128.1, 128.0, 127.2, 126.7, 126.6, 123.4, 120.6, 120.5, 120.4, 119.6, 65.3 ppm. HRMS (ESI) exact mass calculated for $[M+Na]^+$ ($C_{28}H_{18}O_2+Na^+$) requires m/z 409.1204, found m/z 409.1199.

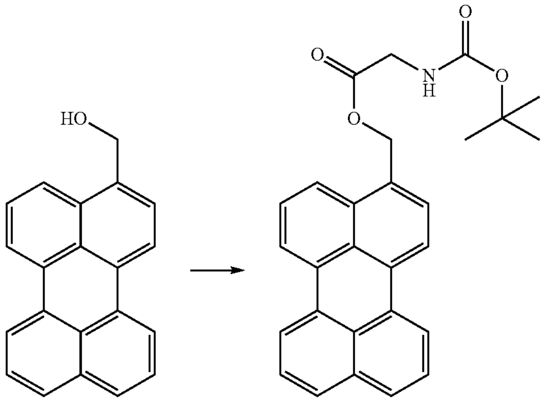

12

Compound 12: 4-benzyl alcohol perylene (140 mg, 0.5 mmol) and Boc-Gly-OH (1.0 mmol) dissolved in dry dichloromethane (DCM) (30 mL) in 0° C. Next, the 4-dimethylaminopyridine (DMAP, 0.1 mmol) and N, N'-dicyclohexylcarbodiimide (DCC, 0.6 mmol) were added to the mixture and then stirred for 12 hours. After the reaction, the solvents were removed under vacuum condition. The raw 12 was purified by silica gel flash column chromatography with DCM/n-hexane=1/1 (v/v) as elute. The shallow yellow band was collected and yield determined to be 78% (171 mg). $^1$H-NMR (500 MHz, $CDCl_3$): δ=8.26-8.20 (m, 3H), 8.17-8.15 (d, 111, J=10.0 Hz), 7.83-7.81 (d, 1H, J=10.0 Hz), 7.72-7.70 (m, 2H), 7.59-7.54 (m, 2H), 7.51-7.48 (m, 2H), 5.59 (s, 2H), 5.01 (s, 1H), 3.99 (s, 2H), 1.44 ppm (s, 9H); $^{13}$CNMR (125 MHz, $CDCl_3$) δ=170.4, 134.6, 133.0, 132.5, 131.9, 131.0, 130.8, 130.2, 129.0, 128.6, 128.5, 128.3, 128.1, 127.3, 126.7, 126.6, 123.2, 120.7, 120.6, 120.4, 119.5, 65.5, 42.5, 28.3 ppm. HRMS (ESI) exact mass calculated for $[M+Na]^+$ ($C_{24}H_{25}NO_4+Na^+$) requires m/z 462.1681, found m/z 462.1676.

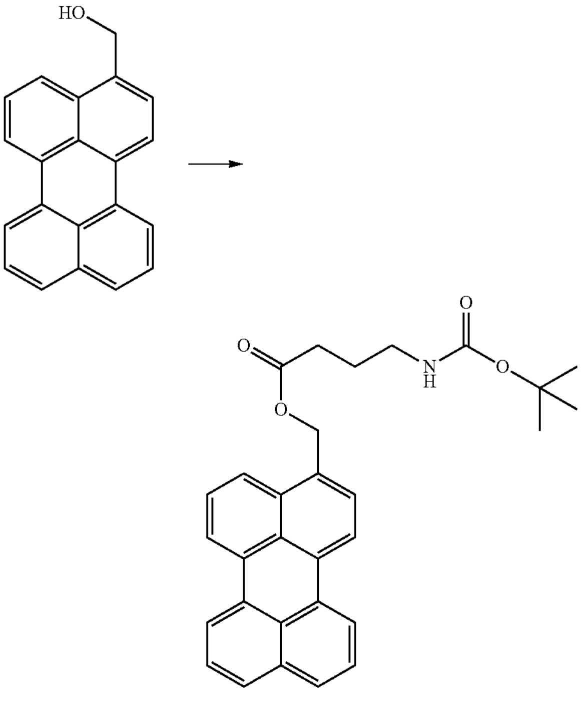

13

Compound 13: 4-benzyl alcohol perylene (140 mg, 0.5 mmol) and Boc-GABA-OH (1.0 mmol) dissolved in dry dichloromethane (DCM) (10 mL) in 0° C. Next, the 4-dimethylaminopyridine (DMAP, 0.2 mmol) and N, N'-dicyclohexylcarbodiimide (DCC, 1.2 mmol) were added to the mixture and then stirred for 12 hours. After the reaction, the solvents were removed under vacuum condition. The raw 13 was purified by silica gel flash column chromatography with DCM/n-hexane=1/1 (v/v) as elute. The shallow yellow band was collected and yield determined to be 69% (156 mg). $^{1}$H-NMR (500 MHz, $CDCl_3$): δ=8.26-8.24 (d, 1H, J=10.0 Hz), 8.23-8.20 (m, 2H), 8.17-8.16 (d, 1H, J=5.0 Hz), 7.84-7.82 (d, 1H, J=10.0 Hz), 7.72-7.70 (m, 2H), 7.58-7.54 (m, 2H), 7.51-7.48 (m, 2H), 5.21 (s, 2H), 4.58 (s, 1H), 3.16 (s, 2H), 2.45-2.42 (m, 2H), 1.86-1.83 (m, 2H), 1.42 ppm (s, 9H); $^{13}$CNMR (125 MHz, $CDCl_3$) δ=173.2, 155.9, 134.6, 133.0, 132.3, 131.8, 131.1, 130.9, 130.8, 129.0, 128.5, 128.4, 128.2, 128.1, 127.2, 126.7, 126.6, 123.3, 120.6, 120.6, 120.4, 119.6, 64.8, 39.9, 31.6, 28.4, 25.3 ppm. HRMS (ESI) exact mass calculated for $[M+Na]^+$ ($C_{30}H_{29}NO_4+Na^+$) requires m/z 490.1994, found m/z 490.1989.

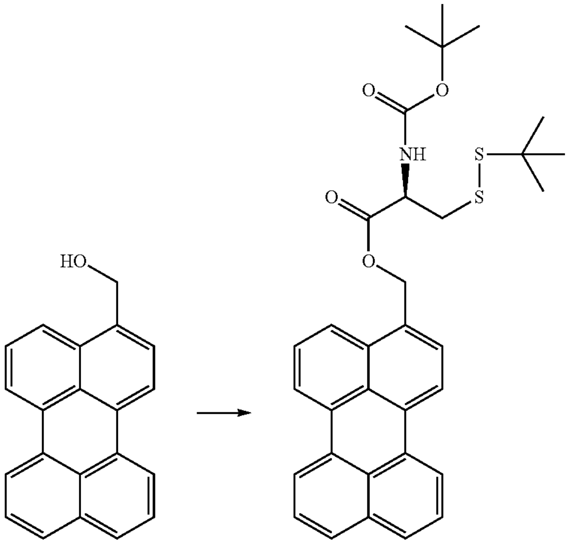

14

Compound 14: 4-benzyl alcohol perylene (140 mg, 0.5 mmol) and Boc-Cys(StBu)-OH (1.0 mmol) dissolved in dry dichloromethane (DCM) (10 mL) in 0° C. Next, the 4-dimethylaminopyridine (DMAP, 0.2 mmol) and N, N'-dicyclohexylcarbodiimide (DCC, 1.2 mmol) were added to the mixture and then stirred for 12 hours. After the reaction, the solvents were removed under vacuum condition. The raw 14 was purified by silica gel flash column chromatography with DCM/n-hexane=1/1 (v/v) as elute. The yellow band was collected and yield determined to be 65% (186 mg). $^{1}$H-NMR (500 MHz, $CDCl_3$): δ=8.24-8.19 (m, 3H), 8.16-8.13 (m, 1H), 7.83-7.82 (m, 1H), 7.71-7.70 (m, 2H), 7.57-7.48 (m, 4H), 5.58 (s, 2H), 5.43-5.41 (m, 1H), 4.66 (s, 1H), 3.21-3.11 (m, 2H), 1.43 (s, 9H), 1.26 ppm (s, 9H). $^{13}$CNMR (125 MHz, $CDCl_3$) δ=170.8, 155.1, 134.6, 133.0, 132.5, 131.8, 131.0, 130.8, 130.1, 129.0, 128.6, 128.4, 128.3, 128.1, 127.2, 126.7, 126.6, 123.3, 120.7, 120.6, 120.4, 119.5, 80.2, 65.9, 48.2, 42.9, 29.7, 28.3 ppm. HRMS (ESI) exact mass calculated for $[M+Na]^+$ ($C_{33}H_{35}NO_4S_2+Na^+$) requires m/z 596.1905, found m/z 596.1900.

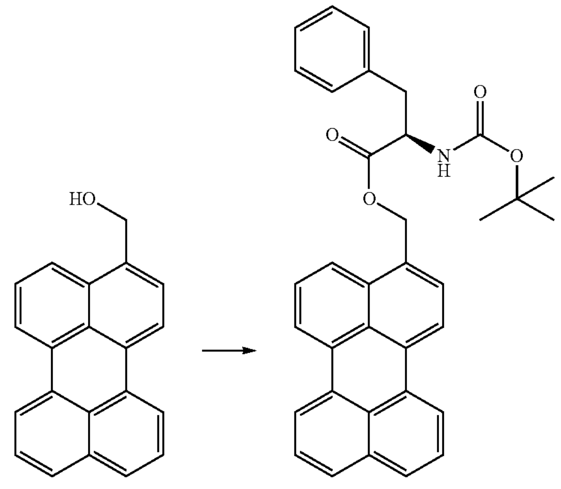

15

Compound 15: 4-benzyl alcohol perylene (140 mg, 0.5 mmol) and Boc-Phen-OH (1.0 mmol) dissolved in dry dichloromethane (DCM) (10 mL) in 0° C. Next, the 4-dimethylaminopyridine (DMAP, 0.2 mmol) and N, N'-dicyclohexylcarbodiimide (DCC, 0.6 mmol) were added to the mixture and then stirred for 12 hours. After the reaction, the solvents were removed under vacuum condition. The raw 15 was purified by silica gel flash column chromatography with DCM/n-hexane=1/1 (v/v) as elute. The shallow yellow band was collected and yield determined to be 65% (163 mg). $^{1}$H-NMR (500 MHz, $CDCl_3$): δ=8.25-8.20 (m, 3H), 8.15-8.13 (d, 1H, J=10.0 Hz), 7.76-7.70 (m, 3H), 7.55-7.48 (m, 4H), 7.14 (s, 3H), 6.99 (s, 2H), 5.58-5.49 (m, 2H), 5.02-4.98 (m, 1H), 4.68-4.64 (m, 1H), 3.09-3.04 (m, 2H), 1.40 ppm (s, 9H). $^{13}$CNMR (125 MHz, $CDCl_3$) δ=171.9, 155.1, 135.7, 134.6, 133.0, 132.4, 131.8, 131.0, 130.8, 130.2, 129.3, 129.0, 128.7, 128.5, 128.3, 128.1, 127.2, 126.9, 126.7, 126.6, 123.2, 120.7, 120.6, 120.4, 119.5, 79.9, 65.4, 54.5, 38.4, 30.3, 28.3 ppm. HRMS (ESI) exact mass calculated for $[M+Na]^+$ ($C_{35}H_{31}NO_4+Na^+$) requires m/z 552.2151, found m/z 552.2145.

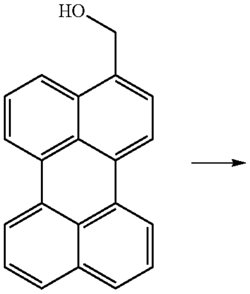

-continued

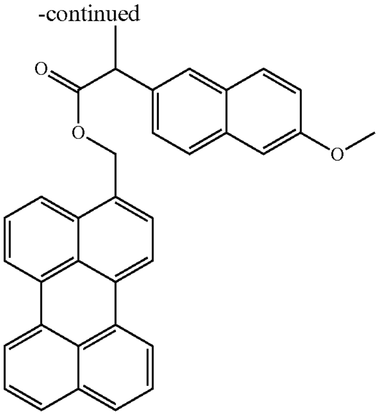

16

Compound 16: 4-benzyl alcohol perylene (140 mg, 0.5 mmol) and naproxen (0.7 mmol) dissolved in dry dichloromethane (DCM) (10 mL) in 0° C. Next, the 4-dimethylaminopyridine (DMAP, 0.2 mmol) and N, N'-dicyclohexylcarbodiimide (DCC, 0.6 mmol) were added to the mixture and then stirred for 12 hours. After the reaction, the solvents were removed under vacuum condition. The raw 16 was purified by silica gel flash column chromatography with DCM/n-hexane=1/1 (v/v) as elute. The shallow yellow band was collected and yield determined to be 57% (141 mg). $^{1}$H-NMR (500 MHz, $CDCl_3$): δ=8.10-8.07 (m, 2H), 8.05-8.04 (d, 1H, J=5.0 Hz), 7.99-7.97 (d, 1H, J=10.0 Hz), 7.65-7.58 (m, 5H), 7.53-7.52 (d, 1H, J=5.0 Hz), 7.46-7.41 (m, 2H), 7.36-7.34 (m, 2H), 7.22-7.19 (m, 1H), 7.09-7.05 (m, 2H), 5.44 (s, 2H), 3.91-3.90 (m, 1H), 3.87 (s, 3H), 1.66-1.58 ppm (d, J=10.0 Hz, 3H); $^{13}$CNMR (125 MHz, $CDCl_3$) δ=174.6, 157.6, 135.4, 134.5, 133.7, 132.8, 132.0, 131.5, 131.1, 130.8, 130.7, 129.3, 128.9, 128.4, 128.1, 127.9, 127.1, 126.7, 126.5, 126.4, 126.2, 126.0, 123.3, 120.5, 120.4, 120.2, 119.4, 118.9, 105.5, 65.2, 55.3, 45.5, 18.3 ppm. HRMS (ESI) exact mass calculated for $[M+Na]^+$ ($C_{35}H_{26}O_3$+$Na^+$) requires m/z 517.1780, found m/z 517.1774.

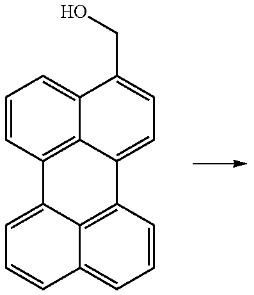

-continued

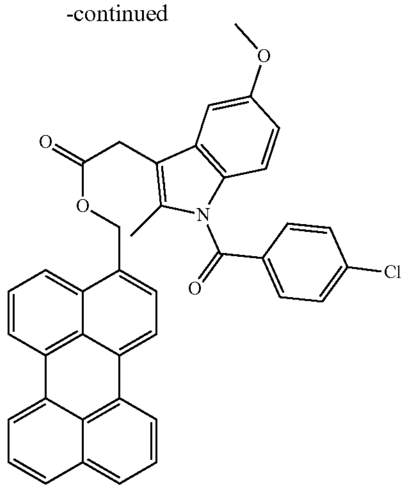

17

Compound 17: 4-benzyl alcohol perylene (140 mg, 0.5 mmol) and indometacin (0.7 mmol) dissolved in dry dichloromethane (DCM) (10 mL) in 0° C. Next, the 4-dimethylaminopyridine (DMAP, 0.2 mmol) and N, N'-dicyclohexylcarbodiimide (DCC, 0.6 mmol) were added to the mixture and then stirred for 12 hours. After the reaction, the solvents were removed under vacuum condition. The raw 17 was purified by silica gel flash column chromatography with DCM/n-hexane=1/1 (v/v) as elute. The shallow yellow band was collected and yield determined to be 53% (164 mg). $^{1}$H-NMR (500 MHz, $CDCl_3$): δ=8.21-8.19 (m, 3H), 8.13-8.11 (d, 1H, J=10.0 Hz), 7.72-7.70 (m, 2H), 7.67-7.65 (d, 1H, J=10.0 Hz), 7.55-7.54 (m, 2H), 7.52-7.49 (m, 3H), 7.39-7.35 (m, 3H), 6.90-6.88 (m, 2H), 6.65-6.63 (m, 1H), 5.52 (s, 2H), 3.72 (s, 2H), 3.66 (s, 3H), 2.29 ppm (s, 3H); $^{13}$CNMR (125 MHz, $CDCl_3$) δ=170.8, 168.3, 156.1, 139.2, 135.8, 134.6, 133.9, 132.9, 132.4, 131.8, 131.1, 131.0, 130.8, 130.7, 130.5, 129.1, 129.0, 128.6, 128.4, 128.3, 128.1, 127.0, 126.7, 126.6, 123.3, 120.7, 120.6, 120.4, 119.5, 115.0, 112.5, 111.9, 101.1, 65.4, 55.5, 30.6, 13.4 ppm; HRMS (ESI) exact mass calculated for $[M+Na]^+$ ($C_{40}H_{28}NO_4Cl$+$Na^+$) requires m/z 644.1605, found m/z 644.1609.

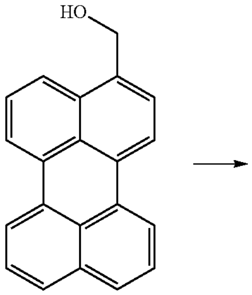

-continued

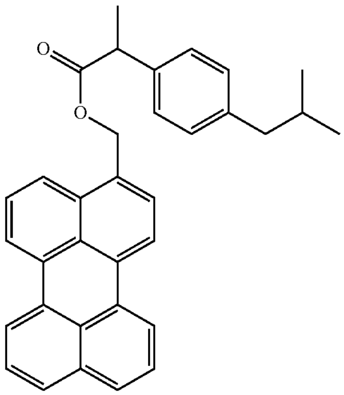

18

-continued

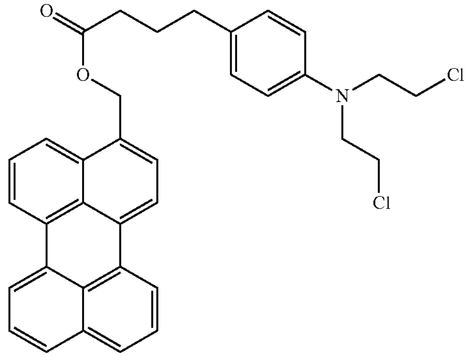

19

Compound 18: 4-benzyl alcohol perylene (140 mg, 0.5 mmol) and ibuprofen (0.7 mmol) dissolved in dry dichloromethane (DCM) (10 mL) in 0° C. Next, the 4-dimethylaminopyridine (DMAP, 0.2 mmol) and N, N'-dicyclohexylcarbodiimide (DCC, 0.6 mmol) were added to the mixture and then stirred for 12 hours. After the reaction, the solvents were removed under vacuum condition. The raw 18 was purified by silica gel flash column chromatography with DCM/n-hexane=1/1 (v/v) as elute. The shallow yellow band was collected and yield determined to be 67% (152 mg). $^1$H-NMR (500 MHz, $CDCl_3$): δ=8.21-8.16 (m, 3H), 8.10-8.08 (m, 1H), 7.70-7.68 (d, 2H, J=10.0 Hz), 7.65-7.63 (d, 1H, J=10.0 Hz), 7.50-7.47 (m, 2H), 7.44-7.41 (m, 2H), 7.21-7.19 (d, 2H, J=10.0 Hz), 7.10-7.01 (m, 4H), 5.48 (s, 2H), 2.45-2.43 (m, 2H), 1.86-1.82 (m, 1H), 1.53-1.51 (d, 3H), 0.90 ppm (s, 6H); $^{13}$CNMR (125 MHz, $CDCl_3$) δ=174.7, 140.6, 137.5, 134.6, 132.8, 132.0, 131.7, 130.9, 129.5, 129.4, 129.3, 128.9, 128.5, 128.1, 128.0, 127.9, 127.3, 126.9, 126.6, 126.5, 120.4, 120.3, 119.5, 65.0, 45.2, 45.0, 30.2, 22.4, 18.3 ppm. HRMS (ESI) exact mass calculated for $[M+Na]^+$ ($C_{34}H_{30}O_2$+$Na^+$) requires m/z 493.2143, found m/z 493.2138.

Compound 19: 4-benzyl alcohol perylene (140 mg, 0.5 mmol) and chlorambucil (0.7 mmol) dissolved in dry dichloromethane (DCM) (10 mL) in 0° C. Next, the 4-dimethylaminopyridine (DMAP, 0.2 mmol) and N, N'-dicyclohexylcarbodiimide (DCC, 0.6 mmol) were added to the mixture and then stirred for 12 hours. After the reaction, the solvents were removed under vacuum condition. The raw 19 was purified by silica gel flash column chromatography with DCM/n-hexane=1/1 (v/v) as elute. The shallow yellow band was collected and yield determined to be 60% (168 mg). $^1$H-NMR (500 MHz, $CDCl_3$): δ=8.26-8.20 (m, 3H), 8.17-8.16 (1H, d, J=5.0 Hz), 7.86-7.84 (1H, d, J=10.0 Hz), 7.71-7.70 (2H, d, J=10.0 Hz), 7.58-7.55 (m, 2H), 7.52-7.48 (m, 2H), 6.98-6.96 (2H, d, J=10.0 Hz), 6.56-6.54 (211, d, J=9.0 Hz), 5.52 (s, 2H), 3.67-3.64 (m, 4H), 3.59-3.56 (m, 4H), 2.53-2.50 (m, 2H), 2.40-2.37 (m, 2H), 1.95-1.89 (m, 2H). $^{13}$CNMR (125 MHz, $CDCl_3$) δ=173.5, 144.3, 134.6, 133.0, 131.9, 131.1, 130.9, 130.5, 129.7, 129.1, 128.5, 128.4, 128.2, 128.1, 127.1, 126.7, 126.6, 123.4, 120.6, 120.5, 120.4, 119.6, 112.1, 64.5, 53.6, 40.5, 33.9, 33.7, 26.8 ppm. HRMS (ESI) exact mass calculated for [M+H]+ ($C_{35}H_{31}Cl_2NO_2$+$H^+$) requires m/z 568.1810, found m/z 568.1805.

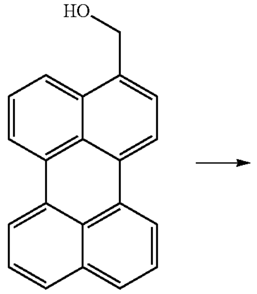

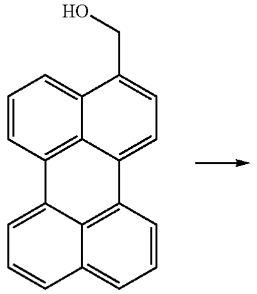

-continued

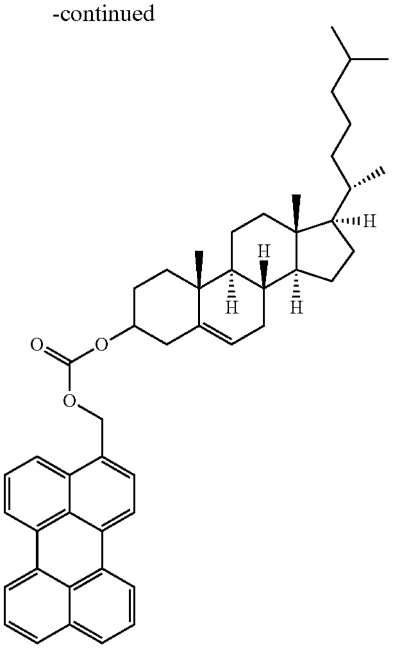

20

Compound 20: 4-benzyl alcohol perylene (140 mg, 0.5 mmol) and pyridine (50 μL) dissolved in dry dichloromethane (DCM) (10 mL) in 0° C. Next, the cholesteryl chloroformate. (0.6 mmol) were added to the mixture and then stirred for 12 hours. After the reaction, the solvents were removed under vacuum condition. The raw 20 was purified by silica gel flash column chromatography with DCM/n-hexane=1/1 (v/v) as elute. The shallow yellow band was collected and yield determined to be 21% (72 mg). $^1$H-NMR (500 MHz, $CDCl_3$): δ=8.25-8.20 (m, 3H), 8.16-8.15 (d, 1H, J=5.0 Hz), 7.89-7.87 (d, 1H, J=10.0 Hz), 7.71-7.69 (m, 2H), 7.59-7.55 (m, 2H), 7.51-7.48 (m, 2H), 5.56 (s, 2H), 5.39-5.38 (d, 1H, J=5.0 Hz), 4.55-4.49 (m, 1H), 2.44-2.38 (m, 2H), 2.01-1.95 (m, 3H), 1.88-1.82 (m, 2H), 1.68-1.63 (m, 1H), 1.50-1.43 (m, 5H), 1.36-1.31 (m, 3H), 1.26-1.24 (m, 3H), 1.17-1.04 (m, 8H), 0.99 (s, 4H), 0.92-0.90 (m, 3H), 0.87-0.85 (m, 6H), 0.67 ppm (s, 3H); $^{13}$CNMR (125 MHz, $CDCl_3$) δ=154.6, 139.4, 134.6, 133.0, 132.4, 131.8, 131.1, 130.9, 130.4, 129.0, 128.4, 128.2, 128.1, 127.2, 126.6, 126.5, 123.3, 123.0, 120.7, 120.6, 120.4, 119.6, 78.2, 67.7, 56.7, 56.1, 50.0, 42.3, 39.7, 39.5, 38.0, 36.9, 36.5, 36.2, 35.8, 31.9, 31.8, 28.2, 27.7, 24.3, 23.8, 22.8, 22.6, 21.0, 19.3, 18.7, 11.9 ppm. HRMS (ESI) exact mass calculated for $[M+Na]^+$ ($C_{49}H_{58}O_3+Na^+$) requires m/z 717.4284, found m/z 717.4278.

Section 2. Photophysical Properties of Photosensitizers and Photoremovable Protecting Groups (PPGs).)

Figure 4:
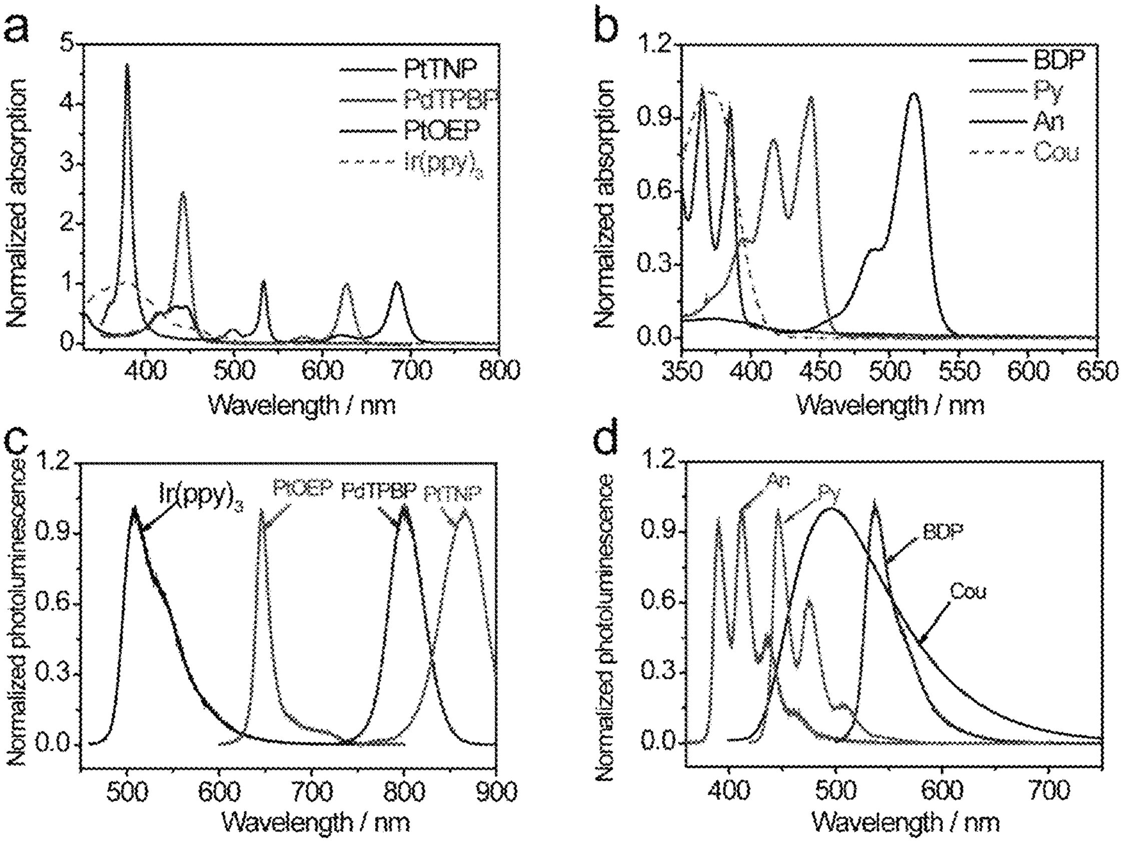
FIG. 4. (a) Normalized UV-vis absorption spectra of $Ir(ppy)_3$, PtOEP, PdTPBP and PtTNP; (b) Normalized UV-vis absorption spectra of Cou (compound 1), An (compound 2), Py (compound 8) and BDP (compound 7); (c) Normalized photoluminescence emission spectra of $Ir(ppy)_3$ ($\lambda_{ex}$=410 nm), PtOEP ($\lambda_{ex}$=530 nm), PdTPBP ($\lambda_{ex}$=630 nm) and PtTNP ($\lambda_{ex}$=700 nm); (d) Normalized photoluminescence emission spectra of Cou (($\lambda_{ex}$=360 nm), An ($\lambda_{ex}$=360 nm), Py ($\lambda_{ex}$=410 nm) and BDP ($\lambda_{ex}$=470 un).

FIG. 4 shows (a) Normalized UV-vis absorption spectra of $Ir(ppy)_3$, PtOEP, PdTPBP and PtTNP; (b) Normalized UV-vis absorption spectra of Cou (compound 1), An (compound 2), Py (compound 8) and BDP (compound 7); (c) Normalized photoluminescence emission spectra of $Ir(ppy)_3$ ($\lambda_{ex}$=410 nm), PtOEP ($\lambda_{ex}$=530 nm), PdTPBP ($\lambda_{ex}$=630 nm) and PtTNP ($\lambda_{ex}$=700 nm); (d) Normalized photoluminescence emission spectra of Cou (($\lambda_{ex}$=360 nm), An ($\lambda_{ex}$=360 nm), Py ($\lambda_{ex}$=410 nm) and BDP ($\lambda_{ex}$=470 nm).

From the absorption and emission spectra of Sen and PPGs, the triplet and singlet energy levels of PPG and Sen can be calculated. The maximum emission wavelength of phosphorescence is the triplet excited state energy level ($T_1$) of the Sen. The maximum emission wavelength of fluorescence is the singlet excited state energy level ($S_1$) of the PPGs. Moreover, according to the literature, we know the triplet excited energy levels of PPGs. The detail information is always in

TABLE 8

The photophysical parameters of Sen and PPGs[a]

| | $\lambda_{abs}$[b] | $\lambda_{em}$[c] | ξ ($10^4$ $M^{-1}$ $cm^{-1}$)[d] | $T_1$ (eV)[e] | $S_1$ (eV)[f] | $\tau_T$ (μs)[g] |
|---|---|---|---|---|---|---|
| PtTNP | 687 | 866 | 13.2 | 1.43 | —[p] | 11.0[h] |
| PdTPBP | 630 | 790 | 11.0 | 1.55 | —[p] | 223.7[i] |
| PtOEP | 533 | 647 | 7.0 | 1.92 | —[p] | 90[j] |
| $Ir(ppy)_3$ | 377 | 513 | 1.7 | 2.40 | —[p] | 1.6[k] |
| BDP | 517 | 537 | 7.3 | 1.49[l] | 2.31 | —[p] |
| Py | 440 | 445 | 4.0 | 1.52[m] | 2.78 | —[p] |
| An | 366 | 411 | 1.1 | 1.77[n] | 3.02 | —[p] |
| Cou | 360 | 460 | 0.62 | 2.18[o] | 2.52 | —[p] |

[a]in toluene, 10 μM;
[b]maximum absorption wavelength;
[c]maximum emission wavelength;
[d] molar extinction coefficient;
[e]triplet excited state;
[f]singlet excited state;
[g] triplet excited lifetime of Sen;
[h]Lebedev, et al. 2009 *ACS Appl. Mater. Interfaces.* 1, 1292;
[i]Cui, et al. 2013 *Chem. Commun.* 49, 10221;
[j]Bansal, et al. 2006 *Chemical Physics.* 330, 118;
[k]Hofbeck, et al. 2010 *Inorg. Chem.* 49, 9290-9299;
[l]Whited, et al. 2011 *J. Am. Chem. Soc.* 133, 88;
[m] Cui, et al. 2014 *J. Am. Chem. Soc.* 136, 9256-9259;
[n] Ji, et al. 2011 *Angew. Chem. Int. Ed.* 50, 1626-1629;
[o] Ma, et al. 2012 *Dalton Trans.* 41, 10680;
[p]no applicable.

Section 3. Analysis of Possible Combinations of Sen and PPGs for TTAP Based on Energy Satisfaction Conditions.

Figure 5:
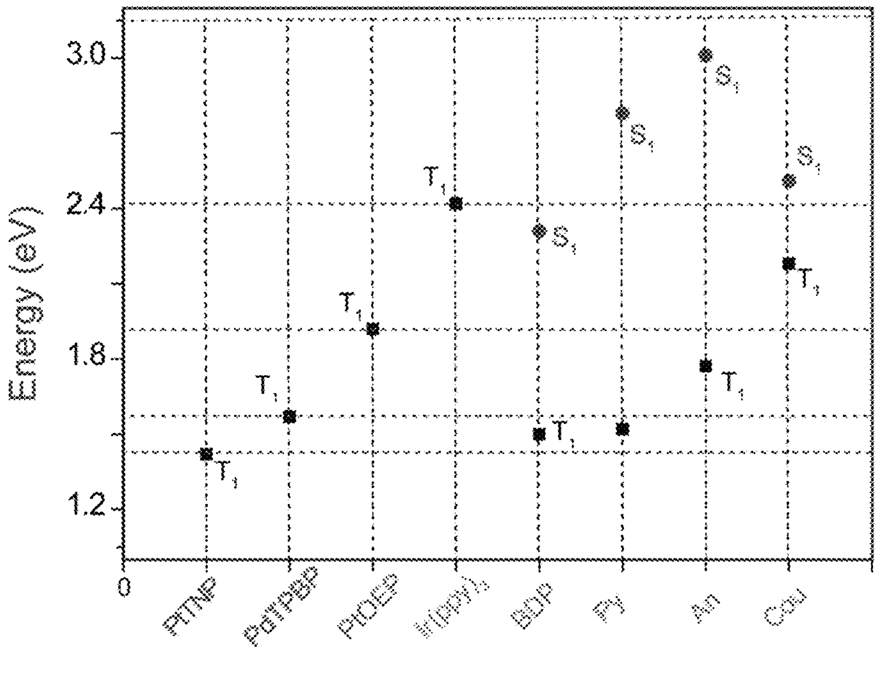
FIG. 5. The comparison of triple excited state and single excited state of Sen and PPGs.

FIG. 5 shows comparison of triple excited state and single excited state of Sen and PPGs.

TABLE 9

| A summary of the singlet excited/triplet excited state energy level of PPGs and Sen. | | | | | | | | |
|---|---|---|---|---|---|---|---|---|
| | PtTNP | PdTPBP | PtOEP | $Ir(ppy)_3$ | BDP | Py | An | Cou |
| $S_1$ (eV) | — | — | — | — | 2.31 | 2.78 | 3.02 | 2.52 |
| $T_1$ (eV) | 1.43 | 1.55 | 1.92 | 2.4 | 1.49 | 1.52 | 1.77 | 2.18 |
| $2 \times T_1 - S_1$ (eV) | | | | | 0.69 | 0.26 | 0.53 | 1.85 |

According to the energetic requirements of TTAP ($^3$[Sen]*>$^3$[PPGs]*; 2x$^3$[PPGs]*>$^1$[PPGs]*) (Table 9), We come to the conclusion that there may be a combination of TTAP in this study (Table 10).

TABLE 10

| The combination of Sen and PPGs in this study | | | | |
|---|---|---|---|---|
| | PtTNP | PdTPBP | PtOEP | Ir $(ppy)_3$ |
| BDP | √ | √ | x | x |
| Py | √ | √ | √ | x |
| An | x | x | √ | x |
| Cou | x | x | x | √ |

"√" means there may be a TTAP process;
"x" means there may not be a TTAP process Section 4. TTAP Process of $Ir(ppy)_3$ and Con (Compound 1) Including the Stern-Volmer Photoluminescence Quenching and Photolytic Experiments.

FIG. 6 shows (a) Molecular structure of $Ir(ppy)_3$ and Cou (compound 1); (b) Phosphorescence intensity quenching of $Ir(ppy)_3$ (10 μM) in the presence of different concentration of compound 1, $\lambda_{ex}$, =410 nm; (c) Stern-Volmer plots generated from the phosphorescence intensity quenching of $Ir(ppy)_3$ as a function of compound 1 concentration.

Section 5. TTAP Process of PtOEP: An (Compound 2) and PtOEP:Py (Compound 8).

Figure 7:
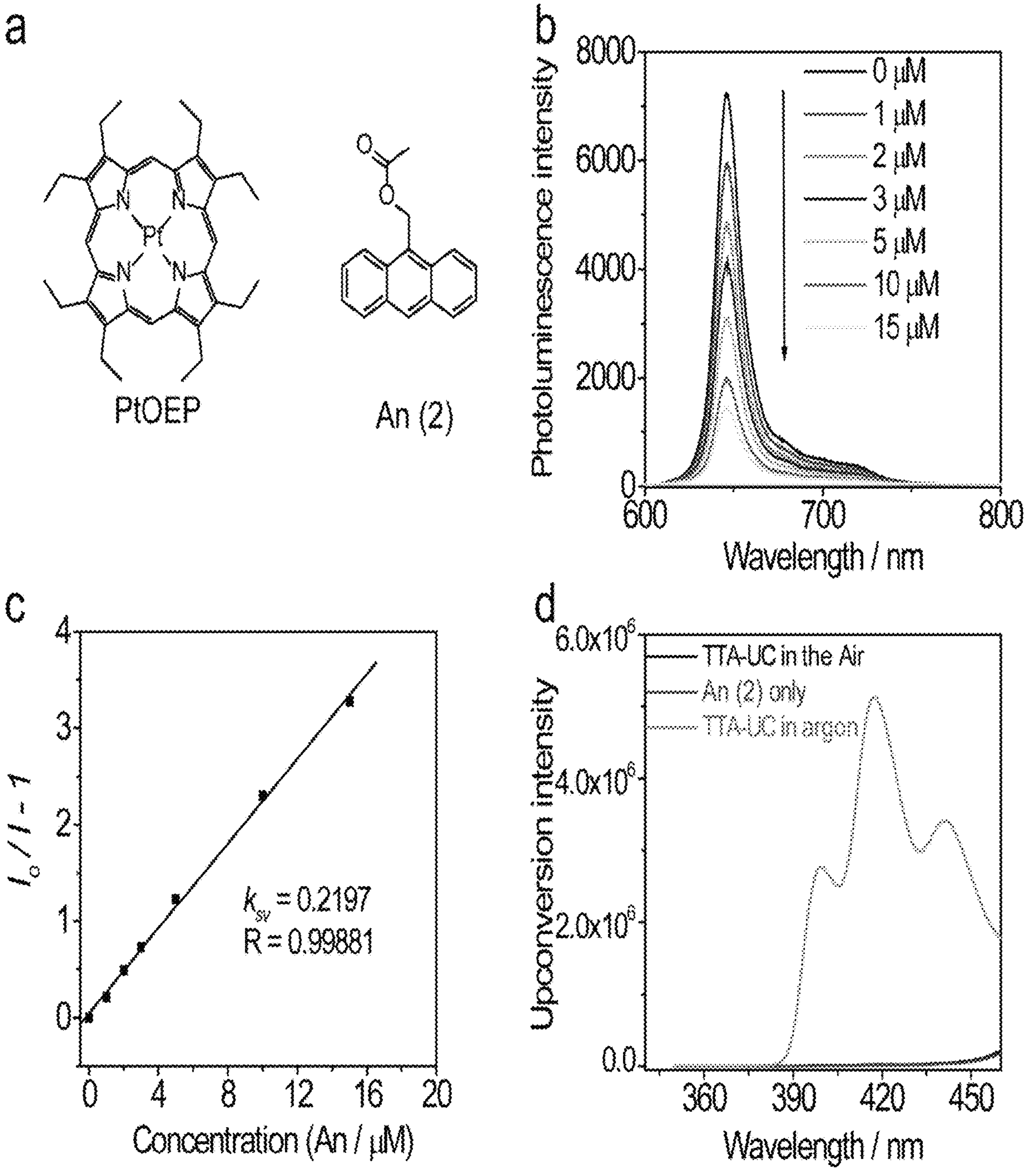
FIG. 7. (a) Molecular structure of PtOEP and An (compound 2); (b) Phosphorescence intensity quenching of PtOEP (10 μM) in the presence of different concentration of An (compound 2), $\lambda_{ex}$=530 nm; (c) Stern-Volmer plots generated from the phosphorescence intensity quenching of PtOEP as a function of compound 2 concentration; (d) The upconversion emission spectra of PtOEP and compound 2 paired in the air, argon and in the absence of PtOEP, $\lambda_{ex}$=530 nm, 20 mW/$cm^2$, in toluene.

FIG. 7 shows (a) Molecular structure of PtOEP and An (compound 2); (b) Phosphorescence intensity quenching of PtOEP (10 μM) in the presence of different concentration of An (compound 2), $\lambda_{ex}$=530 nm; (c) Stern-Volmer plots generated from the phosphorescence intensity quenching of PtOEP as a function of compound 2 concentration; (d) The upconversion emission spectra of PtOEP and compound 2 paired in the air, argon and in the absence of PtOEP, $\lambda_{ex}$=530 nm, 20 mW/$cm^2$, in toluene.

Figure 8:
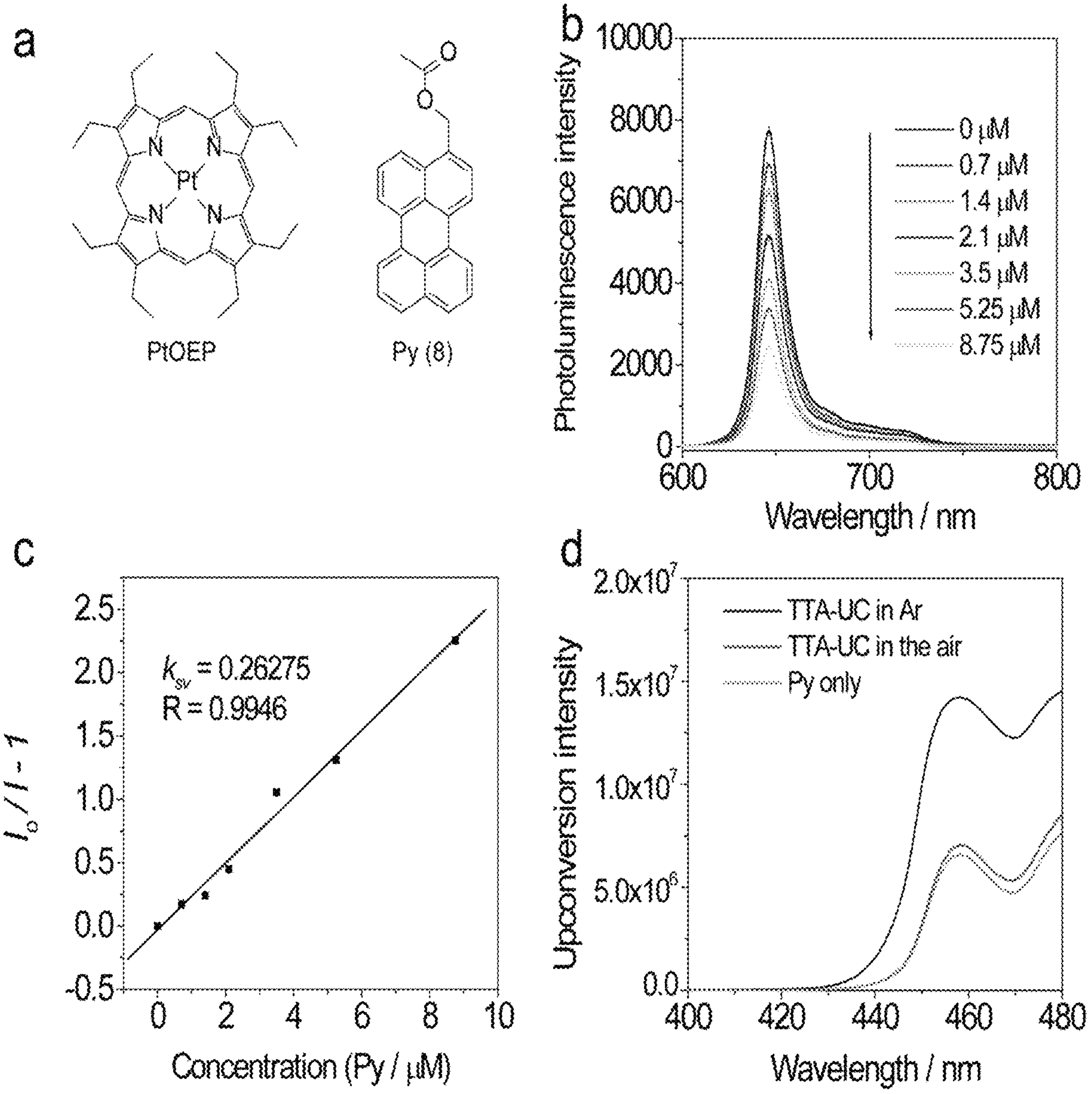
FIG. 8. (a) Molecular structure of PtOEP and Py (compound 8); (b) Phosphorescence intensity quenching of PtOEP (10 μM) in the presence of different concentration of compound 8, $\lambda_{ex}$=530 nm; (c) Stern-Volmer plots generated from the phosphorescence intensity quenching of PtOEP as a function of compound 8 concentration; (d) The upconversion emission spectra of PtOEP and compound 8 paired in the air, argon and in the absence of PtOEP, $\lambda_{ex}$=530 un, 20 mW/$cm^2$, in toluene.

FIG. 8 shows (a) Molecular structure of PtOEP and Py (compound 8); (b) Phosphorescence intensity quenching of PtOEP (10 μM) in the presence of different concentration of compound 8, $\lambda_{ex}$=530 nm; (c) Stern-Volmer plots generated from the phosphorescence intensity quenching of PtOEP as a function of compound 8 concentration; (d) The upconversion emission spectra of PtOEP and compound 8 paired in the air, argon and in the absence of PtOEP, $\lambda_{ex}$=530 nm, 20 mW/$cm^2$, in toluene.

TABLE 11

Photolytic reaction for Ir(ppy)3 and Cou (compound 1)

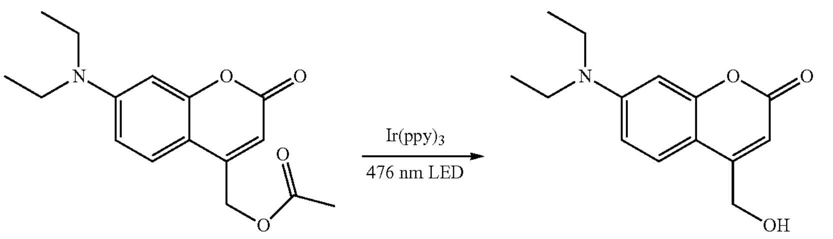

Cou (1)

| Enter | Condition | Reaction time | Yield (%)[a] |
|---|---|---|---|
| 1 | light; air | 20 min | 4 |
| 2 | dark, argon; | 20 min | No reaction |
| 3 | light, Cou only, argon; | 20 min | No reaction |
| 4 | light; argon; | 20 min | 73.6 |

[a]HPLC

TABLE 12

Photolytic reaction for PtOEP and An (compound 2 )

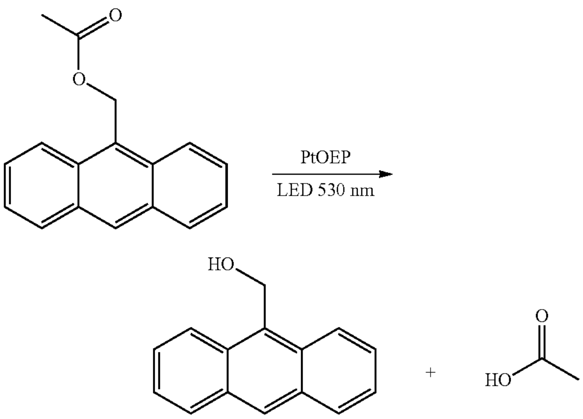

| Enter | Condition | Reaction time | Yield (%)[a] |
|---|---|---|---|
| 1 | Light, air | 1 h | Trace |
| 2 | Dark, argon | 1 h | No reaction |
| 3 | An (compound 2) only, light, argon | 1 h | No reaction |
| 4 | Light, argon | 1 h | 83.2 |

[a]HPLC.

TABLE 13

Photolytic reaction for PtOEP and Py (compound 8)

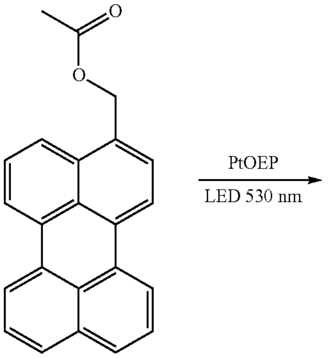 [SMILES: CC(=O)OCc1ccc2c3cccc4cccc(c5cccc1c52)c43]

TABLE 13-continued

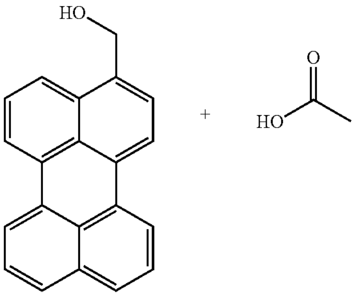

| Enter | Condition | Reaction time | Yield (%)[a] |
|---|---|---|---|
| 1 | Light, air | 1 h | 2 |
| 2 | Dark, argon | 1 h | No reaction |
| 3 | Py (compound 8) only, light, argon | 1 h | No reaction |
| 4 | Light, argon | 1 h | 70.2 |

[a]HPLC.

Section 6. TTAP Process of PdTPBP:Py (Compound 8) and PdTPBP:BDP (Compound 7).

Figure 9:
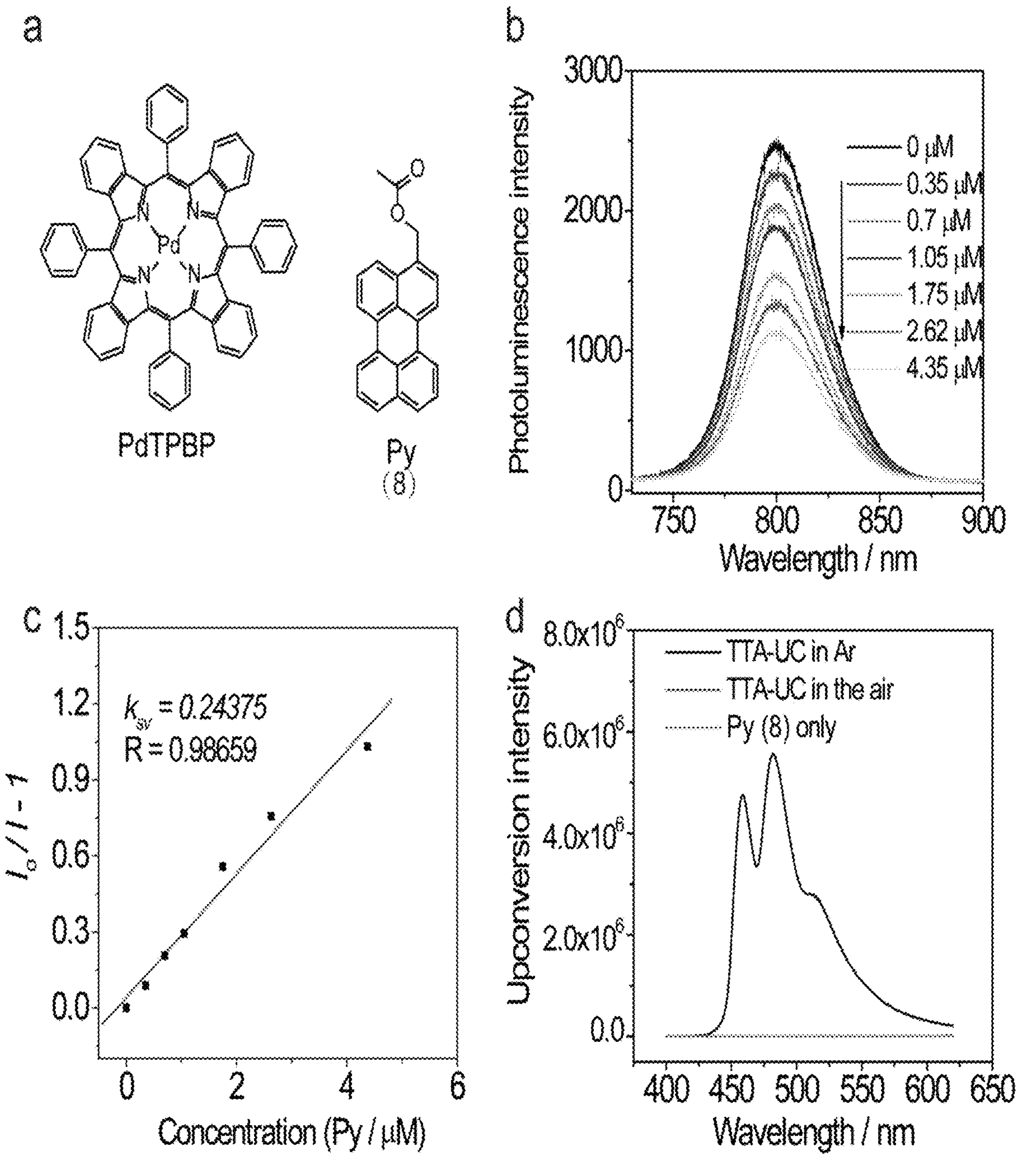
FIG. 9. (a) Molecular structure ofPdTPBP and Py (compound 8); (b) Phosphorescence intensity quenching of PdTPBP (10 μM) in the presence of different concentration of Py (compound 8), $\lambda_{ex}$, =635 un; (c) Stern-Volmer plots generated from the phosphorescence intensity quenching of PdTPBP as a function of Py (compound 8) concentration; (d) The upconversion emission spectra of PdTPBP and Py (compound 8) paired in the air, argon and in the absence of PdTPBP, $\lambda_{ex}$=650 nm, 100 mW/$cm^2$, in toluene.

FIG. 9 shows (a) Molecular structure of PdTPBP and Py (compound 8); (b) Phosphorescence intensity quenching of PdTPBP (10 μM) in the presence of different concentration of Py (compound 8), $\lambda_{ex}$=635 nm; (c) Stern-Volmer plots generated from the phosphorescence intensity quenching of PdTPBP as a function of Py (compound 8) concentration; (d) The upconversion emission spectra of PdTPBP and Py (compound 8) paired in the air, argon and in the absence of PdTPBP, $\lambda_{ex}$=650 nm, 100 mW/cm$^2$, in toluene.

Figure 10:
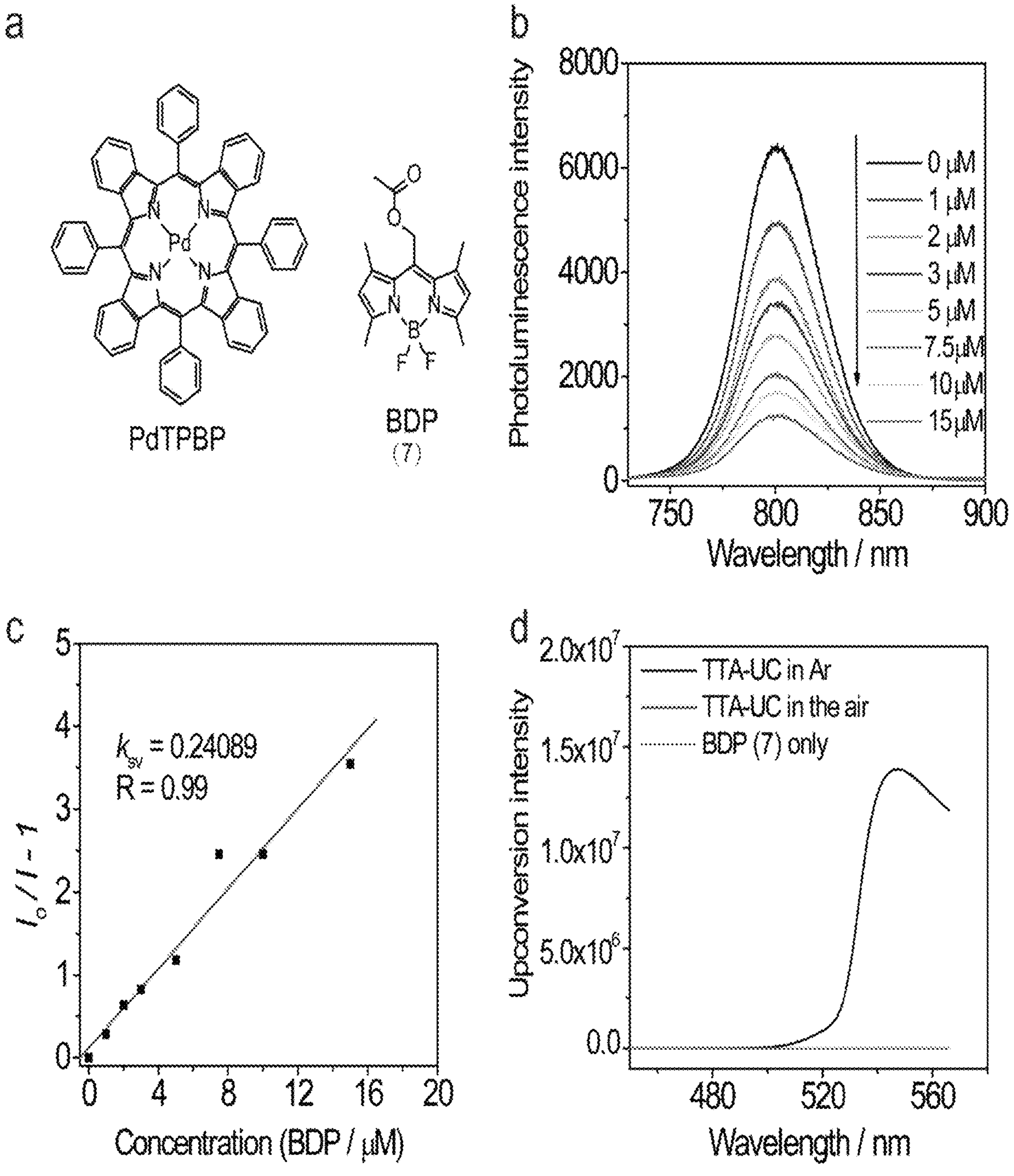
FIG. 10. (a) Molecular structure of PdTPBP and BDP (compound 7); (b) Phosphorescence intensity quenching of PdTPBP (10 μM) in the presence of different concentration of BDP (compound 7), $\lambda_{ex}$=635 nm; (c) Stern-Volmer plots generated from the phosphorescence intensity quenching of PdTPBP as a function of BDP (compound 7) concentration; (d) The upconversion emission spectra of PdTPBP and BDP (compound 7) paired in the air, argon and in the absence of PdTPBP, $\lambda_{ex}$=650 nm, 100 mW/$cm^2$, in toluene.

FIG. 10 shows (a) Molecular structure of PdTPBP and BDP (compound 7); (b) Phosphorescence intensity quenching of PdTPBP (10 M) in the presence of different concentration of BDP (compound 7), $\lambda_{ex}$=635 nm; (c) Stern-Volmer plots generated from the phosphorescence intensity quenching of PdTPBP as a function of BDP (compound 7) concentration; (d) The upconversion emission spectra of PdTPBP and BDP (compound 7) paired in the air, argon and in the absence of PdTPBP, $\lambda_{ex}$=650 nm, 100 mW/cm$^2$, in toluene.

TABLE 14

Photolytic reaction for PdTPBP and Py (compound 8)

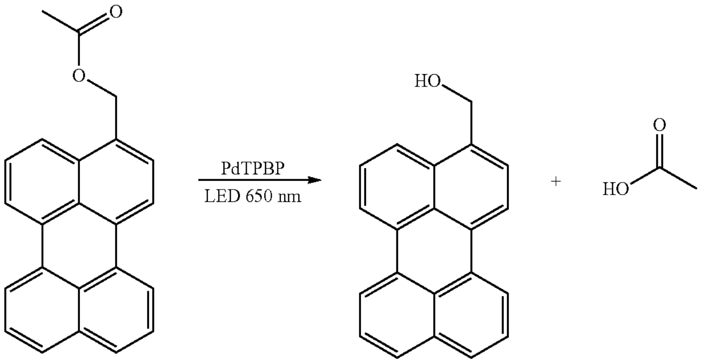

TABLE 14-continued

| Enter | Condition | Reaction time | Yield (%)[a] |
|---|---|---|---|
| 1 | Light, air | 1 h | No reaction |
| 2 | Dark, argon | 1 h | No reaction |
| 3 | Py (compound 8) only, light, argon | 1 h | No reaction |
| 4 | Light, argon | 1 h | 87.1 |

[a]HPLC.

TABLE 15

Photolytic reaction for PdTPBP and BDP (compound 7)

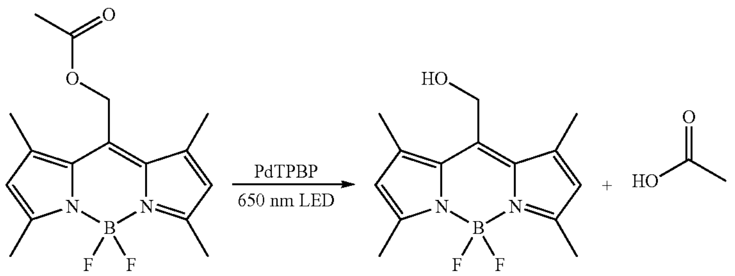

| Enter | Condition | Reaction time | Yield (%)[a] |
|---|---|---|---|
| 1 | Light, air | 1 h | No reaction |
| 2 | Dark, argon | 1 h | No reaction |
| 3 | BDP (compound 7) only, light, argon | 1 h | No reaction |
| 4 | Light, argon | 1 h | 76.0 |

[a]HPLC.

Section 7. TTAP Process of PtTNP:Py (Compound 8) and PtTNP:BDP (Compound 7).

Figure 11:
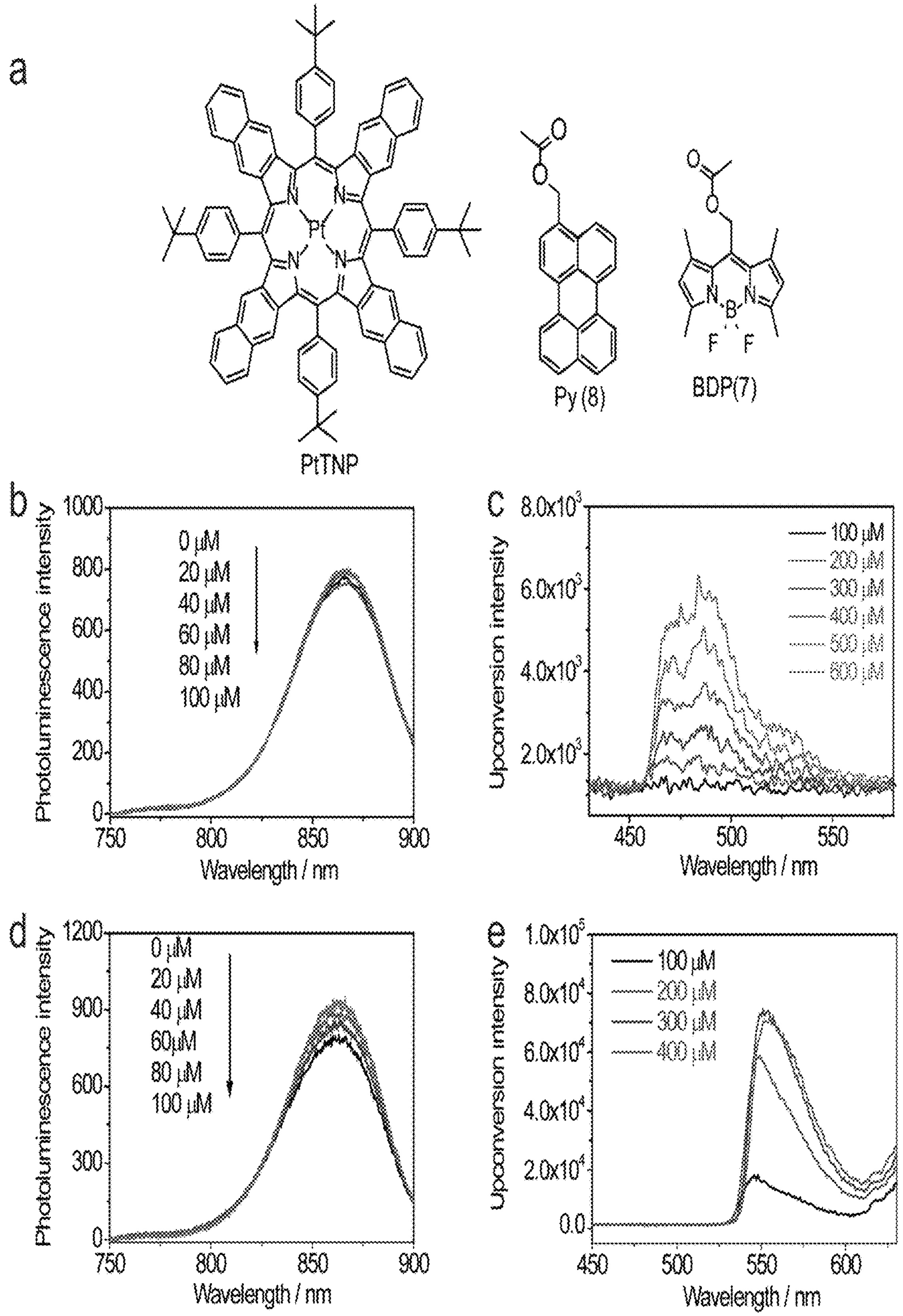
FIG. 11. (a) Molecular structure of PtTNP, Py (compound 8) and BDP (compound 7); (b) Phosphorescence intensity quenching of PtTNP (10 μM) in the presence of different concentration of Py (compound 8), $\lambda_{ex}$=700 nm; (c) The upconversion emission spectra of PtTNP and Py (compound 8) in the different concentration of Py (compound 8), $\lambda_{ex}$=720 nm, 100 mW/$cm^2$, in toluene; (d) Phosphorescence intensity quenching of PtTNP (10 M) in the presence of different concentration of BDP (compound 7), $\lambda_{ex}$=700 nm; (e) The upconversion emission spectra of PtTNP and BDP (compound 7) in the different concentration of BDP (compound 7), $\lambda_{ex}$=720 nm, 100 mW/$cm^2$, in toluene.

FIG. 11 shows (a) Molecular structure of PtTNP, Py (compound 8) and BDP (compound 7); (b) Phosphorescence intensity quenching of PtTNP (10 μM) in the presence of different concentration of Py (compound 8), $\lambda_{ex}$=700 nm; (c) The upconversion emission spectra of PtTNP and Py (compound 8) in the different concentration of Py (compound 8), $\lambda_{ex}$=720 nm, 100 mW/cm$^2$, in toluene; (d) Phosphorescence intensity quenching of PtTNP (10 μM) in the presence of different concentration of BDP (compound 7), $\lambda_{ex}$=700 nm; (e) The upconversion emission spectra of PtTNP and BDP (compound 7) in the different concentration of BDP (compound 7), $\lambda_{ex}$=720 nm, 100 mW/cm$^2$, in toluene.

TABLE 16

Photolytic reaction for PtTNP and Py (compound 8)

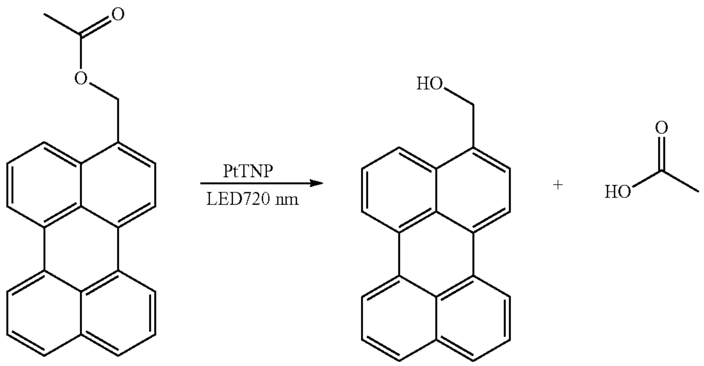

| Enter | Condition | Reaction time | Yield (%)[a] |
|---|---|---|---|
| 1 | Light, air | 1 h | No reaction |
| 2 | Dark, argon | 1 h | No reaction |
| 3 | Py (compound 8) only, light, argon | 1 h | No reaction |
| 4 | Light, argon | 1 h | 14.7 |

[a]HPLC.

TABLE 17

Photolytic reaction for PtTNP and BDP (compound 7)

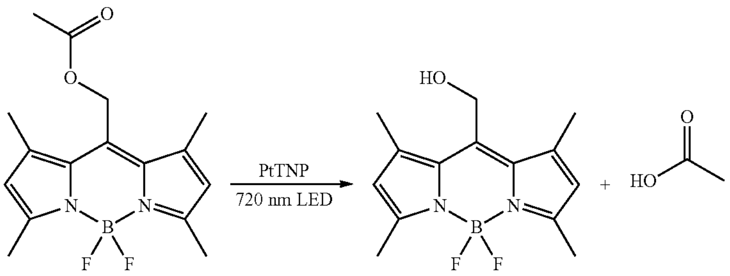

| Enter | Condition | Reaction time | Yield (%)[a] |
|---|---|---|---|
| 1 | Light, air | 1 h | No reaction |
| 2 | Dark, argon | 1 h | No reaction |
| 3 | BDP (compound 7) only, light, argon | 1 h | No reaction |
| 4 | Light, argon | 1 h | 17.7 |

[a]HPLC.

TABLE 18

Photolytic reaction for Py (compound 8) at room light and blue light illumination

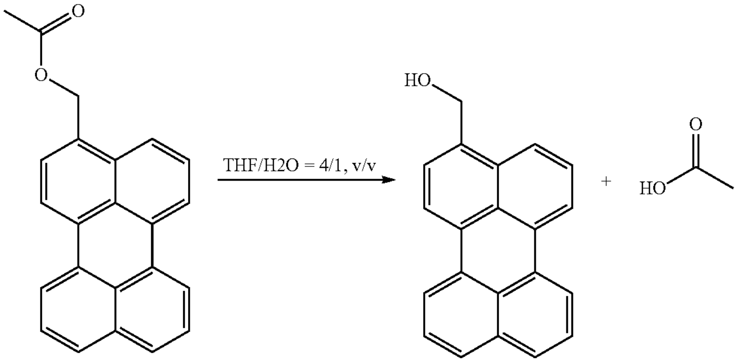

| Enter | Condition | Reaction time | Yield (%)[a] |
|---|---|---|---|
| 1 | Py (compound 8) only, air, dark | 60 min | No reaction |
| 2 | Py (compound 8) only, air, room light | 60 min | No reaction |
| 3 | PdTPBP, Py (compound 8), air, room light | 60 min | No reaction |
| 4 | PdTPBP, Py (compound 8), argon, room light | 60 min | No reaction |
| 5 | Py (compound 8) only, air, blue light (445 nm) | 60 min | 59.0 |

[a]HPLC yield.

Section 8. Photocleavage quantum yield calculation and $k_{sv}$ constants for TTAP systems

TABLE 19

The photocleavage quantum yield and $k_{sv}$ constants for TTAP systems

| | $\Phi_p$ [a] | $\varepsilon_1 \times \Phi_p$ [b] | $\varepsilon_2 \times \Phi_p$ [c] | $k_{sv}$ ($M^{-1}$) [d] | $k_{sv}$ ($M^{-1}S^{-1}$) [e] |
|---|---|---|---|---|---|
| BDP (compound 7) | $9.9 \times 10^{-4}$ [f] | 70 | 108.9 [g]/132.0[h] | $2.40 \times 10^5$ [g] | $1.08 \times 10^9$ [g] |
| Py (compound 8) | 0.093[i] | 3627 | 12400[h]<br>10230 [g]<br>6510 [j] | $2.43 \times 10^5$ [g]<br>$2.62 \times 10^5$ [j] | $1.09 \times 10^9$ [g]<br>$2.9 \times 10^9$ [j] |

TABLE 19-continued

The photocleavage quantum yield and $k_{sv}$ constants for TTAP systems

| | $\Phi_p$ [a] | $\varepsilon_1 \times \Phi_p$ [b] | $\varepsilon_2 \times \Phi_p$ [c] | $k_{sv}$ ($M^{-1}$) [d] | $k_{sv}$ ($M^{-1}S^{-1}$) [e] |
|---|---|---|---|---|---|
| An (compound 2) | 0.089[k] | 979 | 6230[j] | $2.19 \times 10^5$ [j] | $2.43 \times 10^9$ [j] |
| Cou (compound 1) | 0.13 [l] | 806 | 2210 [m] | $3.13 \times 10^3$ [m] | $2.34 \times 10^9$ [m] |

[a] photocleavage quantum yield;
[b] $\varepsilon_{(PPGs)} \times \Phi_{p\ (PPGs)}$;
[c] $\varepsilon_{(Sen)} \times \Phi_{p\ (PPGs)}$;
[d] Stern-Volmer quenching constant.
[e] bimolecular quenching constant, $k_{sv} = k_q \tau_T$;
[f] Goswami, et al. 2015 *J. Am. Chem. Soc.* 137, 3783;
[g] PdTPBP as sensitizer;
[h]PtTNP as photosensitizer;
[i]Jana, et al. 2012 *Tetrahedron*. 68, 1128;
[j] PtOEP as sensitizer;
[k]Atta, etal. 2013 Photochem. *Photobiol. Sci.* 12, 393;
[l] Klán, etal. 2013 *Chem. Rev.* 113, 119-191;
[m] Ir $(ppy)_3$ as sensitizer.

TABLE 20

Comparison of previous reported photolysis systems and our TTAP

| PPGs | Excitation intensity | $\lambda_{ex}$ | Photocleavage quantum yield | Overall photocleavage quantum yield |
|---|---|---|---|---|
| Perylene[1] | 110 mW/$cm^2$ Hg lamp | >410 nm | 0.093 | 3627 |
| Perylene[2] | 125 WHg lamp | ≥410 nm | 0.093 | 3627 |
| Coumarin[3] | One photon: 120 mW/$cm^2$; | $\lambda$ > 400 nm | 0.13 | 806 |
| Coumarin[3] | femtosecond laser ($10^6$ W) | $\lambda$ = 800 nm | | |
| Coumarin[4] | upconversion nanophosphors (UCNPs) as photo transducers, 570 mW $cm^{-2}$ | $\lambda$ = 980 nm | 0.13 | <0.02873 |
| Perylene | 20 mW/$cm^2$ | $\lambda$ = 650 nm | 0.093 | 12400 |

[1]Jana, et al. 2014 *ACS Nano*. 8, 5939;
[2]Jana, et al. 2012 *J. Am. Chem. Soc.* 134, 7656;
[3]Lin, et al. 2010 *J. Am. Chem. Soc.* 132, 10645;
[4]Zhao, et al. 2014 *Adv. Funct. Mater.* 24, 363.

We compared photolytic quantum efficiency of the widely used PPG of Cou by using the UCNPs as phototransducer. In the UCNPs-assist photolysis, the UV upconversion quantum yield is less than 0.1%. Moreover, the luminescence resonance energy transfer (LRET) efficiency is less than 10%) Therefore, these systems not only consider the (p of PPGs, but also the upconversion quantum yield and luminescence resonance energy transfer (LRET) as important in calculating the true $\Phi_p$ $$\eta(\text{upconversion})=\Phi_p \times \Phi_{uc} \times \Phi_{LRET} \lambda \varepsilon_{(PPG)}.$$

According to the reported results in the literature (Zhao, et al. 2014 *Adv. Funct. Mater.* 24, 363), we calculated overall photolysis quantum yield of Cou (note: other PPGs including Py, BDP and An have not been reported in the literature combination with UCNPs-assist photolysis). $\eta$ (upconversion)<0.13×0.001×0.1×6200=0.02873

Section 9. Photolytic Reaction for PdTPBP: Compound 19 and PtTNP: Compound 19.

TABLE 21

Photolytic reaction for PdTPBP: compound 19 under far red LED irradiation

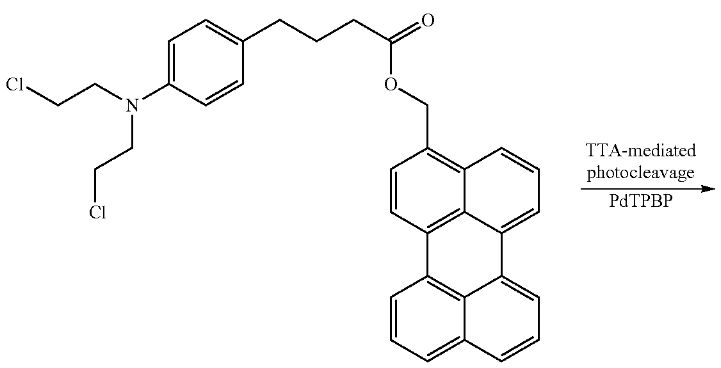

19

TABLE 21-continued

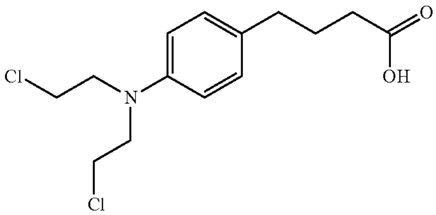

Chlorambucil

+

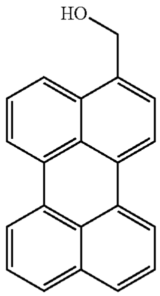

| Enter | Condition | Reaction time (h) | Yield[a] |
|---|---|---|---|
| 1 | Compound 19 only; red light; | 2 | No reaction |
| 2 | Compound 19 only; argon; red light; | 2 | No reaction |
| 3 | PdTPBP, compound 19; argon; red light; | 1 | 72.8 |
| 4 | PdTPBP, compound 19; argon; red light; | 2 | 67.0 |
| 5 | PdTPBP, compound 19; air, red light; | 2 | 7 |
| 6 | PdTPBP, compound 19; argon, dark; | 2 | No reaction |

[a]HPLC yield.

TABLE 22

Photolytic reaction for PtTNP: pro-chlorambucil under 720 nm LED irradiation

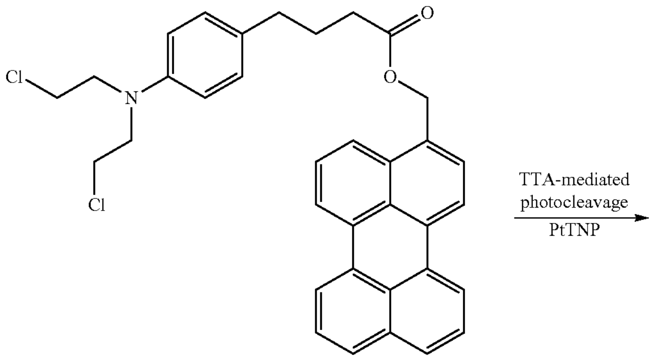

19

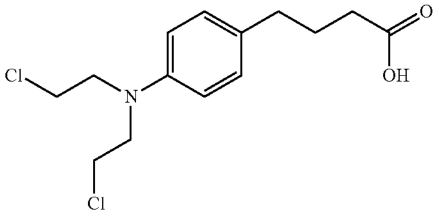

Chlorambucil

+

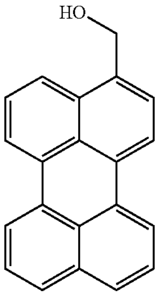

TABLE 22-continued

| Enter | Condition | Reaction time (h) | Yield[a] |
|---|---|---|---|
| 1 | Compound 19 only; 720 nm LED; | 1 | No reaction |
| 2 | Compound 19 only; argon; 720 nm LED; | 1 | No reaction |
| 3 | PtTNP, compound 19; argon; 720 nm LED; | 1 | 30.4 |
| 4 | PtTNP, compound 19; air, 720 nm LED; | 1 | No reaction |
| 6 | PtTNP, compound 19; argon, dark; | 1 | No reaction |

[a]HPLC yield.

Section 10. The Polymer of PSMA-PEG-OAm Reduce the Oxygen the TTAP Process.

Figure 12:
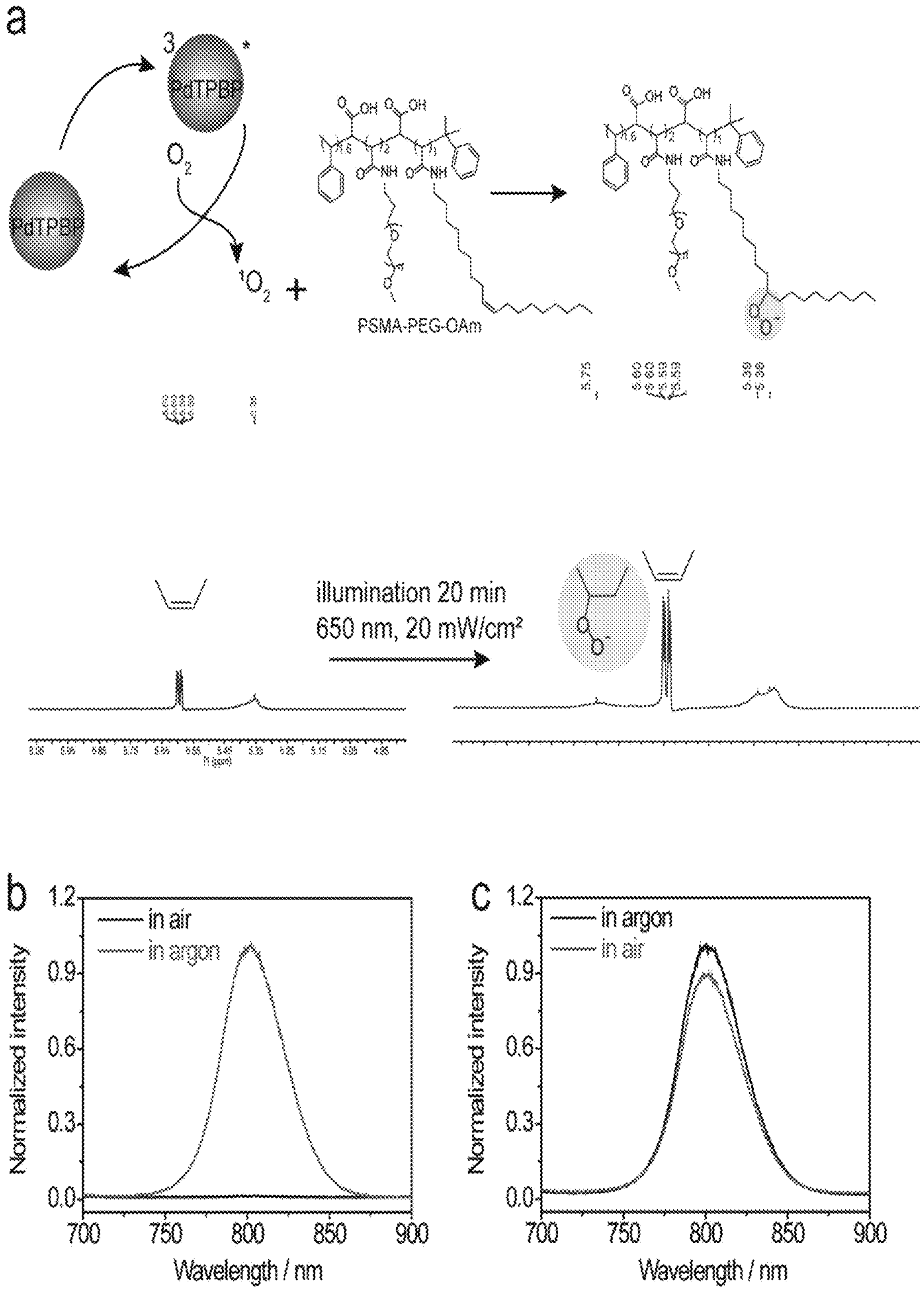
FIG. 12. (a) Up: A schematic diagram of the mechanism of PSMA-PEG-OAm scavenge oxygen and molecular structure of PSMA-PEG-OAm, bottom: $^1$HNMR monitor PSMA-PEG-OAm reacting with singlet oxygen. (b) the normalized phosphorescence spectra of PdTPBP in toluene, in air and in argon, $\lambda_{ex}$=630 nm; (c) The normalized phosphorescence spectra of PdTPBP NPs in PBS buffer, in air and in argon, $\lambda_{ex}$=630 nm.

FIG. 12 shows (a) Up: A schematic diagram of the mechanism of PSMA-PEG-OAm scavenge oxygen and molecular structure of PSMA-PEG-OAm, bottom: $^1$HNMR monitor PSMA-PEG-OAm reacting with singlet oxygen. (b) the normalized phosphorescence spectra of PdTPBP in toluene, in air and in argon, $\lambda_{ex}$=630 nm; (c) The normalized phosphorescence spectra of PdTPBP NPs in PBS buffer, in air and in argon, $\lambda_{ex}$=630 nm.

For the polymer PSMA-PEG-OAm, it is noteworthy that the hydrophilic properties of PEG and carboxylic acids of the polymer enhance the biocompatibility of the nanoparticle. The unsaturated alkene sidechains of such amphiphilic polymers act as active decoys to react with and exhaust the oxygen from the external environment (FIG. 12*a*). We determined the molecular structure change of PSMA-PEG-OAm under light irradiation by nuclear magnetic resonance (NMR). Along with the illumination, the photosensitizer converts di-oxygen into singlet oxygen, which reacts with unsaturated double bonds, thus generation new peaks at 5.75 ppm. (FIG. 12*a*). Moreover, since phosphorescence is extremely sensitive to di-oxygen, the phosphorescence of PdTPBP is further used to validate the oxygen scavenger role of PAA-OAm. (FIG. 12*b*) The phosphorescence of PSMA-PEG-OAm encased PdTPBP nanoparticles (PdTPBP NPs) was measured in air and argon. (FIG. 12*c*). The phosphorescence intensity in air was found to be quite similar to that under argon. These results demonstrated that PSMA-PEG-OAm can provide a hypoxia microenvironment to reduce oxygen quenching triplet state of PdTPBP.

Section 11. Preparation and Characterization of TTAP Nanoparticles.

Figure 84:
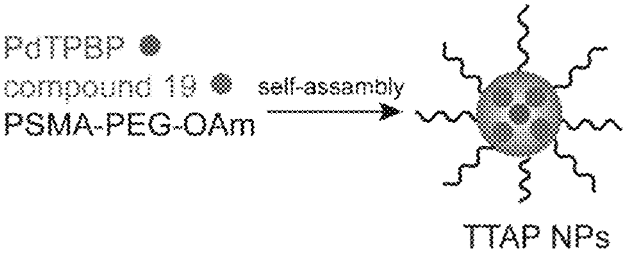
FIG. 84 shows a schematic of preparation of a nanoparticle.

Preparation of TTAP NPs. As schematically illustrated in FIG. 84, TTAP NPs was prepared via self-assembly of PdTPBP and compound 19, and PSMA-PEG-OAm with a single-step. Briefly, 0.25 mg PdTPBP, 20 mg compound 19, and 100 mg PSMA-PEG-OAm were dissolved in 8 mL THF. The mixture was added to 10 mL PBS buffer. The mixture solution was stirred at 40° C. in dark for 30 min to let THF remove out. In order to let the absolutely remove out the THF, we used the air flow to accelerates THF evaporation at 40° C. for 30 min. Afterward, the TTAP NPs was centrifuged at 6000×g for 60 min. large nanoparticles precipitated and the supernatant containing small nanoparticles was decanted. And then the TTAP NPs solution was purified by dialysis tube (cut off M, =3500). Finally, TTA NPs was stored at 4° C. until use. Similar procedures were used to prepare the PdTPBP nanoparticles (PdTPBP NPs) and Py nanoparticles (Py NPs).

The entrapment efficiency (%) was calculated by collecting UV-vis absorption spectra using a molar absorption coefficient of 40000 $M^{-1}$ $cm^{-1}$ with $\lambda_{max}$, =449 nm for compound 19. Firstly, the TTAP NPs was dissolved in THF/water=1/1, v/v and tested the UV-vis absorption spectra, according to the molar absorption coefficient of compound 19, the concentration of compound 19 was calculated in TTAP NPs.

The entrapment efficiency (%) was calculated using the following equation:

Entrapment efficiency (%)=absorption of the loaded prodrug/absorption initial of the prodrug×100%.

The entrapment efficiency of prodrug is 89%.

According the entrapment efficiency of prodrug, the mass of prodrug was calculated in TTAP NPs. And then the TTAP NPs was dried by lyophilization and weight the mass of TTAP NPs. The prodrug loading efficiency (%)=the mass of prodrug in TTAP NPs/total mass of TTAP NPs×100%.

The prodrug loading efficiency of prodrug is up to 16%.

Figure 13:
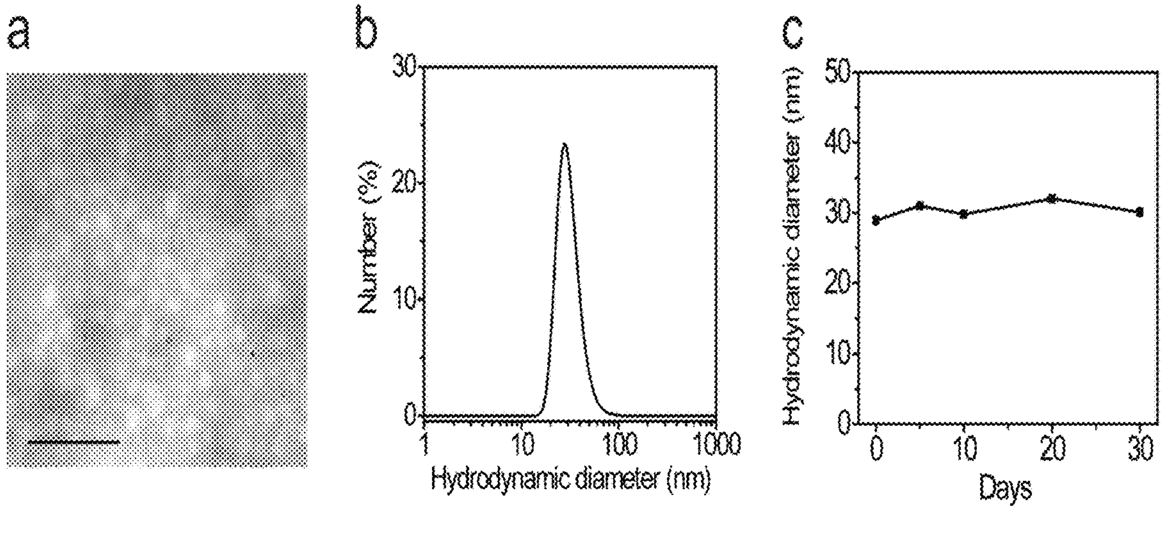
FIG. 13. (a) TEM imaging of TTAP NPs, scar bar is 100 nm; (b) hydrodynamic diameter of TTAP NPs in PBS via DLS; (c) colloidal storage stability of TTAP NPs in PBS.

FIG. 13 shows (a) TEM imaging of TTAP NPs, scar bar is 100 nm; (b) hydrodynamic diameter of TTAP NPs in PBS via DLS; (c) colloidal storage stability of TTAP NPs in PBS.

Section 12. Photolytic Reaction in TTAP NPs Under 650 nm LED Irradiation.

Far red LED photocleave drug release of TTAP NPs in solution. We found that the fluorescence of compound 19 reduced along with compound 19 photoactivation process at 487 nm. Based on the property, the photocleavage chlorambucil releasing process also was monitored by measured the fluorescence spectra of compound 19. In addition, we also utilized HPLC to monitor the photo-cleave pro-chlorambucil process.

Figure 14:
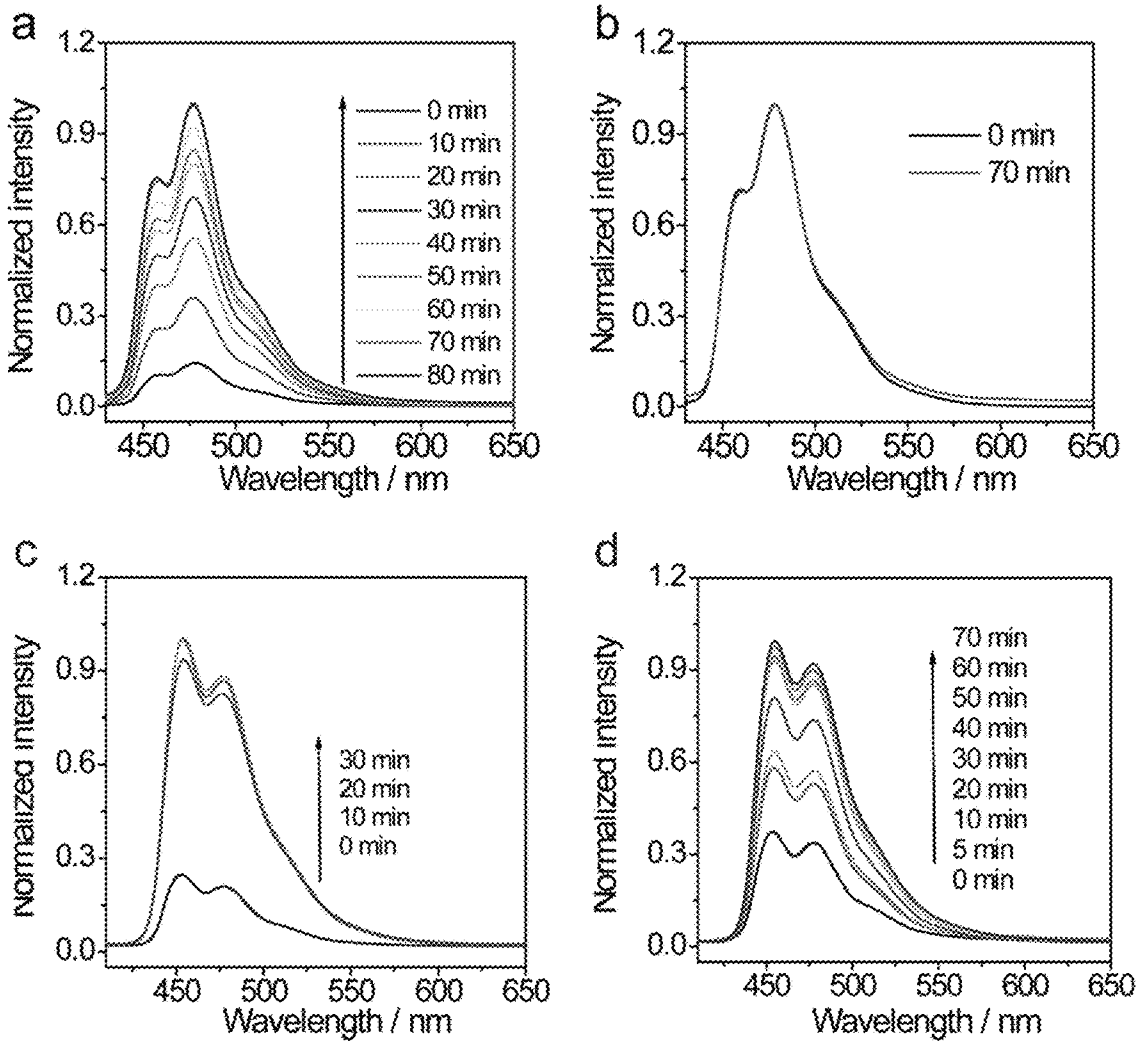
FIG. 14. (a) Blue light mediated photolytic reaction (455 nm LED, 20 mW/$cm^2$) for Py NPs; (b) Far red light mediated photolytic reaction (650 nm LED, 20 mW/$cm^2$) for Py NPs; (c) Far red light mediated photolytic reaction (650 nm laser, 100 mW/$cm^2$) for TTAP NPs; (d) Far red light mediated photolytic reaction (650 nm LED, 20 mW/$cm^2$) for TTAP NPs.

FIG. 14 shows (a) Blue light mediated photolytic reaction (455 nm LED, 20 mW/$cm^2$) for Py NPs; (b) Far red light mediated photolytic reaction (650 nm LED, 20 mW/$cm^2$) for Py NPs; (c) Far red light mediated photolytic reaction (650 nm laser, 100 mW/$cm^2$) for TTAP NPs; (d) Far red light mediated photolytic reaction (650 nm LED, 20 mW/$cm^2$) for TTAP NPs.

As shown in FIG. 14*b*, A similar nanoparticle consisting of the prodrug (compound 19) without the PdTPBP (Py NPs) was prepared as a stringent control. Upon 650 nm illumination of Py NPs for 60 min, no observable uncaged chlorambucil was detected, excluding the possibility of the direct uncaging of chlorambucil by 650 nm light. However, after uncaging via long wavelength light for TTAP NPs, after uncaging, the prodrug (compound 19) is able to convert into hydrophilic chlorambucil, which can be released from the nanoparticles and kill tumor cells. When we illuminated TTAP NPs with a 650 nm light emitting diode (LED; 20 mWcm$^2$), we found that the prodrug was uncaged, resulting in greater than 48% activation of the prodrug within 30 min, and a maximum photo-release of approximately 64% of the prodrug after 60 min (FIG. 14*b-c*, 15*a*).

Figure 15:
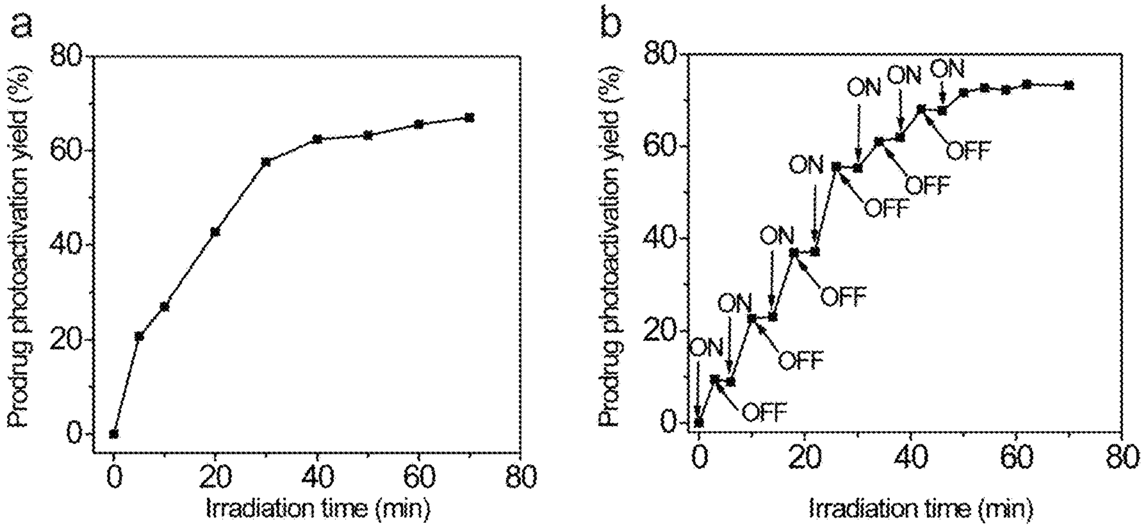
FIG. 15. (a) The release profiles of chlorambucil from TTAP NPs in PBS buffer with 650 nm LED irradiation, 20 mW/$cm^2$. (b) The photolytic process for compound 19 from TTAP NPs with 650 nm LED irradiation. "ON" and "OFF" indicate the initiation and termination of LED irradiation, respectively; the LED (650 nm, 20 mW/$cm^2$).

FIG. 15 shows (a) The release profiles of chlorambucil from TTAP NPs in PBS buffer with 650 nm LED irradiation, 20 mW/$cm^2$. (b) The photolytic process for compound 19 from TTAP NPs with 650 nm LED irradiation. "ON" and "OFF" indicate the initiation and termination of LED irradiation, respectively; the LED (650 nm, 20 $mW/cm^2$).

Section 13. In Vitro Experiments for TTAP NPs.

(1) Cell culture. Human cervical carcinoma (HeLa cell lines) and mice breast cancer cells (4T1 cell lines) were cultured in Dulbecco's modified Eagle's medium (DMEM) containing 10% fetal bovine serum (FBS), 100 μg $mL^{-1}$ streptomycin and 100 U $mL^{-1}$ penicillin at 37° C. in a humidified incubator containing 5% $CO_2$ and 95% air. The medium was replenished every other day and the cells were subcultured after reaching confluence.

(2) Cell viability assay: Cell viability was verified by MTT assay. HeLa and 4T1 cell lines were used. Firstly, the cells (100 μL, 5000) were plated in a 96-well plate. After 12 h, the nanoparticles were added at different concentrations (0, 5, 10, 15, 20, 25 μg $mL^{-1}$). The nanoparticles were taken up over 12 h. The cells were irradiated with far red LED light (650 nm, 20 mW $cm^2$). After 30 min irradiation, the cells were incubated another 24 h under 5% $CO_2$ atmosphere at 37° C. MTT solution (5.0 mg $mL^{-1}$, 50 μL) was added to every well and left for 4 h. The old cell culture medium was removed carefully and 200 μL DMSO was added to every well. A microplate reader (Bio-Rad) was used to record the absorption at 595 nm.

Cell viability (%)=OD value test/OD value control×100%.

Figure 16:
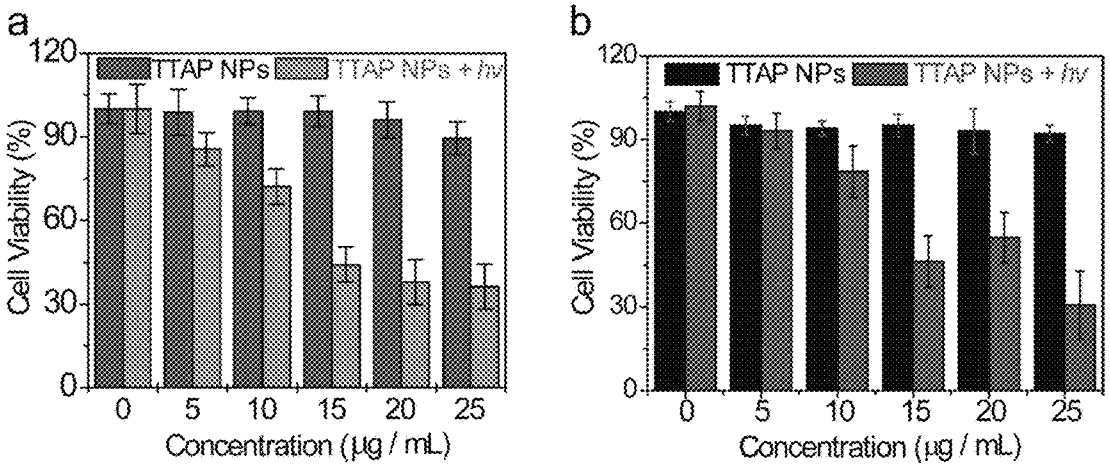
FIG. 16. (a) MTT assay of Hela cells viability of different concentrations of TTAP NPs and TTAP NPs+hv. (b) 4T1 cell viability in different concentrations of TTAP NPs with and without light irradiation.

FIG. 16 shows (a) MTT assay of Hela cells viability of different concentrations of TTAP NPs and TTAP NPs+hv. (b) 4T1 cell viability in different concentrations of TTAP NPs with and without light irradiation.

FIG. 17 shows Hela cell viability in different concentrations of PdTPBP NPs with and without light irradiation.

Section 14. In Vivo Anti-Tumor Immunotherapy Via Combination TTAP NPs and α-PD-L1.

(1) In vivo studies of combination TTAP NPs mediated phototherapeutic with check-point blockade metastasis immunotherapy in 4T1 tumor bearing mice: the 5 week's BALB/c female mice order from Jackson lab. The 4T1 cells ($2\times10^6$) was seeded at mice right back and the left mice back seeded the 4T1 cells ($2\times10^5$), waiting for the right side tumor volume reached to 100 $mm^3$, the 4T1 bearing mice were subjected to six different treatments: (1) PBS+hv; (2) PdTPBP+hv; (3) α-PD-L1 only; (4) TTAP NPs+dark; (5) TTAP NPs+hv; (6) TTAP+hv+α–PD-L1. The TTAP NPs (1 mg/mL, 100 μL) or PdTPBP NPs (10 μg/mL, 100 μL) was intratumorally injected in right side tumor in group 2, 4-6 groups. After 4 hours, the right tumor site was exposed to far red LED (650 un) for 30 mins. The α-PD-L1 (75 μg per mouse) was injected by intraperitoneal during 7-9 day in group 3 and 6. After 15 days treatment, the mice were euthanized and spleen, right and left tumor tissue was isolated to analysis the immunity responses. Different treatment groups were monitored by measuring the right and left tumor size using a Vernier caliper for 15 d. Tumor size=width×width×length/2.

In group 1 (PBS+hv), we did not observe tumor growth inhibition; after 15 days, the tumor volume increased 7.5-fold. This result indicated that low power intensity far red light did not have obvious photothermal effects in regard to cancer therapy. In group 2 (PdTPBP NPs+hv), the tumor volume also increased 6.5-fold and we did not observe significant tumor growth inhibition by PdTPBP NPs. This is likely due to the presence of an unsaturated bond on these nanoparticles that can exhaust singlet oxygen to reduce the possible photodynamic effect. In group 4 (TTAP NPs only), the tumor volume also increased 7.0-fold, indicating a low inherent toxicity of TTAP NPs in the dark. However, in group 5 (TTAP NPs+hv), the tumor volume only increased 3.9-fold. These results demonstrated that the anticancer drug was efficiently photolyzed and released for tumor cell killing. In group 3, the injection of α-PD-L1 also led to tumor growth inhibition; a result that is consistent with previously reported results. In contrast, in group 6, the tumor showed a slow growth rate from days 1 to 6, but post α-PD-L1 injection at $7^{th}$, $8^{th}$ and $9^{th}$ day, the tumor volume was remarkably suppressed. More significantly, we also measured the left tumor growth rates. In groups 1, 2, and 4, we did not observe tumor inhibition. In group 3, the tumor presented a slower tumor growth rate than seen in group 1, as α-PD-L1 can mitigate the metastasis. However, compared to group 5, group 6 presented significant tumor suppression. (FIG. 3*b*.) We also measured tumor weight after 15 treatments. In group 6, both the right and left tumor showed obvious reduction. (FIG. 3*d*.) These experimental results clearly demonstrated that the TTABP mediated prodrug photolytic system improves the checkpoint blockade immunotherapy efficacy and promotes abscopal effects.

(2) Flow cytometry test the immune cells in the right and left tumor tissue: The tumor (right and left side) were isolated from the mice after different treatments. The tumor tissue was divided into small pieces, treated with 1 mg $ml^{-1}$ collagenase I (Gibco) for 1 h at 37° C. and ground using the rubber end of a syringe (BD, 10 mL syringe). Cells were filtered through nylon mesh filters (Coming, cell strainer, 70 μm nylon). The single cells were collected by centrifugation (800×g, 5 min), the blood cells in the tumor tissue was eliminated by cold $NH_4Cl$ lysis. The single suspensions tumor cells were washed by cold PBS containing 2% FBS. The tumor cells were stained with fluorescence-labeled antibodies PerCP-Cy™5.5 Hamster Anti-Mouse TCR β chain (BD bioscience, clone H57-597, catalog No. 560657), PerCP-Cy™5.5 Rat Anti-Mouse CD3 Molecular Complex Clone (BD bioscience, catalog No. 560527), Pacific Blue™ Rat Anti-Mouse CD45R (clone RA3-6B2, BD bioscience, catalog No. 558108), PE-Cy™7 Rat Anti-Mouse CD4 (Clone GK1.5, BD bioscience, catalog No. 563933), PE Rat Anti-Mouse CD8a (Clone 53-6.7, BD bioscience, catalog No. 553032), APC Mouse Anti-Mouse NK-1.1 (Clone PK136, BD biosciences, catalog No.561117), FITC Rat Anti-Mouse CD44 (Clone IM7, BD biosciences, catalog No. 561859), APC-Cy™7 Rat Anti-Mouse CD62L (Clone MEL-14, BD biosciences, catalog No. 560514) following the manufacturer's instructions. All antibodies were diluted 200 times. Flow cytometric analyses were performed on an LSRFortessa (BD Biosciences) and analyzed using FlowJo Software (Tree Star).

(3) Flow cytometry test the immune cells in the spleen: The spleens were isolated from the mice after different treatments. We grinded the spleen and cells were filtered by nylon mesh filters. The blood cells were lysis by twice NH4Cl solution, and then washed cold PBS containing 2% FBS. The single cells were collected by centrifugation (800×g, 5 min), the blood cells in the tumor tissue was eliminated by cold $NH_4Cl$ lysis. The cells were incubated with 50 ng/ml PMA (Sigma) and 500 ng/ml ionomycin (Sigma) in the presence of GolgiStop (BD) in complete T cell media at 37° C. for 4 h. Cells were washed with PBS buffer containing, stained with Live/Dead fixable aqua dead cell marker (Invitrogen). The following antibodies were used for staining: PerCP-Cy™5.5 Hamster Anti-Mouse TCR β chain (BD bioscience, clone H57-597, catalog No. 560657), PerCP-Cy™5.5 Rat Anti-Mouse CD3 Molecular Complex Clone (BD bioscience, catalog No. 560527), Pacific Blue™ Rat Anti-Mouse CD45R (clone RA3-6B2, BD bioscience, catalog No. 558108), PE-Cy™7 Rat Anti-Mouse CD4 (Clone GK1.5, BD bioscience, catalog No. 563933), PE Rat Anti-Mouse CD8a (Clone 53-6.7, BD bioscience, catalog No. 553032), APC Mouse Anti-Mouse NK-1.1 (Clone PK136, BD biosciences, catalog No. 561117). Intracellular staining for FITC Rat Anti-Mouse IFN-γ (Clone XMG1.2, BD biosciences, catalog No. 562019). Intracellular cytokine staining was performed by fixing cells in 2% paraformaldehyde, followed by permeabilization and staining (BD Biosciences). Flow cytometric analyses were performed on an LSRFortessa (BD Biosciences) and analyzed using FlowJo Software (Tree Star).

Statistical analyses: The results are showed as the mean L standard error of the mean (s.e.m.), Moreover, Student's t-test was used for two-group comparisons. The Origin 9.0 was used to all statistical analyses. The threshold for statistical significance was *p<0.001, p<0.01, or *p<0.05.

Figure 18:
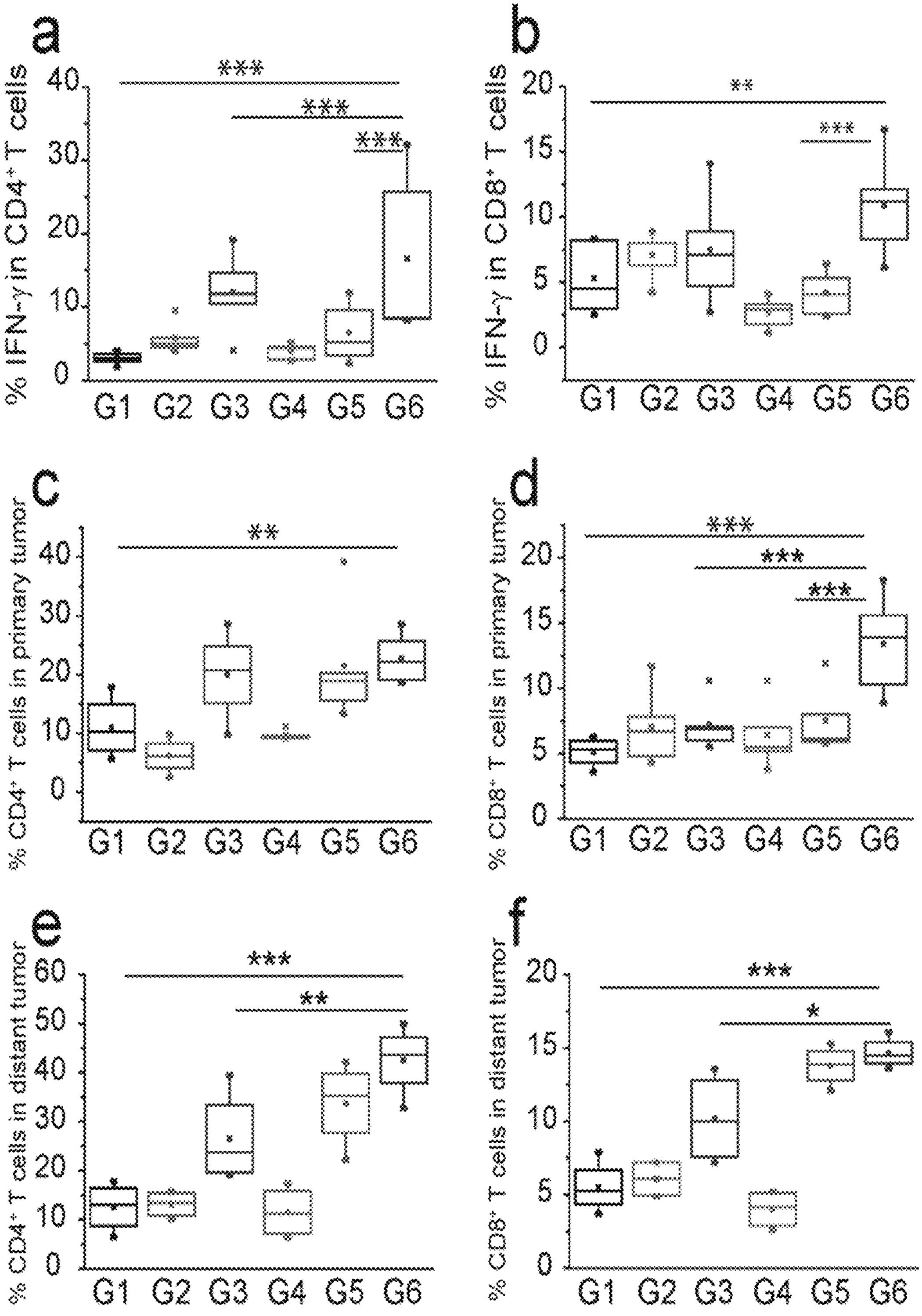
FIG. 18. Tumor-specific immune responses. (a-b) Splenocytes were stimulated for 4 h with PMA/ionomycin, the frequency of IFN-γ-producing $CD4^+$ and $CD8^+$ T cells was measured by flow cytometry. (c-d) the percentage of tumor-infiltrating (c) $CD4^+$ T cells, (d) $CD8^+$ T cells in the primary tumor. (e-f) the percentage of tumor-infiltrating (e) $CD4^+$ T cells, (f) $CD8^+$ T cells in the distant tumor. Data are expressed as means ±s.d. (n=5). *P<0.05, P<0.01, and *P<0.001.

FIG. 18 shows Tumor-specific immune responses. (a-b) Splenocytes were stimulated for 4 h with PMA/ionomycin, the frequency of IFN-γ-producing $CD4^+$ and $CD8^+$ T cells was measured by flow cytometry. (c-d) the percentage of tumor-infiltrating (c) $CD4^+$ T cells, (d) $CD8^+$ T cells in the primary tumor. (e-f) the percentage of tumor-infiltrating (e) $CD4^+$ T cells, (f) $CD8^+$ T cells in the distant tumor. Data are expressed as means ±s.d. (n=5). *P<0.05, P<0.01, and *P<0.001.

Figure 19:
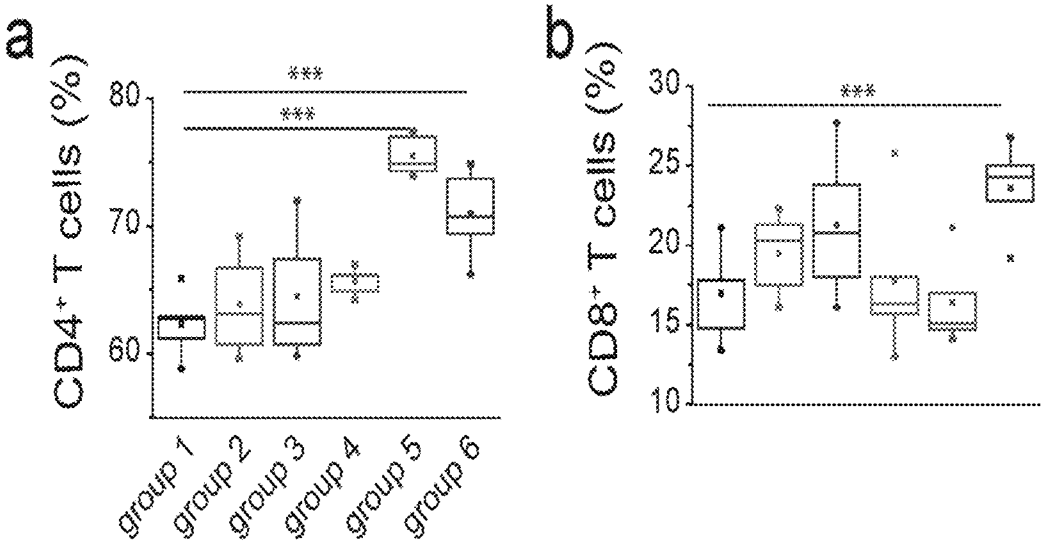
FIG. 19. (a) The percentage of tumor-infiltrating (a) $CD4^+$ T cells (b), $CD8^+$ T cells in the spleen. Data are expressed as means±s.d. (n=5). *P<0.05, P<0.01, and P<0.001.

FIG. 19 shows (a) The percentage of tumor-infiltrating (a) $CD4^+$ T cells (b), $CD8^+$ T cells in the spleen. Data are expressed as means±s.d. (n=5). *P<0.05, P<0.01, and *P<0.001.

Figure 20:
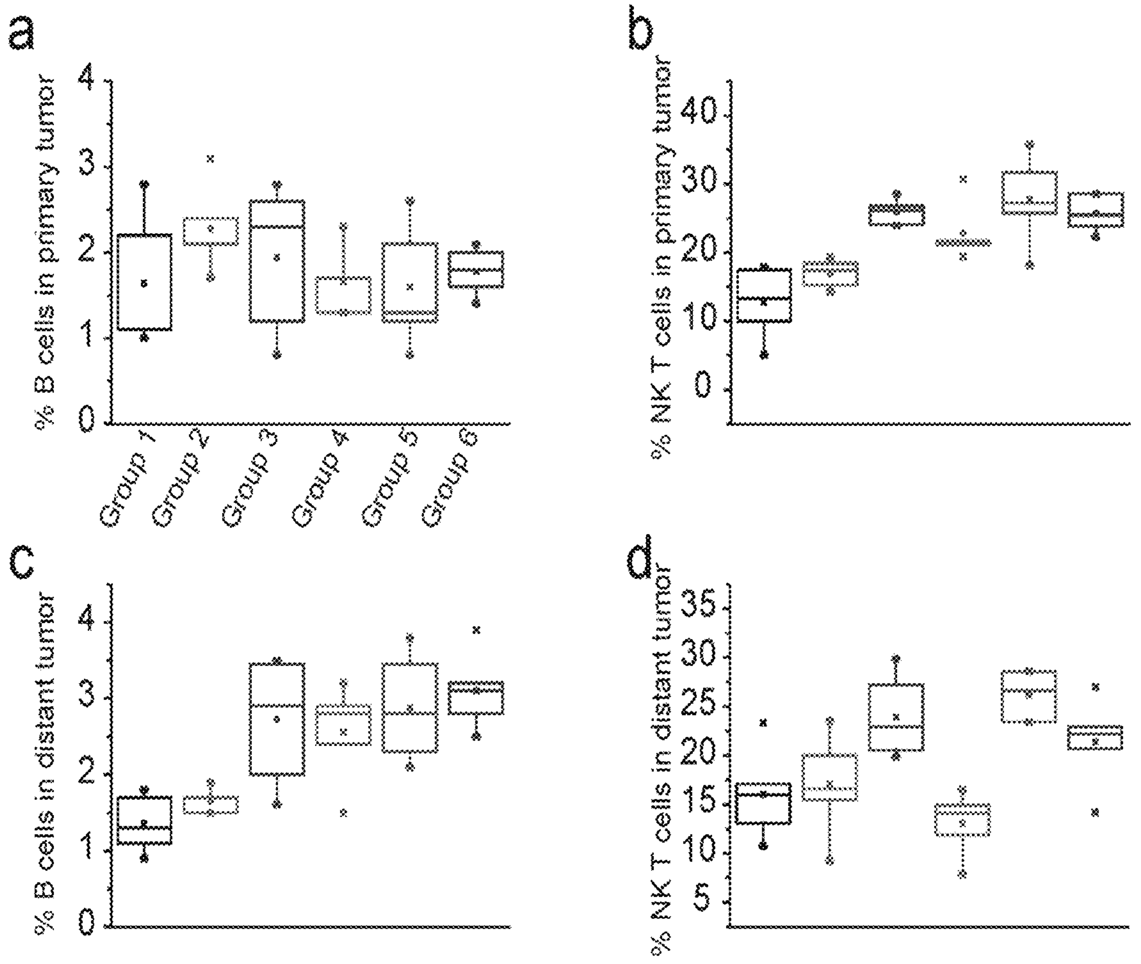
FIG. 20. the percentage of tumor-infiltrating (a) B cells, (b) NK T cells in the primary tumor. (c) B cells, (d) NK T cells in the distant tumor. Data are expressed as means±s.d. (n=5).

FIG. 20 shows the percentage of tumor-infiltrating (a) B cells, (b) NK T cells in the primary tumor. (c) B cells, (d) NK T cells in the distant tumor. Data are expressed as means±s.d. (n=5).

Section 15. In Vivo Study the Toxicity of TTAP NPs and Biosafe.

(1) Pathological section to explore the toxicity of TTAP NPs to major organs: On the 14th day after injection of TTAP NPs, mice were sacrificed major organs (heart, liver, spleen, lung, and kidney) were dissected for H&E staining.

(2) Blood biochemistry and complete blood panel analysis: The Balb/c mice were i.v.-injected with TTAP (100 μg $mL^{-1}$, 150 μL) and then sacrificed at the various time points (3, 6, 12, 24, 48, 96 hour) after injection. Another four Balb/c mice were used as the control. Before the mice were euthanatized, blood samples (~0.5 mL) were collected for blood panel analyses and blood chemistry tests.

Figure 21:
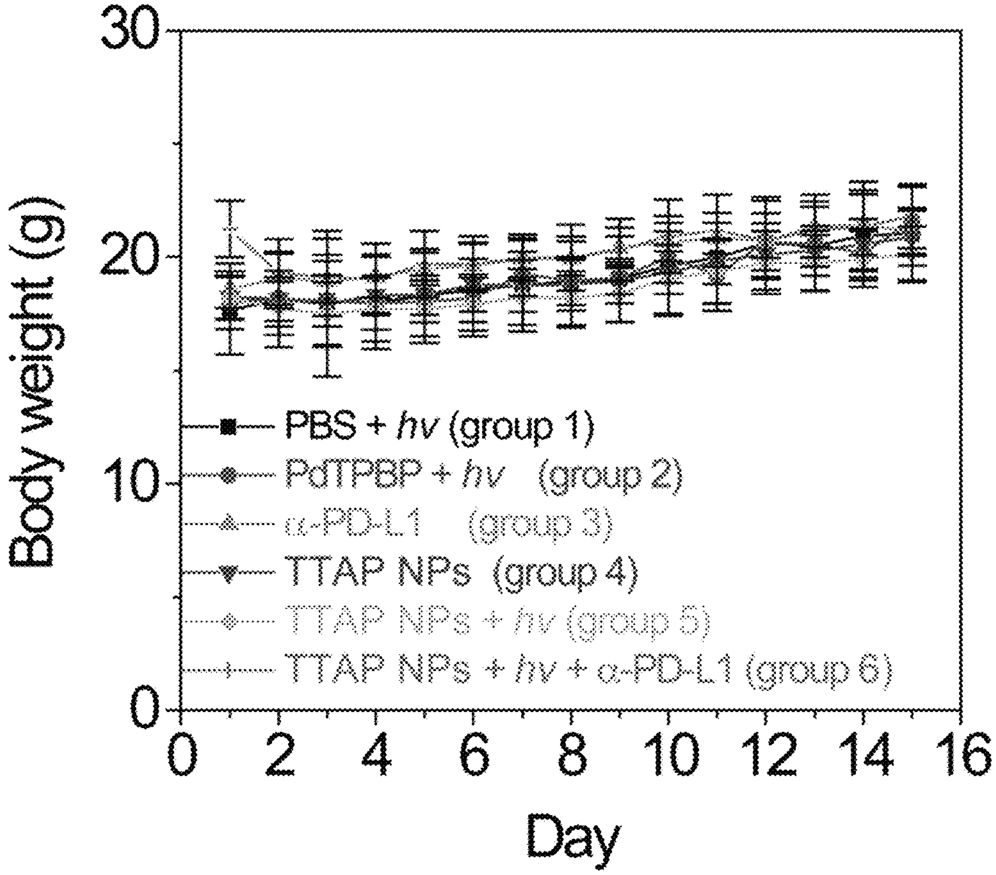
FIG. 21. The mice body weight change of anti-tumor immunotherapy model.

FIG. 21 shows the mice body weight change of anti-tumor immunotherapy model.

Figure 22:
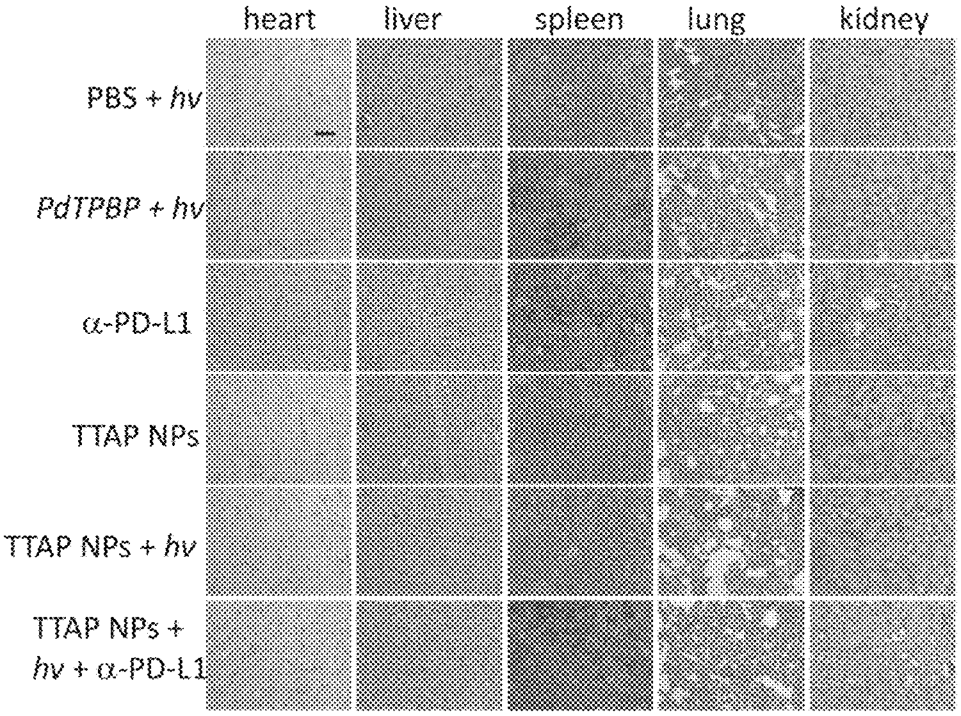
FIG. 22. H&E staining images of major organs (heart, liver, spleen, lung and kidney) of 4T1 tumor bearing mice, scale bar represents 100 μm.

FIG. 22 shows H&E staining images of major organs (heart, liver, spleen, lung and kidney) of 4T1 tumor bearing mice, scale bar represents 100 μm.

TABLE 23

Blood biochemistry and complete blood panel analysis of mice

| | Normal range | Control | 3 h | 6 h | 12 h | 24 h | 48 h | 96 h |
|---|---|---|---|---|---|---|---|---|
| WBC (K/μL) | 1.8-10.7 | 6.42 | 9.78 | 10.08 | 8.90 | 6.22 | 6.04 | 6.4 |
| NE (K/μL) | 0.1-2.4 | 2.29 | 2.00 | 2.07 | 1.46 | 2.27 | 1.6 | 0.12 |
| LY (K/μL) | 0.9-9.3 | 3.59 | 6.55 | 6.70 | 4.82 | 3.38 | 4.08 | 4.0 |
| MO (K/μL) | 0.0-0.4 | 0.39 | 0.16 | 0.28 | 0.38 | 0.28 | 0.27 | 0.02 |
| EO (K/μL) | 0.0-0.2 | 0.11 | 0.05 | 0.02 | 0.18 | 0.08 | 0.07 | 0.01 |
| BA (K/μL) | 0.0-0.2 | 0.02 | 0.01 | 0.01 | 0.06 | 0.01 | 0.01 | 0.02 |
| RBC (M/μL) | 6.36-9.42 | 8.83 | 9.31 | 8.90 | 8.95 | 9.36 | 9.07 | 8.76 |
| HGB (g/dL) | 11.0-15.1 | 13.3 | 13.5 | 13.7 | 13.6 | 13.6 | 12.8 | 13.1 |
| HCT (%) | 35.1-45.4 | 44.1 | 40.6 | 45.1 | 43.7 | 41.3 | 38.7 | 36.3 |
| MCV (fL) | 45.4-60.3 | 55.0 | 54.4 | 55.7 | 54.0 | 54.8 | 53.7 | 53.8 |
| MCH (pg) | 14.1-19.3 | 14.5 | 14.5 | 16.8 | 17.7 | 14.5 | 14.1 | 14.6 |
| MCHC (K/μL) | 30.2-34.2 | 31.6 | 31.7 | 32.9 | 33.3 | 32.5 | 32.2 | 30.2 |
| RDW (K/μL) | 12.4-27.0 | 16.8 | 18.3 | 17.2 | 17.7 | 16.8 | 17.5 | 17.4 |
| PLT (K/μL) | 592-2972 | 630 | 669 | 649 | 743 | 605 | 671 | 778 |
| MPV (fL) | 5.0-20.0 | 5.6 | 6.1 | 6.2 | 5.3 | 5.6 | 5.7 | 6.2 |

White blood cell (WBC), Neutrophils (NE), Lymphocytes (LY), Monocytes (MO), Eosinophils (EO), Basophils (BA), Red blood cell (RBC), Hemoglobin (HGB), Hematocrit (HCT), Mean corpuscular volume (MCV), Mean corpuscular hemoglobin (MCH), Mean corpuscular hemoglobin concentration (MCHC), Red blood cell distribution width (RDW), Platelet Thrombocyte (PLT), Mean platelet volume (MPV).

Figure 85:
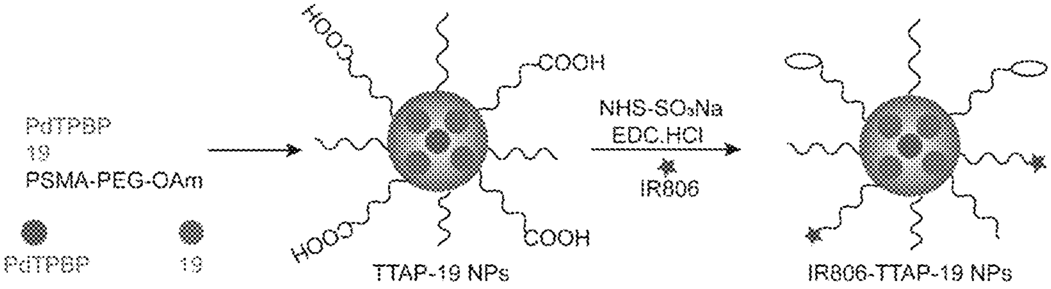
FIG. 85 shows a schematic of preparation of a nanoparticle.

Preparation of IR806-TTAP NPs. As schematically illustrated in FIG. 85, 5 mL TTAP NPs in PBS buffer, 10 mg sodium sulfonate N-hydroxysuccinimide ($NHS{\cdot}SO_3Na$) and 10 mg N-(3-dimethylaminopropyl)-N'-ethylcarbodiimide hydrochloride (EDC.HCl) were added to the nanoparticle solution and the mixture was then stirred at room temperature for 5 hours. After that the amine substituted IR806 (0.5 mg) was added into the mixture, and stirred for another 24 hours. Finally, the nanoparticles were purified by dialysis ($M_r$=12000).

Body clearance of TTA NPs: IR806-TTAP NPs were studied in $4T_1$ tumor-bearing mice. They were subjected to the following treatments: group 1, intravenous injection of IR806-TTAP NPs (150 μL, 100 μg mL-1); group 2, intravenous injection of PBS. We collect the mice fences during 48 hours, and then measured the fluorescence of IR806 with IVS animal imaging. Excitation filter was ICG (750-790 nm) and emission filter was ICG (815-850 nm).

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A compound having the formula,

PPG-X, wherein

PPG is a photoremovable protecting group comprising a moiety selected from the group consisting of coumarin, anthracene, perylene and boron-dipyrromethene; and X is L-Y, wherein L is a photolabile linker comprising an ester, carbonate, carbamate, quaternary ammonium salt moiety and Y a therapeutic moiety.

2. The compound of claim 1, wherein the PPG comprises a perylene.

3. The compound of claim 1, wherein the PPG comprises a coumarin thereof.

4. The compound of claim 1, wherein the PPG comprises an anthracene thereof.

5. The compound of claim 1, wherein L comprises an ester moiety.

6. The compound of claim 1, wherein Y is an anti-nonsteroidal or anti-inflammatory agent.

7. A pharmaceutical composition comprising a compound of claim 1.

8. Alight-activatable prodrug having the structure

PPG-X, wherein

PPG is a photoremovable protecting group comprising a moiety selected from the group consisting of coumarin, anthracene, perylene and boron-dipyrromethene; and X is L-Y, wherein L is a photolabile linker comprising an ester, carbonate, carbamate, quaternary ammonium salt moiety and Y an amino acid or peptide moiety.

9. The light-activatable prodrug of claim 8, wherein Y is an amino acid moiety.

10. The light-activatable prodrug of claim 8, wherein Y is a peptide moiety.

11. A pharmaceutical composition comprising a light-activatable prodrug of claim 8.

12. A composition comprising a pair of a photosensitizer and a photolytic compound, wherein the photosensitizer and the photolytic compound are selected as follows:

the photosensitizer is capable of light absorption of single low energy photon in the range of about 400 nm to about 1,000 nm thereby reaching a singlet excited state and subsequently generating a photosensitizer triplet excited state through rapid intersystem crossing; and the triplet excited state is characterized by a lifetime sufficient to allow collision with the photolytic molecule to occur thereby capable of transferring energy to the photolytic molecule via triplet-triplet annihilation so as to cause a photolytic reaction of the photolytic compound, wherein the photolytic compound has the formula,

PPG-X, wherein

PPG is a photoremovable protecting group comprising a moiety selected from the group consisting of coumarin, anthracene, perylene and boron-dipyrromethene; and X is L-Y, wherein L is a photolabile linker comprising an ester, carbonate, carbamate, quaternary ammonium salt moiety and Y a therapeutic moiety.

* * * * *